(12) United States Patent
Jorand-Lebrun et al.

(10) Patent No.: US 11,001,561 B2
(45) Date of Patent: May 11, 2021

(54) PYRIMIDINONE DERIVATIVES AS SHP2 ANTAGONISTS

(71) Applicant: MERCK PATENT GMBH, Darmstadt (DE)

(72) Inventors: Catherine Jorand-Lebrun, Arlington, MA (US); Roch Boivin, North Chelmsford, MA (US); Theresa Johnson, Salem, MA (US); Yanping Wang, Billerica, MA (US); Yufang Xiao, Lexington, MA (US); Xiaoling Chen, Chestnut Hill, MA (US); Nina Linde, Frankfurt AM Main (DE); Doreen Musch, Reinheim (DE); Deepak Kumar, Canton (MA)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/843,735

(22) Filed: Apr. 8, 2020

(65) Prior Publication Data

US 2020/0317622 A1  Oct. 8, 2020

Related U.S. Application Data

(60) Provisional application No. 63/000,257, filed on Mar. 26, 2020, provisional application No. 62/879,816, filed on Jul. 29, 2019.

(30) Foreign Application Priority Data

Apr. 8, 2019  (EP) ..................... 19167897

(51) Int. Cl.

| | | |
|---|---|---|
| *C07D 239/36* | (2006.01) |
| *C07D 239/42* | (2006.01) |
| *C07D 401/04* | (2006.01) |
| *C07D 401/14* | (2006.01) |
| *C07D 403/04* | (2006.01) |
| *C07D 471/10* | (2006.01) |
| *C07D 487/10* | (2006.01) |
| *C07D 491/052* | (2006.01) |
| *C07D 491/107* | (2006.01) |
| *C07D 491/20* | (2006.01) |
| *A61P 35/00* | (2006.01) |

(52) U.S. Cl.
CPC ............ *C07D 239/36* (2013.01); *A61P 35/00* (2018.01); *C07D 239/42* (2013.01); *C07D 401/04* (2013.01); *C07D 401/14* (2013.01); *C07D 403/04* (2013.01); *C07D 471/10* (2013.01); *C07D 487/10* (2013.01); *C07D 491/052* (2013.01); *C07D 491/107* (2013.01); *C07D 491/20* (2013.01)

(58) Field of Classification Search
CPC .. C07D 239/35; C07D 239/42; C07D 401/04; C07D 401/14; C07D 403/04; C07D 471/10; C07D 487/10; C07D 491/052; C07D 491/107; C07D 491/20
See application file for complete search history.

(56) References Cited

U.S. PATENT DOCUMENTS

| | | | |
|---|---|---|---|
| 4,125,828 A | 11/1978 | Resnick et al. |
| 4,207,554 A | 6/1980 | Resnick et al. |

FOREIGN PATENT DOCUMENTS

| | | | |
|---|---|---|---|
| WO | WO97/22596 A1 | 6/1997 |
| WO | WO97/30035 A1 | 8/1997 |
| WO | WO97/32856 A1 | 9/1997 |
| WO | WO98/13354 A1 | 4/1998 |
| WO | WO99/02166 A1 | 1/1999 |
| WO | WO00/40529 A1 | 7/2000 |
| WO | WO00/41669 A2 | 7/2000 |
| WO | WO01/92224 A1 | 12/2001 |
| WO | WO02/04434 A1 | 1/2002 |
| WO | WO02/08213 A1 | 1/2002 |
| WO | WO 2015/107493 A1 | 7/2015 |
| WO | WO 2015/107494 A1 | 7/2015 |
| WO | WO 2015/107495 A1 | 7/2015 |
| WO | WO 2016/203404 A1 | 12/2016 |
| WO | WO 2016/203405 A1 | 12/2016 |
| WO | WO 2016/203406 A1 | 12/2016 |

(Continued)

OTHER PUBLICATIONS

N. Aceto et al., Nature Medicine, 2012, 28, 529-538.

(Continued)

*Primary Examiner* — Erich A Leeser
(74) *Attorney, Agent, or Firm* — Kathryn M. Bishop; EMD Serono Research and Development Institute

(57) ABSTRACT

The invention relates to pyrimidinone derivatives of the general Formula I,

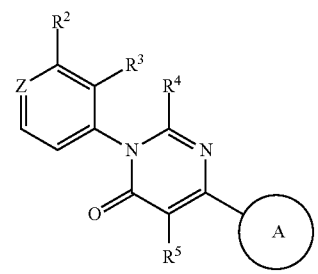

or a pharmaceutically acceptable salt thereof, and the use of the compounds of the present invention for the treatment of hyperproliferative diseases and disorders in mammals, especially humans, and pharmaceutical compositions containing such compound.

19 Claims, 7 Drawing Sheets

(56) References Cited

FOREIGN PATENT DOCUMENTS

| WO | WO 2017/216706 A1 | 12/2017 | | |
|---|---|---|---|---|
| WO | WO2017211303 A1 | 12/2017 | | |
| WO | WO2018/013597 A1 | 1/2018 | | |
| WO | WO2018/057884 A1 | 3/2018 | | |
| WO | WO2018/081091 A1 | 5/2018 | | |
| WO | WO2018/130928 A1 | 7/2018 | | |
| WO | WO2018/136264 A1 | 7/2018 | | |
| WO | WO2018/136265 A1 | 7/2018 | | |
| WO | WO 2018/172984 | * | 9/2018 | ........... C07D 241/18 |
| WO | WO2018/172984 A1 | 9/2018 | | |
| WO | WO2019/051084 A1 | 3/2019 | | |
| WO | WO2019/051469 A1 | 3/2019 | | |
| WO | WO2019/067843 A1 | 4/2019 | | |
| WO | WO2019/118909 A1 | 6/2019 | | |
| WO | WO2019/165073 A1 | 8/2019 | | |
| WO | 2019/182960 | 9/2019 | | |
| WO | WO2019/83364 A1 | 9/2019 | | |
| WO | WO2019/183367 A1 | 9/2019 | | |
| WO | 2020/033828 | 3/2020 | | |

OTHER PUBLICATIONS

M. Bentires-Alj et al., in Cancer Res. 2004, 64, 8816-8820.
Cai et al., Biomedicine & Pharmacotherapy 2014, 68, 285-29.
Chen et al., Nature, 2016, doi. 10.1038/nature/18621.
J. G. Fortanet et al., J. Med. Chem. 2016, doi: 10.1021/acs.jmedchem. 6b00600.
P.J. Fraker et al., Proc. Nat. Acad. Sci. USA, vol. 75, No. 11, 1978, 5660-5664.
CM Furcht, Oncogene, 2013, 32, 2346-2355.
K. S. Grossman et al., Adv. Cancer Res., 2010, 106, 53-89.
J. Schaffer et al., Journal of Pharmaceutical Sciences, 1999, vol. 88, No. 3, 313-318.
V. E. Schneeberger et al., Oncotarget, 2015, 6, 6191-6202.
P. Tyle, Pharmaceutical Research, 1986, vol. 3, No. 6, 318-326.
J. Wang et al., J. Clin. Invest., 2016, 126, 6, 2077-2092.
M. Yosida et al., International Journal of Pharmaceutics, 995, 115, 61-67.
Sarver et al., Journal of Medicinal Chemistry 2019, 62, 4, 1793-1802, Jan. 28, 2019.
Bagdanoff et al., Journal of Medicinal Chemistry 2019, 62, 4, 1781-1792, Jan. 28, 2019.

* cited by examiner

PYRIMIDINONE DERIVATIVES AS SHP2 ANTAGONISTS

REFERENCE TO RELATED APPLICATIONS

This application claims the benefit of priority to European Application Number 19167897.8, filed on Apr. 8, 2019, U.S. Provisional Application No. 62/879,816 filed Jul. 29, 2019, and U.S. Provisional Application No. 63/000,257 filed Mar. 26, 2020. All of the above-referenced applications are incorporated by reference herein.

The invention relates to pyrimidinone derivatives of the general Formula I,

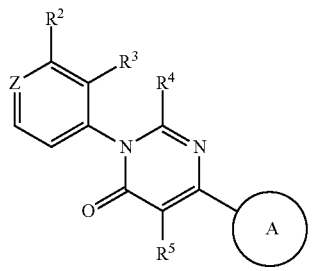

or a pharmaceutically acceptable salt thereof, and the use of the compounds of the present invention for the treatment of hyperproliferative diseases and disorders in mammals, especially humans, and pharmaceutical compositions containing such compounds.

BACKGROUND OF THE INVENTION

Src homology region 2 (SH2) containing protein tyrosine phosphatase 2 (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

SHP2 is ubiquitously expressed in various tissues and cell types. It plays an important role in diverse signaling pathways to regulate cellular biological processes and is involved in the signaling pathways of a variety of growth factors and cytokines. Within a single signaling pathway, SHP2 can play both positive (signal enhancing) and negative (signal diminishing) roles intracellular signaling processes. SHP2 is believed to function by dephosphorylating its associated signaling molecules, thereby attenuating the local signaling flow. However, the main effect of SHP2 action in most signaling pathways (e.g. growth factor, cytokine and extracellular matrix receptors) is to enhance signal transduction. For example, SHP2 is a positive regulator of the ERK/MAPK signaling pathway, playing a key role in regulating cellular proliferation and survival (K. S. Grossman et al., Adv. Cancer Res., 2010, 106, 53-89 and references cited therein).

Mutations in the PTPN11 gene that affect the N-SH2 or PTP domain residues involved in basal inhibition of SHP2 result in more readily activatable forms of SHP2 protein, which can lead to unregulated or increased SHP2 activity. Such activated mutants of SHP2 have been associated with developmental disorders such as Noonan syndrome, where nearly all mutated forms of SHP2 demonstrate increased PTP activity. Activating SHP2 mutations have also been detected in juvenile myelomonocytic leukemia (e g. Q506P), chronic myelomonocytic leukemia (e.g. Y63C), neuroblastoma (e.g. T507K), melanoma (e.g. RI38Q), acute myeloid leukemia (e.g, G503V), breast cancer, lung cancer (e.g. E76V) and colorectal cancer (e.g. E76G) (M. Bentires-Alj et al., in Cancer Res. 2004, 64, 8816-8820; and references cited therein). Additional PTPN1 mutations associated with cancers are disclosed in WO 2015/107495 and references cited therein.

Mutations in the PTPN11 gene and subsequently in SHP2 have been identified in several human diseases, such as Noonan Syndrome (NS), Leopard Syndrome, diabetes, neutropenia (Kostmann's syndrome), systemic lupus erythematosus, neuroblastoma, melanoma, juvenile myelomonocytic leukemia, acute myeloid leukemia, juvenile leukemia, chronic myelomonocytic leukemia and other cancers associated with SHP2 deregulation such as cancers of the lung, colon and breast such as HER2-positive breast cancer, triple-negative breast cancer, ductal carcinoma of the breast, invasive ductal carcinoma of the breast, non-small cell lung cancer (including adenocarcinoma of the lung), esophageal cancer, gastric cancer, squamous-cell carcinoma of the head and neck (SCCHN) and colon cancer. (N. Aceto et al., Nature Medicine, 2012, 28, 529-538; C. M. Furcht et al., Oncogene, 2013, 32, 2346-2355; V. E. Schneeberger et al., Oncotarget, 2015, 6, 6191-6202; P. Cai et al., Biomedicine & Pharmacotherapy 2014, 6, 285-290; and references cited therein).

Therefore, SHP2 represents a highly attractive target for the development of novel therapies for the treatment of various diseases. The compounds of the present disclosure fulfill the need for small molecules to that inhibit the activity of SHP2.

SHP2 phosphatase inhibitors are disclosed e.g. in WO 2015/107493. WO 2015/107494, WO 2015/107495, WO 2016/203404, WO 2016/203405, WO 2016/203406, WO2017/216706, WO2018/013597, WO2018/136264, WO2018/136265, WO2018/057884, WO2018/081091 and J. G. Fortanet et al., J. Med. Chem. 2016, doi: 10.1021/acs.jmedchem.6b00600 and references cited therein. The effects of SHP2 phosphatase inhibition are described e.g. in Y.-N. P. Chen et al., Nature, 2016, doi. 10.1038/nature/18621; J. Wang et al., J. Clin. Invest., 2016, 126, 2077-2092 and references cited therein. SHP2 phosphatase inhibitors include e.g. 8-Hydroxy-7-[(6-sulfo-2-naphthyl)azo]-5-quinolinesulfonic acid (NSC 87077) and SHP099.

However, known compounds such as SHP099 (or the compounds of the WO2015/107493) or RMC-4550 (the compounds of the WO2018/013597) do not show a high selectivity over hErg but which is very important for the safety of compounds which are intended to be used for the treatment of diseases. hErg expression has been definitely linked to QT elongation, which is a type of cardiac toxicity. Compounds which have the tendency to inhibit hERG, thereby lengthening the QT, can potentially lead to irregularity of the heartbeat called a ventricular tachyarrhythmia, and death.

Furthermore, compounds of the present invention show superior pharmacokinetic properties (e.g., low clearance and/or high exposure) as compared to compounds such as SHP099 (or the compounds of the WO2015/107493) or RMC-4550 (or the compounds of WO2018/013597).

Thus, there remains a need for highly effective SHP2 inhibitors which have improved toxicity and/or pharmacokinetic properties as compared to prior art compounds. It is a specific object of the invention to provide improved methods of preventing or treating hyperproliferative diseases and disorders in a host, especially to provide effective SHP2 antagonists for the treatment and prevention of such diseases.

SUMMARY OF THE INVENTION

Surprisingly, it has been found that the pyrimidinone derivatives according to the invention are highly effective inhibitors of SHP2 and thus they can be used for the treatment of hyperproliferative diseases and disorders such as cancer.

Additionally, the compounds of the present invention are highly effective inhibitors of ERK1 2, a target downstream form SHP2 in the signaling pathway (as mentioned above SHP2 is a positive regulator of the ERK/MAPK signaling pathway, ERK phosphorylation depends on SHP2 activation), which is playing a key role in regulating cellular proliferation and survival. This also confirms that the compounds of the present invention can be used for the treatment of hyperproliferative diseases and disorders such as cancer.

At the same time, the compounds of the present invention in comparison with the known SHP2 antagonists SHP099, RMC-4550 and similar pyrimidine derivatives surprisingly have a much higher selectivity over hErg (the ion channel Kv11.1). The high hErg inhibitory activity of SHP099, RMC-4550 and similar pyrimidine derivatives clearly point to a potential cardiotoxicity risk, which is avoided by compounds of the present invention. This improved safety profile of the compounds of the present invention is combined with more desirable pharmacokinetic properties and enhanced target engagement (lower IC50s). The surprising properties of the compounds of the present invention show a significant needed advancement in the field of SHP2 inhibitors.

The invention relates to pyrimidinone derivatives of the general Formula I*,

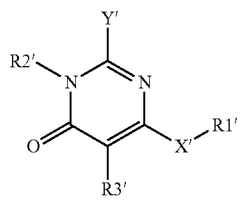

wherein

R1' is mono-, bi or tricyclic alkyl, alkenyl, heterocyclyl, heteroaryl or bicyclic alkylaryl, containing 3 to 14 carbon atoms and 0-4 heteroatoms, independently selected from N, O and S, which is unsubstituted or mono-, di- or trisubstituted by $(CH_2)_n NHR4'$, $(CH_2)_n CONH_2$, $(CH_2)_n CF_2H$, $(CH_2)_n CF_3$, $(CH_2)_n OH$, alkyl, =O, Hal or by N-alkyl or alkyl-$NH_2$ which is unsubstituted or mono or disubstituted with OR4', X' is a single bond, —NH—, —N($CH_3$)—, —$(CH_2)_n$— or —O—, R2' is aryl or heteroaryl, S-aryl or S-heteroaryl which is unsubstituted or mono-, di- or trisubstituted by $(CH_2)_n NH_2$, $(CH_2)_n OR_4$, $(CH_2)_n COOR4'$, $(CH_2)_n CONH_2$, alkyl, =S, =O, =NH, CN, $CF_3$ or Hal, Y' is H, $NH_2$, alkyl, S-alkyl, $CF_3$, $CF_2H$, COOR4, $CONH_2$, OH or Hal, R3' is H, alkyl, $NH_2$, $CF_3$, $CF_2H$, COOR4, $CONH_2$, $CD_3$, OH or Hal, R4' is H or alkyl Hal is F, Cl, Br, or I, n is 0, 1, 2 or 3, and pharmaceutically acceptable salts thereof.

One embodiment of the invention is a compound according to Formula (I):

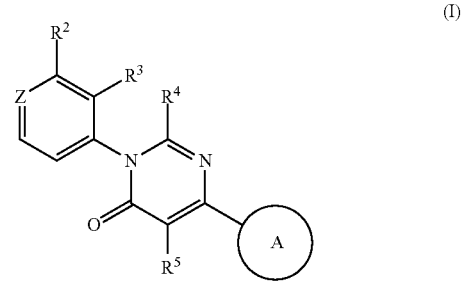

or a pharmaceutically acceptable salt thereof,
wherein
Ring A is

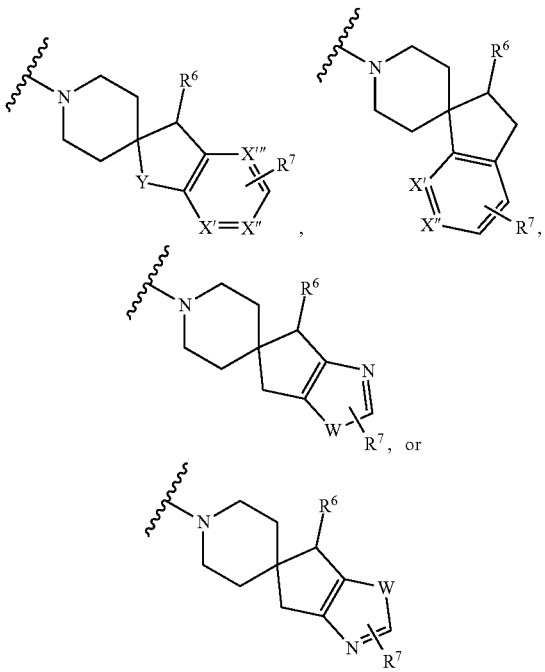

R¹ is hydrogen, —F, —Cl, —Br, —OPh,

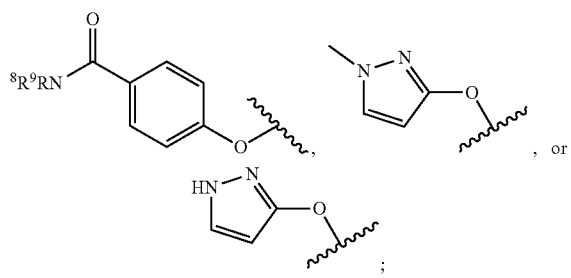

, or each of R², and R³ are independently selected from hydrogen, —CF₃, —Cl, —Br, —F, —CN, —NH₂, —OCH₃, and —CH₃;

each of R⁴ and R⁵ are independently selected from hydrogen, —Br, —Cl, —CF₃, —CH₃, —CD₃ and —NH₂;

R⁶ is —NH₂;

R⁷ is hydrogen, —Cl, —Br, —F, —CN, —OCH₃, —CH₃, or —NH₂;

each of R⁸ and R⁹ is independently hydrogen or methyl;

each W is S or O;

Z is N or —CR¹;

each X' and X" is either —CH— or —N—, provided that both X' and X" are not N at the same time; and Y, where present, is —CH₂— or —O—.

One aspect of this embodiment is a compound of Formula (I), or a pharmaceutically acceptable salt thereof, wherein Z is N.

Another aspect of this embodiment is a compound of Formula (I), or a pharmaceutically acceptable salt thereof, wherein Z is C—R¹.

DETAILED DESCRIPTION

Figure 1:
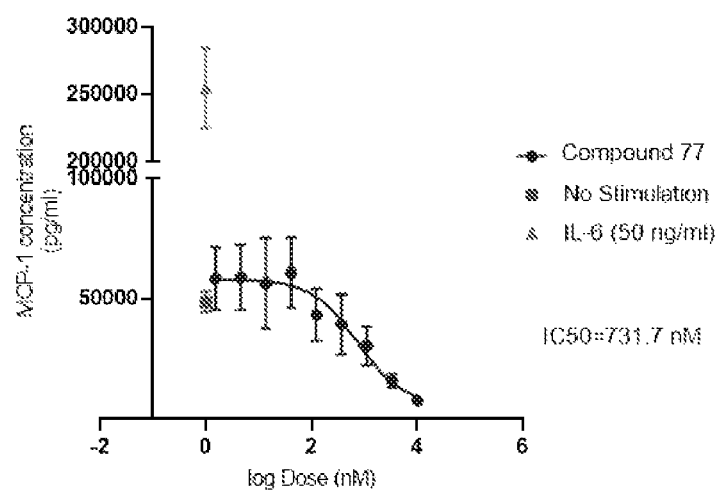
FIG. 1 depicts compound 77 suppressed MCP-1 production in U937 cells stimulated with IL-6.

A further embodiment of the invention is a compound according to Formula (Ia') or Formula (Ib'):

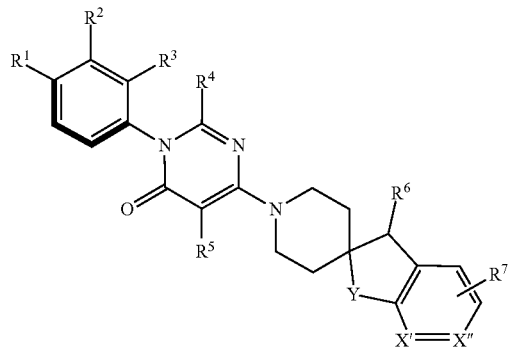

Ia'

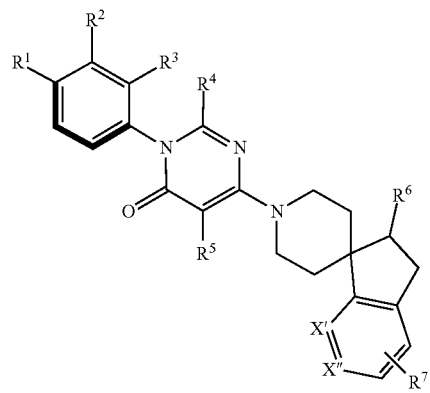

Ib' or a pharmaceutically acceptable salt thereof.

A further embodiment of the present invention is a compound according to Formula (Ia") or Formula (Ib"):

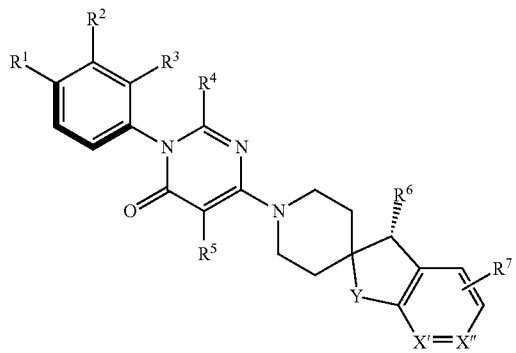

Ia"

-continued

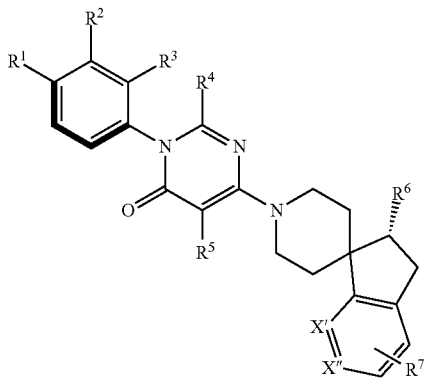

or a pharmaceutically acceptable salt thereof.

One aspect of the invention is a compound according to any one of Formulae I, Ia', Ib', Ia", or Ib", or a pharmaceutically acceptable salt thereof, wherein $R^1$ is hydrogen or —F.

A second aspect of the invention is a compound according to any one of Formulae I, Ia', Ib', Ia", or Ib", or a pharmaceutically acceptable salt thereof, wherein $R^1$ is hydrogen.

A third aspect of the invention is a compound according to any one of Formulae I, Ia', Ib', Ia", or Ib", or a pharmaceutically acceptable salt thereof, wherein $R^2$ and $R^3$ are independently —Cl, —Br, —F, —CN, —OCH$_3$, or —CH$_3$.

A fourth aspect of the invention is a compound according to any one of Formulae I, Ia', Ib', Ia", or Ib", or a pharmaceutically acceptable salt thereof, wherein $R^2$ and $R^3$ are both —Cl.

A fifth aspect of the invention is a compound according to any one of Formulae I, Ia', Ib', a", or Ib", or a pharmaceutically acceptable salt thereof, wherein $R^4$ and $R^5$ are independently —CH$_3$ or —NH$_2$.

A sixth aspect of the invention is a compound according to any one of Formulae I, Ia', Ib', Ia", or Ib", or a pharmaceutically acceptable salt thereof, wherein $R^4$ and $R^5$ are both —CH$_3$.

A seventh aspect of the invention is a compound according to any one of Formulae I, Ia', Ib', Ia", or Ib", or a pharmaceutically acceptable salt thereof, wherein $R^6$ is —NH$_2$.

An eighth aspect of the invention is a compound according to any one of Formulae I, Ia', Ib', Ia", or Ib", or a pharmaceutically acceptable salt thereof, wherein $R^7$ is hydrogen.

A ninth aspect of the invention is a compound according to any one of Formulae I, Ia', Ib', Ia", or Ib", or a pharmaceutically acceptable salt thereof, wherein X' is N and X" is CH.

A tenth aspect of the invention is a compound according to any one of Formulae I, Ia', Ib', Ia", or Ib", or a pharmaceutically acceptable salt thereof, wherein X' is CH and X" is N.

An eleventh aspect of the invention is a compound according to any one of Formulae I, Ia', Ib', Ia", or Ib", or a pharmaceutically acceptable salt thereof, wherein both X' and X" are CH.

A twelfth aspect of the invention is a compound according to any one of Formulae I, Ia', Ib', Ia", or Ib", or a pharmaceutically acceptable salt thereof, wherein Y, when present, is O.

A thirteenth aspect of the invention is a compound according to any one of Formulae I, Ia', Ib', Ia", or Ib", or a pharmaceutically acceptable salt thereof, wherein Y, when present, is CH$_2$.

A fourteenth embodiment of the invention is a compound according to any one of Formulae I, Ia', Ib', Ia", or Ib", selected from the group consisting of:

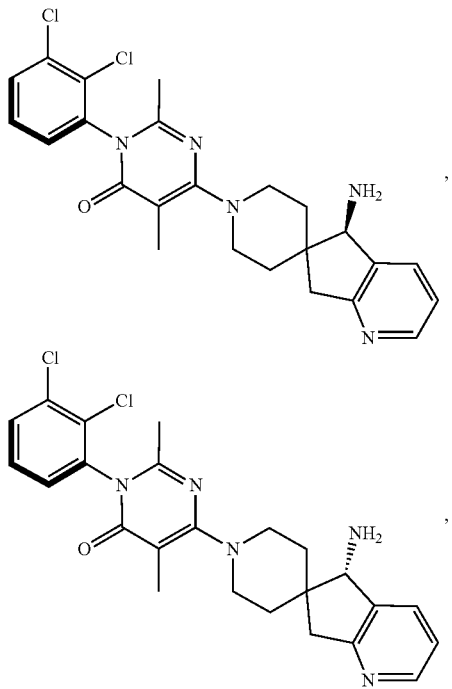

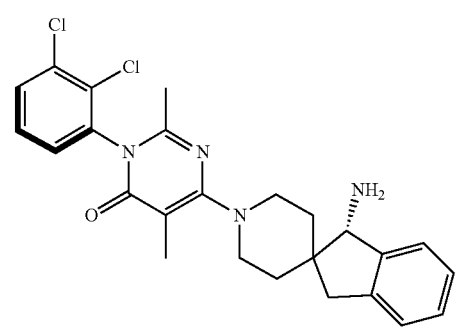

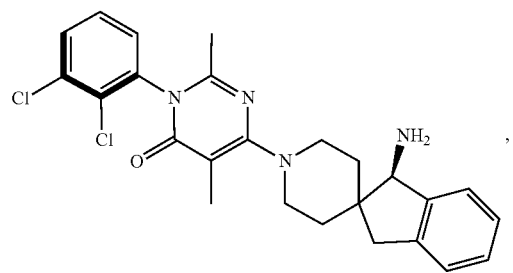

-continued
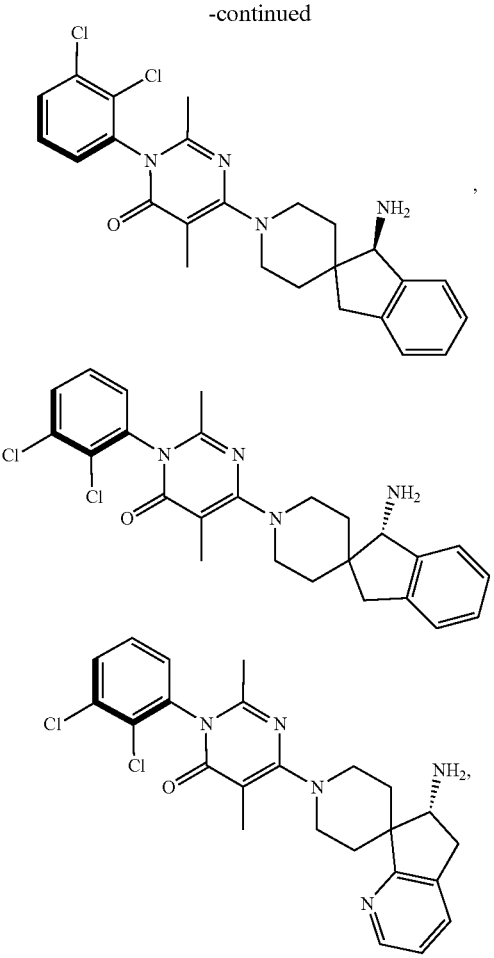
-continued
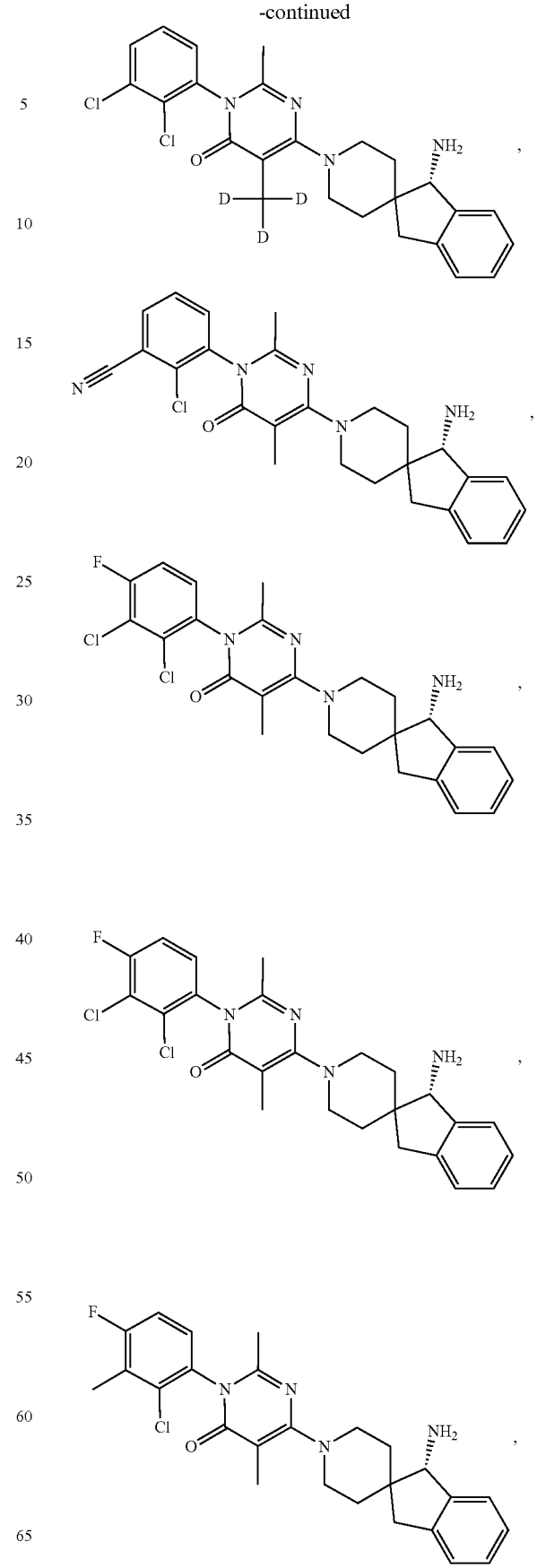

11
-continued
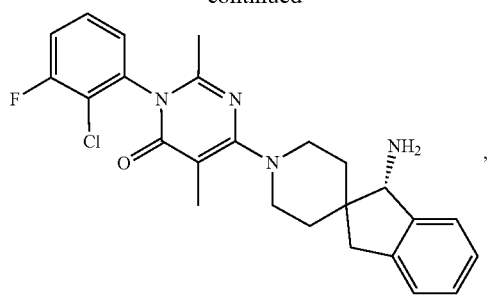
,
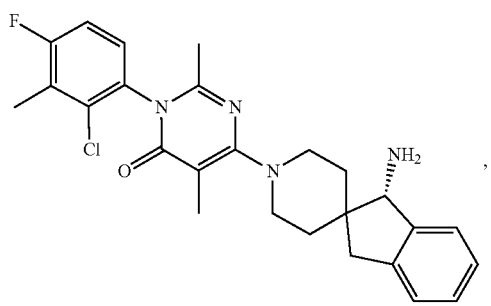
,
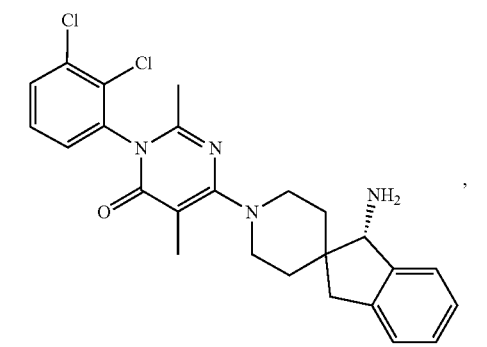
,
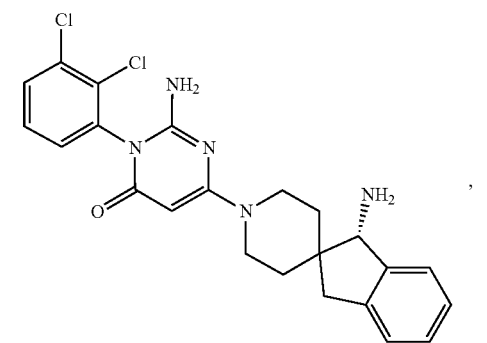
,
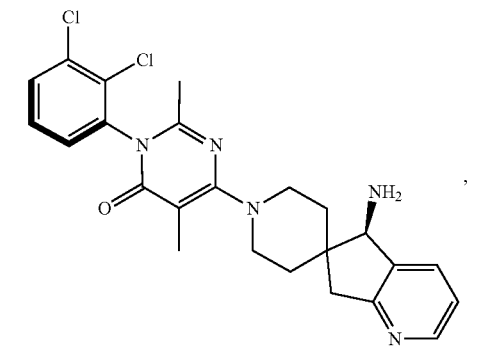
,
12
-continued
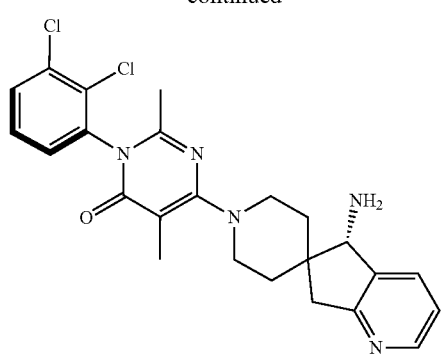
,
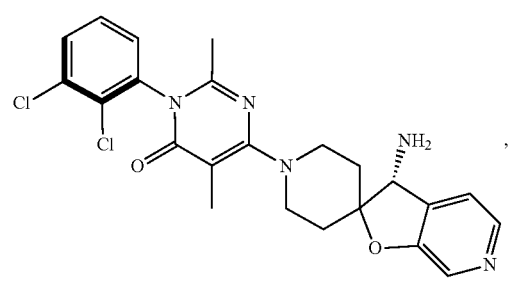
,
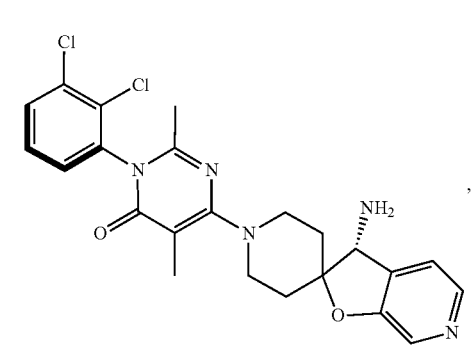
79b
,
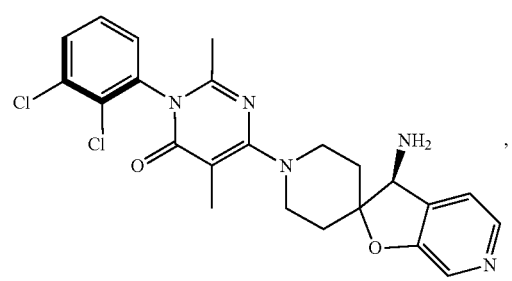
,
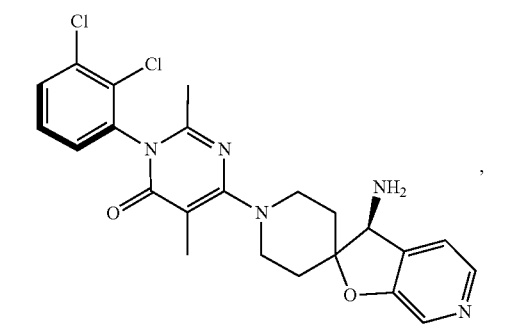
,

13

-continued

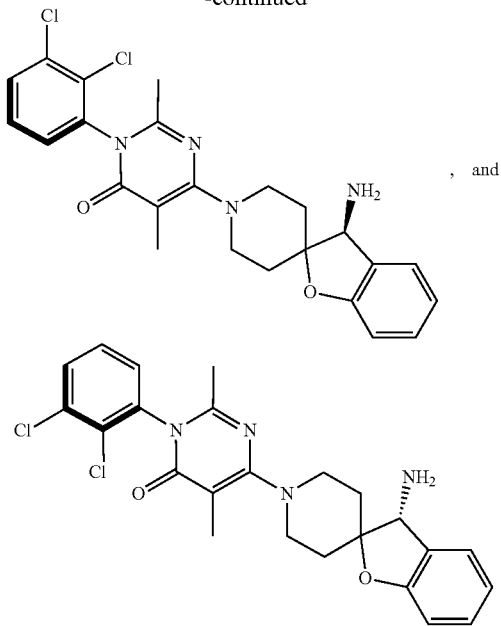

, and

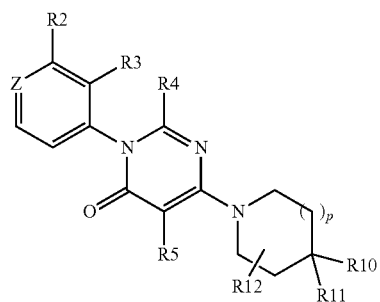

or a pharmaceutically acceptable salt thereof.

A further embodiment is a compound selected from Table 1, or a pharmaceutically acceptable salt thereof.

Another embodiment of the present invention is a compound according to Formula II:

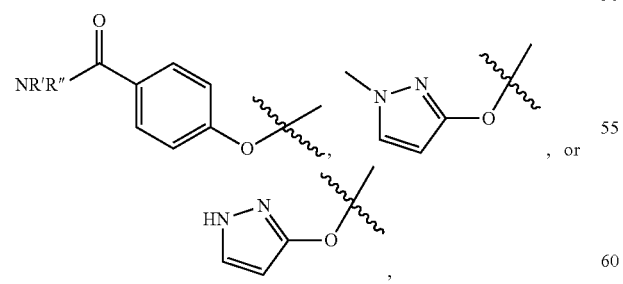

or a pharmaceutically acceptable salt thereof, wherein
Z is $CR^1$ or N;
$R^1$ is hydrogen, —OH, —OCH$_3$, —F, —Cl, —Br, —OPh,

[structures: NR'R"-benzoyl-O-, N-methylpyrazolyl-O-, pyrazolyl-O-]
, or
, each of $R^2$ and $R^3$ are independently selected from hydrogen, —CF$_3$, —Cl, —Br, —F, —CN, —NH$_2$, —OCH$_3$, and —CH$_3$;
each of $R^4$ and $R^5$ are independently selected from hydrogen, —Br, —Cl, $C_1$-$C_3$ alkyl, $C_1$-$C_3$ haloalkyl, —CD$_3$, cyclopropyl, $C_1$-$C_3$ aminoalkyl, $C_1$-$C_3$ alkoxy, $C_1$-$C_3$ hydroxyalkyl, $C_1$-$C_3$ thioalkyl and —NH$_2$;

each of $R^{10}$ and $R_{11}$ are independently selected from hydrogen, —OH, —NR'R", $C_1$-$C_3$ aminoalkyl, $C_1$-$C_3$ hydroxyalkyl, $C_1$-$C_3$ hydroxy(amino)alkyl, $C_1$-$C_3$ haloalkyl, and a 5-7 membered heterocyclyl, wherein the heterocyclyl is optionally substituted with 1-3 groups selected from methyl, ethyl, —OH, —NH$_2$, —CH$_2$NH$_2$, and —CH$_2$OH;
or $R^{10}$ and $R^{11}$ can be taken together with the carbon atom to which they are attached to form a 3-10 membered cycloalkyl or a 4-11 membered heterocyclyl, each of which is optionally substituted with 1 to 3 groups independently selected from methyl, ethyl, propyl, isopropyl, —OH, —NH$_2$, —Br, —Cl, —F, $C_1$-$C_3$ haloalkyl, $C_1$-$C_3$ aminoalkyl, and $C_1$-$C_3$ hydroxyalkyl;
$R^{12}$ is hydrogen, —OH, $C_1$-$C_3$ alkyl, —NH$_2$, —Cl, —Br, —F, $C_1$-$C_3$ hydroylalkyl, $C_1$-$C_3$ alkoxy, $C_1$-$C_3$ aminoalkyl; or
when $R^{12}$ is on a carbon atom alpha to $R^{10}$, $R^{12}$ can be taken together with $R^{10}$ and the two carbon atoms of the nitrogen containing ring to which they are each attached to form a 5-6 membered fused bicyclic or tricyclic heterocyclyl ring which is optionally substituted with 1 to 3 groups independently selected from methyl, ethyl, propyl, isopropyl, —OH, —NH$_2$, —Br, —Cl, —F, $C_1$-$C_3$ haloalkyl, $C_1$-$C_3$ aminoalkyl, and $C_1$-$C_3$ hydroxyalkyl;
each of R' and R" are independently —H, $C_1$-$C_3$ alkyl, —OH, —CH$_2$ (4-hydroxycyclohexyl), $C_1$-$C_4$ hydroxyalkoxy, and $C_1$-$C_3$ hydroxyalkyl; and
p is 0, 1 or 2;

and wherein the compound is not

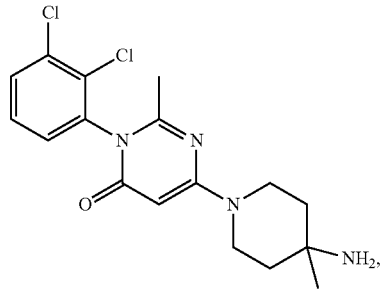

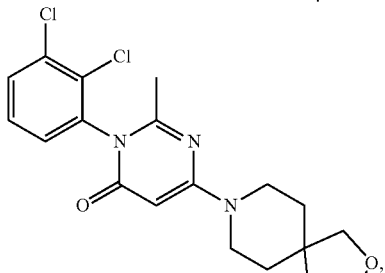

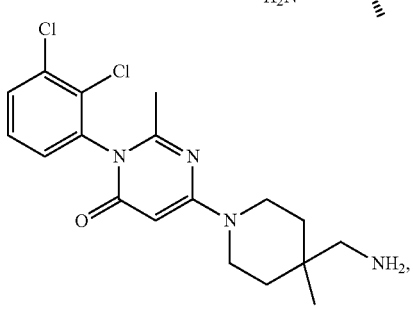

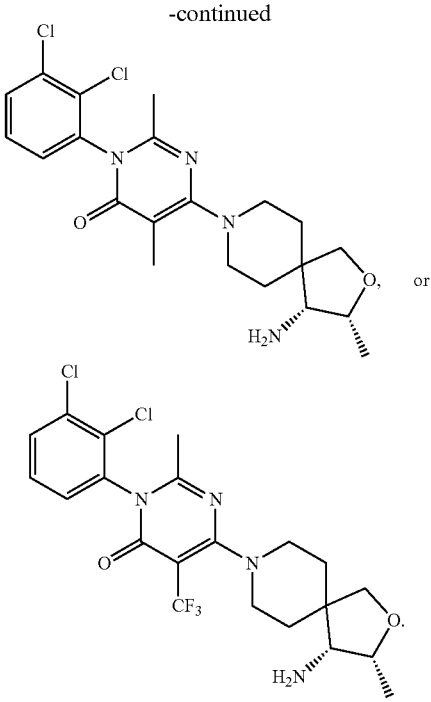

A further embodiment is a compound according to Formula II wherein Z is N.

Another embodiment is a compound according to Formula II wherein Z is C—R$^1$. In one aspect of this embodiment, R$^1$ is hydrogen, —OCH$_3$ or —F. In a further aspect of the embodiment, R$^1$ is hydrogen.

One embodiment of the invention is a compound according to Formula II wherein R$^2$ and R$^3$ are independently selected from —Cl, —Br, —F, —CF$_3$, —OCH$_3$, and —CN. A further embodiment is a compound according to Formula II wherein R$^3$ is —Cl, —Br or —F. One aspect of this embodiment is wherein both R$^2$ and R$^3$ are —Cl.

One embodiment, is a compound according to Formula II wherein Z is CR$^1$, R$^1$ is H, and both R$^2$ and R$^3$ are —Cl.

A further embodiment is a compound according to Formula II wherein R$^4$ is selected from —CH$_3$, —NH$_2$, —CF$_2$H, hydrogen, —CF$_3$, ethyl, isopropyl, —CD$_3$, —OCH$_3$, and —CH$_2$CH$_2$OH. In one aspect of this embodiment, R$^4$ is selected from —CH$_3$, —NH$_2$, hydrogen and —CF$_2$H. In a further aspect of this embodiment, R$^4$ is —CH$_3$ or —NH$_2$. In a further aspect of this embodiment, R$^4$ is —CH$_3$.

Another embodiment is a compound according to Formula II wherein R$^5$ is selected from —CH$_3$, —NH$_2$, —CF$_2$H, hydrogen, —CF$_3$, ethyl, isopropyl, —CD$_3$, —OCH$_3$, and —CH$_2$CH$_2$OH. In one aspect of this embodiment, R$^5$ is selected from hydrogen, —CH$_3$, —CF$_3$, ethyl, isopropyl, —CD$_3$, —OCH$_3$, and —CH$_2$CH$_2$OH. In another aspect of this embodiment, R$^S$ is —CH$_3$.

One embodiment of the present invention is a compound according to Formula II wherein both R$^4$ and R$^5$ are —CH$_3$.

One embodiment of the present invention is a compound according to Formula II wherein each of R$^{10}$ and R$^{11}$ are independently selected from hydrogen, —OH, —NR'R", C$_1$-C$_3$ aminoalkyl, C$_1$-C$_3$ hydroxyalkyl, C$_1$-C$_3$ hydroxy (amino)alkyl, C$_1$-C$_3$ haloalkyl, and a 5-7 membered heterocyclyl, wherein the heterocyclyl is optionally substituted with 1-3 groups selected from methyl, ethyl, —OH, —NH$_2$, —CH$_2$NH$_2$, and —CH$_2$OH.

One embodiment of the present invention is a compound of Formula II wherein p is 0 and each of R$^{10}$ and R$^{11}$ are independently selected from hydrogen, —OH, —NR'R", C$_1$-C$_3$ aminoalkyl, C$_1$-C$_3$ hydroxyalkyl, C$_1$-C$_3$ hydroxy (amino)alkyl, C$_1$-C$_3$ haloalkyl, and a 5-7 membered heterocyclyl, wherein the heterocyclyl is optionally substituted with 1-3 groups selected from methyl, ethyl, —OH, —NH$_2$, —CH$_2$NH$_2$, and —CH$_2$OH. In one aspect of this embodiment, the nitrogen containing ring on which R$^{10}$ and R$^{11}$ are attached is:

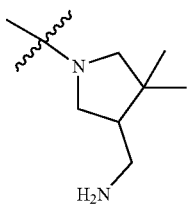

Another embodiment of the present invention is a compound of Formula II wherein p is 0 and R10 and R12 are taken together with the two adjacent carbon atoms to which they are attached to form a fused bicyclic or tricyclic ring as shown:

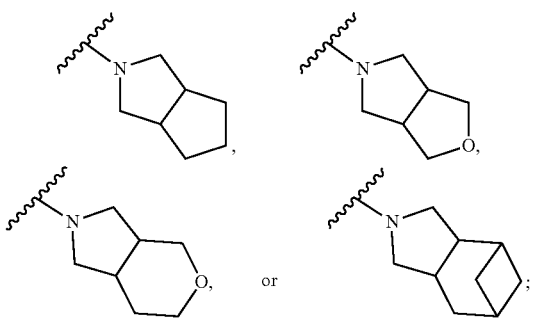

wherein each ring formed by R$^{10}$ and R$^{12}$ is independently and optionally substituted with 1-3 groups selected from —NH$_2$, —CH$_2$NH$_2$, —CH$_3$, —OH and —CH$_2$OH. One aspect of this embodiment is selected from the fused pyrrolidinyl moieties as shown:

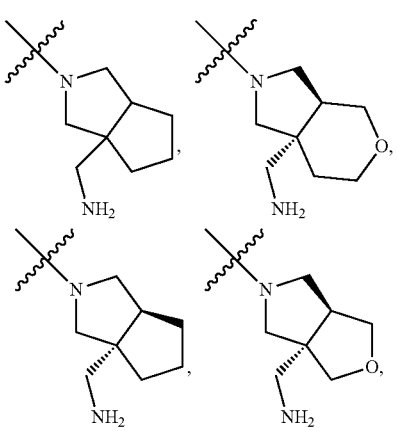

-continued

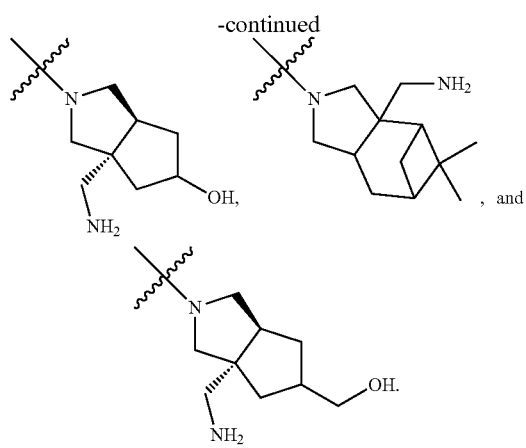

A further embodiment of the present invention is a compound of Formula II wherein p is 1 and R10 and R12 are taken together with the two adjacent carbon atoms to which they are attached to form the fused bicyclic ring

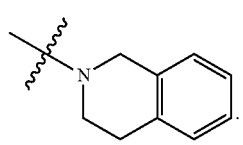

In one aspect of this embodiment, the fused bicyclic moiety is selected from

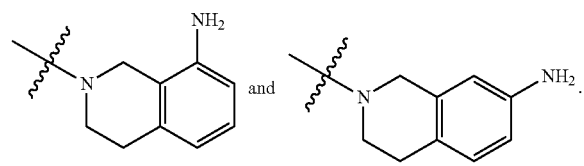 [SMILES: *N1CCc2cccc(N)c2C1 ; *N1CCc2ccc(N)cc2C1]

One embodiment of the present invention is a compound according to Formula II wherein each of $R^{10}$ and $R^{11}$ are independently selected from hydrogen, —OH, —NR'R", $C_1$-$C_3$ aminoalkyl, $C_1$-$C_3$ hydroxyalkyl, $C_1$-$C_3$ hydroxy (amino)alkyl, $C_1$-$C_3$ haloalkyl, and a 5-7 membered heterocyclyl, wherein the heterocyclyl is optionally substituted with 1-3 groups selected from methyl, ethyl, —OH, —NH$_2$, —CH$_2$NH$_2$, and —CH$_2$OH. A further embodiment of the present invention is a compound of Formula II wherein p is 1 or 2; and $R^{10}$ and $R^{11}$ are selected from hydrogen, —NH$_2$, $C_1$-$C_3$ aminoalkyl, $C_1$-$C_3$ alkyl, $C_1$-$C_3$ hydroxyalkyl, and —OH, wherein $R^{10}$ and $R^{11}$ are not both hydrogen. In a further aspect of this embodiment, p is 1; and $R^{10}$ and R are selected from hydrogen, —NH$_2$, —CH$_2$NH$_2$, —(CH$_2$)$_2$NH$_2$, —C(O)NH$_2$, —OH, —CH$_2$CH$_2$F, —CH$_2$OH, —CH$_2$CH$_2$OH, —NHCH$_3$, —NH(CH$_2$CHOHCH$_2$OH), —NH(CH$_2$CHOHCH$_2$OCH$_3$), —CHOHCH$_2$NH$_2$,

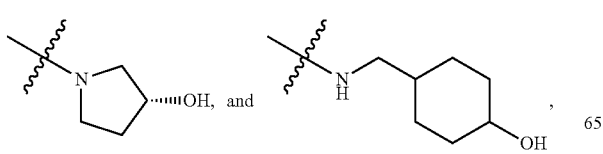

wherein $R^{10}$ and $R^{11}$ are not both hydrogen. In an additional aspect of this embodiment, one of $R^{10}$ and $R^{11}$—NH$_2$ or —CH$_2$NH$_2$. In one aspect of this embodiment, the piperidinyl moiety is selected from the group consisting of:

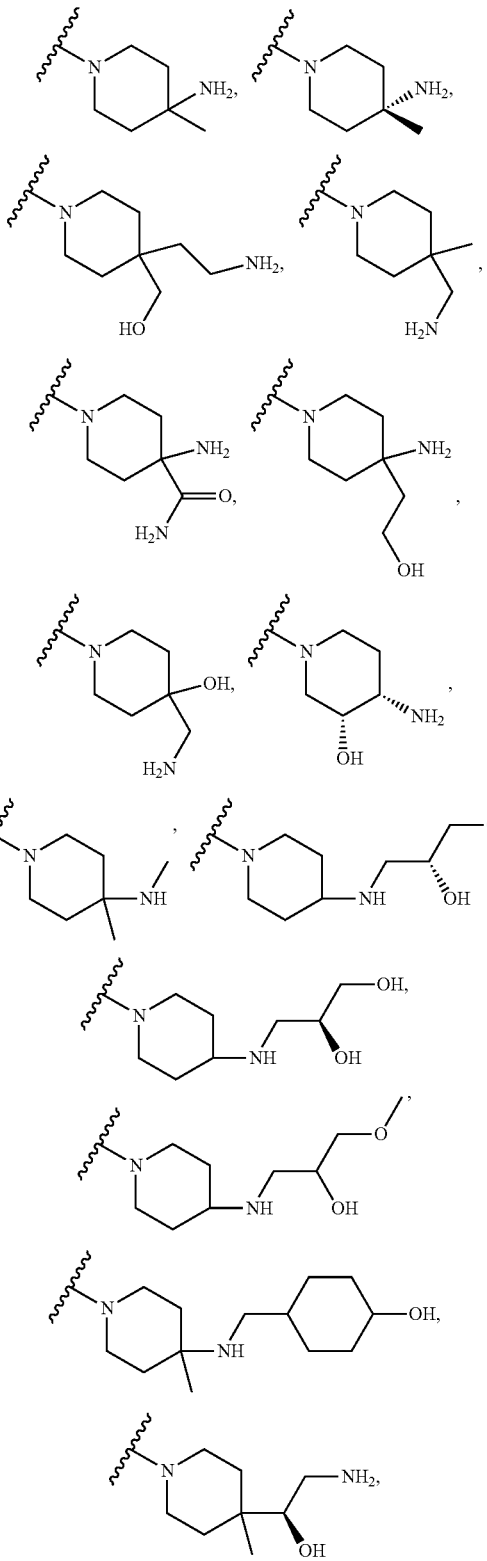

-continued

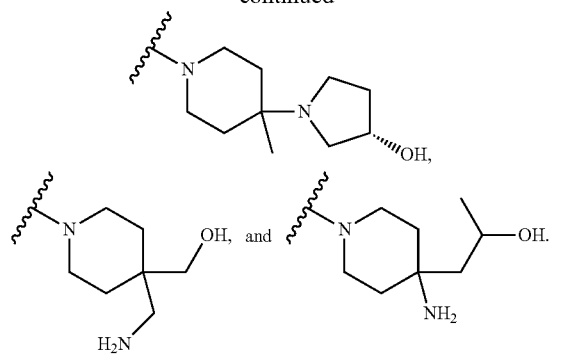

One embodiment of the present invention is a compound according to Formula II wherein p is 2, and $R^{10}$ and $R^{11}$ are selected from —$NH_2$ and —$C_1$-$C_3$ hydroxyalkyl. In one aspect of this embodiment, the nitrogen containing ring substituted with $R^{10}$ and $R^{11}$ is selected from:

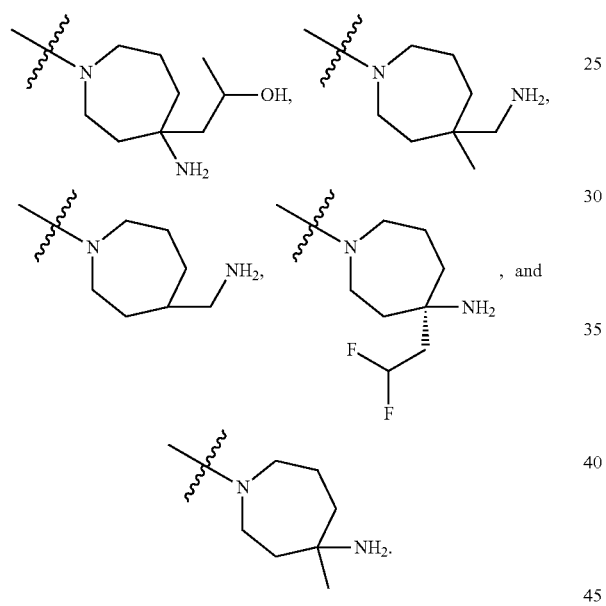

A further embodiment of the present invention is a compound according to Formula II wherein $R^{10}$ and $R^{11}$ are taken together with the carbon atom to which they are attached to form a 3-10 membered cycloalkyl or a 4-11 membered heterocyclyl, each of which is optionally substituted with 1 to 3 groups independently selected from methyl, ethyl, propyl, isopropyl, —OH, —$NH_2$, —Br, —Cl, —F, $C_1$-$C_3$ haloalkyl, $C_1$-$C_3$ aminoalkyl, and $C_1$-$C_3$ hydroxyalkyl. In one aspect of this embodiment, p is 1; and $R^{10}$ and $R^{11}$ are taken together with the carbon atom of the piperidinyl moiety to which they are bonded to form a group as shown (including the piperidinyl moiety):

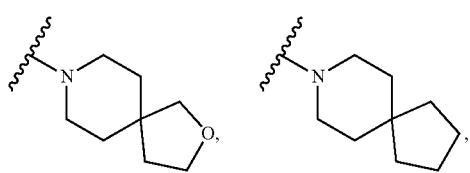

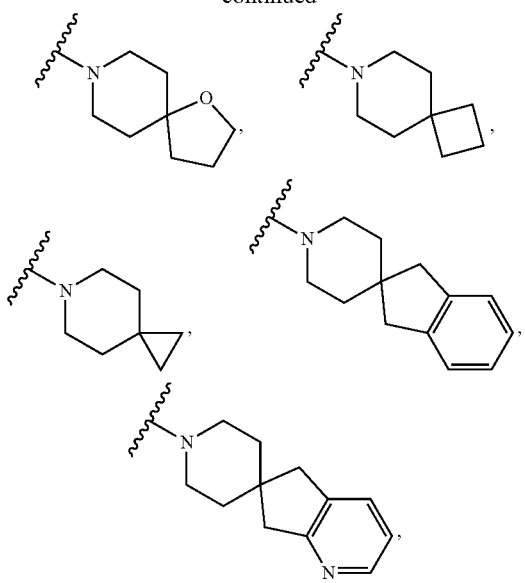

wherein each ring formed by $R^{10}$ and $R^{11}$ is independently and optionally substituted with 1-3 groups selected from —$NH_2$, —OH, —$CH_2OH$, —$CH_2NH_2$, —$CH_3$, and —F. In one aspect of this embodiment, the ring formed by $R^{10}$ and $R^{11}$ is substituted with at least one of —$NH_2$ or —$CH_2NH_2$.

A further embodiment of the present invention is a compound according to Formula II wherein $R^{10}$ and $R^{11}$ are taken together with the carbon atom to which they are attached to form a group selected from:

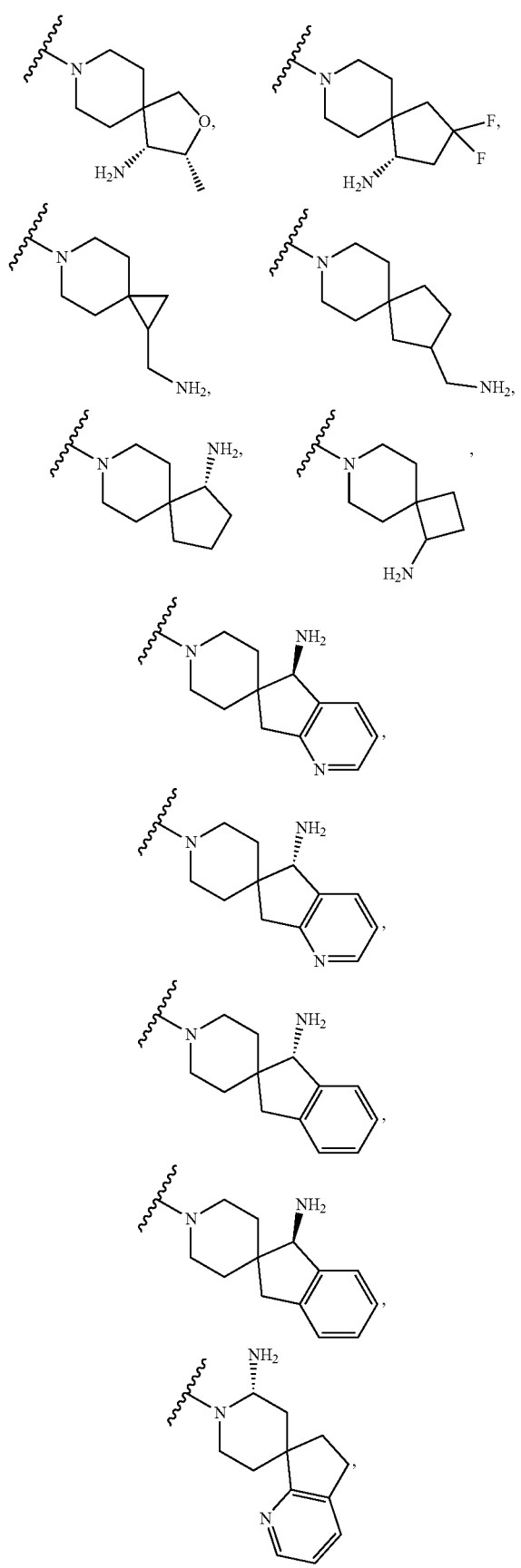
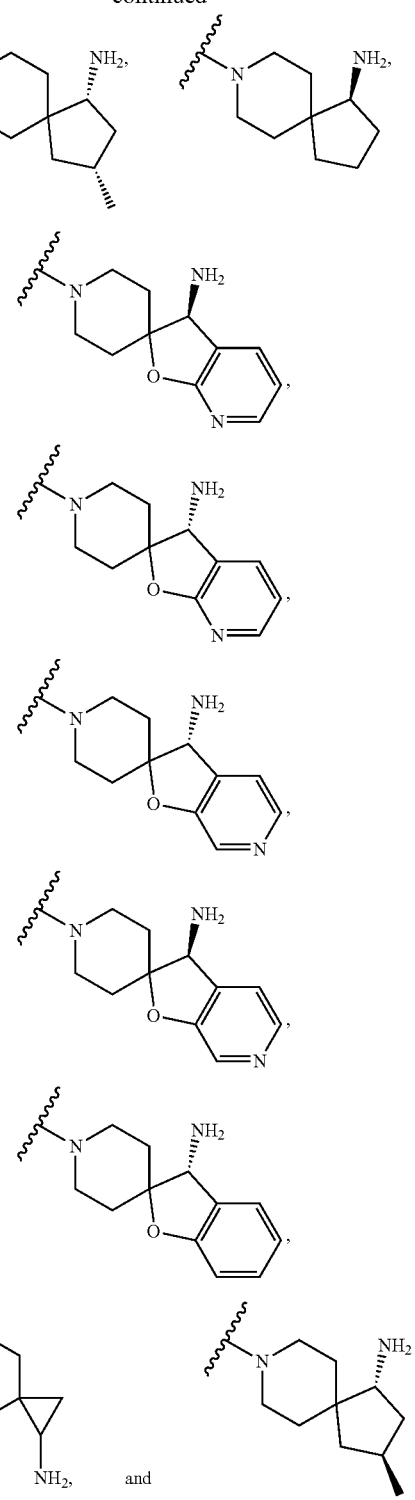
A further embodiment is a compound according to Formula II wherein $R^{12}$ is hydrogen.
One embodiment of the present invention is a compound according to Formula II selected from the group consisting of:

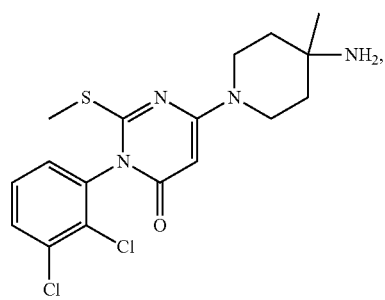
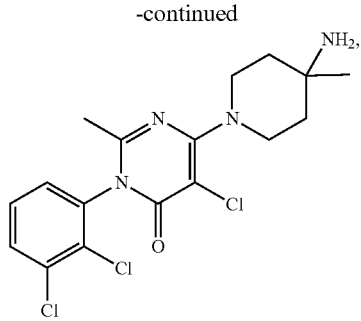
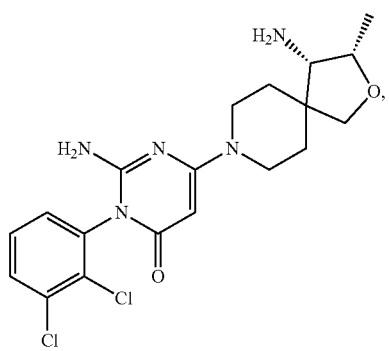
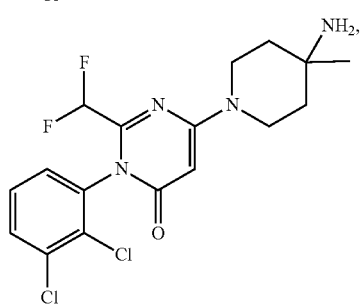
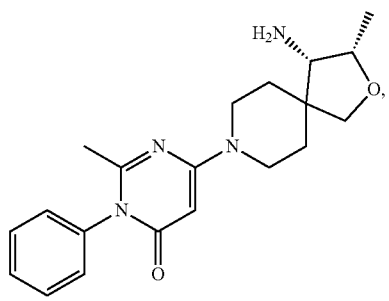
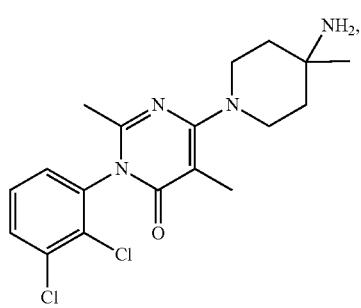
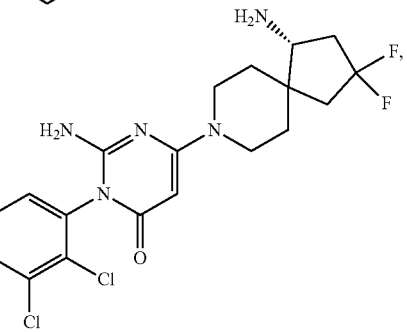
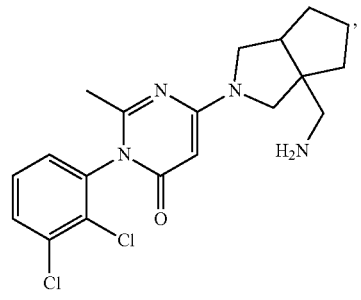
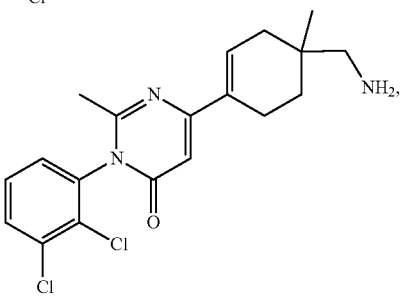
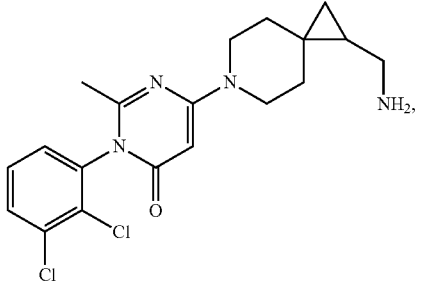

25
-continued
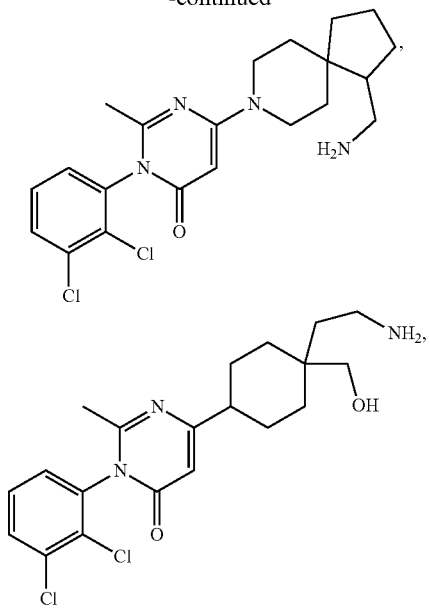
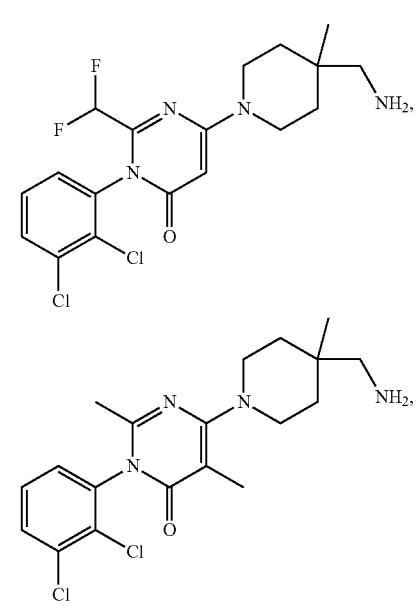
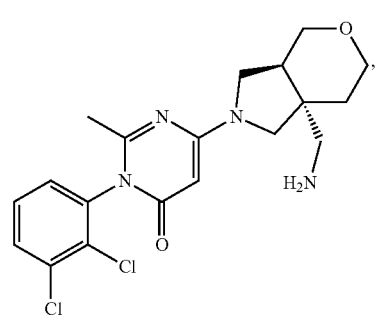
26
-continued
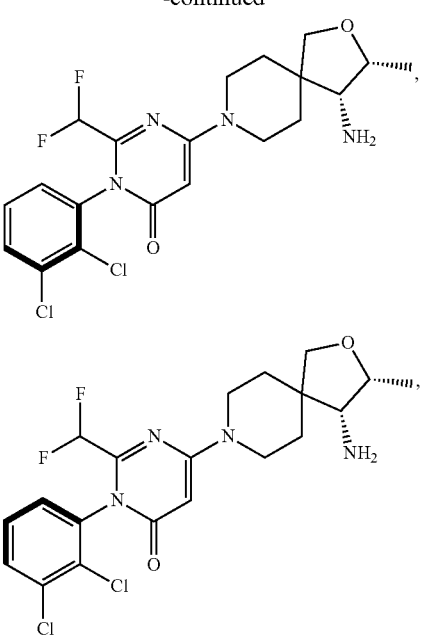
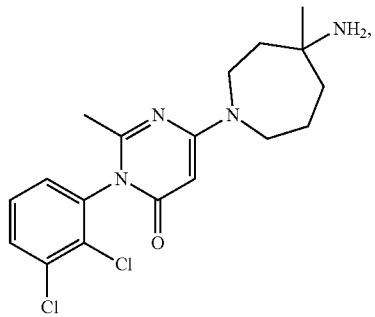
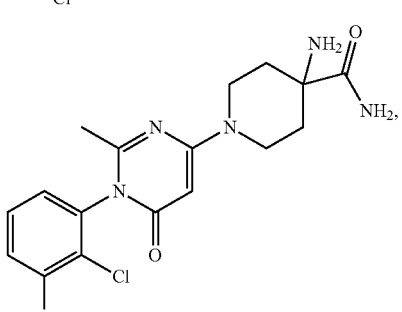
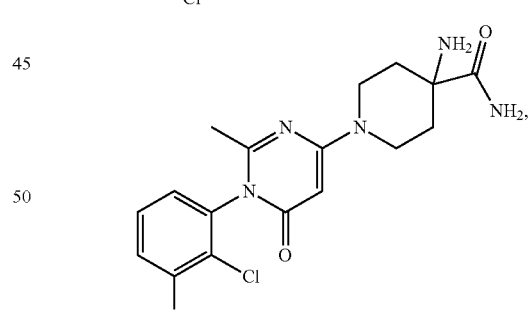
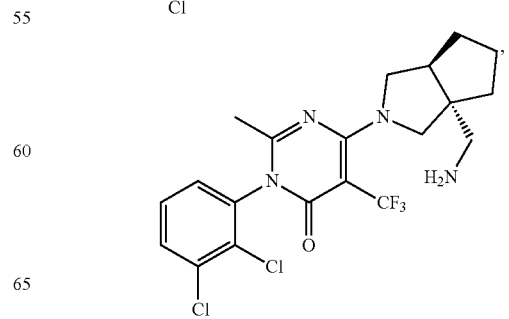

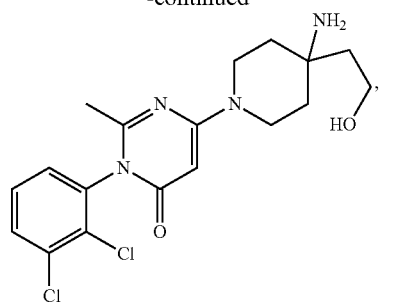
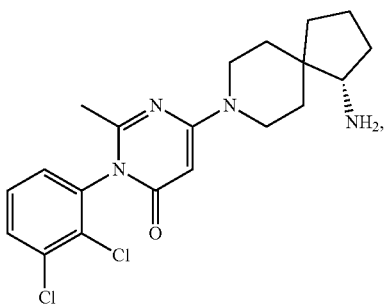
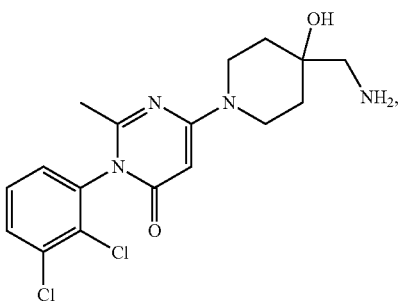
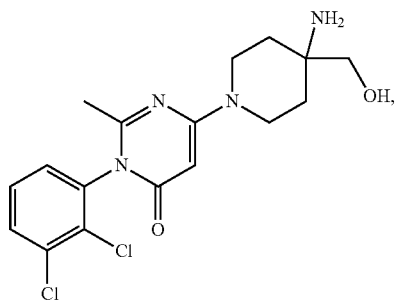
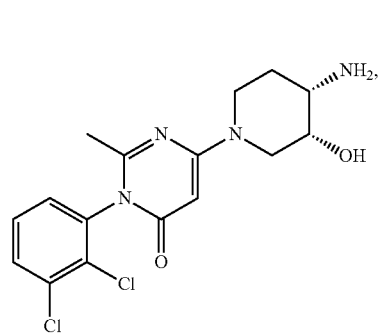
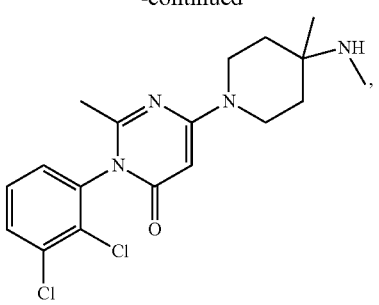
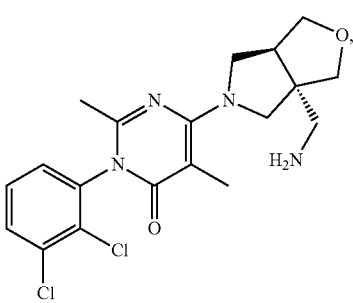
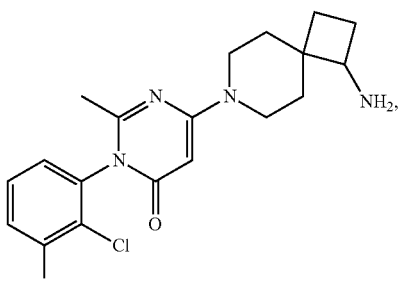
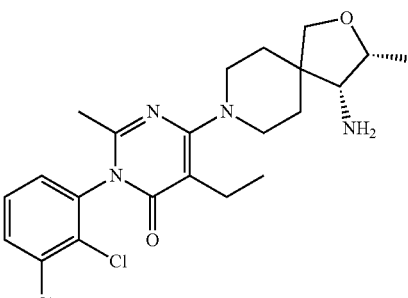
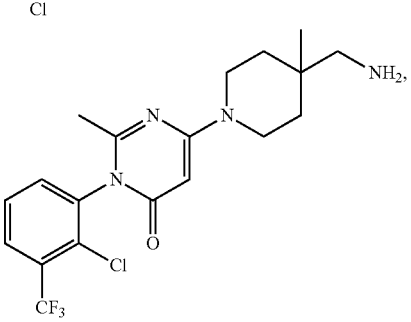

-continued
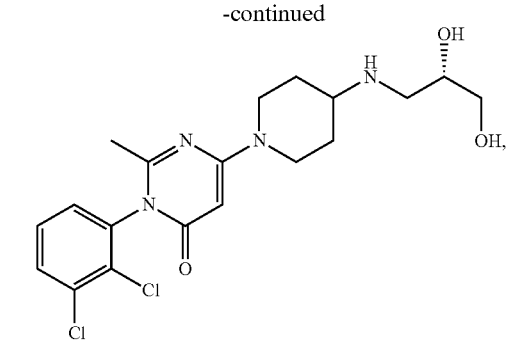
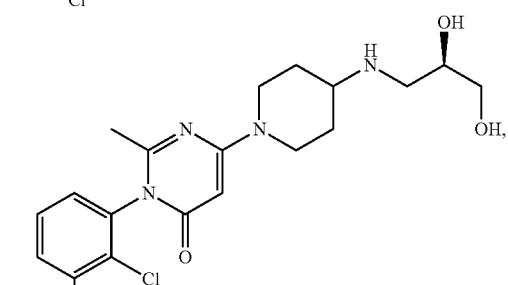
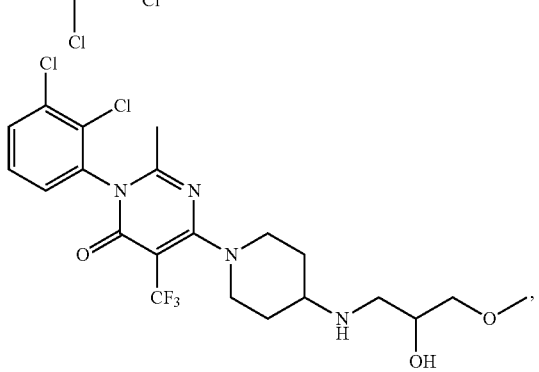
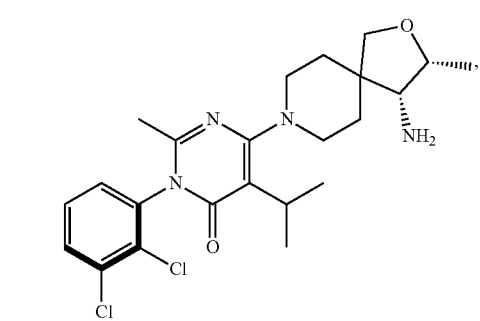
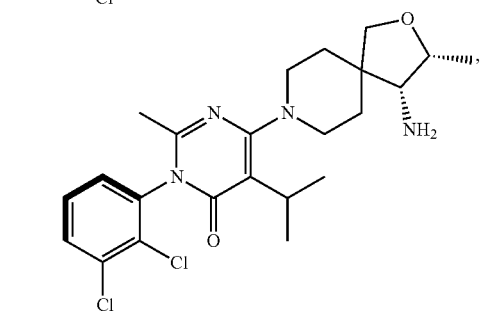
-continued
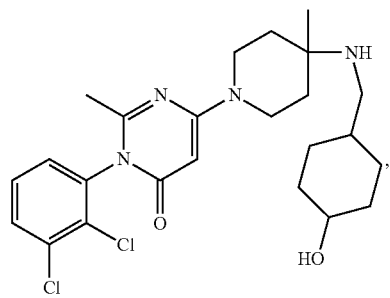
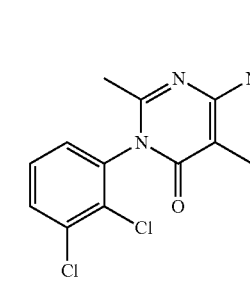
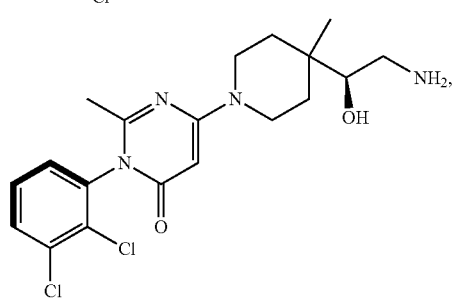
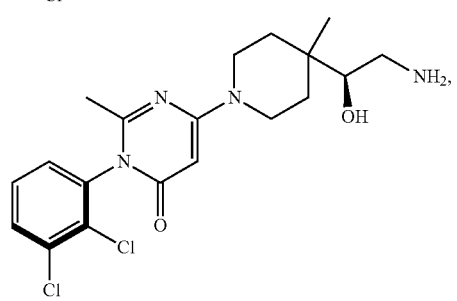
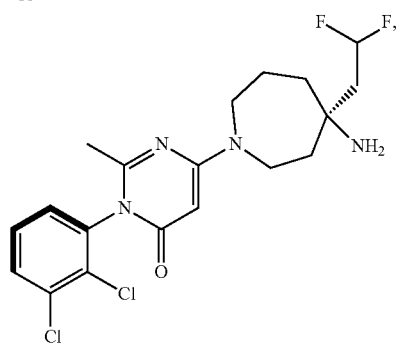

31
-continued
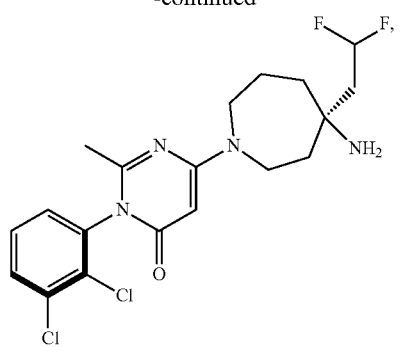
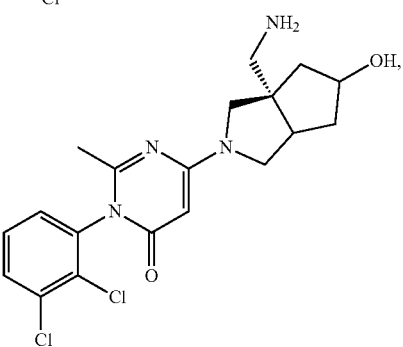
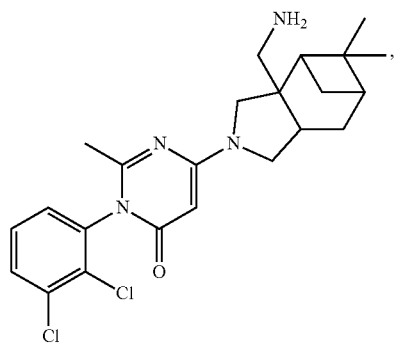
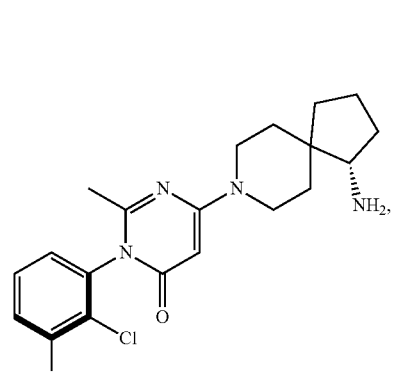
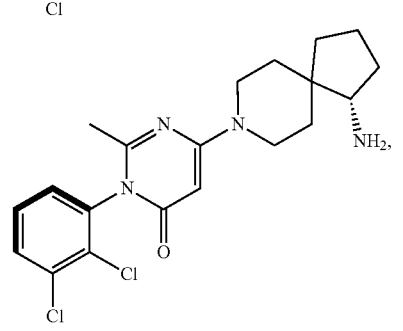
32
-continued
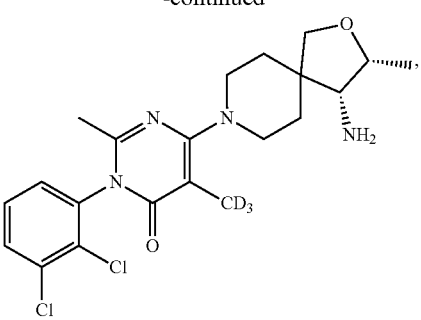
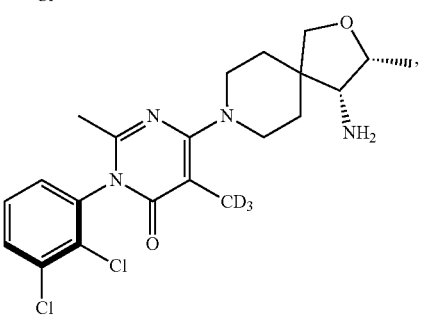
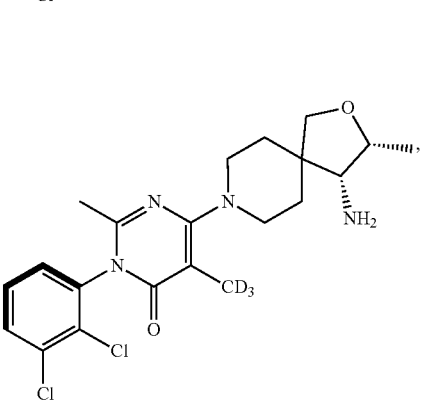
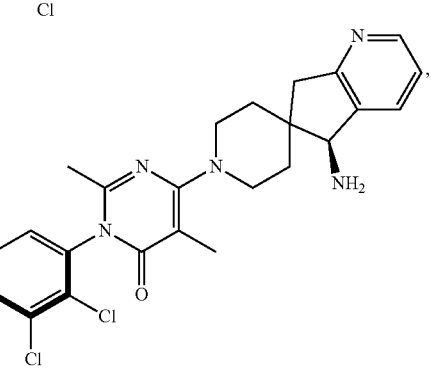
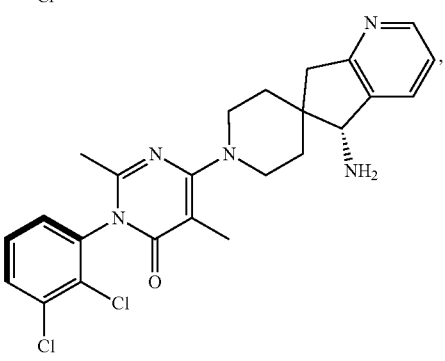

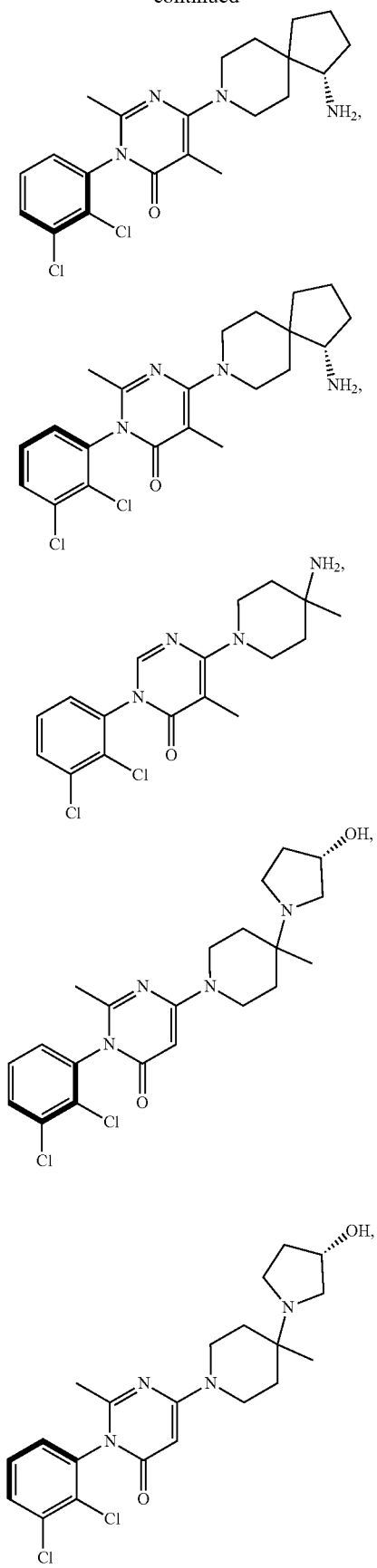
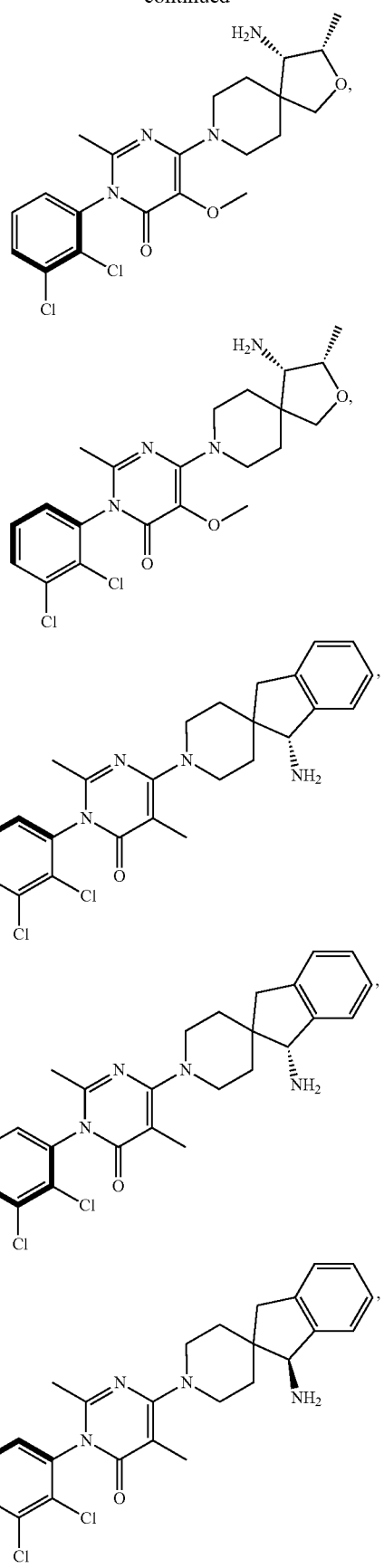

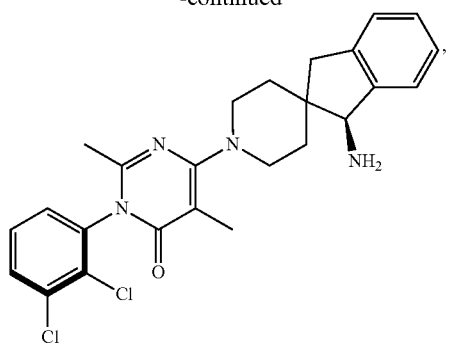
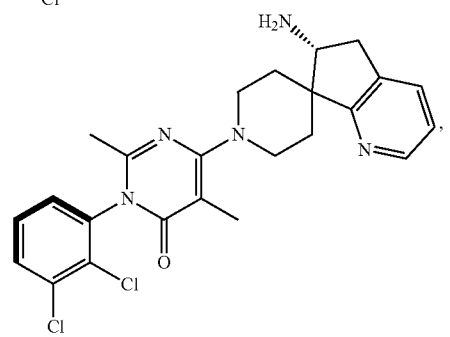
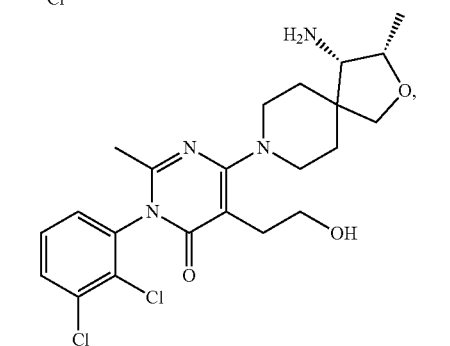
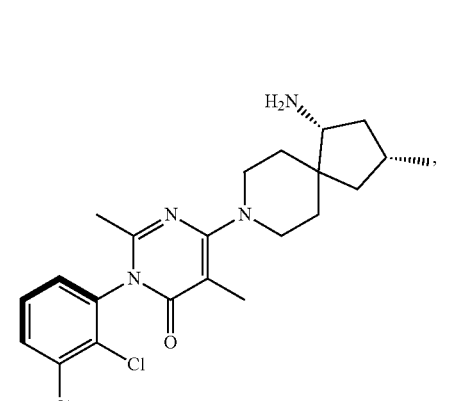
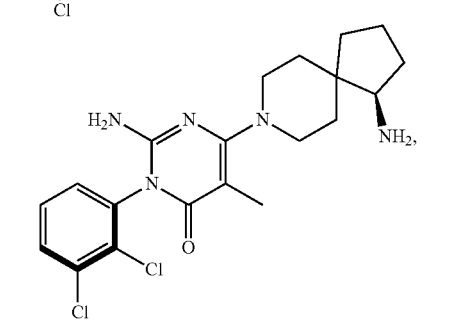
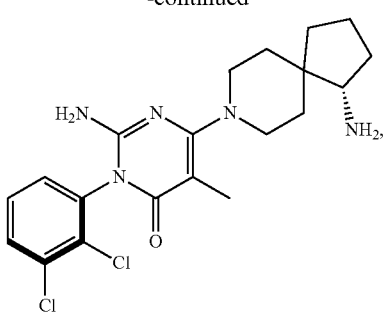
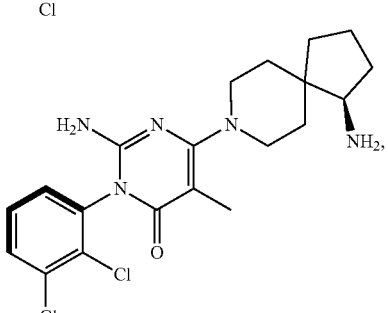
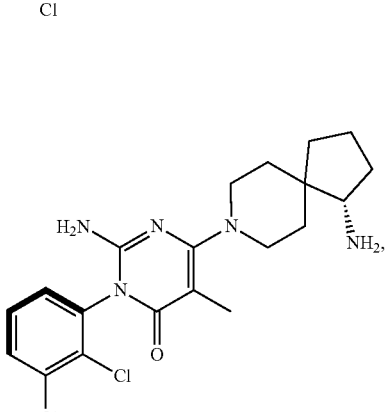
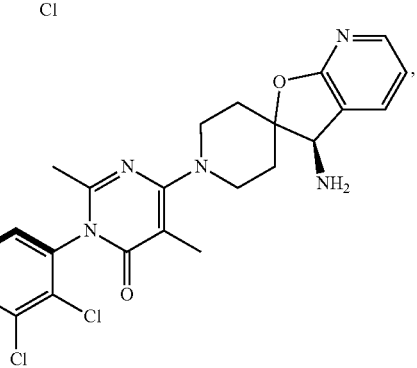
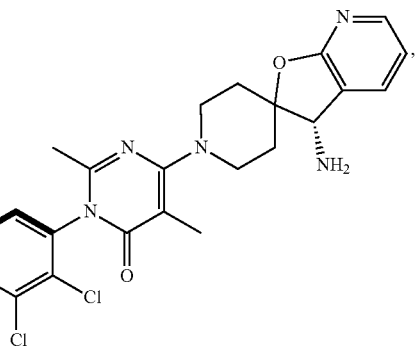

-continued
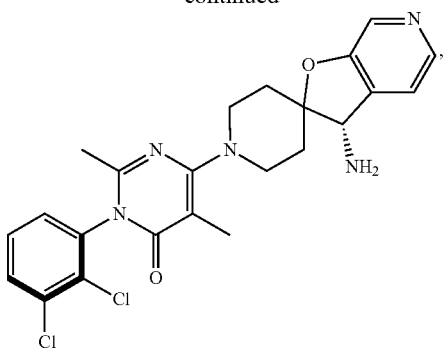
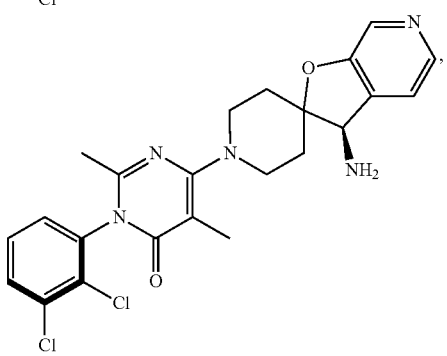
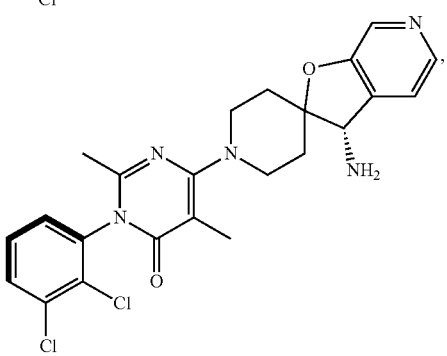
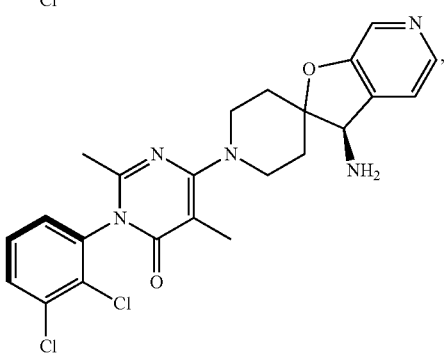
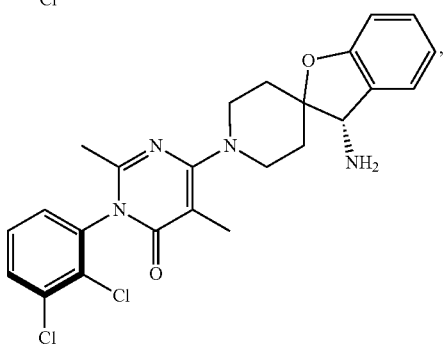
-continued
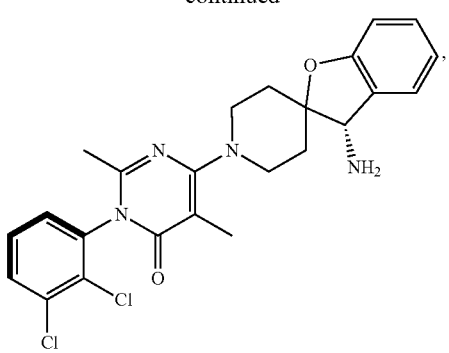
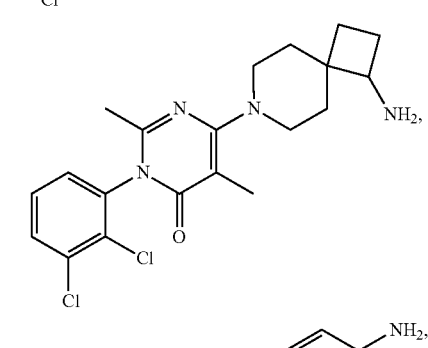
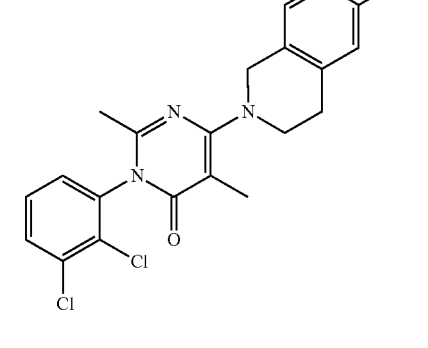
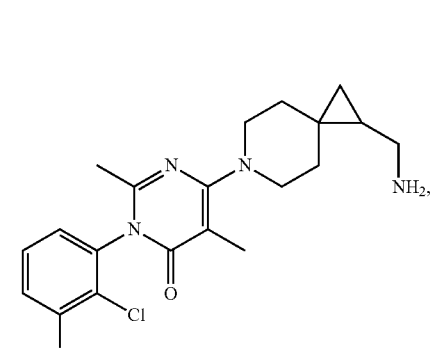
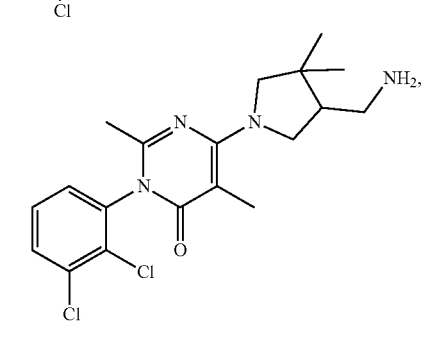

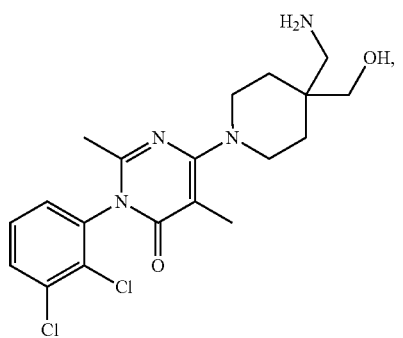
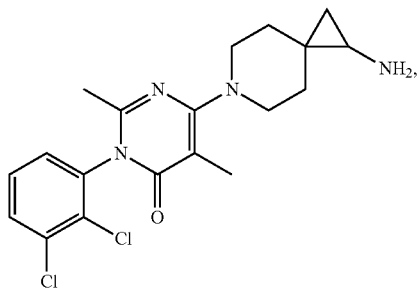
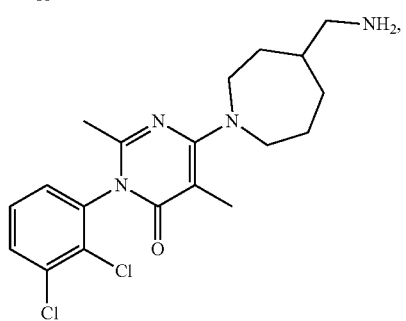
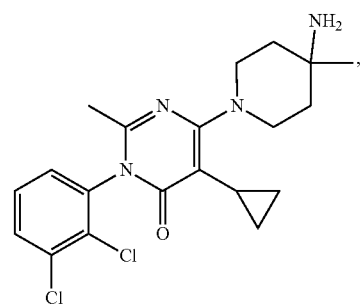
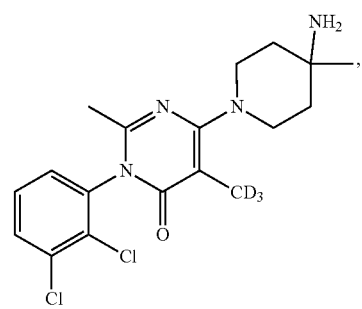
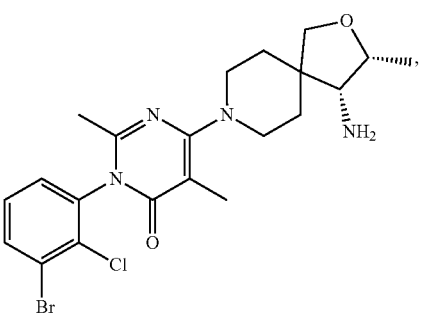
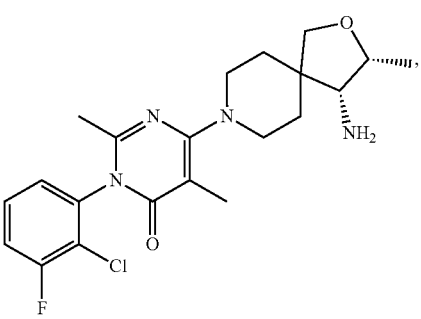
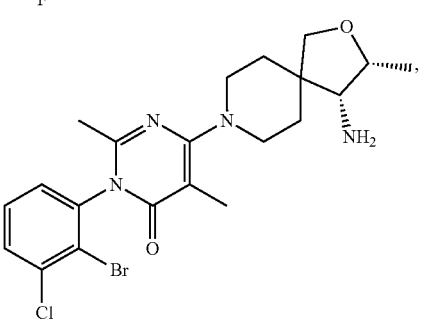
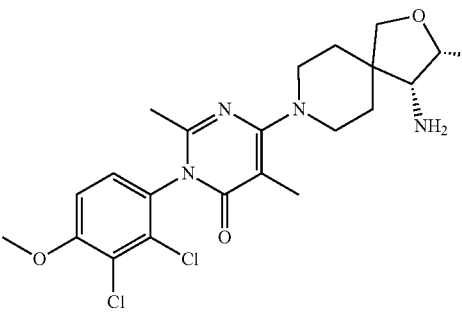
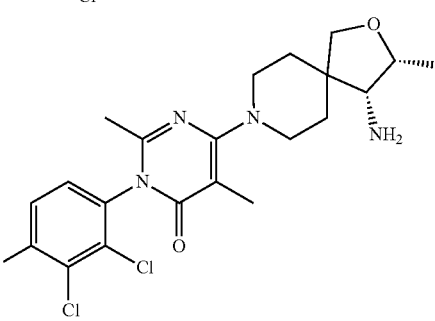

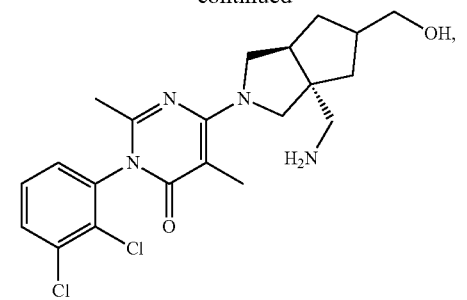
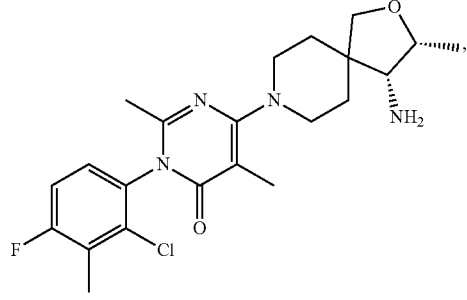
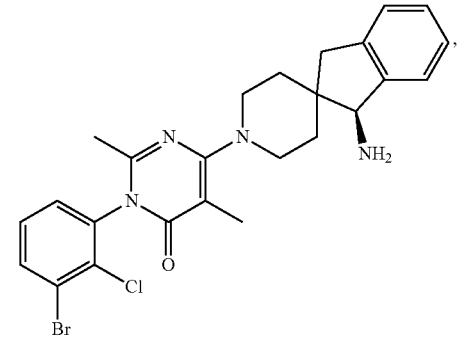
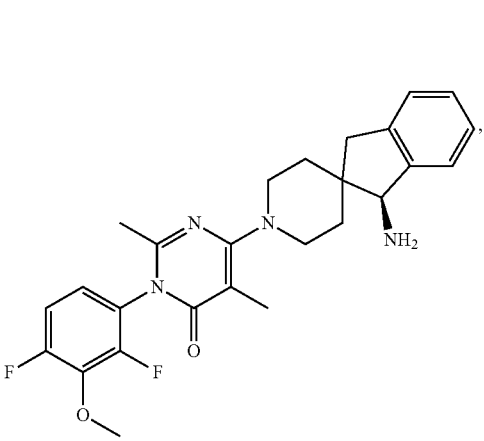
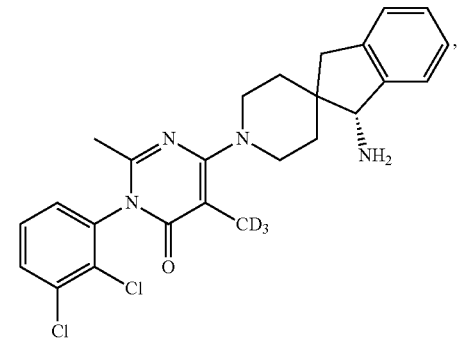
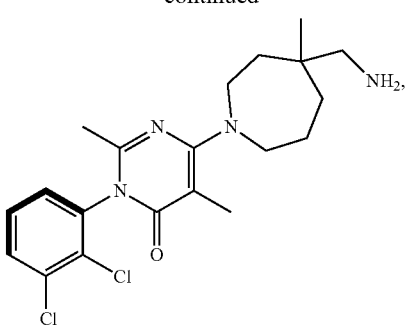
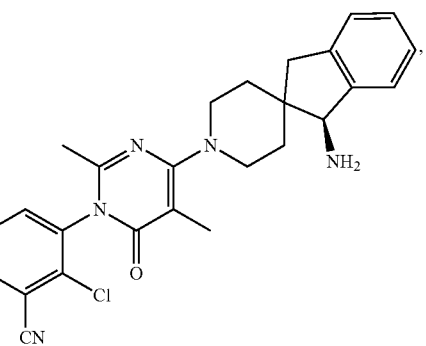
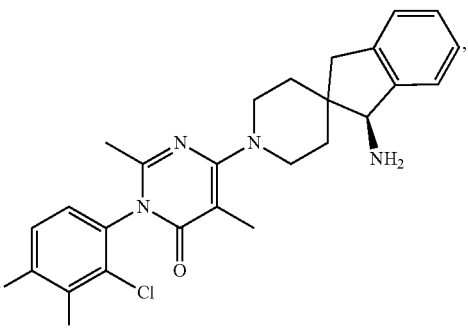
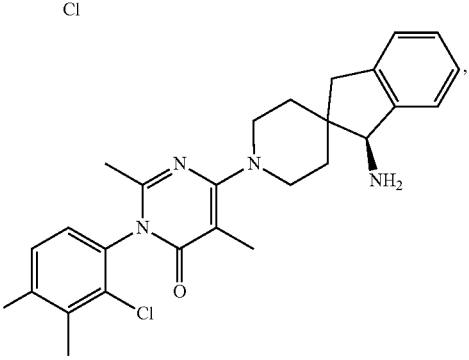
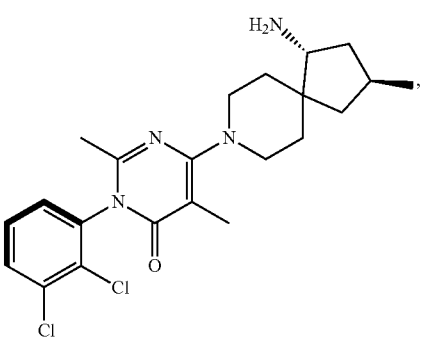

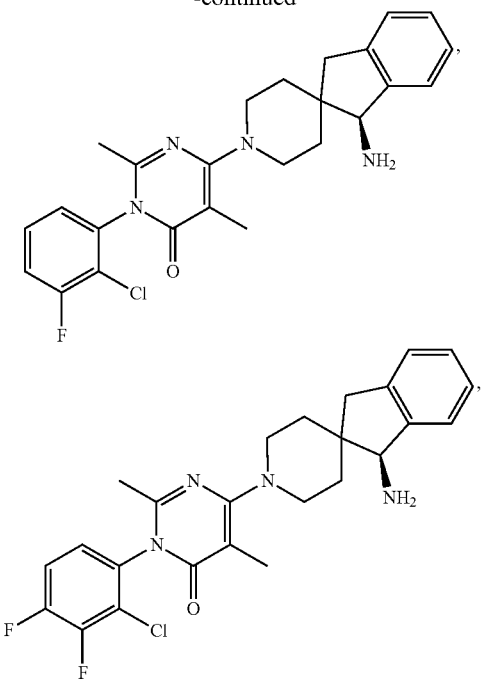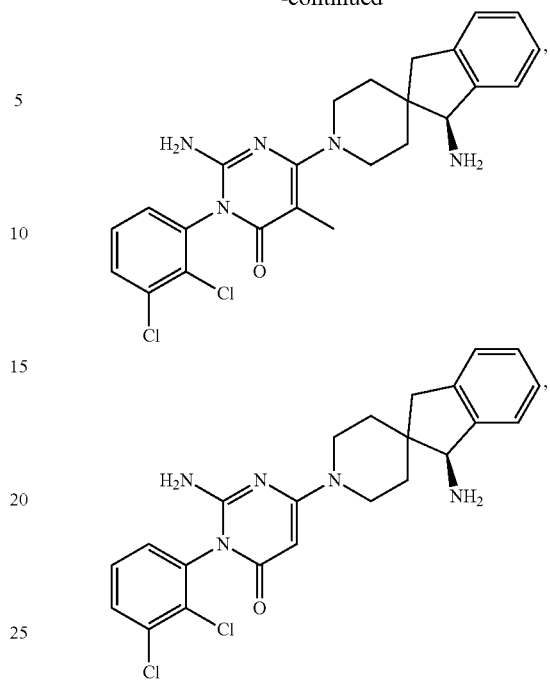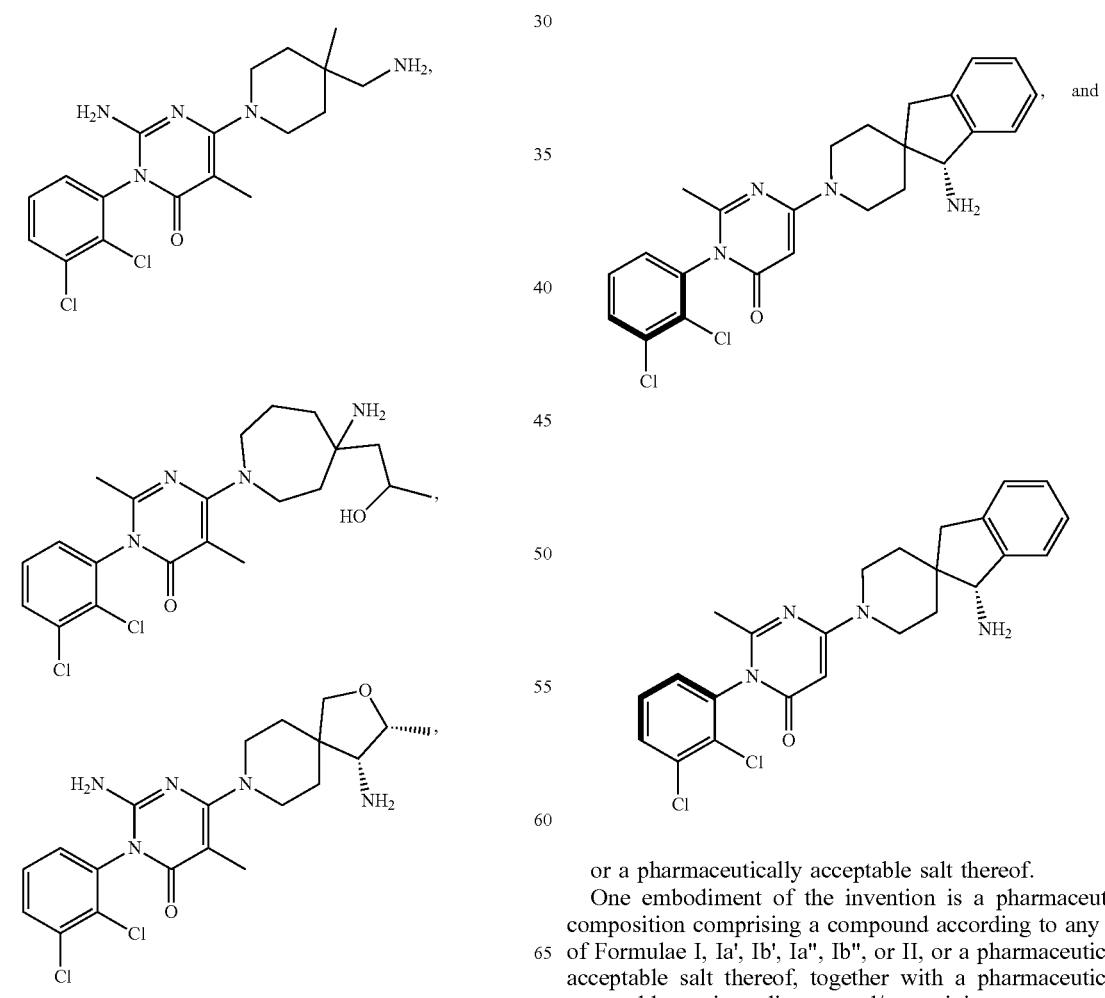
or a pharmaceutically acceptable salt thereof.
One embodiment of the invention is a pharmaceutical composition comprising a compound according to any one of Formulae I, Ia', Ib', Ia'', Ib'', or II, or a pharmaceutically acceptable salt thereof, together with a pharmaceutically acceptable carrier, adjuvant and/or excipient.

One embodiment of the present invention is a compound according to any one of Formulae I, Ia', Ib', Ia", Ib", or II, or a pharmaceutically acceptable salt thereof, for the treatment of cancer.

In one aspect of this embodiment, the cancer is selected from acute lymphocytic leukemia, chronic lymphocytic leukemia, acute granulocytic leukemia, adrenal cortex cancer, bladder cancer, brain cancer, breast cancer, cervical cancer, cervical hyperplasia, chorio cancer, colorectal cancer, endometrial cancer, esophageal cancer, essential thrombocytosis, gastric cancer, genitourinary carcinoma, glioma, glioblastoma, neurofibromatosis, hairy cell leukemia, head and neck carcinoma, Hodgkin's disease, Kaposi's sarcoma, kidney cancer, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid leukemia, lymphocytic leukemia, neuroblastoma, non-Hodgkin's lymphoma, non-small cell lung cancer, osteogenic sarcoma, ovarian carcinoma, pancreatic carcinoma, polycythemia vera, primary brain carcinoma, primary macroglobulinemia, prostatic cancer, renal cell carcinoma, rhabdomygsarcoma, skin cancer, small-cell lung cancer, soft-tissue sarcoma, squamous cell cancer, stomach cancer, testicular cancer, thyroid cancer and Wilm's tumor.

In a further aspect of this embodiment, the cancer is selected from non-small cell lung cancer, small cell lung cancer, breast cancer, esophageal cancer, gastric cancer, colorectal cancer, glioblastoma, pancreatic cancer, osteosarcoma, melanoma and kidney cancer.

In another aspect of this embodiment, the compound according to any one of Formulae I, Ia', Ib', Ia", Ib", or II, or a pharmaceutically acceptable salt thereof, is administered in combination with one or more additional therapeutic agent.

In one aspect of this embodiment, the one or more additional therapeutic agent is an EGFR inhibitor, MET inhibitor, PD-L1 inhibitor, MEK 1/2 inhibitor, TGF-βR pathway inhibitor, or a combination thereof.

In a further aspect of this embodiment, the one or more additional therapeutic agent is Erbitux, tepotinib, avelumab, Muc1-TGFβR2 Nb, EGFR-Muc1-ADC, pimasertib, pembrolizumab, nivolumab, cemiplimab, atezolizumab, durvalumab, or a combination thereof.

In a further aspect of this embodiment, the one or more additional therapeutic agents is Erbitux, tepotinib, avelumab, pimasertib or a combination thereof.

One embodiment of the present invention is a compound according to any one of Formulae I, Ia', Ib', Ia", Ib", or II, or a pharmaceutically acceptable salt thereof, for the treatment of a disease or disorder selected from the group consisting of age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation, inflammatory bowel disease, psoriasis, rheumatoid arthritis, systemic lupus erythematosus (SLE), vascular hyperproliferation secondary to retinal hypoxia and vasculitis.

One embodiment of the present invention is a method of treating cancer in a patient in need thereof, comprising administering an effective amount of a compound according to one of Formulae I, Ia', Ib', Ia", Ib", or II, or a pharmaceutically acceptable salt thereof, to said patient.

In one aspect of this method, the cancer is selected from acute lymphocytic leukemia, chronic lymphocytic leukemia, acute granulocytic leukemia, adrenal cortex cancer, bladder cancer, brain cancer, breast cancer, cervical cancer, cervical hyperplasia, chorio cancer, colorectal cancer, endometrial cancer, esophageal cancer, essential thrombocytosis, gastric cancer, genitourinary carcinoma, glioma, glioblastoma, neurofibromatosis, hairy cell leukemia, head and neck carcinoma, Hodgkin's disease, Kaposi's sarcoma, kidney cancer, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid leukemia, lymphocytic leukemia, neuroblastoma, non-Hodgkin's lymphoma, non-small cell lung cancer, osteogenic sarcoma, ovarian carcinoma, pancreatic carcinoma, polycythemia vera, primary brain carcinoma, primary macroglobulinemia, prostatic cancer, renal cell carcinoma, rhabdomyosarcoma, skin cancer, small-cell lung cancer, soft-tissue sarcoma, squamous cell cancer, stomach cancer, testicular cancer, thyroid cancer and Wilm's tumor.

In another aspect of this method, the cancer is selected from non-small cell lung cancer, small cell lung cancer, breast cancer, esophageal cancer, gastric cancer, colorectal cancer, glioblastoma, pancreatic cancer, osteosarcoma, melanoma and kidney cancer.

In a further embodiment of this method, the method further comprises administering to the subject one or more additional therapeutic agents.

In one aspect of this embodiment, the one or more additional therapeutic agents is an EGFR inhibitor, MET inhibitor, PD-L1 inhibitor, MEK 1/2 inhibitor, TGF-βR pathway inhibitor, or a combination thereof.

In another aspect of this embodiment, the one or more additional therapeutic agents is Erbitux, tepotinib, avelumab, pimasertib or a combination thereof.

One embodiment of the present invention is a method of treating a proliferative disease or disorder in a patient in need thereof, comprising administering an effective amount of a compound according to one of Formulae I, Ia', Ib', Ia", Ib", or II, or a pharmaceutically acceptable salt thereof, to said patient.

In one aspect of this embodiment, the proliferative disease or disorder is selected from the group consisting of age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation, inflammatory bowel disease, psoriasis, rheumatoid arthritis, systemic lupus erythematosus (SLE), vascular hyperproliferation secondary to retinal hypoxia and vasculitis.

In a further embodiment of this invention, the method further comprises administering to the subject an effective amount of one or more additional therapeutic agents.

One embodiment of the invention is a compound selected from Table 1, or a pharmaceutically acceptable salt thereof, which includes the group consisting of:

| No. | Structure | Chemical Name |
|---|---|---|
| 1 | 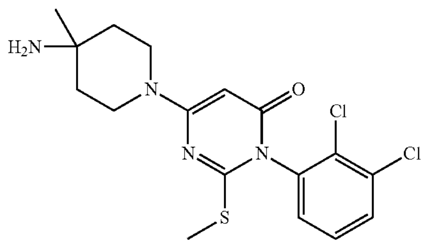 [SMILES: CSc1nc(N2CCC(C)(N)CC2)cc(=O)n1-c1cccc(Cl)c1Cl] | 6-(4-amino-4-methylpiperidin-1-yl)-3-(2,3-dichlorophenyl)-2-(methylsulfanyl)-3,4-dihydropyrimidin-4-one |
| 2 | 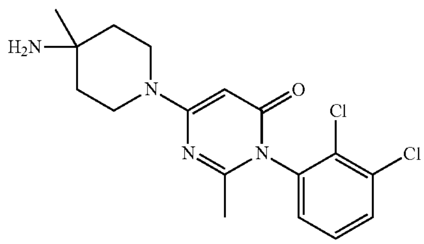 [SMILES: Cc1nc(N2CCC(C)(N)CC2)cc(=O)n1-c1cccc(Cl)c1Cl] | 6-(4-amino-4-methylpiperidin-1-yl)-3-(2,3-dichlorophenyl)-2-methyl-3,4-dihydropyrimidin-4-one |
| 2a | 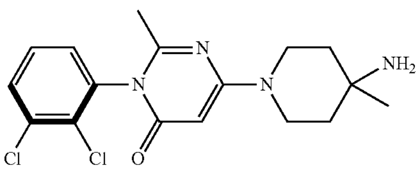 | (3P)-6-(4-amino-4-methylpiperidin-1-yl)-3-(2,3-dichlorophenyl)-2-methyl-3,4-dihydropyrimidin-4-one |
| 2b | 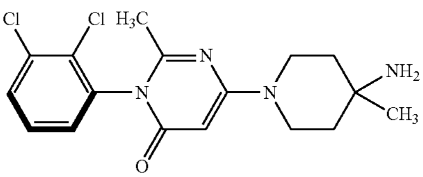 | (3M)-6-(4-amino-4-methylpiperidin-1-yl)-3-(2,3-dichlorophenyl)-2-methyl-3,4-dihydropyrimidin-4-one |
| 3 | 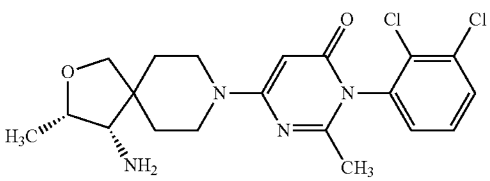 [SMILES: Cc1nc(N2CCC3(CC2)CO[C@@H](C)[C@H]3N)cc(=O)n1-c1cccc(Cl)c1Cl] | 6-[(3S,4S)-4-amino-3-methyl-2-oxa-8-azaspiro[4.5]decan-8-yl]-3-(2,3-dichlorophenyl)-2-methyl-3,4-dihydropyrimidin-4-one |
| 3a | 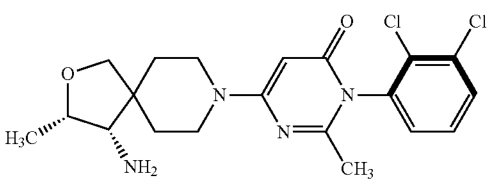 | (3P)-6-[(3S,4S)-4-amino-3-methyl-2-oxa-8-azaspiro[4.5]decan-8-yl]-3-(2,3-dichlorophenyl)-2-methyl-3,4-dihydropyrimidin-4-one |
| 3b | 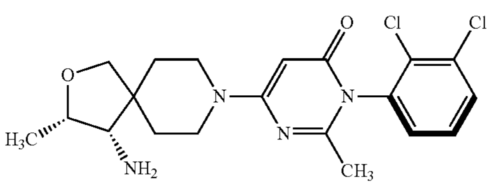 | (3M)-6-[(3S,4S)-4-amino-3-methyl-2-oxa-8-azaspiro[4.5]decan-8-yl]-3-(2,3-dichlorophenyl)-2-methyl-3,4-dihydropyrimidin-4-one |
| 4 | 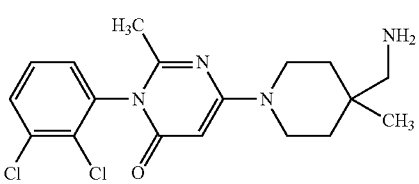 [SMILES: Cc1nc(N2CCC(C)(CN)CC2)cc(=O)n1-c1cccc(Cl)c1Cl] | 6-[4-(aminomethyl)-4-methylpiperidin-1-yl]-3-(2,3-dichlorophenyl)-2-methyl-3,4-dihydropyrimidin-4-one |

| No. | Structure | Chemical Name |
|---|---|---|
| 5 | 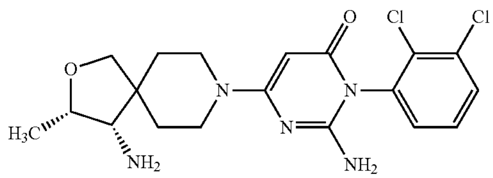 [SMILES: C[C@@H]1OCC2(CCN(c3cc(=O)n(-c4cccc(Cl)c4Cl)c(N)n3)CC2)[C@@H]1N] | 2-amino-6-[(3S,4S)-4-amino-3-methyl-2-oxa-8-azaspiro[4.5]decan-8-yl]-3-(2,3-dichlorophenyl)-3,4-dihydropyrimidin-4-one |
| 6a | 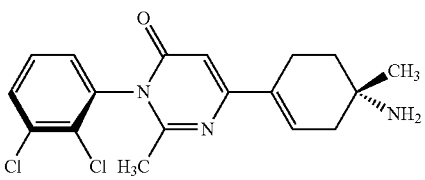 | (+/−)-(3M)-6-[(4S)-4-amino-4-methylcyclohex-1-en-1-yl]-3-(2,3-dichlorophenyl)-2-methyl-3,4-dihydropyrimidin-4-one |
| 6b | 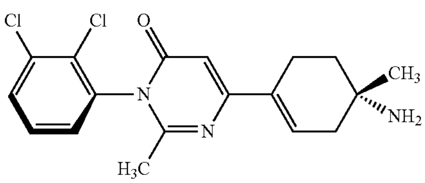 | (+/−)-(3P)-6-[(4S)-4-amino-4-methylcyclohex-1-en-1-yl]-3-(2,3-dichlorophenyl)-2-methyl-3,4-dihydropyrimidin-4-one |
| 7 | 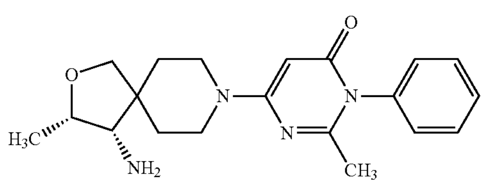 [SMILES: Cc1nc(N2CCC3(CC2)CO[C@@H](C)[C@H]3N)cc(=O)n1-c1ccccc1] | 6-[(3S,4S)-4-amino-3-methyl-2-oxa-8-azaspiro[4.5]decan-8-yl]-2-methyl-3-phenyl-3,4-dihydropyrimidin-4-one |
| 8 | 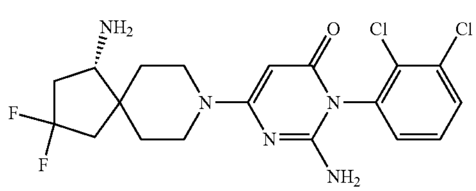 [SMILES: Nc1nc(N2CCC3(CC2)CC(F)(F)C[C@@H]3N)cc(=O)n1-c1cccc(Cl)c1Cl] | 2-amino-6-[(1R)-1-amino-3,3-difluoro-8-azaspiro[4.5]decan-8-yl]-3-(2,3-dichlorophenyl)-3,4-dihydropyrimidin-4-one |
| 9 | 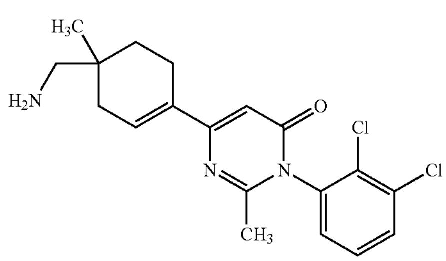 [SMILES: Cc1nc(C2=CCC(C)(CN)CC2)cc(=O)n1-c1cccc(Cl)c1Cl] | 6-[4-(aminomethyl)-4-methylcyclohex-1-en-1-yl]-3-(2,3-dichlorophenyl)-2-methyl-3,4-dihydropyrimidin-4-one |
| 10 | 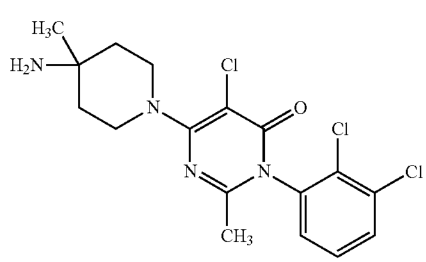 [SMILES: Cc1nc(N2CCC(C)(N)CC2)c(Cl)c(=O)n1-c1cccc(Cl)c1Cl] | 6-(4-amino-4-methylpiperidin-1-yl)-5-chloro-3-(2,3-dichlorophenyl)-2-methyl-3,4-dihydropyrimidin-4-one |

-continued

| No. | Structure | Chemical Name |
|---|---|---|
| 11 | 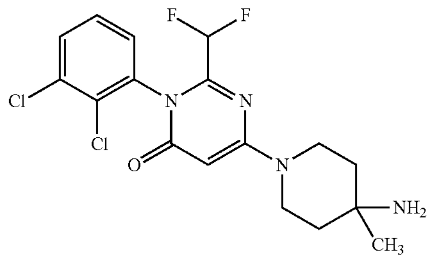 [SMILES: CC1(N)CCN(c2cc(=O)n(-c3cccc(Cl)c3Cl)c(C(F)F)n2)CC1] | 6-(4-amino-4-methylpiperidin-1-yl)-3-(2,3-dichlorophenyl)-2-(difluoromethyl)-3,4-dihydropyrimidin-4-one |
| 12 | 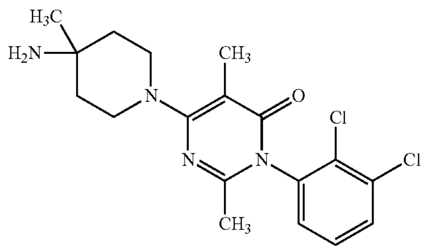 [SMILES: Cc1c(N2CCC(C)(N)CC2)nc(C)n(-c2cccc(Cl)c2Cl)c1=O] | 6-(4-amino-4-methylpiperidin-1-yl)-3-(2,3-dichlorophenyl)-2,5-dimethyl-3,4-dihydropyrimidin-4-one |
| 13 | 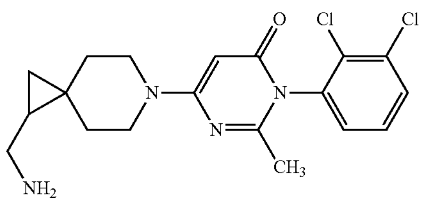 [SMILES: Cc1nc(N2CCC3(CC2)CC3CN)cc(=O)n1-c1cccc(Cl)c1Cl] | 6-[1-(aminomethyl)-6-azaspiro[2.5]octan-6-yl]-3(2,3-dichlorophenyl)-2-methyl-3,4-dihydropyrimidin-4-one |
| 14 | 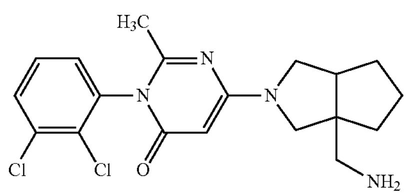 [SMILES: Cc1nc(N2CC3CCCC3(CN)C2)cc(=O)n1-c1cccc(Cl)c1Cl] | 6-[3a-(aminomethyl)-octahydrocyclopenta[c]pyrrol-2-yl]-3-(2,3-dichlorophenyl)-2-methyl-3,4-dihydropyrimidin-4-one |
| 15 | 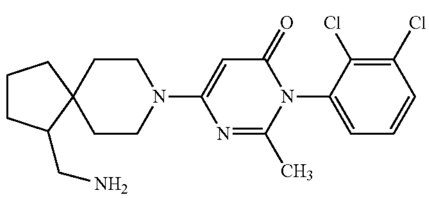 [SMILES: Cc1nc(N2CCC3(CCCC3CN)CC2)cc(=O)n1-c1cccc(Cl)c1Cl] | 6-[1-(aminomethyl)-8-azaspiro[4.5]decan-8-yl]-3-(2,3-dichlorophenyl)-2-methyl-3,4-dihydropyrimidin-4-one |
| 16 | 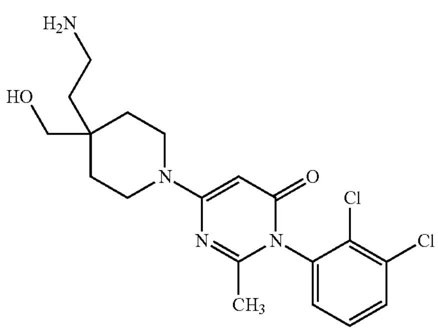 [SMILES: Cc1nc(N2CCC(CO)(CCN)CC2)cc(=O)n1-c1cccc(Cl)c1Cl] | 6-[4-(2-aminoethyl)-4-(hydroxymethyl)piperidin-1-yl]-3-(2,3-dichlorophenyl)-2-methyl-3,4-dihydropyrimidin-4-one |

-continued

| No. | Structure | Chemical Name |
|---|---|---|
| 17 | 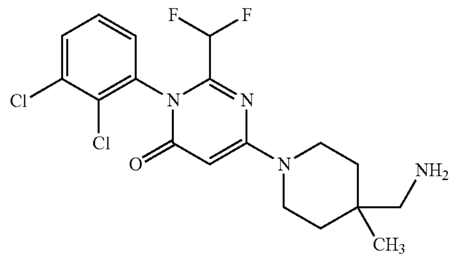 [SMILES: CC1(CN)CCN(c2cc(=O)n(-c3cccc(Cl)c3Cl)c(C(F)F)n2)CC1] | 6-[4-(aminomethyl)-4-methylpiperidin-1-yl]-3-(2,3-(2,3-dichlorophenyl)-2-(difluoromethyl)-3,4-dihydropyrimidin-4-one |
| 18 | 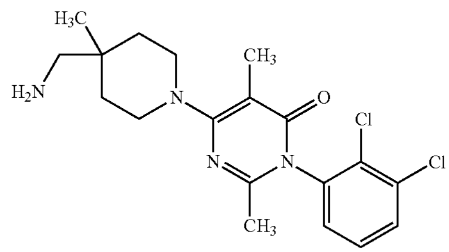 [SMILES: Cc1c(N2CCC(C)(CN)CC2)nc(C)n(-c2cccc(Cl)c2Cl)c1=O] | 6-[4-(aminomethyl)-4-methylpiperidin-1-yl]-3-(2,3-dichlorophenyl)-2,5-dimethyl-3,4-dihydropyrimidin-4-one |
| 19 | 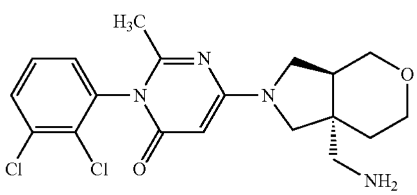 [SMILES: Cc1nc(N2C[C@H]3COCC[C@@]3(CN)C2)cc(=O)n1-c1cccc(Cl)c1Cl] | (+/−)-6-[(3aS,7aR)-7a-(aminomethyl)-octahydropyrano[3,4-c]pyrrol-2-yl]-3-(2,3-dichlorophenyl)-2-methyl-3,4-dihydropyrimidin-4-one |
| 20a | 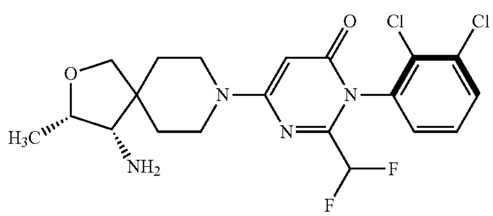 | (3P)-6-[(3S,4S)-4-amino-3-methyl-2-oxa-8-azaspiro[4.5]decan-8-yl]-3-(2,3-dichlorophenyl)-2-(difluoromethyl)-3,4-dihydropyrimidin-4-one |
| 20b | 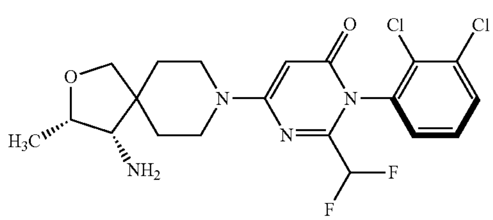 | (3M)-6-[(3S,4S)-4-amino-3-methyl-2-oxa-8-azaspiro[4.5]decan-8-yl]-3-(2,3-dichlorophenyl)-2-(difluoromethyl)-3,4-dihydropyrimidin-4-one |
| 21 | 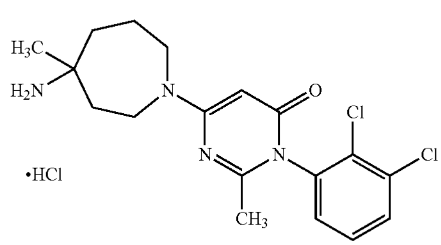 [SMILES: Cl ; Cc1nc(N2CCCC(C)(N)CC2)cc(=O)n1-c1cccc(Cl)c1Cl] | 6-(4-amino-4-methyl]azepan-1-yl)-3-(2,3-dichlorophenyl)-2-methyl-3,4-dihydropyrimidin-4-one hydrochloride |

-continued

| No. | Structure | Chemical Name |
|---|---|---|
| 22 | 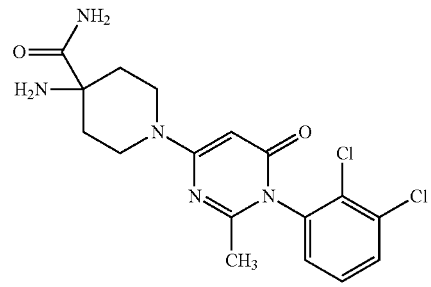 [SMILES: Cc1nc(N2CCC(N)(C(N)=O)CC2)cc(=O)n1-c1cccc(Cl)c1Cl] | 4-amino-1-[1-(2,3-dichlorophenyl)-2-methyl-6-oxo-1,6-dihydropyrimidin-4-yl]piperidine-4-carboxamide |
| 23a | 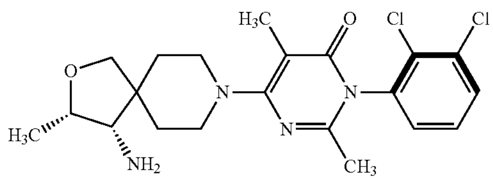 | (3P)-6-[(3S,4S)-4-amino-3-methyl-2-oxa-8-azaspiro[4.5]decan-8-yl]-3-(2,3-dichlorophenyl)-2,5-dimethyl-3,4-dihydropyrimidin-4-one |
| 23b | 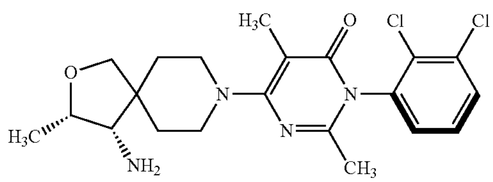 | (3M)-6-[(3S,4S)-4-amino-3-methyl-2-oxa-8-azaspiro[4.5]decan-8-yl]-3-(2,3-dichlorophenyl)-2,5-dimethyl-3,4-dihydropyrimidin-4-one |
| 24 | 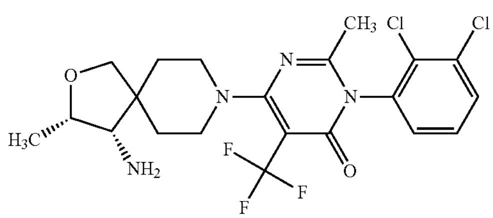 [SMILES: Cc1nc(N2CCC3(CC2)CO[C@@H](C)[C@H]3N)c(C(F)(F)F)c(=O)n1-c1cccc(Cl)c1Cl] | 6-[(3S,4S)-4-amino-3-methyl-2-oxa-8-azaspiro[4.5]decan-8-yl]-3-(2,3-dichlorophenyl)-2-methyl-5-(trifluoromethyl)-3,4-dihydropyrimidin-4-one |
| 25 | 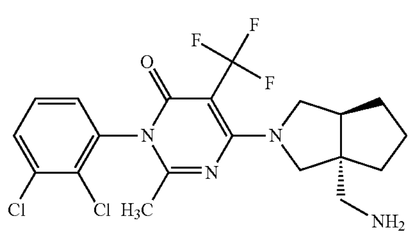 [SMILES: Cc1nc(N2C[C@H]3CCC[C@@]3(CN)C2)c(C(F)(F)F)c(=O)n1-c1cccc(Cl)c1Cl] | (+/−)-6-[(3aS,6aR)-3a-(aminomethyl)-octahydrocyclopenta[c]pyrrol-2-yl]-3-(2,3-dichlorophenyl)-2-methyl-5-(trifluoromethyl)-3,4-dihydropyrimidin-4-one |
| 26 | 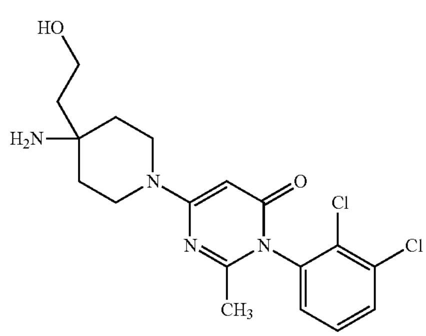 [SMILES: Cc1nc(N2CCC(N)(CCO)CC2)cc(=O)n1-c1cccc(Cl)c1Cl] | 6-[4-amino-4-(2-hydroxyethyl)piperidin-1-yl]-3-(2,3-dichlorophenyl)-2-methyl-3,4-dihydropyrimidin-4-one |

| No. | Structure | Chemical Name |
|---|---|---|
| 27 | 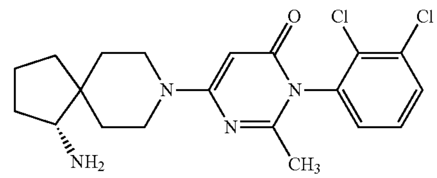 [SMILES: Cc1nc(N2CCC3(CCC[C@H]3N)CC2)cc(=O)n1-c1cccc(Cl)c1Cl] | 6-{(R)-1-amino-8-azaspiro[4.5]decan-8-yl]-3-(2,3-dichlorophenyl)-2-methyl-3,4-dihydropyrimidin-4-one |
| 28 | 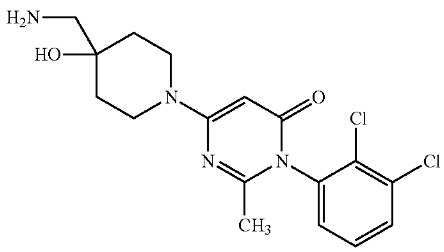 [SMILES: Cc1nc(N2CCC(O)(CN)CC2)cc(=O)n1-c1cccc(Cl)c1Cl] | 6-[4-(aminomethyl)-4-hydroxypiperidin-1-yl]-3-(2,3-dichlorophenyl)-2-methyl-3,4-dihydropyrimidin-4-one |
| 29 | 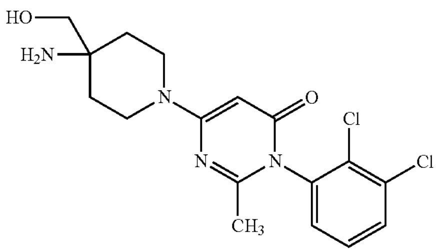 [SMILES: Cc1nc(N2CCC(N)(CO)CC2)cc(=O)n1-c1cccc(Cl)c1Cl] | 6-[4-amino-4-(hydroxymethyl)piperidin-1-yl]-3-(2,3-dichlorophenyl)-2-methyl-3,4-dihydropyrimidin-4-one |
| 30 | 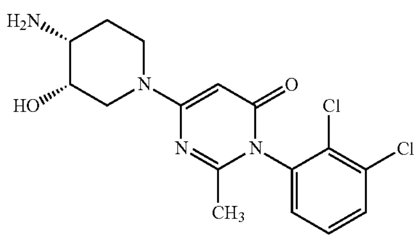 [SMILES: Cc1nc(N2CC[C@@H](N)[C@@H](O)C2)cc(=O)n1-c1cccc(Cl)c1Cl] | (+/−)-6-[(3S,4R)-4-amino-3-hydroxypiperidin-1-yl]-3-(2,3-dichlorophenyl)-2-methyl-3,4-dihydropyrimidin-4-one |
| 31 | 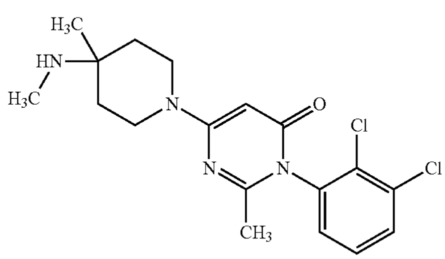 [SMILES: CNC1(C)CCN(c2cc(=O)n(-c3cccc(Cl)c3Cl)c(C)n2)CC1] | 3-(2,3-dichlorophenyl)-2-methyl-6-[4-methyl-4-(methylamino)piperidin-1-yl]-3,4-dihydropyrimidin-4-one |
| 32a | 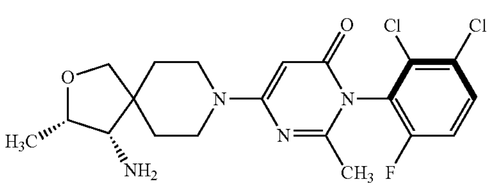 | (3P)-6-[(3S,4S)-4-amino-3-methyl-2-oxa-8-azaspiro[4.5]decan-8-yl]-3-(2,3-dichloro-6-fluorophenyl)-2-methyl-3,4-dihydropyrimidin-4-one |
| 32b | 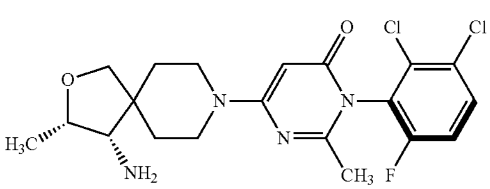 | (3M)-6-[(3S,4S)-4-amino-3-methyl-2-oxa-8-azaspiro[4.5]decan-8-yl]-3-(2,3-dichloro-6-fluorophenyl)-2-methyl-3,4-dihydropyrimidin-4-one |

| No. | Structure | Chemical Name |
|-----|-----------|---------------|
| 33a | 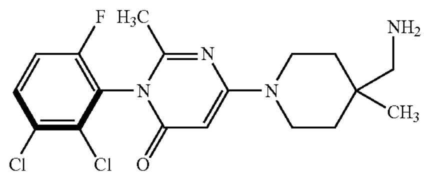 | (3P)-6-[4-(aminomethyl)-4-methylpiperidin-1-yl]-3-(2,3-dichloro-6-fluorophenyl)-2-methyl-3,4-dihydropyrimidin-4-one |
| 33b | 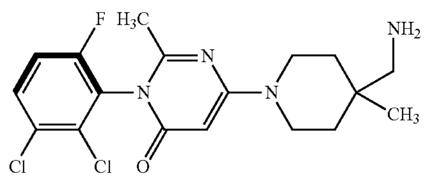 | (3M)-6-[4-(aminomethyl)-4-methylpiperidin-1-yl]-3-(2,3-dichloro-6-fluorophenyl)-2-methyl-3,4-dihydropyrimidin-4-one |
| 34 | 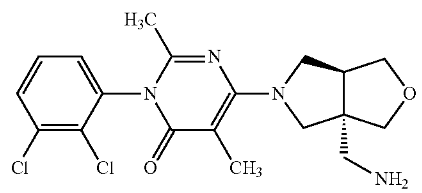 [SMILES: Cc1c(N2C[C@H]3COC[C@@]3(CN)C2)nc(C)n(-c2cccc(Cl)c2Cl)c1=O] | (+/−)-6-[(3aS,6aS)-3a-(aminomethyl)-hexahydro-1H-furo[3,4-c]pyrrol-5-yl]-3-(2,3-dichlorophenyl)-2,5-dimethyl-3,4-dihydropyrimidin-4-one |
| 35 | 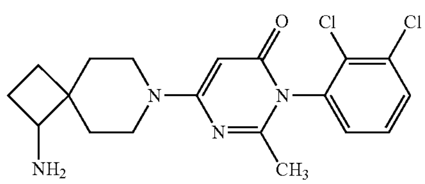 [SMILES: Cc1nc(N2CCC3(CCC3N)CC2)cc(=O)n1-c1cccc(Cl)c1Cl] | 6-1-amino-7-azaspiro[3.5]nonan-7-yl-3-(2,3-dichlorophenyl)-2-methyl-3,4-dihydropyrimidin-4-one |
| 36 | 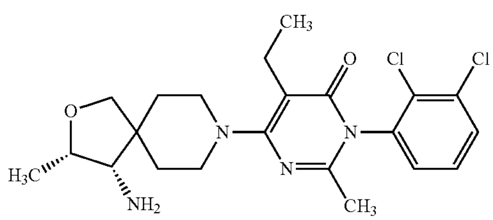 [SMILES: CCc1c(N2CCC3(CC2)CO[C@@H](C)[C@H]3N)nc(C)n(-c2cccc(Cl)c2Cl)c1=O] | 6-[(3S,4S)-4-amino-3-methyl-2-oxa-8-azaspiro[4.5]decan-8-yl]-3-(2,3-dichlorophenyl)-5-ethyl-2-methyl-3,4-dihydropyrimidin-4-one |
| 37a | 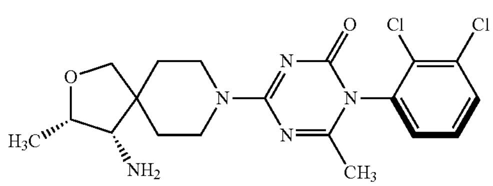 | (1M)-4-[(3S,4S)-4-amino-3-methyl-2-oxa-8-azaspiro[4.5]decan-8-yl]-1-(2,3-dichlorophenyl)-6-methyl-1,2-dihydro-1,3,5-triazin-2-one |
| 37b | 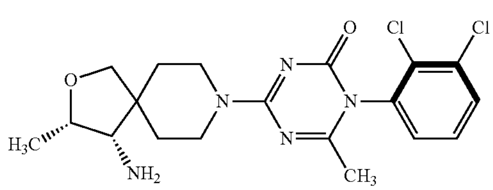 | (1P)-4-[(3S,4S)-4-amino-3-methyl-2-oxa-8-azaspiro[4.5]decan-8-yl]-1-(2,3-dichlorophenyl)-6-methyl-1,2-dihydro-1,3,5-triazin-2-one |

-continued

| No. | Structure | Chemical Name |
|---|---|---|
| 38 | 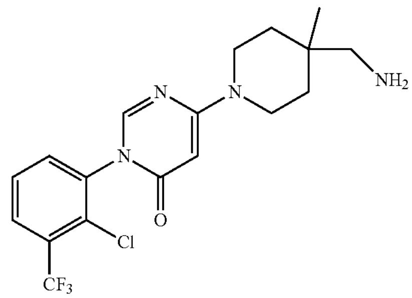 [SMILES: CC1(CN)CCN(c2cc(=O)n(-c3cccc(C(F)(F)F)c3Cl)cn2)CC1] | 6-[4-(aminomethyl)-4-methylpiperidin-1-yl]-3-[2-chloro-3-(trifluoromethyl)phenyl]-2-methyl-3,4-dihydropyrimidin-4-one |
| 39 | 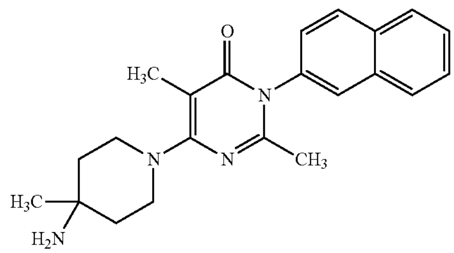 [SMILES: Cc1c(N2CCC(C)(N)CC2)nc(C)n(-c2ccc3ccccc3c2)c1=O] | 6-(4-Amino-4-methyl-piperidin-1-yl)-2,5-dimethyl-3-naphthalen-2-yl-3H-pyrimidin-4-one |
| 41 | 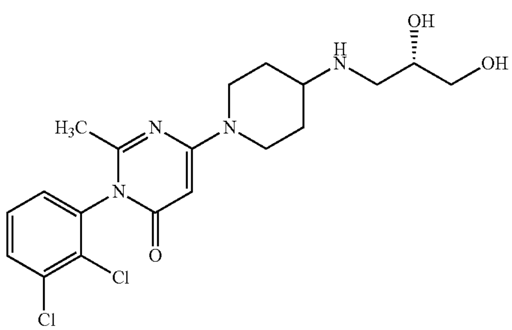 [SMILES: Cc1nc(N2CCC(NC[C@H](O)CO)CC2)cc(=O)n1-c1cccc(Cl)c1Cl] | 3-(2,3-dichlorophenyl)-6-(4-{[(2R)-2,3-dihydroxypropyl]amino}piperidin-1-yl)-2-methyl-3,4-dihydropyrimidin-4-one |
| 42 | 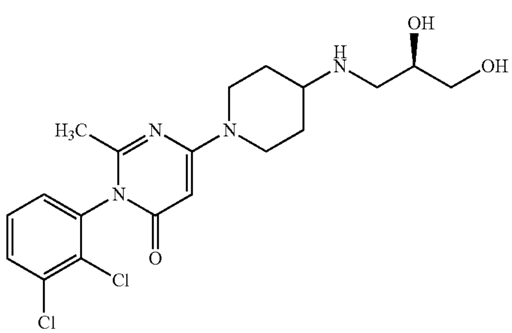 [SMILES: Cc1nc(N2CCC(NC[C@@H](O)CO)CC2)cc(=O)n1-c1cccc(Cl)c1Cl] | 3-(2,3-dichlorophenyl)-6-(4-{[(2S)-2,3-dihydroxypropyl]amino}piperidin-1-yl)-2-methyl-3,4-dihydropyrimidin-4-one |
| 43 | 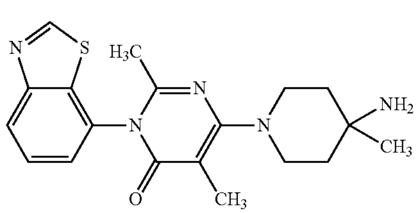 [SMILES: Cc1c(N2CCC(C)(N)CC2)nc(C)n(-c2cccc3ncsc23)c1=O] | 6-(4-Amino-4-methyl-piperidin-1-yl)-3-benzothiazol-7-yl-2,5-dimethyl-3H-pyrimidin-4-one |

| No. | Structure | Chemical Name |
|-----|-----------|---------------|
| 44 | 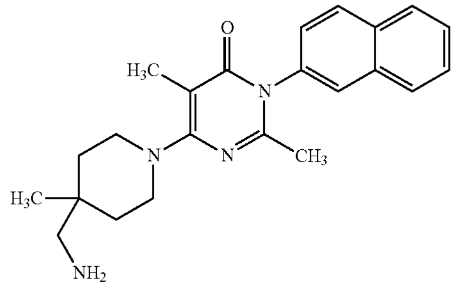 [SMILES: Cc1c(N2CCC(C)(CN)CC2)nc(C)n(-c2ccc3ccccc3c2)c1=O] | 6-(4-Aminomethyl-4-methyl-piperidin-1-yl)-2,5-dimethyl-3-naphthalen-2-yl-3H-pyrimidin-4-one |
| 45 | 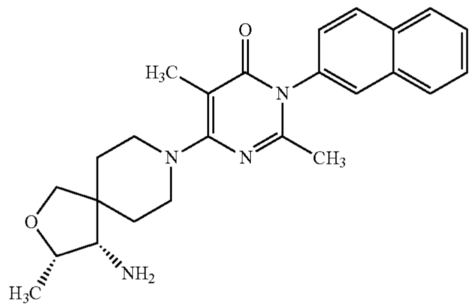 [SMILES: Cc1c(N2CCC3(CC2)CO[C@@H](C)[C@H]3N)nc(C)n(-c2ccc3ccccc3c2)c1=O] | 6-((3S,4S)-4-Amino-3-methyl-2-oxa-8-aza-spiro[4.5]dec-8-yl)-2,5-dimethyl-3-naphthalen-2-yl-3H-pyrimidin-4-one |
| 46 | 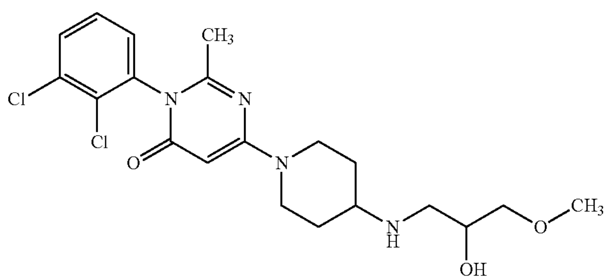 [SMILES: COCC(O)CNC1CCN(c2cc(=O)n(-c3cccc(Cl)c3Cl)c(C)n2)CC1] | 3-(2,3-dichlorophenyl)-6-{4-[(2-hydroxy-3-methoxypropyl)-amino]piperidin-1-yl}-2-methyl-3,4-dihydropyrimidin-4-one |
| 47 | 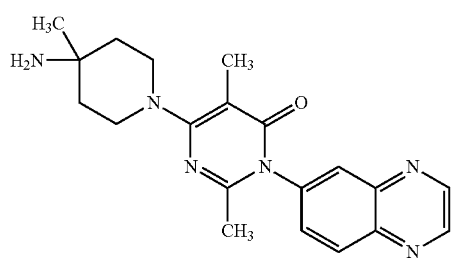 [SMILES: Cc1c(N2CCC(C)(N)CC2)nc(C)n(-c2ccc3nccnc3c2)c1=O] | 6-(4-Amino-4-methyl-piperidin-1-yl)-2,5-dimethyl-3-quinoxalin-6-yl-3H-pyrimidin-4-one |
| 48 | 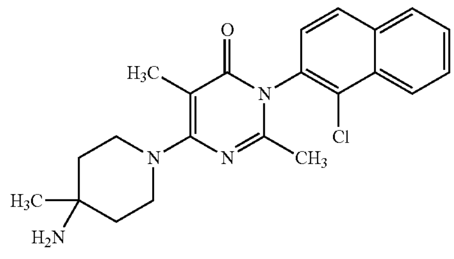 [SMILES: Cc1c(N2CCC(C)(N)CC2)nc(C)n(-c2ccc3ccccc3c2Cl)c1=O] | 6-(4-Amino-4-methyl-piperidin-1-yl)-3-(1-chloro-naphthalen-2-yl)-2,5-dimethyl-3H-pyrimidin-4-one |

-continued

| No. | Structure | Chemical Name |
|---|---|---|
| 49a | 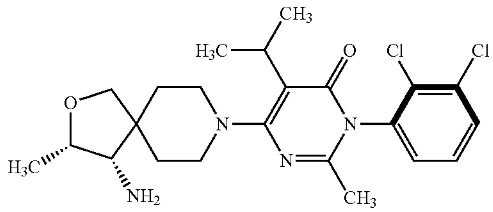 | (3P)-6-[(3S,4S)-4-amino-3-methyl-2-oxa-8-azaspiro[4.5]decan-8-yl]-3-(2,3-dichlorophenyl)-2-methyl-5-(propan-2-yl)-3,4-dihydropyrimidin-4-one |
| 49b | 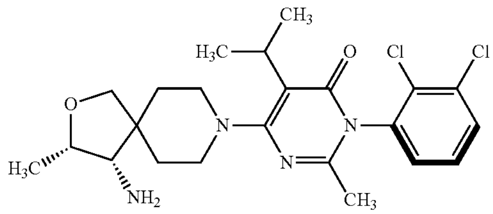 | (3M)-6-[(3S,4S)-4-amino-3-methyl-2-oxa-8-azaspiro[4.5]decan-8-yl]-3-(2,3-dichlorophenyl)-2-methyl-5-(propan-2-yl)-3,4-dihydropyrimidin-4-one |
| 50 | 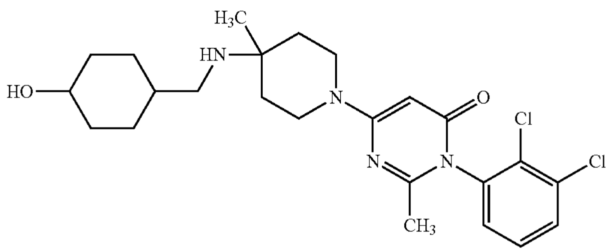 [SMILES: Cc1nc(N2CCC(C)(NCC3CCC(O)CC3)CC2)cc(=O)n1-c1cccc(Cl)c1Cl] | 3-(2,3-dichlorophenyl)-6-(4-{[(4-hydroxycyclohexyl)methyl]amino)-4-methylpiperidin-1-yl)-2-methyl-3,4-dihydropyrimidin-4-one |
| 51 | 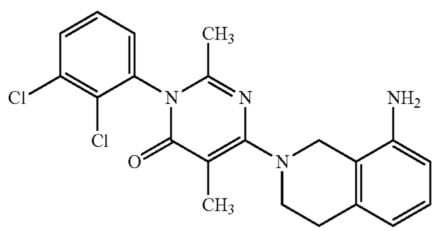 [SMILES: Cc1c(N2CCc3cccc(N)c3C2)nc(C)n(-c2cccc(Cl)c2Cl)c1=O] | 6-(8-amino-1,2,3,4-tetrahydroisoquinolin-2-yl)-3-(2,3-dichlorophenyl)-2,5-dimethyl-3,4-dihydropyrimidin-4-one |
| 52 | 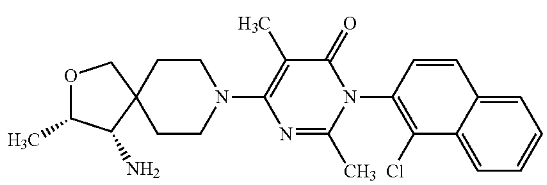 [SMILES: Cc1c(N2CCC3(CC2)CO[C@@H](C)[C@H]3N)nc(C)n(-c2ccc3ccccc3c2Cl)c1=O] | 6-((3S,4S)-4-Amino-3-methyl-2-oxa-8-aza-spiro[4.5]dec-8-yl)-3-(1-chloro-naphthalen-2-yl)-2,5-dimethyl-3H-pyrimidin-4-one |
| 53 | 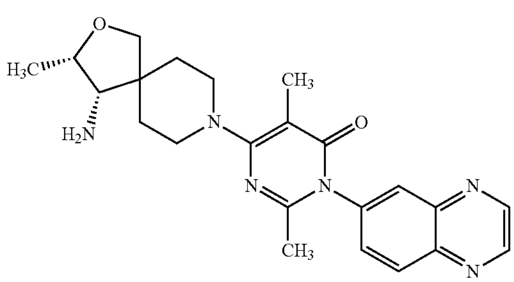 [SMILES: Cc1c(N2CCC3(CC2)CO[C@@H](C)[C@H]3N)nc(C)n(-c2ccc3nccnc3c2)c1=O] | 6-((3S,4S)-4-Amino-3-methyl-2-oxa-8-aza-spiro[4.5]dec-8-yl)-2,5-dimethyl-3-quinoxalin-6-yl-3H-pyrimidin-4-one |
| 54 | 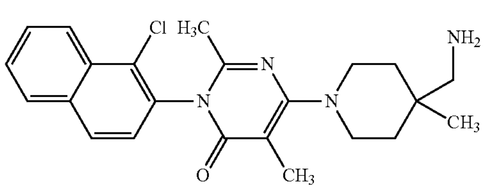 [SMILES: Cc1c(N2CCC(C)(CN)CC2)nc(C)n(-c2ccc3ccccc3c2Cl)c1=O] | 6-(4-Aminomethyl-4-methyl-piperidin-1-yl)-3-(1-chloro-naphthalen-2-yl)-2,5-dimethyl-3H-pyrimidin-4-one |

-continued

| No. | Structure | Chemical Name |
|---|---|---|
| 55 | 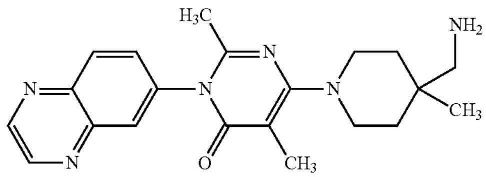 [SMILES: Cc1c(N2CCC(C)(CN)CC2)nc(C)n(-c2ccc3nccnc3c2)c1=O] | 6-(4-Aminomethyl-4-methyl-piperidin-1-yl)-2,5-dimethyl-3-quinoxalin-6-yl-3H-pyrimidin-4-one |
| 56 | 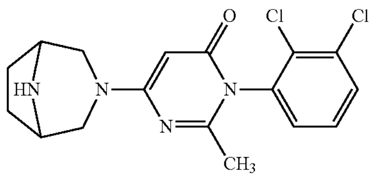 [SMILES: Cc1nc(N2CC3CCC(C2)N3)cc(=O)n1-c1cccc(Cl)c1Cl] | 6-3,8-diazabicyclo[3.2.1]octan-3-yl-3-(2,3-dichlorophenyl)-2-methyl-3,4-dihydropyrimidin-4-one |
| 57a | 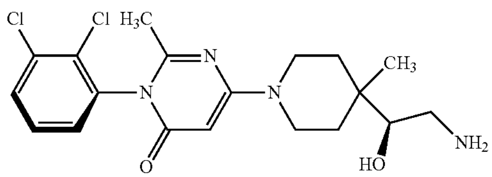 | (+/−)-(3M)-6-{4-[(1S)-2-amino-1-hydroxyethyl]-4-methylpiperidin-1-yl}-3-(2,3-dichlorophenyl)-2-methyl-3,4-dihydropyrimidin-4-one |
| 57b | 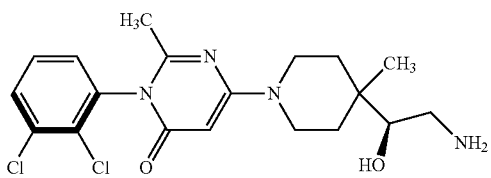 | (+/−)-(3P)-6-{4-[(1S)-2-amino-1-hydroxyethyl]-4-methylpiperidin-1-yl}-3-(2,3-dichlorophenyl)-2-methyl-3,4-dihydropyrimidin-4-one |
| 58a | 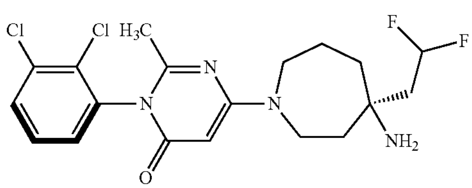 | (+/−)-(3M)-6-4-[(1R)-4-amino-4-(2,2-difluoroethyl)azepan-1-yl]-3-(2,3-dichlorophenyl)-2-methyl-3,4-dihydropyrimidin-4-one |
| 58b | 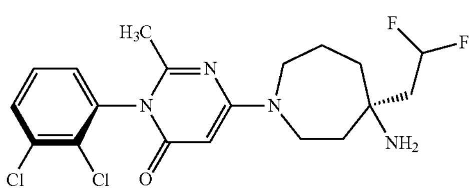 | (+/−)-(3P)-6-4-[(1R)-4-amino-4-(2,2-difluoroethyl)azepan-1-yl]-3-(2,3-dichlorophenyl)-2-methyl-3,4-dihydropyrimidin-4-one |
| 59 | 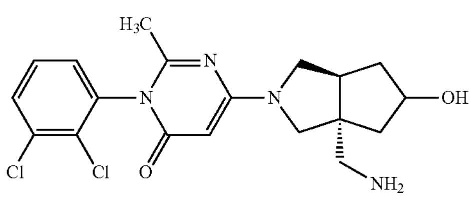 [SMILES: Cc1nc(N2C[C@H]3CC(O)C[C@@]3(CN)C2)cc(=O)n1-c1cccc(Cl)c1Cl] | 6-[(3aR,6aS)-3a-(aminomethyl)-5-hydroxy-octahydrocyclopenta[c]pyrrol-2-yl]-3-(2,3-dichlorophenyl)-2-methyl-3,4-dihydropyrimidin-4-one |
| 60 | 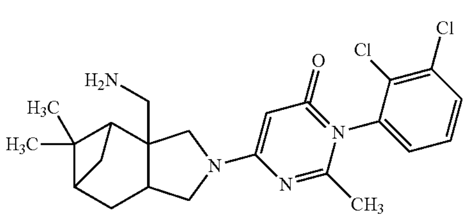 | 6-[2-(aminomethyl)-9,9-dimethyl-4-azatricyclo[6.1.1.0$^{2,6}$]decan-4-yl]-3-(2,3-dichlorophenyl)-2-methyl-3,4-dihydropyrimidin-4-one |

-continued

| No. | Structure | Chemical Name |
|---|---|---|
| 61 | 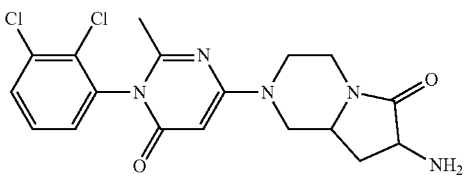 [SMILES: Cc1nc(N2CCN3C(=O)C(N)CC3C2)cc(=O)n1-c1cccc(Cl)c1Cl] | 6-7-amino-6-oxo-octahydropyrrolo[1,2-a]pyrazin-2-yl-3-(2,3-dichlorophenyl)-2-methyl-3,4-dihydropyrimidin-4-one |
| 62a | 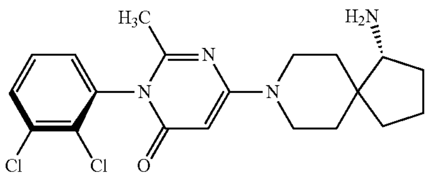 | (3P)-6-{(R)-1-amino-8-azaspiro[4.5]decan-8-yl}-3-(2,3-dichlorophenyl)-2-methyl-3,4-dihydropyrimidin-4-one |
| 62b | 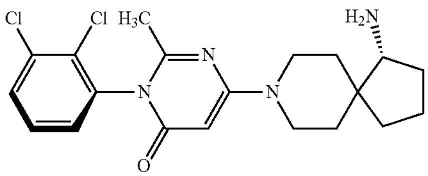 | (3M)-6-{(R)-1-amino-8-azaspiro[4.5]decan-8-yl}-3-(2,3-dichlorophenyl)-2-methyl-3,4-dihydropyrimidin-4-one |
| 63 | 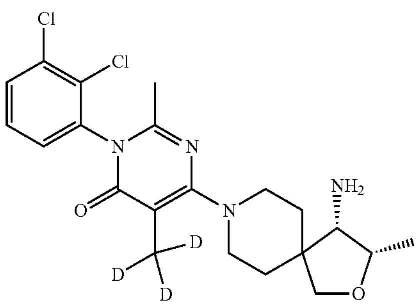 [SMILES: [2H]C([2H])([2H])c1c(N2CCC3(CC2)CO[C@@H](C)[C@H]3N)nc(C)n(-c2cccc(Cl)c2Cl)c1=O] | 6-[(3S,4S)-4-amino-3-methyl-2-oxa-8-azaspiro[4.5]decan-8-yl]-3-(2,3-dichlorophenyl)-5-($^2$H3)methyl-2-methyl-3,4-dihydropyrimidin-4-one |
| 63a | 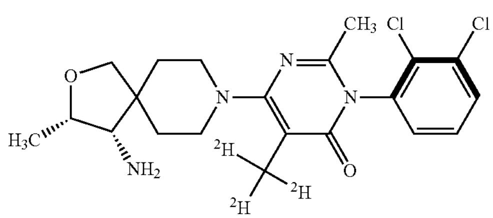 | (3P)-6-[(3S,4S)-4-amino-3-methyl-2-oxa-8-azaspiro[4.5]decan-8-yl]-3-(2,3-dichlorophenyl)-5-(D$_3$)methyl-2-methyl-3,4-dihydropyrimidin-4-one |
| 63b | 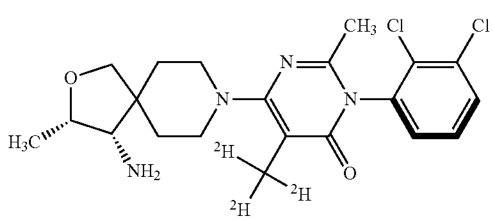 | (3M)-6-[(3S,4S)-4-amino-3-methyl-2-oxa-8-azaspiro[4.5]decan-8-yl]-3-(2,3-dichlorophenyl)-5-(D$_3$)methyl-2-methyl-3,4-dihydropyrimidin-4-one |
| 66a | 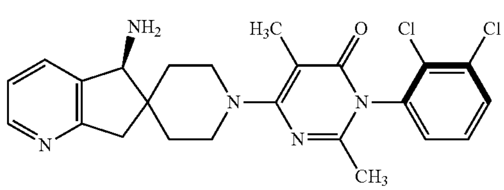 | (3P)-6-[(5R)-5-amino-5,7-dihydrospiro[cyclopenta[b]pyridine-6,4'-piperidin]-1'-yl]-3-(2,3-dichloropheny))-2,5-dimethyl-3,4-dihydropyrimidin-4-one |

| No. | Structure | Chemical Name |
|---|---|---|
| 66b | 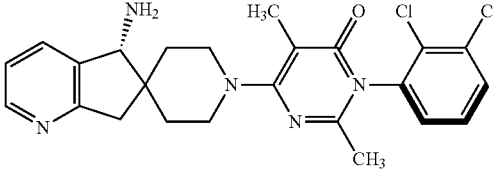 | (3M)-6-[(5S)-5-amino-5,7-dihydrospiro[cyclopenta[b]pyridine-6,4'-piperidin]-1'-yl]-3-(2,3-dichlorophenyl)-2,5-dimethyl-3,4-dihydropyrimidin-4-one |
| 67a | 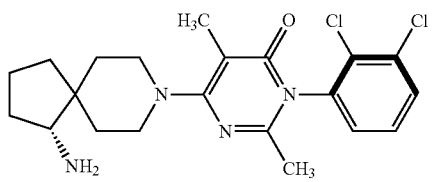 | (3P)-6-[(1R)-1-amino-8-azaspiro[4.5]decan-8-yl]-3-(2,3-dichlorophenyl)-2,5-dimethyl-3,4-dihydropyrimidin-4-one |
| 67b | 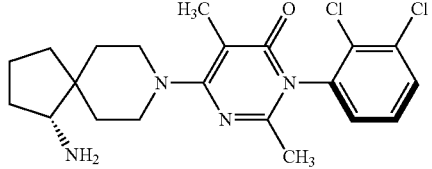 | (3M)-6-[(1R)-1-amino-8-azaspiro[4.5]decan-8-yl]-3-(2,3-dichlorophenyl)-2,5-dimethyl-3,4-dihydropyrimidin-4-one |
| 70 | 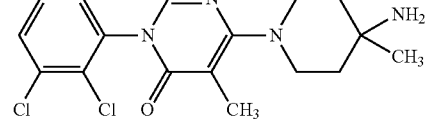 | 6-(4-Amino-4-methyl-piperidin-1-yl)-3-(2,3-dichloro-phenyl)-5-methyl-3H-pyrimidin-4-one |
| 71a | 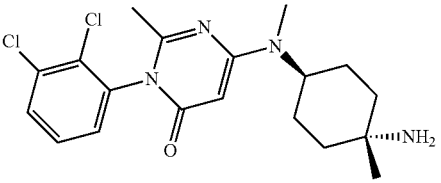 [SMILES: Cc1nc(N(C)[C@H]2CC[C@](C)(N)CC2)cc(=O)n1-c1cccc(Cl)c1Cl] | 3-(2,3-dichlorophenyl)-2-methyl-6-methyl[(trans)-4-amino-4-methylcyclohexyl]amino-3,4-dihydropyrimidin-4-one |
| 71b | 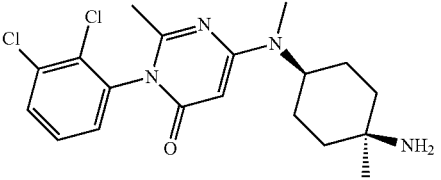 [SMILES: Cc1nc(N(C)[C@H]2CC[C@@](C)(N)CC2)cc(=O)n1-c1cccc(Cl)c1Cl] | 3-(2,3-dichlorophenyl)-2-meyhyl-6-methyl[(cis)-4-amino-4-methylcyclohexyl]amino-3,4-dihydropyrimidin-4-one |
| 72a | 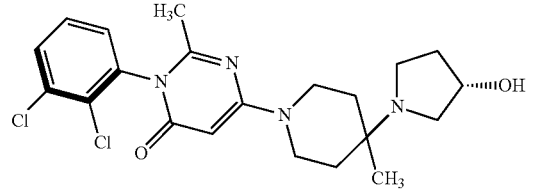 | (+/−)-(3P)-3-(2,3-dichlorophenyl)-6-{4-[(3R)-3-hydroxypyrrolidin-1-yl]-4-methylpiperidin-1-yl}-2-methyl-3,4-dihydropyrimidin-4-one |
| 72b | 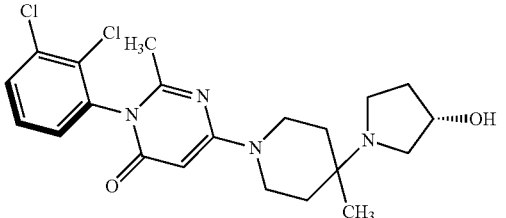 | (+/−)-(3M)-3-(2,3-dichlorophenyl)-6-{4-[(3R)-3-hydroxypyrrolidin-1-yl]-4-methylpiperidin-1-yl}-2-methyl-3,4-dihydropyrimidin-4-one |

| No. | Structure | Chemical Name |
|---|---|---|
| 73a | 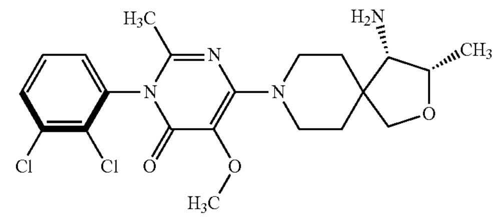 | (3P)-6-[(3S,4S)-4-amino-3-methyl-2-oxa-8-azaspiro[4.5]decan-8-yl]-3-(2,3-dichlorophenyl)-5-methoxy-2-methyl-3,4-dihydropyrimidin-4-one |
| 73b | 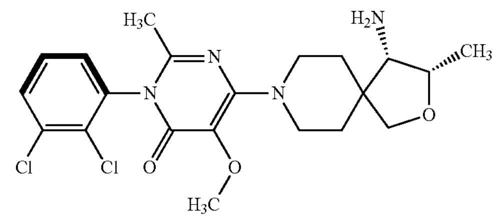 | (3M)-6-[(3S,4S)-4-amino-3-methyl-2-oxa-8-azaspiro[4.5]decan-8-yl]-3-(2,3-dichlorophenyl)-5-methoxy-2-methyl-3,4-dihydropyrimidin-4-one |
| 74a | 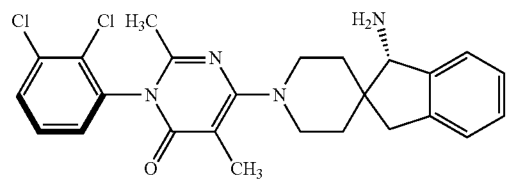 | (3M)-6-[(1S)-1-amino-1,3-dihydrospiro[indene-2,4'-piperidin]-1'-yl]-3-(2,3-dichlorophenyl)-2,5-dimethyl-3,4-dihydropyrimidin-4-one |
| 74b | 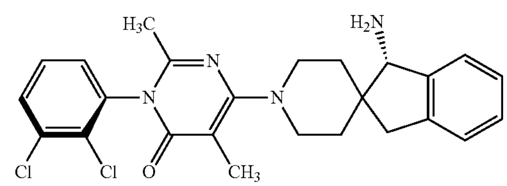 | (3P)-6-[(1S)-1-amino-1,3-dihydrospiro[indene-2,4'-piperidin]-1'-yl]-3-(2,3-dichlorophenyl)-2,5-dimethyl-3,4-dihydropyrimidin-4-one |
| 74c | 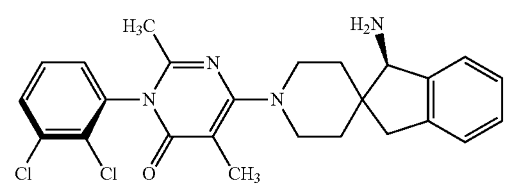 | (3M)-6-[(1R)-1-amino-1,3-dihydrospiro[indene-2,4'-piperidin]-1'-yl]-3-(2,3-dichlorophenyl)-2,5-dimethyl-3,4-dihydropyrimidin-4-one |
| 74d | 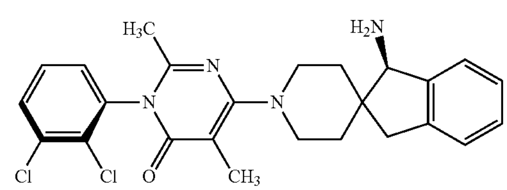 | (3P)-6-[(1R)-1-amino-1,3-dihydrospiro[indene-2,4'-piperidin]-1'-yl]-3-(2,3-dichlorophenyl)-2,5-dimethyl-3,4-dihydropyrimidin-4-one |
| 75 | 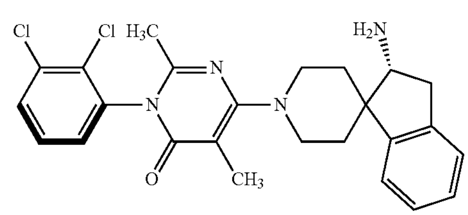 | (3M)-6-[(6R)-6-amino-5,6-dihydrospiro[cyclopenta[b]pyridine-7,4'-piperidin]-1'-yl]-3-(2,3-dichlorophenyl)-2,5-dimethyl-3,4-dihydropyrimidin-4-one |

-continued

| No. | Structure | Chemical Name |
|---|---|---|
| 76 | 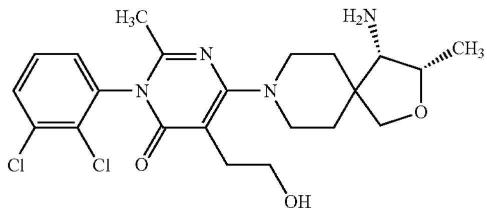 [SMILES: Cc1nc(N2CCC3(CC2)CO[C@@H](C)[C@H]3N)c(CCO)c(=O)n1-c1cccc(Cl)c1Cl] | 6-((3S,4S)-4-amino-3-methyl-2-oxa-8-azaspiro[4.5]dec-8-yl)-3-(2,3-dichlorophenyl)-5-(2-hydroxyethyl)-2-methyl-3,4-dihydropyrimidin-4-one hydrochloride |
| 77 | 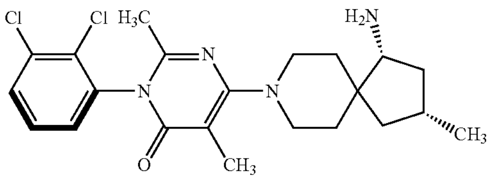 | (3M)-6-[(1R,3R)-1-amino-3-methyl-8-azaspiro[4.5]decan-8-yl]-3-(2,3-dichlorophenyl)-2,5-dimethyl-3,4-dihydropyrimidin-4-one |
| 78a | 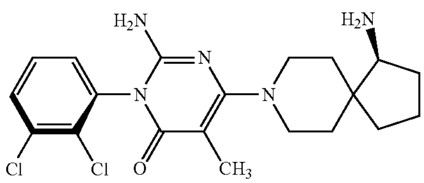 | (3P)-2-amino-6-[(1S)-1-amino-8-azaspiro[4.5]decan-8-yl]-3-(2,3-dichlorophenyl)-5-methyl-3,4-dihydropyrimidin-4-one |
| 78b | 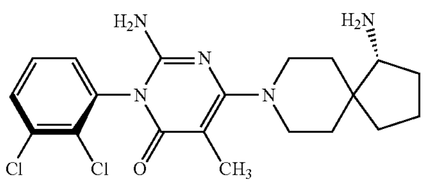 | (3P)-2-amino-6-[(1R)-1-amino-8-azaspiro[4.5]decan-8-yl]-3-(2,3-dichlorophenyl)-5-methyl-3,4-dihydropyrimidin-4-one |
| 78c | 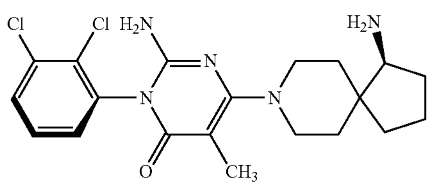 | (3M)-2-amino-6-[(1S)-1-amino-8-azaspiro[4.5]decan-8-yl]-3-(2,3-dichlorophenyl)-5-methyl-3,4-dihydropyrimidin-4-one |
| 78d | 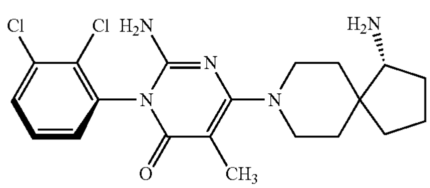 | (3M)-2-amino-6-[(1R)-1-amino-8-azaspiro[4.5]decan-8-yl]-3-(2,3-dichlorophenyl)-5-methyl-3,4-dihydropyrimidin-4-one |
| 79a | 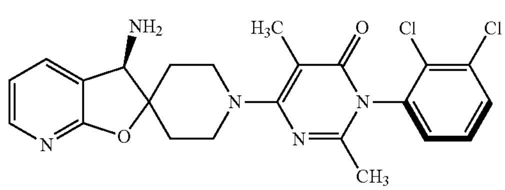 | (3M)-6-[(3R)-3-amino-3H-spiro[furo[2,3-b]pyridine-2,4'-piperidin]-1'-yl]-3-(2,3-dichlorophenyl)-2,5-dimethyl-3,4-dihydropyrimidin-4-one |
| 79b | 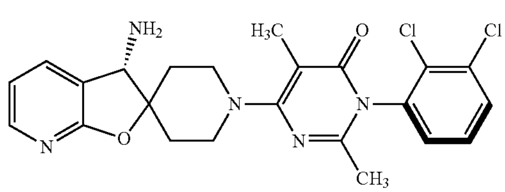 | (3M)-6-[(3S)-3-amino-3H-spiro[furo[2,3-b]pyridine-2,4'-piperidin]-1'-yl]-3-(2,3-dichlorophenyl)-2,5-dimethyl-3,4-dihydropyrimidin-4-one |

-continued

| No. | Structure | Chemical Name |
|---|---|---|
| 80a | 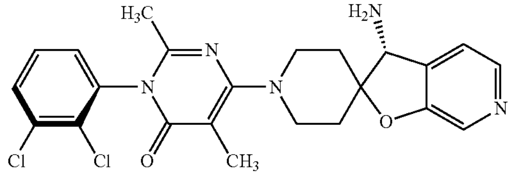 | (3P)-6-[(3S)-3-amino-3H-spiro[furo[2,3-c]pyridine-2,4'-piperidin]-1'-yl]-3-(2,3-dichlorophenyl)-2,5-dimethylpyrimidin-4-one |
| 80b | 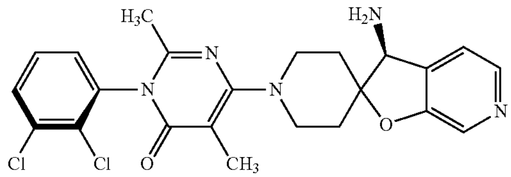 | (3P)-6-[(3R)-3-amino-3H-spiro[furo[2,3-c]pyridine-2,4'-piperidin]-1'-yl]-3-(2,3-dichlorophenyl)-2,5-dimethylpyrimidin-4-one |
| 80c | 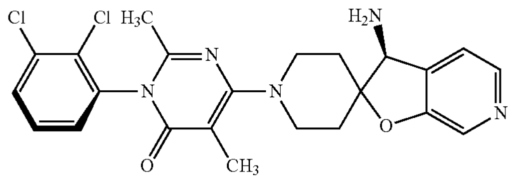 | (3M)-6-[(3R)-3-amino-3H-spiro[furo[2,3-c]pyridine-2,4'-piperidin]-1'-yl]-3-(2,3-dichlorophenyl)-2,5-dimethylpyrimidin-4-one |
| 80d | 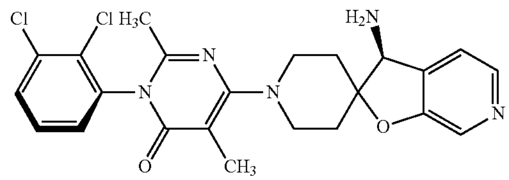 | (3M)-6-[(3S)-3-amino-3H-spiro[furo[2,3-c]pyridine-2,4'-piperidin]-1'-yl]-3-(2,3-dichlorophenyl)-2,5-dimethylpyrimidin-4-one |
| 81a | 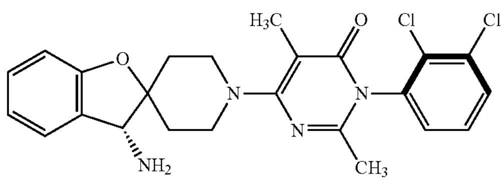 | (3P)-6-[(3R)-3-amino-3H-spiro[1-benzofuran-2,4'-piperidin]-1'-yl]-3-(2,3-dichlorophenyl)-2,5-dimethyl-3,4-dihydropyrimidin-4-one |
| 81b | 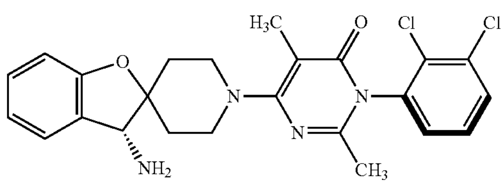 | (3M)-6-[(3R)-3-amino-3H-spiro[1-benzofuran-2,4'-piperidin]-1'-yl]-3-(2,3-dichlorophenyl)-2,5-dimethyl-3,4-dihydropyrimidin-4-one |
| 82 | 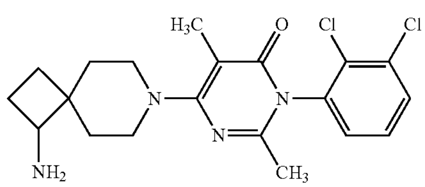 [SMILES: Cc1c(N2CCC3(CCC3N)CC2)nc(C)n(-c2cccc(Cl)c2Cl)c1=O] | 6-1-amino-7-azaspiro[3.5]nonan-7-yl-3-(2,3-dichlorophenyl)-2,5-dimethyl-3,4-dihydropyrimidin-4-one |
| 83 | 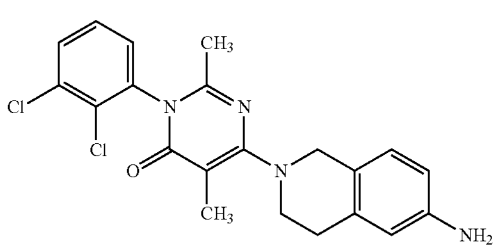 [SMILES: Cc1c(N2CCc3cc(N)ccc3C2)nc(C)n(-c2cccc(Cl)c2Cl)c1=O] | 6-(6-amino-1,2,3,4-tetrahydroisoquinolin-2-yl)-3-(2,3-dichlorophenyl)-2,5-dimethyl-3,4-dihydropyrimidin-4-one |

| No. | Structure | Chemical Name |
|---|---|---|
| 84 | 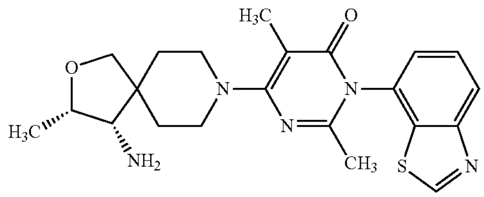 [SMILES: Cc1c(N2CCC3(CC2)CO[C@@H](C)[C@H]3N)nc(C)n(-c2cccc3ncsc23)c1=O] | 6-((3S,4S)-4-Amino-3-methyl-2-oxa-8-aza-spiro[4.5]dec-8-yl)-3-benzothiazol-7-yl-2,5-dimethyl-3H-pyrimidin-4-one |
| 85 | 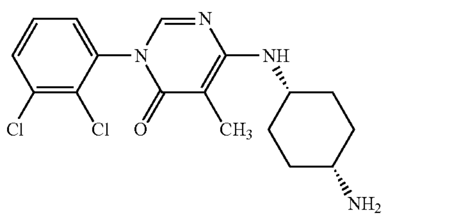 [SMILES: Cc1c(N[C@H]2CC[C@@H](N)CC2)ncn(-c2cccc(Cl)c2Cl)c1=O] | 6-(4-Amino-cyclohexylamino)-3-(2,3-dichloro-phenyl)-5-methyl-3H-pyrimidin-4-one |
| 86 | 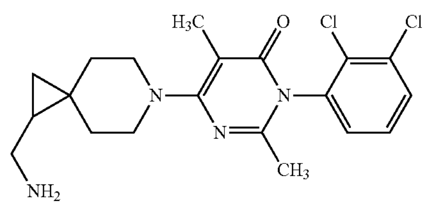 [SMILES: Cc1c(N2CCC3(CC2)CC3CN)nc(C)n(-c2cccc(Cl)c2Cl)c1=O] | 6-[1-(aminomethyl)-6-azaspiro[2.5]octan-6-yl]-3-(2,3-dichlorophenyl)-2,5-dimethyl-3,4-dihydropyrimidin-4-one |
| 87 | 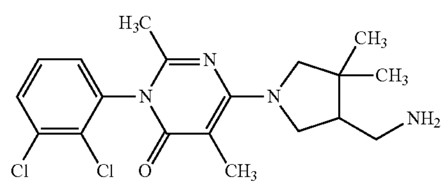 [SMILES: Cc1c(N2CC(CN)C(C)(C)C2)nc(C)n(-c2cccc(Cl)c2Cl)c1=O] | 6-[4-(aminomethyl)-3,3-dimethylpyrrolidin-1-yl]-3-(2,3-dichlorophenyl)-2,5-dimeihyl-3,4-dihydropyrimidin-4-one |
| 88 | 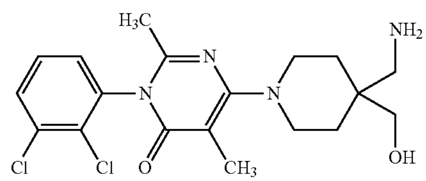 [SMILES: Cc1c(N2CCC(CN)(CO)CC2)nc(C)n(-c2cccc(Cl)c2Cl)c1=O] | 6-[4-(aminomethyl)-4-(hydroxymethyl)piperidin-1-yl]-3-(2,3-dichlorophenyl)-2,5-dimethyl-3,4-dihydropyrimidin-4-one |
| 89 | 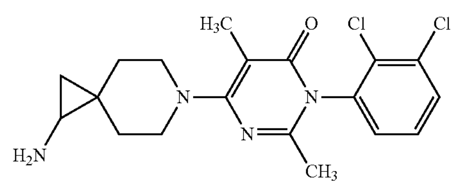 [SMILES: Cc1c(N2CCC3(CC2)CC3N)nc(C)n(-c2cccc(Cl)c2Cl)c1=O] | 6-1-amino-6-azaspiro[2.5]octan-6-yl-3-(2,3-dichlorophenyl)-2,5-dimethyl-3,4-dihydropyrimidin-4-one |
| 90 | 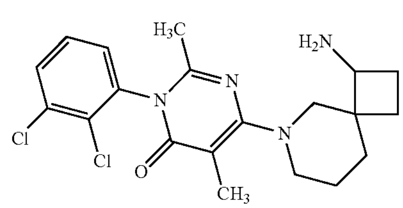 [SMILES: Cc1c(N2CCCC3(CCC3N)C2)nc(C)n(-c2cccc(Cl)c2Cl)c1=O] | 6-1-amino-6-azaspiro[3.5]nonan-6-yl-3-(2,3-dichlorophenyl)-2,5-dimethyl-3,4-dihydropyrimidin-4-one |
| 91 | 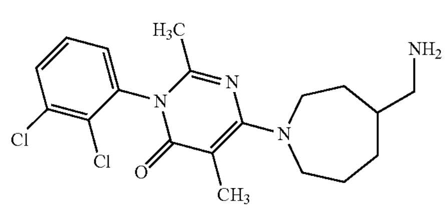 [SMILES: Cc1c(N2CCCC(CN)CC2)nc(C)n(-c2cccc(Cl)c2Cl)c1=O] | 6-[4-(aminomethyl)azepan-1-yl]-3-(2,3-dichlorophenyl)-2,5-dimethyl-3,4-dihydropyrimidin-4-one |

-continued

| No. | Structure | Chemical Name |
|---|---|---|
| 92 | 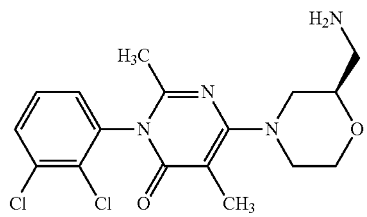 [SMILES: Cc1c(N2CCO[C@H](CN)C2)nc(C)n(-c2cccc(Cl)c2Cl)c1=O] | 6-[(2R)-2-(aminomethyl)morpholin-4-yl]-3-(2,3-dichlorophenyl)-2,5-dimethyl-3,4-dihydropyrimidin-4-one |
| 93 | 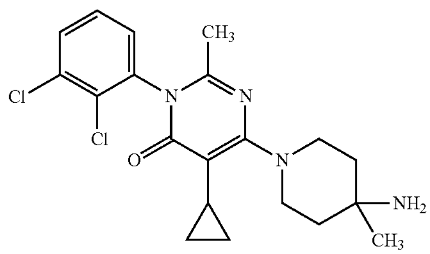 [SMILES: Cc1nc(N2CCC(C)(N)CC2)c(C2CC2)c(=O)n1-c1cccc(Cl)c1Cl] | 6-(4-Amino-4-methyl-piperidin-1-yl)-5-cyclopropyl-3-(2,3-dichloro-phenyl)-2-methyl-3H-pyrimidin-4-one |
| 94 | 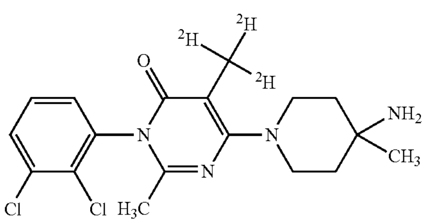 [SMILES: [2H]C([2H])([2H])c1c(N2CCC(C)(N)CC2)nc(C)n(-c2cccc(Cl)c2Cl)c1=O] | 6-(4-amino-4-methylpiperidin-1-yl)-3-(2,3-dichlorophenyl)-5-(D$_3$)methyl-2-methyl-3,4-dihydropyrimidin-4-one |
| 95 | 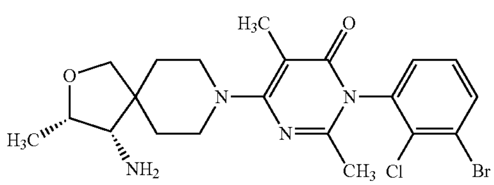 [SMILES: Cc1c(N2CCC3(CC2)CO[C@@H](C)[C@H]3N)nc(C)n(-c2cccc(Br)c2Cl)c1=O] | 6-((3S,4S)-4-Amino-3-methyl-2-oxa-8-aza-spiro[4.5]dec-8-yl)-3-(3-bromo-2-chloro-phenyl)-2,5-dimethyl-3H-pyrimidin-4-one |
| 96 | 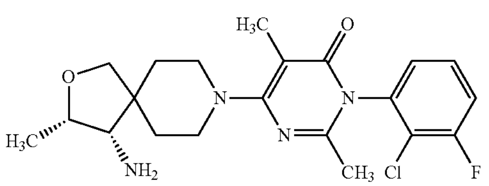 [SMILES: Cc1c(N2CCC3(CC2)CO[C@@H](C)[C@H]3N)nc(C)n(-c2cccc(F)c2Cl)c1=O] | 6-((3S,4S)-4-Amino-3-methyl-2-oxa-8-aza-spiro[4.5]dec-8-yl)-3-(2-chloro-3-fluoro-phenyl)-2,5-dimethyl-3H-pyrimidin-4-one |
| 97 | 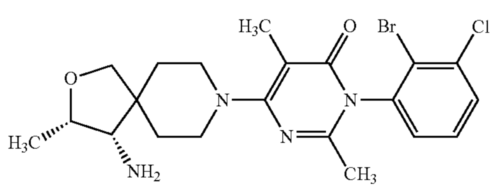 [SMILES: Cc1c(N2CCC3(CC2)CO[C@@H](C)[C@H]3N)nc(C)n(-c2cccc(Cl)c2Br)c1=O] | 6-((3S,4S)-4-Amino-3-methyl-2-oxa-8-aza-spiro[4.5]dec-8-yl)-3-(2-bromo-3-chloro-phenyl)-2,5-dimethyl-3H-pyrimidin-4-one |
| 98 | 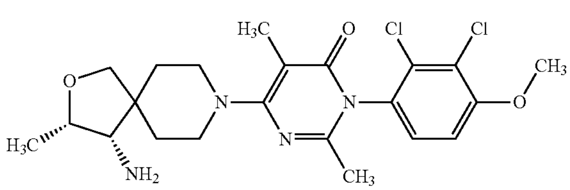 | 6-((3S,4S)-4-Amino-3-methyl-2-oxa-8-aza-spiro[4.5]dec-8-yl)-3-(2,3-dichloro-4-methoxy-phenyl)-2,5-dimethyl-3H-pyrimidin-4-one |

-continued

| No. | Structure | Chemical Name |
|---|---|---|
| 99 | 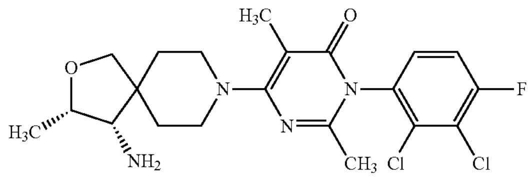 [SMILES: Cc1c(N2CCC3(CC2)CO[C@@H](C)[C@H]3N)nc(C)n(-c2ccc(F)c(Cl)c2Cl)c1=O] | 6-((3S,4S)-4-Amino-3-methyl-2-oxa-8-aza-spiro[4.5]dec-8-yl)-3-(2,3-dichloro-4-fluoro-phenyl)-2,5-dimethyl-3H-pyrimidin-4-one |
| 100 | 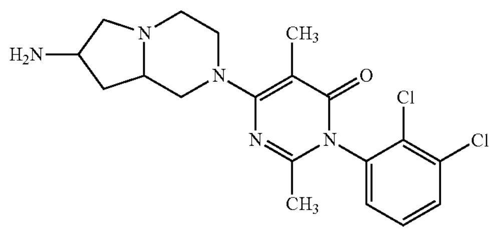 [SMILES: Cc1c(N2CCN3CC(N)CC3C2)nc(C)n(-c2cccc(Cl)c2Cl)c1=O] | (3M)-6-7-amino-octahydropyrrolo[1,2-a]pyrazin-2-yl-3-(2,3-dichlorophenyl)-2,5-dimethyl-3,4-dihydropyrimidin-4-one |
| 101 | 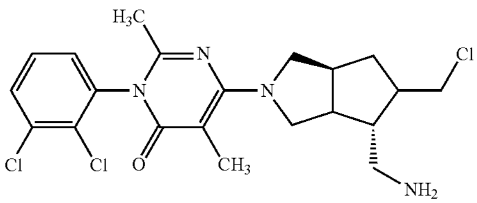 | (3M)-6-[(3aR,6aS)-3a-(aminomethyl)-5-(hydroxymethyl)-octahydrocyclopenta[c]pyrrol-2-yl]-3-(2,3-dichlorophenyl)-2,5-dimethyl-3,4-dihydropyrimidin-4-one |
| 102 | 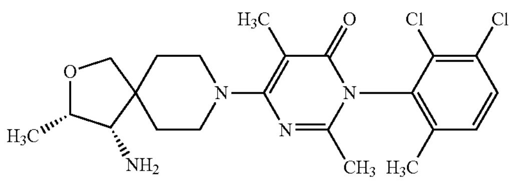 [SMILES: Cc1ccc(Cl)c(Cl)c1-n1c(C)nc(N2CCC3(CC2)CO[C@@H](C)[C@H]3N)c(C)c1=O] | 6-((3S,4S)-4-Amino-3-methyl-2-oxa-8-aza-spiro[4.5]dec-8-yl)-3-(2,3-dichloro-6-methyl-phenyl)-2,5-dimethyl-3H-pyrimidin-4-one |
| 103 | 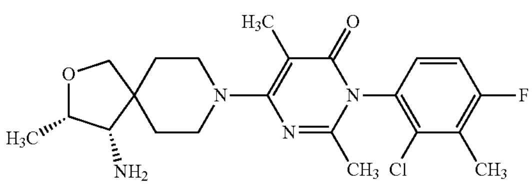 [SMILES: Cc1c(F)ccc(-n2c(C)nc(N3CCC4(CC3)CO[C@@H](C)[C@H]4N)c(C)c2=O)c1Cl] | 6-((3S,4S)-4-Amino-3-methyl-2-oxa-8-aza-spiro[4.5]dec-8-yl)-3-(2-chloro-4-fluoro-3-methyl-phenyl)-2,5-dimethyl-3H-pyrimidin-4-one |
| 104 | 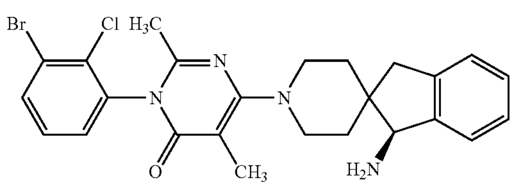 [SMILES: Cc1c(N2CCC3(CC2)Cc2ccccc2[C@H]3N)nc(C)n(-c2cccc(Br)c2Cl)c1=O] | 6-[(1S)-1-amino-1,3-dihydrospiro[indene-2,4'-piperidin]-1'-yl]-3-(3-bromo-2-chlorophenyl)-2,5-dimethyl-3,4-dihydropyrimidin-4-one |
| 105 | 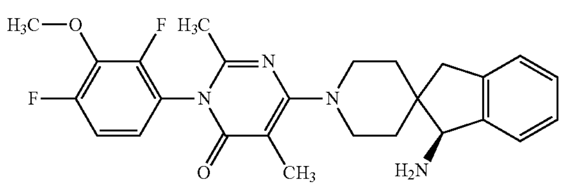 [SMILES: COc1c(F)ccc(-n2c(C)nc(N3CCC4(CC3)Cc3ccccc3[C@H]4N)c(C)c2=O)c1F] | 6-[(1S)-1-amino-1,3-dihydrospiro[indene-2,4'-piperidin]-1'-yl]-3-(2,4-difluoro-3-methoxyphenyl)-2,5-dimethyl-3,4-dihydropyrimidin-4-one |
| 106 | 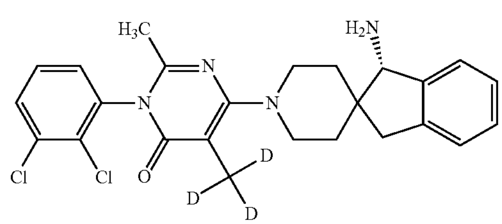 [SMILES: [2H]C([2H])([2H])c1c(N2CCC3(CC2)Cc2ccccc2[C@H]3N)nc(C)n(-c2cccc(Cl)c2Cl)c1=O] | 6-[(1S)-1-amino-1,3-dihydrospiro[indene-2,4'-piperidin]-1'-yl]-3-(2,3-dichlorophenyl)-5-(2H3)methyl-2-methyl-3,4-dihydropyrimidin-4-one |

-continued

| No. | Structure | Chemical Name |
|---|---|---|
| 107 | 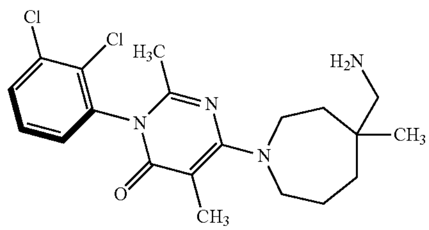 | (3M)-6-[4-(aminomethyl)-4-methylazepan-1-yl]-3-(2,3-dichlorophenyl)-2,5-dimethyl-3,4-dihydropyrimidin-4-one |
| 108 | 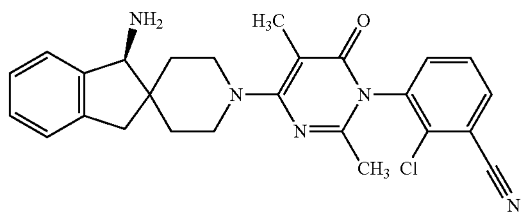 [SMILES: Cc1c(N2CCC3(CC2)Cc2ccccc2[C@H]3N)nc(C)n(-c2cccc(C#N)c2Cl)c1=O] | 3-4-[(1S)-1-amino-1,3-dihydrospiro[indene-2,4'-piperidin]-1'-yl]-2,5-dimethyl-6-oxo-1,6-dihydropyrimidin-1-yl-2-chlorobenzonitrile |
| 109 | 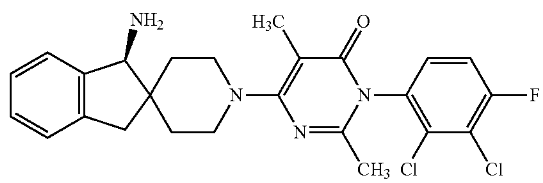 | 6-((1S)-1-amino-1,3-dihydrospiro[indene-2,4'-piperidin]-1'-yl]-3-(2,3-dichloro-4-fluorophenyl)-2,5-dimethyl-3,4-dihydropyrimidin-4-one |
| 110 | 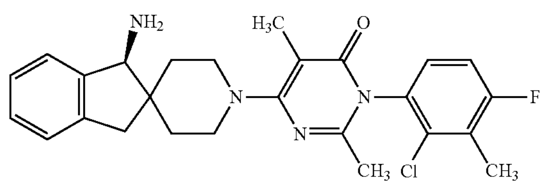 [SMILES: Cc1c(F)ccc(-n2c(C)nc(N3CCC4(CC3)Cc3ccccc3[C@H]4N)c(C)c2=O)c1Cl] | 6-[(1S)-1-amino-1,3-dihydrospiro[indene-2,4'-piperidin]-1'-yl]-3-(2-chloro-4-fluoro-3-methylphenyl)-2,5-dimethyl-3,4-dihydropyrimidin-4-one |
| 111a | 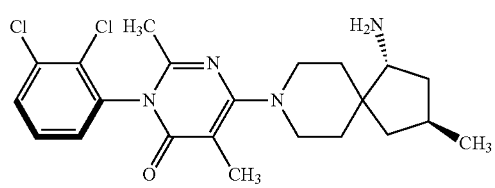 | (3M)-6-[(1R,3S)-1-amino-3-methyl-8-azaspiro[4.5]decan-8-yl]-3-(2,3-dichlorophenyl)-2,5-dimethyl-3,4-dihydropyrimidin-4-one |
| 112 | 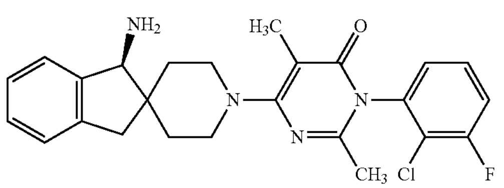 [SMILES: Cc1c(N2CCC3(CC2)Cc2ccccc2[C@H]3N)nc(C)n(-c2cccc(F)c2Cl)c1=O] | 6-[(1S)-1-amino-1,3-dihydrospiro[indene-2,4'-piperidin]-1'-yl]-3-(2-chloro-3-fluorophenyl)-2,5-dimethyl-3,4-dihydropyrimidin-4-one |
| 113 | 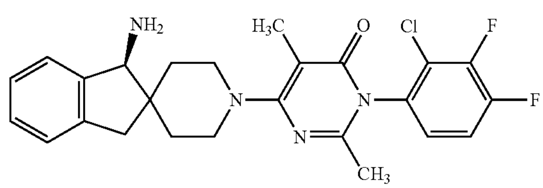 [SMILES: Cc1c(N2CCC3(CC2)Cc2ccccc2[C@H]3N)nc(C)n(-c2ccc(F)c(F)c2Cl)c1=O] | 6-[(1S)-1-amino-1,3-dihydrospiro[indene-2,4'-piperidin]-1'-yl)-3-(2-chloro-3,4-difluorophenyl)-2,5-dimethyl-3,4-dihydropyrimidin-4-one |
| 114 | 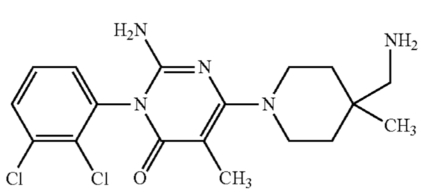 | 2-Amino-6-(4-aminomethyl-4-methyl-piperidin-1-yl)-3-(2,3-dichloro-phenyl)-5-methyl-3H-pyrimidin-4-one |

| No. | Structure | Chemical Name |
|---|---|---|
| 115 | 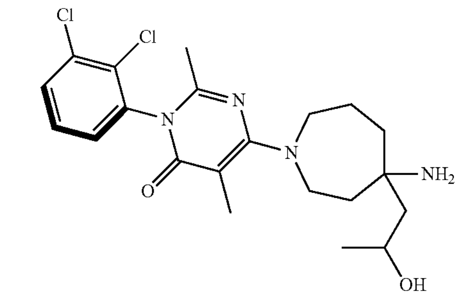 | (3M)-6-[4-amino-4-(2-hydroxypropyl)azepan-1-yl]-3-(2,3-dichlorophenyl)-2,5-dimethyl-3,4-dihydropyrimidin-4-one |
| 116 | 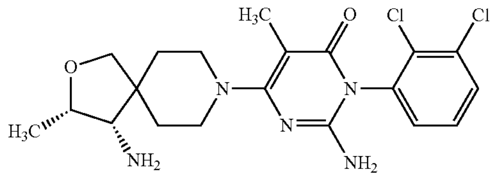 [SMILES: Cc1c(N2CCC3(CC2)CO[C@@H](C)[C@H]3N)nc(N)n(-c2cccc(Cl)c2Cl)c1=O] | 2-Amino-6-((3S,4S)-4-amino-3-methyl-2-oxa-8-aza-spiro[4.5]dec-8-yl)-3-(2,3-dichloro-phenyl)-5-methyl-3H-pyrimidin-4-one |
| 117 | 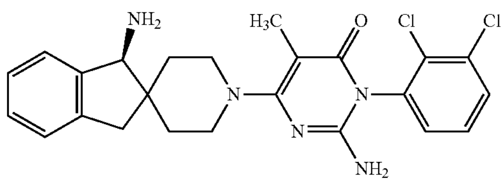 [SMILES: Cc1c(N2CCC3(CC2)Cc2ccccc2[C@H]3N)nc(N)n(-c2cccc(Cl)c2Cl)c1=O] | 2-amino-6-[(3S)-3-amino-1,3-dihydrospiro[indene-2,4'-piperidin]-1'-yl]-3-(2,3-dichlorophenyl)-5-methyl-3,4-dihydropyrimidin-4-one |
| 118 | 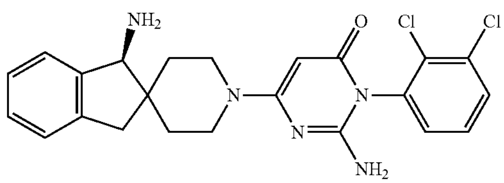 [SMILES: Nc1nc(N2CCC3(CC2)Cc2ccccc2[C@H]3N)cc(=O)n1-c1cccc(Cl)c1Cl] | 2-amino-6-[(3S)-3-amino-1,3-dihydrospiro[indene-2,4'-piperidin]-1'-yl]-3-(2,3-dichlorophenyl)-3,4-dihydropyrimidin-4-one |
| 119a | 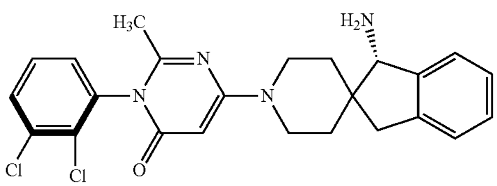 | (3P)-6-[(1S)-1-amino-1,3-dihydrospiro[indene-2,4'-piperidin]-1'-yl]-3-(2,3-dichlorophenyl)-2-methyl-3,4-dihydropyrimidin-4-one |
| 119b | | (3M)-6-[(1S)-1-amino-1,3-dihydrospiro[indene-2,4'-piperidin]-1'-yl]-3-(2,3-dichlorophenyl)-2-methyl-3,4-dihydropyrimidin-4-one | and pharmaceutically acceptable salts thereof.

All above-mentioned embodiments and aspects of embodiments which define the meanings of the specific variables of any one of Formulae I, Ia', Ib', Ia'', Ib'', or II should be understood in such a way that these specific embodiments and/or aspects of embodiments can be combined with one another in any possible definition of variables to give compounds of the Formulae I, Ia', Ib', Ia'', Ib'', or II.

"Alkyl" is a saturated unbranched or branched hydrocarbon chain and has 1, 2, 3, 4, 5, 6, 7, 8, 9 or 10 C atoms. Examples of "alkyl" groups include methyl, ethyl, propyl, isopropyl, butyl, isobutyl, sec-butyl or tert-butyl, and the like.

"Aminoalkyl" is an alkyl as described above, which is substituted with 1-3 —NH$_2$ group. Examples include —CH$_2$NH$_2$, —CH$_2$CH$_2$NH$_2$, and the like.

"Hydroxyalkyl" is an alkyl as described above, which is substituted with 1-3 —OH groups. Examples include —CH$_2$OH, —CH$_2$CH$_2$OH, and the like.

"Hydroxy(amino)alkyl" is an alkyl group which is substituted with at least 1 —OH and at least 1 —NH$_2$ group. Generally, a hydroxy(amino)alkyl will have the —OH and —NH2 groups on separate carbon atoms. Examples include —CH₂CHOHCH₂NH₂ and the like.

"Haloalkyl" is an alkyl group as described above which is substituted with 1-3 halogen atoms selected from —F, —Br and —Cl. Examples of haloalkyl groups include —CF₃, —CH₂F, —CF₂H, —CH₂CHF₂, —CCl₃, —CClFH, and the like.

"Alkoxy" is a saturated unbranched or branched hydrocarbon chain which has 1-10 C atoms, according to the formula —O(CH₂)ₙCH₃, wherein n is 0-9. Examples of an alkoxy include methoxy, ethoxy, isopropoxy, and the like.

"Cycloalkyl" is a saturated cyclic hydrocarbon chain which has 3-15 carbon atoms and can be in the form of a bridged ring system, a mono-cyclic ring system, a bicyclic ring system and/or a spiro-connected ring system. Monocyclic cycloalkyl groups are preferably 3-7 C atoms and preferably denotes cyclopropyl, cyclobutyl, cyclopentyl, cyclohexyl or cycloheptyl. Cycloalkyl may also denote a partially unsaturated cyclic akyl, such as, for example, cyclohexenyl or cyclohexynyl. When the cycloalkyl group is a part of a bicyclic ring system, at least one of the rings is a 3-7 membered cycloalkyl group, which may be fused to a 5 or 6 membered heteroaryl, phenyl group, a 5-7 membered heterocyclyl, or a 5-7 membered cycloalkyl group. Examples of bicyclic ring systems that are embodied in the definition of cycloalkyl include, for example, 2,3-dihydro-1H-indenyl, 4H,5H,6H-cyclopenta[d][1,3]thiazolyl, 1,2,3,4-tetrahydronaphthalenyl, 5,6,7,8-tetrahydroquinolinyl, 5,6,7,8-tetrahydroisoquinolinyl, 5H,6H,7H-cyclopenta(b)pyridinyl, 5H,6H,7H-cyclopenta(c)pyridinyl, and the like.

"Aryl" denotes a mono- or polycyclic aromatic or fully unsaturated cyclic hydrocarbon chain, for example unsubstituted phenyl, naphthyl or biphenyl, furthermore preferably phenyl, naphthyl or biphenyl, each of which is mono-, di- or trisubstituted, for example, by fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, and/or amidyl.

"Heterocycle" and "heterocyclyl" refer to saturated or unsaturated non-aromatic monocyclic rings, or partially or fully non-aromatic ring systems which may be bridged, bicyclic ("fused") and/or spiro-connected. Heterocyclyls contain at least one heteroatom selected from O, S and N, and further may include the oxidized forms of sulfur, namely SO and SO₂. Monocyclic heterocyclyl groups are preferably 3-7 atoms and includes azetidine, tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, oxolane, oxane, azepane, and the like. When the heterocyclyl group is a part of a bicyclic ring system, at least one of the rings is a 3-7 membered heterocyclic group, which may be fused to a 5 or 6 membered heteroaryl, phenyl group, a 5-7 membered heterocyclyl, or a 5-7 membered cycloalkyl group. Examples of bicyclic ring systems that are embodied in the definition of heterocyclyl include, for example, 2H,3H-furo[2,3-b]pyridine, 2H,3H-furo[2,3-c]pyridine, 2H,3H-furo[2,3-d]pyridine, 2,3-dihydrobenzofuran, octahydro-1H-isoindole, octahydrocyclopenta[c]pyrrole, octahydropyrrolo[3,4-c]pyrrole, 3-azabicyclo[3.1.0]hexane, 3,9-diazabicyclo[4.2.1]non-3-yl, and the like.

"Heteroaryl" means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoxazolyl, isoindolyl, dihydrobenzothienyl, indolizinyl, cinnolinyl, phthalazinyl, quinazolinyl, naphthyridinyl, carbazolyl, benzdioxinyl, benzodioxolyl, quinoxalinyl, purinyl, furazanyl, thiophenyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Spiro-connected" cyclic moieties denote those in which two rings, or ring systems, are connected through a single, common, carbon atom. Spiro compounds may be fully carbocyclic (all carbon) or heterocyclic (having one or more non-carbon atom). Spiro connected cyclic moieties which include two cycles are considered bicyclic; spiro connected cyclic moieties which connect a monocycle with a bicyclic moiety are considered tricyclic moieties. Examples of spiro connected bicyclic moieties include 8-azaspiro[4.5]decane, 2-oxa-8-azaspiro[4.5]decane,2-azaspiro[3.4]octane, 6-azaspiro[3.4]octane, 2-oxa-6-azaspiro[3.4]octane, 2-azaspiro[4.4]nonane,1-oxa-9-azaspiro[5.5]undecane,5-azaspiro[2.4]heptane, 1,3-dihydrospiro-[indene-2,4'-piperidine], 5,7-dihydrospiro[cyclopenta[b]pyridine-6,4'-piperidine], 3H-spiro[furo[2,3-b]pyridine-2,4'-piperidine], 3H-spiro[1-benzofuran-2,4'-piperidine], 4,6-dihydrospiro[cyclopenta[d][1,3]thiazole-5,4'-piperidine], and the like.

Compounds of the present invention may form atropisomers, which are conformational isomers in relation to the pyrimidine moiety present in Formulae I, Ia', Ib', Ia", Ib", or II. Atropisomers are stereoisomers arising because of hindered rotation about a single bond, where energy differences due to steric strain or other contributors create a barrier to rotation that is high enough to allow for isolation of individual conformers. There are two different atropisomers that were observed in the compounds of the present invention, which are shown, for example below when Z is CR1 and R is a substituted phenyl ring.

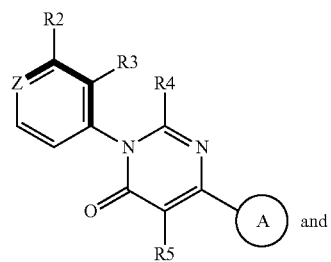

and

-continued

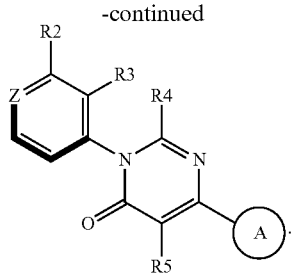

These forms are denoted in the nomenclature of the compounds as being of the M or P forms, depending on the orientation of the aryl or heteroaryl group and the substituent R4 on the pyrimidine ring. Examples of the M and P forms are provided in the examples. Particularly preferred compounds are those with the orientation:

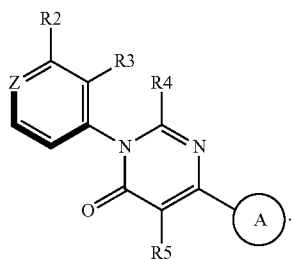

The invention also relates to a pharmaceutical preparation comprising the compound according to the present invention and/or one of its pharmaceutically acceptable salts. The invention also relates to a pharmaceutical preparation as described above, comprising further excipients and/or adjuvants.

In addition, the invention relates to an above pharmaceutical preparation according to the invention, comprising one or more additional therapeutic agent.

The compound of the present invention can be used in its freebase form. On the other hand, the present invention also encompasses the use of the compounds of the present invention in the form of their pharmaceutically acceptable salts, which can be derived from various organic and inorganic bases by procedures known in the art. The term pharmaceutical salt is used to refer to an ionisable drug that has been combined with a counter-ion to form a neutral complex. Converting a drug into a salt through this process can increase its chemical stability, render the complex easier to administer and allow manipulation of the agent's pharmacokinetic profile. Salt selection is now a common standard operation performed with small ionisable molecules during drug development, and in many cases the drug salts display preferential properties as compared with the parent molecule. Pharmaceutically acceptable salt forms of the compounds of the present invention are for the most part prepared by conventional methods.

In one embodiment, the pharmaceutically acceptable salt of the compound of the invention may be selected from hydrochloride, sodium, sulfate, acetate, phosphate or diphosphate, chloride, potassium, maleate, calcium, citrate, mesylate, nitrate, tartrate, aluminium, gluconate, benzoate, besylate, and edisylate. In one aspect of this embodiment, the pharmaceutically acceptable salt is benzoate, besylate, or edisylate.

A pharmaceutically acceptable salt of the compound of the present invention includes solvates of said salts. The term solvate is taken to mean adductions of inert solvent molecules of the compounds of the present invention which form owing to their mutual attractive force. Solvates are, for example, hydrates, such as monohydrates or dihydrates, or alcoholates, i.e. addition compounds with alcohols, such as, for example, with methanol or ethanol.

Compounds of the general Formulae I, Ia', Ib', Ia'', Ib'', or II may contain one or more centres of chirality, so that all stereoisomers, enantiomers, diastereomers, etc., of the compounds of the general formula I are also claimed in the present invention Thus, the invention also relates to the optically active forms (stereoisomers), the enantiomers, the racemates, the diastereomers and hydrates and solvates of these compounds.

It is furthermore intended that a compound of Formulae I, Ia', Ib', Ia'', Ib'', or II includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^{2}H$, $^{3}H$, $^{13}C$, $^{14}C$, $^{5}N$, $^{18}O$, $^{17}O$, $^{31}P$, $^{32}P$, S, $^{18}F$ and $^{36}Cl$, respectively. A compound of the formula I, or a pharmaceutically acceptable salt thereof, which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as 3H or $^{14}C$, has been incorporated is suitable for medicament and/or substrate tissue distribution assays. These radioisotopes, i.e. tritium (3H) and carbon-14 ($^{4}C$), are particularly preferred owing to their simple preparation and excellent detectability. Incorporation of heavier isotopes, for example deuterium ($^{2}H$), into a compound of the formula I has therapeutic advantages owing to the higher metabolic stability of this isotope-labelled compound. Higher metabolic stability translates directly into an increased in-vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant with a readily available isotope-labelled reactant.

In order to manipulate the oxidative metabolism of the compound by way of the primary kinetic isotope effect, deuterium ($^{2}H$) can also be incorporated into a compound of Formulae I, Ia', Ib', Ia'', Ib'', or II. The primary kinetic isotope effect is a change in the rate of a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom in a non-exchangeable position, rate differences of $k_M/k_D$=2-7 are typical. If this rate difference is successfully applied to a compound of the formula I that is susceptible to oxidation, the profile of this compound in vivo can thereby be drastically modified and result in improved pharmacokinetic properties.

The replacement of hydrogen by deuterium in a compound of Formulae I, Ia', Ib', Ia", Ib", or II can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the undesired metabolite, even if the particular oxidation is not a rate-determining step. Further information on the state of the art with respect to deuterium-hydrogen exchange is given, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al., Biochemistry 33(10), 2927-2937, 1994, and Jarman et al., Carcinogenesis 16(4), 683-688, 1993.

The invention also relates to mixtures of the compounds of Formulae I, Ia', Ib', Ia", Ib", or II according to the invention, for example mixtures of two atropisomers and/or two or more diastereomers, for example in the ratio 1:1, 1:2, 1:3, 1:4, 1:5, 1:10, 1:100 or 1:1000. These are particularly preferably mixtures of two stereoisomeric compounds. In one embodiment of the present invention, mixtures of atropisomers and/or diastereomers contain at least 80% of the desired conformation. In one aspect of this embodiment, the mixture of atropisomers and/or diastereomers contain at least 85% of the desired conformation. In another aspect of this embodiment, the mixture of atropisomers and/or diastereomers contain at least 90% of the desired conformation. In one aspect of this embodiment, the mixture of atropisomers and/or diastereomers contain at least 95% of the desired conformation.

In one aspect of this embodiment, the mixture of atropisomers and/or diastereomers contain at least 98% of the desired conformation.

If desired, the starting materials can also be formed in situ by not isolating them from the reaction mixture, but instead immediately converting them further into the compounds of Formulae I, Ia', Ib', Ia", Ib", or I.

The compounds of Formulae I, Ia', Ib', Ta", Ib", or II are preferably obtained by liberating them from their functional derivatives by solvolysis, in particular by hydrolysis, or by hydrogenolysis. Preferred starting materials for the solvolysis or hydrogenolysis are those which contain correspondingly protected amino, carboxyl and/or hydroxyl groups instead of one or more free amino, carboxyl and/or hydroxyl groups, preferably those which carry an amino-protecting group instead of an H atom which is connected to an N atom. Preference is furthermore given to starting materials which carry a hydroxyl-protecting group instead of the H atom of a hydroxyl group. Preference is also given to starting materials which carry a protected carboxyl group instead of a free carboxyl group. It is also possible for a plurality of identical or different protected amino, carboxyl and/or hydroxyl groups to be present in the molecule of the starting material. If the protecting groups present are different from one another, they can in many cases be cleaved off selectively.

The term "amino-protecting group" is generally known and relates to groups which are suitable for protecting (blocking) an amino group against chemical reactions, but which can easily be removed after the desired chemical reaction has been carried out elsewhere in the molecule. Typical of such groups are, in particular, unsubstituted or substituted acyl groups, furthermore unsubstituted or substituted aryl (for example 2,4-dinitophenyl) or aralkyl groups (for example benzyl, 4-nitrobenzyl, triphenylmethyl). Since the amino-protecting groups are removed after the desired reaction or reaction sequence, their type and size is, in addition, not crucial, but preference is given to those having 1-20, in particular 1-8, C atoms. The term "acyl group" is to be understood in the broadest sense in connection with the present process. It encompasses acyl groups derived from aliphatic, araliphatic, aromatic or heterocyclic carboxylic acids or sulfonic acids and, in particular, alkoxycarbonyl, aryloxycarbonyl and especially aralkoxycarbonyl groups. Examples of such acyl groups are alkanoyl, such as acteyl, propionyl, buturyl, aralkanoyl, such as phenylacetyl, aroyl, such as benzoyl or toluyl, aryoxyaklanoyl, such as phenoxyacetyl, alkyoxycarbonyyl, such as methoxycarbonyl, ethoxycarbonyl, 2,2,2-trichloroethoxycarbonyl, BOC, 2-iodoethoxycaronyl, aralkoxycarbonyl. such as CBZ, 4-methoxybenzyloxycarbonyl or FMOC. Preferred acyl groups are CBZ, FMOC, benzyl and acetyl.

The term-"acid-protecting group" or "carboxyl-protecting group" is likewise generally known and relates to groups which are suitable for protecting a —COOH group against chemical reactions, but which can easily be removed after the desired chemical reaction has been carried out elsewhere in the molecule. The use of esters instead of the free acids, for example of substituted and unsubstituted alkyl esters (such as methyl, ethyl, tert-butyl and substituted derivatives thereof), of substituted and unsubstituted benzyl esters or silyl esters, is typical. The type and size of the acid-protecting groups is not crucial, but preference is given to those having 1-20, in particular 1-10, C atoms.

The term "hydroxyl-protecting group" is likewise generally known and relates to groups which are suitable for protecting a hydroxyl group against chemical reactions, but which can easily be removed after the desired chemical reaction has been carried out elsewhere in the molecule. Typical of such groups are the above-mentioned unsubstituted or substituted aryl, aralkyl or acyl groups, furthermore also alkyl groups. Their type and size of the hydroxyl-protecting groups is not crucial, but preference is given to those having 1-20, in particular 1-10, C atoms. Examples of hydroxyl-protecting groups are, inter alia, benzyl, p-nitrobenzoyl, p-toluenesulfonyl and acetyl, where benzyl and acetyl are preferred.

Further typical examples of amino-, acid- and hydroxyl-protecting groups are found, for example, in "Greene's Protective Groups in Organic Synthesis", fourth edition, Wiley-Interscience, 2007.

The resultant compounds according to the invention can be separated from the corresponding solution in which they are prepared (for example by centrifugation and washing) and can be stored in another composition after separation, or they can remain directly in the preparation solution. The resultant compounds according to the invention can also be taken up in desired solvents for the particular use.

Conventional work-up steps, such as, for example, addition of water to the reaction mixture and extraction, enable the compounds to be obtained after removal of the solvent. It may be advantageous, for further purification of the product, to follow this with a distillation or crystallisation or to carry out a chromatographic purification.

It has been surprisingly found that the compounds of the formula I may have advantageous efficacy, selectivity, pharmacokinetic properties, dosing schedule, lower toxicity, and/or physical properties as compared to prior art compounds.

The invention furthermore relates to the use of compounds according to the invention for the preparation of a medicament for the treatment of diseases which are caused, promoted and/or propagated by SHP2 or its agonists.

The invention thus also relates, in particular, to a medicament comprising at least one compound according to the invention and/or one of its pharmaceutically acceptable salts, for use in the treatment of physiological and/or pathophysiological states. Particular preference is given, in particular, to physiological and/or pathophysiological states which are connected to SHP2. Physiological and/or pathophysiological states are taken to mean physiological and/or pathophysiological states which are medically relevant, such as, for example, diseases or illnesses and medical disorders, complaints, symptoms or complications and the like, in particular diseases.

The invention furthermore relates to a medicament comprising at least one compound according to the invention and/or one of its pharmaceutically acceptable salts, for use in the treatment of physiological and/or pathophysiological states selected from the group consisting of hyperproliferative diseases and disorders. in one embodiment, the hyperproliferative disease or disorder is cancer.

The invention thus particularly relates to a medicament comprising at least one compound according to the invention and/or one of its pharmaceutically acceptable salts, wherein the cancer is selected from the group consisting of acute and chronic lymphocytic leukemia, acute granulocytic leukemia, adrenal cortex cancer, bladder cancer, brain cancer, breast cancer, cervical cancer, cervical hyperplasia, chorio cancer, colon cancer, endometrial cancer, esophageal cancer, essential thrombocytosis, genitourinary carcinoma, glioma, glioblastoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, non-small cell lung cancer, osteogenic sarcoma, ovarian carcinoma, pancreatic carcinoma, polycythemia vera, primary brain carcinoma, primary macroglobulinemia, prostatic cancer, renal cell cancer, rhabdomyosarcoma, skin cancer, small-cell lung cancer, soft-tissue sarcoma, squamous cell cancer, stomach cancer, testicular cancer, thyroid cancer and Wilms' tumor. In one embodiment of the invention, the cancer is selected from non-small cell lung cancer, small cell lung cancer, head and neck carcinoma, breast cancer, esophageal cancer, gastric cancer, colorectal cancer, glioblastoma, pancreatic cancer, osteosarcoma, melanoma and kidney cancer. In one aspect of this embodiment, the cancer is head and neck carcinoma. In another aspect of this embodiment, the cancer is lung cancer. In one aspect of this embodiment, the lung cancer is non-small cell lung cancer. In another aspect of this embodiment, the lung cancer is small cell lung cancer. In another aspect of this embodiment, the cancer is colorectal cancer. In a further aspect of this embodiment, the cancer is esophageal cancer. In another aspect of this embodiment, the cancer is gastric cancer.

The invention further relates to a medicament comprising at least one compound according to the invention and/or one of its pharmaceutically acceptable salts, for use in the treatment of physiological and/or pathophysiological states selected from the group consisting of hyperproliferative and infectious diseases and disorders, wherein the hyperproliferative disease or disorder is selected from the group consisting of age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation and an immunoproliferative disease or disorder selected from the group consisting of inflammatory bowel disease, psoriasis, rheumatoid arthritis, systemic lupus erythematosus (SLE), vascular hyperproliferation secondary to retinal hypoxia and vasculitis.

It is intended that the medicaments disclosed above include a corresponding use of the compounds according to the invention for the preparation of a medicament for the treatment of the above physiological and/or pathophysiological states.

It is additionally intended that the medicaments disclosed above include a corresponding method for the treatment of the above physiological and/or pathophysiological states in which at least one compound according to the invention is administered to a patient in need of such a treatment.

The compounds according to the invention preferably exhibit an advantageous biological activity which can easily be demonstrated in enzyme assays and animal experiments, as described in the examples. In such enzyme-based assays, the compounds according to the invention preferably exhibit and cause an inhibiting effect, which is usually documented by $IC_{50}$ values in a suitable range, preferably in the micromolar range and more preferably in the nanomolar range.

The compounds according to the invention can be administered to humans or animals, in particular mammals, such as apes, dogs, cats, rats or mice, and can be used in the therapeutic treatment of the human or animal body and in the combating of the above-mentioned diseases. They can furthermore be used as diagnostic agents or as reagents.

Furthermore, compounds according to the invention can be used for the isolation and investigation of the activity or expression of SHP2. In addition, they are particularly suitable for use in diagnostic methods for diseases in connection with disturbed SHP2 activity. The invention therefore furthermore relates to the use of the compounds according to the invention for the isolation and investigation of the activity or expression of SHP2 or as binders and inhibitors of SHP2.

For diagnostic purposes, the compounds according to the invention can, for example, be radioactively labelled. Examples of radioactive labels are $^3H$, $^4C$, $^{231}I$ and $^{125}I$. A preferred labelling method is the iodogen method (Fraker et al., 1978). In addition, the compounds according to the invention can be labelled by enzymes, fluorophores and chemophores. Examples of enzymes are alkaline phosphatase, J-galactosidase and glucose oxidase, an example of a fluorophore is fluorescein, an example of a chemophore is luminol, and automated detection systems, for example for fluorescent colorations, are described, for example, in U.S. Pat. Nos. 4,125,828 and 4,207,554.

The invention therefore furthermore relates to pharmaceutical preparations comprising at least one compound of the formula I and/or pharmaceutically acceptable salts thereof. In particular, the invention also relates to pharmaceutical preparations which comprise further excipients and/or adjuvants, and also to pharmaceutical preparations which comprise at least one further medicament active compound.

In particular, the invention also relates to a process for the preparation of a pharmaceutical preparation, characterised in that a compound of the formula I and/or one of its pharmaceutically acceptable salts, is brought into a suitable dosage form together with a solid, liquid or semi-liquid excipient or adjuvant and optionally with one or more additional therapeutic agent.

The pharmaceutical preparations according to the invention can be used as medicaments in human or veterinary medicine. The patient or host can belong to any mammal species, for example a primate species, particularly humans; rodents, including mice, rats and hamsters; rabbits; horses, cattle, dogs, cats, etc. Animal models are of interest for experimental investigations, where they provide a model for the treatment of a human disease.

Suitable carrier substances are organic or inorganic substances which are suitable for enteral (for example oral), parenteral or topical administration and do not react with the novel compounds, for example water, vegetable oils (such as sunflower oil or cod-liver oil), benzyl alcohols, polyethylene glycols, gelatine, carbohydrates, such as lactose or starch, magnesium stearate, talc, lanolin or Vaseline. Owing to his expert knowledge, the person skilled in the art is familiar with which adjuvants are suitable for the desired medicament formulation. Besides solvents, for example water, physiological saline solution or alcohols, such as, for example, ethanol, propanol or glycerol, sugar solutions, such as glucose or mannitol solutions, or a mixture of the said solvents, gel formers, tablet assistants and other active-ingredient carriers, it is also possible to use, for example, lubricants, stabilisers and/or wetting agents, emulsifiers, salts for influencing the osmotic pressure, antioxidants, dispersants, antifoams, buffer substances, flavours and/or aromas or flavour correctants, preservatives, solubilisers or dyes. If desired, preparations or medicaments according to the invention may comprise one or more further active compounds, for example one or more vitamins.

If desired, preparations or medicaments according to the invention may comprise one or more further active compounds and/or one or more action enhancers (adjuvants).

The terms "pharmaceutical formulation" and "pharmaceutical preparation" are used as synonyms for the purposes of the present invention.

As used here, "pharmaceutically acceptable" relates to medicaments, precipitation reagents, excipients, adjuvants, stabilisers, solvents and other agents which facilitate the administration of the pharmaceutical preparations obtained therefrom to a mammal without undesired physiological side effects, such as, for example, nausea, dizziness, digestion problems or the like.

In pharmaceutical preparations for parenteral administration, there is a requirement for isotonicity, euhydration and tolerability and safety of the formulation (low toxicity), of the adjuvants employed and of the primary packaging. Surprisingly, the compounds according to the invention preferably have the advantage that direct use is possible and further purification steps for the removal of toxicologically unacceptable agents, such as, for example, high concentrations of organic solvents or other toxicologically unacceptable adjuvants, are thus unnecessary before use of the compounds according to the invention in pharmaceutical formulations.

The invention particularly preferably also relates to pharmaceutical preparations comprising at least one compound according to the invention in precipitated non-crystalline, precipitated crystalline or in dissolved or suspended form, and optionally excipients and/or adjuvants and/or further pharmaceutical active compounds.

The compounds according to the invention preferably enable the preparation of highly concentrated formulations without unfavourable, undesired aggregation of the compounds according to the invention occurring. Thus, ready-to-use solutions having a high active-ingredient content can be prepared with the aid of compounds according to the invention with aqueous solvents or in aqueous media.

The compounds and/or physiologically acceptable salts and solvates thereof can also be lyophilised and the resultant lyophilisates used, for example, for the preparation of injection preparations.

Pharmaceutical preparations according to the invention may also comprise mixtures of a plurality of compounds according to the invention.

The preparations according to the invention are physiologically well tolerated, easy to prepare, can be dispensed precisely and are preferably stable with respect to assay, decomposition products and aggregates throughout storage and transport and during multiple freezing and thawing processes. They can preferably be stored in a stable manner over a period of at least three months to two years at refrigerator temperature (2-8° C.) and at room temperature (23-27° C.) and 60% relative atmospheric humidity (R.H.).

For example, the compounds according to the invention can be stored in a stable manner by drying and when necessary converted into a ready-to-use pharmaceutical preparation by dissolution or suspension. Possible drying methods are, for example, without being restricted to these examples, nitrogen-gas drying, vacuum-oven drying, lyophilisation, washing with organic solvents and subsequent air drying, liquid-bed drying, fluidised-bed drying, spray drying, roller drying, layer drying, air drying at room temperature and further methods.

The term "effective amount" denotes the amount of a compound of Formulae I, Ia', Ib', Ia", Ib", or II, or a pharmaceutically acceptable salt thereof, which causes in a tissue, system, animal or human a biological or medical response which is sought or desired, for example, by a researcher or physician.

In addition, the term "therapeutically effective amount" denotes an amount which, compared with a corresponding subject who has not received this amount, has the following consequence: improvement of one or more symptoms, healing, or elimination of a disease, syndrome, disease state, complaint, disorder or prevention of side effects. "Therapeutically effective amount" also encompasses a reduction in the progress of a disease, complaint or disorder. In the context of cancer treatment, a "therapeutically effective amount" can lead to lessening the tumor burden of a subject, delaying the progression of disease ("progression-free survival"), prolonging the life expectancy of the subject (improving the overall survival), slowing or preventing the metastasis of the primary tumor to other tissues and/or improving the quality of life of the subject undergoing treatment. The term "therapeutically effective amount" also encompasses the amounts which are effective for increasing normal physiological function.

One embodiment of the present invention is the use of preparations or medicaments consisting of compounds according to the invention, and/or pharmaceutically acceptable salts thereof, for preparations in dosages of between 0.1 and 500 mg, in particular 1 and 300 mg, per use unit. The daily dose is preferably between 0.001 and 250 mg/kg, in particular 0.01 and 100 mg/kg, of body weight. The preparation can be administered one or more times per day, for example two, three or four times per day. However, the individual dose for a patient depends on a large number of individual factors, such as, for example, on the efficacy of the particular compound used, on the age, body weight, general state of health, sex, nutrition, on the time and method of administration, on the excretion rate, on the combination with other medicaments and on the severity and duration of the particular disease.

A measure of the uptake of a medicament active compound in an organism is its bioavailability. If the medicament active compound is delivered to the organism intravenously in the form of an injection solution, its absolute bioavailability, i.e. the proportion of the pharmaceutical which reaches the systemic blood, i.e. the major circulation, in unchanged form, is 100%. In the case of oral administration of a therapeutic active compound, the active compound is generally in the form of a solid in the formulation and must therefore first be dissolved in order that it is able to overcome the entry barriers, for example the gastrointestinal tract, the oral mucous membrane, nasal membranes or the skin, in particular the stratum corneum, or can be absorbed by the body. Data on the pharmacokinetics, i.e. on the bioavailability, can be obtained analogously to the method of J. Shaffer et al., J. Pharm. Sciences, 88 (1999), 313-318.

Furthermore, medicaments of this type can be prepared by means of one of the processes generally known in the pharmaceutical art.

Medicaments can be adapted for administration via any desired suitable route, for example by the oral (including buccal or sublingual), rectal, pulmonary, nasal, topical (including buccal, sublingual or transdermal), vaginal or parenteral (including subcutaneous, intramuscular, intravenous, intradermal and in particular intra-articular) routes. Medicaments of this type can be prepared by means of all processes known in the pharmaceutical art by, for example, combining the active compound with the excipient(s) or adjuvant(s).

Suitable for enteral administration (oral or rectal) are, in particular, tablets, dragees, capsules, syrups, juices, drops or suppositories, and suitable for topical use are ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one another and/or with water) or powders. Also, particularly suitable for topical uses are liposomal preparations.

It goes without saying that, besides the constituents particularly mentioned above, the medicaments according to the invention may also comprise other agents usual in the art with respect to the particular type of pharmaceutical formulation.

The invention also relates to a set (kit) consisting of separate packs of
a) an effective amount of a compound of Formulae I, Ia', Ib', Ia", Ib", or II and/or a pharmaceutically acceptable salt thereof, and
b) an effective amount of one or more additional therapeutic agent.

The set comprises suitable containers, such as boxes or cartons, individual bottles, bags or ampoules. The set may, for example, comprise separate ampoules each containing an effective amount of a compound of Formulae I, Ia', Ib', Ia", Ib", or II and/or a pharmaceutically acceptable salt thereof, and an effective amount of one or more additional therapeutic agents in dissolved or lyophilised form.

Furthermore, the medicaments according to the invention can be used in order to provide additive or synergistic effects in certain known therapies and/or can be used in order to restore the efficacy of certain existing therapies.

Furthermore, the medicaments according to the invention can be used in order to provide additive or synergistic effects in certain known therapies and/or can be used in order to restore the efficacy of certain existing therapies.

Besides the compounds according to the invention, the pharmaceutical preparations according to the invention may also comprise one or more additional therapeutic agents, for example for use in the treatment of cancer, other anti-tumor medicaments. For the treatment of the other diseases mentioned, the pharmaceutical preparations according to the invention may also, besides the compounds according to the invention, comprise further medicament active compounds which are known to the person skilled in the art in the treatment thereof.

In one embodiment, a compound of the present invention, or a pharmaceutically acceptable salt thereof, is administered in combination with one or more additional therapeutic agent. In one aspect of this invention, the one or more additional therapeutic agent is an EGFR inhibitor, MET inhibitor, PD-L1 inhibitor, MEK 1/2 inhibitor, TGF-βR pathway inhibitor, or a combination thereof. In another aspect of this embodiment, the one or more additional therapeutic agent is Erbitux, tepotinib, avelumab, Muc1-TGFβR2 Nb, EGFR-Muc1-ADC, pimasertib, pembrolizumab, nivolumab, cemiplimab, atezolizumab, durvalumab, or a combination thereof. In one aspect of this embodiment, the one or more additional therapeutic agents is Erbitux, tepotinib, avelumab, pimasertib or a combination thereof.

In one principal embodiment, methods are provided for enhancing an immune response in a host in need thereof. The immune response can be enhanced by reducing T cell tolerance, including by increasing IFN-γ release, by decreasing regulatory T cell production or activation, or by increasing antigen-specific memory T cell production in a host. In one embodiment, the method comprises administering a compound of the present invention to a host in combination or alternation with an antibody. In one aspect of this embodiment, the antibody is a therapeutic antibody. In one particular embodiment, a method of enhancing efficacy of passive antibody therapy is provided comprising administering a compound of the present invention in combination or alternation with one or more passive antibodies. This method can enhance the efficacy of antibody therapy for treatment of abnormal cell proliferative disorders such as cancer or can enhance the efficacy of therapy in the treatment or prevention of infectious diseases. The compound of the present invention can be administered in combination or alternation with antibodies such as rituximab, herceptin or erbitux, for example.

In another principal embodiment, a method of treating or preventing abnormal cell proliferation is provided comprising administering a compound of the present invention to a host in need thereof substantially in the absence of another anti-cancer agent.

In another principal embodiment, a method of treating or preventing abnormal cell proliferation in a host in need thereof is provided, comprising administering a first a compound of the present invention substantially in combination with a first anti-cancer agent to the host and subsequently administering a second SHP2 antagonist. In one aspect of this embodiment, the second antagonist is administered substantially in the absence of another anti-cancer agent. In another principal embodiment, a method of treating or preventing abnormal cell proliferation in a host in need thereof is provided, comprising administering a compound of the present invention substantially in combination with a first anti-cancer agent to the host and subsequently administering a second anti-cancer agent in the absence of the antagonist.

Thus, the cancer treatment disclosed here can be carried out as therapy with a compound of the present invention or in combination with an operation, irradiation or chemotherapy. Chemotherapy of this type can include the use of one or more additional therapeutic agents selected from the group consisting of:

(i) antiproliferative/antineoplastic/DNA-damaging active compounds and combinations thereof, as used in medical oncology, such as alkylating active compounds (for example cis-platin, parboplatin, cyclophosphamide, nitrogen mustard, melphalan, chlorambucil, busulphan and nitrosoureas); antimetabolites (for example antifolates such as fluoropyrimidines such as 5-fluorouracil and tegafur, raltitrexed, methotrexate, cytosine arabinoside, hydroxyurea and gemcitabine); anti-tumour antibiotics (for example anthracyclines, such as adriamycin, bleomycin, doxorubicin, daunomycin, epirubicin, idarubicin, mitomycin-C, dactinomycin and mithramycin); antimitotic active compounds (for example vinca alkaloids, such as vincristine, vin-blastine, vindesine and vinorelbine, and taxoids, such as taxol and taxotere); topoisomerase inhibitors (for example epipodophyllotoxins, such as etoposide and teniposide, amsacrine, topotecan, irinotecan and camptothecin) and cell-differentiating active compounds (for example all-trans-retinoic acid, 13-cis-retinoic acid and fenretinide);

(ii) cytostatic active compounds, such as anti-oestrogens (for example tamoxifen, toremifene, raloxifene, droloxifene and iodoxyfene), oestrogen receptor regulators (for example fulvestrant), anti-androgens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example anastrozole, letrozole, vorazole and exemestane) and inhibitors of 5α-reductase, such as finasteride;

(iii) active compounds which inhibit cancer invasion including for example metalloproteinase inhibitors, like marimastat, and inhibitors of urokinase plasmino-gen activator receptor function;

(iv) inhibitors of growth factor function, for example growth factor antibodies, growth factor receptor antibodies, for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynyl-phenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033), for example inhibitors of the platelet-derived growth factor family and, for example, inhibitors of the hepatocyte growth factor family;

(v) anti-angiogenic active compounds, such as bevacizumab, angiostatin, endostatin, linomide, batimastat, captopril, cartilage derived inhibitor, genistein, interleukin 12, lavendustin, medroxypregesterone acetate, recombinant human platelet factor 4, tecogalan, thrombospondin, TNP-470, anti-VEGF monoclonal antibody, soluble VEGF-receptor chimaeric protein, anti-VEGF receptor antibodies, anti-PDGF receptors, inhibitors of integrins, tyrosine kinase inhibitors, serine/thieonine kinase inhibitors, antisense oligonucleotides, antisense oligodexoynucleotides, siRNAs, anti-VEGF aptamers, pigment epithelium derived factor and compounds which have been published in the international patent applications WO 97/22596, WO 97/30035, WO 97/32856 and WO 98/13354);

(vi) vessel-destroying agents, such as combretastatin A4 and compounds which have been published in the international patent applications WO 99/02166, WO 00/40529, WO 00/41669, WO 01/92224, WO 02/04434 and WO 02/08213;

(vii) antisense therapies, for example those directed to the targets mentioned above, such as ISIS 2503, an anti-Ras antisense;

(viii) gene therapy approaches, including, for example, approaches for replacement of abnormal, modified genes, such as abnormal p53 or abnormal BRCA1 or BRCA2, GDEPT approaches (gene-directed enzyme pro-drug therapy), such as those which use cytosine deaminase, thymidine kinase or a bacterial nitroreductase enzyme, and approaches which increase the tolerance of a patient to chemotherapy or radiotherapy, such as multi-drug resistance therapy; and (ix) immunotherapy approaches, including, for example, ex-vivo and in-vivo approaches for increasing the immunogenicity of tumor cells of a patient, such as transfection with cytokines, such as interleukin 2, interleukin 4 or granulocyte macrophage colony stimulating factor, approaches for decreasing T-cell anergy, approaches using transfected immune cells, such as cytokine-transfected dendritic cells, approaches for use of cytokine-transfected tumor cells and approaches for use of anti-idiotypic antibodies (x) chemotherapeutic agents including foor example abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chorambucil, cinacalcet, cisplatin, cladribine, cyclophosphamide, cytarabine, dacarbazine, dactinomycin, darbepoetinalfa, daunorubicin, denileukindiftitox, dexrazoxane, docetaxel, doxorubicin, dromostanolone, epirubicin, epoetinalfa, estramustine, etoposide, exemestane, filgrastim, floxuridine, fludarabine, fluorouracil, fulvestrantandgemcitabine.

Additional therapeutic agents from Table 2 can preferably, but not exclusively, be combined with the compounds of any one of Formulae I, Ia', Ib', Ia'', Ib'', or II, or a pharmaceutically acceptable salt thereof.

TABLE 2

| | | |
|---|---|---|
| Alkylating active compounds | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum active compounds | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson |
| | Tetraplatin | Matthey) |

TABLE 2-continued

| Category | Column 2 | Column 3 |
|---|---|---|
| | Ormiplatin | BBR-3464 |
| | Iproplatin | (Hoffmann-La Roche) |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-Fluorouracil | Fludarabine |
| | Floxuridine | Pentostatin |
| | 2-Chlorodesoxyadenosin | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-Fluorodesoxycytidin | Irofulven (MGI Pharma) |
| | Methotrexattable e | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analoge (Exelixis) | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxo-rubicin | GPX-100 (Gem Pharmaceuticals) |
| | Mitoxantron (Novantron) | |
| Antimitotic active compounds | Paclitaxel | SB 408075 (GlaxoSmithKline) |
| | Docetaxel | E7010 (Abbott) |
| | Colchicine | PG-TXL (Cell-Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA-Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B (PharmaMar) |
| | RPR 109881A (Aventis) | ZD 6126 (AstraZeneca) |
| | TXD 258 (Aventis) | PEG-Paclitaxel (Enzon) |
| | Epothilone B (Novartis) | AZ10992 (Asahi) |
| | T 900607 (Tularik) | !DN-5109 (Indena) |
| | T 138067 (Tularik) | AVLB (Prescient NeuroPharma) |
| | Cryptophycin 52 (Eli-Lilly) | Azaepothilon B (BMS) |
| | Vinflunine (Fabre) | BNP-7787 |
| | Auristatin PE (Teikoku Hormone) | |
| | BMS 247550 (BMS) | |
| | BMS 184476 (BMS) | |
| | BMS 188797 (BMS) | (BioNumerik) |
| | Taxoprexin (Protarga) | CA-4-prodrug (OXiGENE) |
| | | Dolastatin-10 (NrH) |
| | | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate Synthase inhibitors | Pemetrexed (Eli Lilly) | Nolatrexed (Eximias) |
| | ZD-9331 (BTG) | CoFactor™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (isotope solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Lonafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Schering AG) | |
| Histone acetyl transferase inhibitors | Tacedinaline (Pfizer) | Pivaloyloxymethyl butyrate (Titan) |
| | SAHA (Aton Pharma) | Depsipeptide (Fujisawa) |
| | MS-275 (Schering AG) | |
| Metalloproteinase inhibitors | Neovastat (Aeterna Laboratories) | CMT -3 (CollaGenex) |
| Ribonucleoside reductase inhibitors | Marimastat (British Bio-tech) | BMS-275291 (Celltech) |
| | Gallium maltolate (Titan) | Tezacitabine (Aventis) |
| | Triapin (Vion) | Didox (Molecules for Health) |
| TNF-alpha agonists/antagonists | Virulizin (Lorus Therapeutics) | Revimid (Celgene) |
| | CDC-394 (Celgene) | |
| Endothelin -A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (ligand) | |
| Immunomoculators | Interferon | Dexosome therapy (Anosys) |
| | Oncophage (Antigenic) | Pentrix (Australian Cancer Technology) |
| | GMK (Progenics) | |
| | Adenocarcinoma vaccine (Biomira) | |
| | CTP-37 (AVI BioPharma) | JSF-154 (Tragen) |
| | JRX-2 (Immuno-Rx) | Cancer vaccine (Intercell) |
| | PEP-005 (Peplin Biotech) | Norelin (Biostar) |
| | Synchrovax vaccines (CTL Immuno) | BLP-25 (Biomira) |
| | Melanoma vaccines (CTL Immuno) | MGV (Progenics) |
| | p21-RAS vaccine (Gem Vax) | !3-Alethin (Dovetail) |
| | | CLL-Thera (Vasogen) |
| Hormonal and antihormonal active compounds | Oestrogens | Prednisone |
| | Conjugated oestrogens | Methylprednisolone |
| | Ethynyloestradiol | Prednisolone |
| | Chlorotrianisene | Aminoglutethimide |
| | Idenestrol | Leuprolide |
| | Hydroxyprogesterone caproate | Goserelin |
| | Medroxyprogesterone | Leuporelin |
| | Testosterone | Bicalutamide |
| | Testosterone propionate | Flutamide |
| | Fluoxymesterone | Octreotide |
| | Methyltestosterone | Nilutamide |
| | Diethylstilbestrol | Mitotan |
| | | P-04 (Novogen) |

TABLE 2-continued

| | | |
|---|---|---|
| | Megestrol | 2-Methoxyoestradiol |
| | Tamoxifen | (En-treMed) |
| | Toremofin | Arzoxifen (Eli Lilly) |
| | Dexamethasone | |
| Photodynamic active compounds | Talaporfin (Light Sciences) | Pd bacteriopheophorbide (Yeda) |
| | Theralux (Theratechnologies) | Lutetium texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide(Sugen/Pharmacia) | CEP- 701 (Cephalon) |
| | ZD1839 (AstraZeneca) | CEP-751 (Cephalon) |
| | Erlotinib (Oncogene Sience) | MLN518 (Millenium) |
| | Canertjnib (Pfizer) | PKC412 (Novartis) |
| | Squalamine (Genaera) | Phenoxodiol O |
| | SU5416 (Pharmacia) | Trastuzumab (Genentech) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | Vatalanib (Novartis) | 2C4 (Genentech) |
| | PKI166 (Novartis) | MDX-447 (Medarex) |
| | GW2016 (GlaxoSmith Kline) | ABX-EGF (Abgenix) |
| | EKB-509 (Wyeth) | IMC-1C11 (ImClone) |
| | EKB-569 (Wyeth) | |
| Various other active compounds | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol ™ (triclosan mouthwash, Endo) |
| | CP-461 (PDE-V inhibitor, Cell Pathways) | Triacetyluridine |
| | AG-2037 (GART inhibitor, Pfizer) | (uridine prodrug, Wellstat) |
| | WX-UK1 (plasminogen activator inhibitor, Wilex) | SN-4071 (sarcoma agent, Signature BioScience) |
| | PBI-1402 (PMN stimulant, ProMetic LifeSciences) | TransMID-107 ™ (immunotoxin, KS Biomedix) |
| | Bortezomib (proteasome inhibitor, Millennium) | PCK-3145 (apoptosis promoter, Procyon) |
| | SRL-172 (T-cell stimulant, SR Pharma) | Doranidazole (apoptosis promoter, Pola) |
| | TLK-286 (glutathione-S transferase inhibitor, Telik) | CHS-828 (cytotoxic agent, Leo) |
| | PT-100 (growth factor agonist, Point Therapeutics) | trans-Retinoic acid (differentiator, NIH) |
| | Midostaurin (PKC inhibitor, Novartis) | MX6 (apoptosis promoter, MAXIA) |
| | Bryostatin-1 (PKC stimulant, GPC Biotech) | Apomine (apoptosis promoter, ILEX Oncology) |
| | CDA-II (apoptosis promoter, Everlife) | Urocidin (apoptosis promoter, Bioniche) |
| | SDX-101 (apoptosis promoter, Salmedix) | Ro-31-7453 (apoptosis promoter, La Roche) |
| | Ceflatonin (apoptosis promoter, ChemGenex) | Brostallicin (apoptosis promoter, Pharmacia) |

Even without further embodiments, it is assumed that a person skilled in the art will be able to use the above description in the broadest scope. The preferred embodiments should therefore merely be regarded as descriptive disclosure which is absolutely not limiting in any way.

The following examples are thus intended to explain the invention without limiting it. Unless indicated otherwise, percent data denote percent by weight. All temperatures are indicated in degrees Celsius. "Conventional work-up": water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, filtered and evaporated, and the product is purified by chromatography on silica gel and/or by crystallisation.

List of Abbreviations

° C. degrees Celcius
Ac Acetate
ACN Acetonitrile
AIBN Azobisisobutyronitrile
AUC Area under the plasma drug concentration-time curve
BOP benzotriazol-1-yloxytris(dimethylamino)phosphonium hexafluorophosphate
$C_{max}$ Maximum plasma concentration
CL Clearance
CV Coefficient of variation
CYP Cytochrome P450
DBU 1,8-Diazabicyclo[5.4.0]undec-7-ene
DCM Dichloromethane
dppf 1,1'-bis-diphenyl phosphine ferrocene
DIEA N,N-diisopropylethylamine DMA Dimethylacetamide
DMF Dimethylformamide
DMSO Dimethyl sulfoxide
Et Ethyl
EtOAc Ethylacetate
% F Bioavailability
$f_a$ Fraction absorbed
g gram
h or hr hour
HOBt Hydroxybenzotriazole
HPLC High Performance Liquid Chromatography
iv Intravenous
LC liquid Chromatography
LC-MS/MS Liquid chromatography tandem mass spectrometry
LDA Lithium diisopropylamide
LLOQ Lower limit of quantification
mCPBA meta-Chloroperoxybenzoic acid
Me Methyl
MeOH methanol
min minute
mL milliliter
mmol millimole
MS Mass spectroscopy
NaHMDS Sodium bis(trimethylsilyl)amide
NBS N-bromosuccinimide
ND Not determined
NMP N-Methyl-2-Pyrrolidone
NT Not tested
O/N overnight
PE Petroleum ether
PEG Polyethylene glycol
Pgp Permeability glycoprotein
PK Pharmacokinetic(s)
po Per os (oral)
RT room temperature
$t_{1/2}$ Half-life
$t_{max}$ Time at which maximum plasma concentration of drug is reached
TEA triethylamine
TFA Trifluoroacetic acid
THF Tetrahydrofuran
UPLC Ultra performance liquid chromatography
$V_{ss}$ Volume of distribution (at steady state)
v/v Volume to volume Example 1: Examples of Compounds of the Present Invention The invention especially relates to the compounds of Table 1 (shown above) and pharmaceutically acceptable salts thereof. Compounds of the invention include the atropisomers, stereoisomers, and/or enantiomers thereof, when applicable. Unless the synthetic methodology described in Example 2 indicates otherwise, the structural designations for stereoisomers and/or enantiomers were assigned based on retention times and activities. The compounds of the invention include all atropisomers, stereoisomers and/or enantiomers thereof, even if the structural depiction shows only one possible permutation. Preferred compounds are those that conform to the specific structural depictions shown in Table 1.

Example 2: Preparation of the Compounds of the Present Invention and Analytical Methods In general, the compounds according to Formula (I) and related formulae of this invention can be prepared from readily available starting materials. If such starting materials are not commercially available, they may be prepared by standard synthetic techniques. In general, the synthesis pathways for any individual compound of Formulae 1, Ia', Ib', Ia", Ib", or II will depend on the specific substituents of each molecule, such factors being appreciated by those of ordinary skilled in the art. The following general methods and procedures described hereinafter in the examples may be employed to prepare compounds of Formulae I, Ia', Ib', Ia", Ib", or II. Those methods are illustrative and are not meant to limit the possible methods one skilled in the art may use to prepare compounds disclosed herein. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Depending on the nature of Z, R1, R2, R3, R4, R5, R10, R11, R12 and Ring A different synthetic strategies may be selected for the synthesis of compounds of Formulae I, Ia', Ib', Ia", Ib", or II. In the process illustrated in the following schemes, Z, R1, R2, R3, R4, R5, R10, R11, R12 and Ring A are as above defined in the description unless otherwise mentioned.

All NMR experiments were recorded on Bruker Avance III 400 NMR Spectrometer equipped with a Bruker PABBO BB-1H/D Z GRD probe at 400 MHz for proton NMR or a Bruker DPX-300 MHz. Most deuterated solvents contained typically 0.03% to 0.05% v/v tetramethylsilane, which was used as the reference signal (set at 0.00 for both $^1$H and $^3$C). In cases where the deuterated solvents did not contain tetramethylsilane, the residual non-deuterated solvent peaks were used as a reference signal, as per published guidelines (*J. Org. Chem.*, Vol. 62, No. 21, 1997). Chemical shifts are expressed in parts per million (ppm, 6 units). Coupling constants are in units of hertz (Hz). Splitting patterns describe apparent multiplicities and are designated as s (singlet), d (doublet), t (triplet), q (quartet), m (multiplet), qt (quintuplet) or brs (broad singlet).

UPLC/MS analyses were performed on a Waters AquityH with SQ detector (ESI) and LC/MS on an Agilent 1200 Series with a quadupole detector or a SHIMADZU LC-MS machine consisting of an UFLC 20-AD system and a LCMS 2020 MS detector.

Unless reported differently, analytical chiral SFC were performed using reported column and solvent with the following gradient: from 95% to 40% in 3.5 min, then 40% for 1.5 min, then 40% to 95% in 0.5 min and 95% for 1 min.

The microwave reactions were conducted using Biotage Initiator Microwave Synthesizer using standard protocols that are known in the art.

The commercially available starting materials used in the following experimental description were purchased from Sigma-Aldrich or Fisher unless otherwise reported.

Intermediate 1: 6-chloro-3-(2,3-dichlorophenyl)-2-(methylsulfanyl)-3,4-dihydropyrimidin-4-one

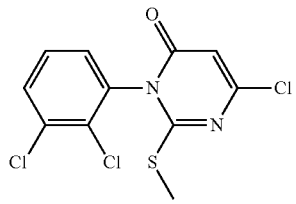 [SMILES: CSc1nc(Cl)cc(=O)n1-c1cccc(Cl)c1Cl]

Step 1: 3-(2,3-dichlorophenyl)-6-hydroxy-2-sulfanylidene-1,2,3,4-tetrahydro-pyrimidin-4-one (2,3-dichlorophenyl)thiourea (103 g, 466 mmol) was added portion-wise to a solution of sodium methylate (12 g, 500 mmol) in methanol (1000 mL) at RT. The reaction mixture was stirred for 10 min before the addition of diethyl malonate (76 g, 474 mmol). It was then refluxed for 3 h and concentrated under reduced pressure. Water was added to the residue (1000 mL) and the precipitate was filtered off. The filtrate was acidified by HCl until white solid precipitates. This solid was filtered, washed with water and dried to give the title compound (71 g, 52%).

Step 2: 3-(2,3-dichlorophenyl)-6-hydroxy-2-(methylsulfanyl)-3,4-dihydropyrimidin-4-one Potassium hydroxide (17 g, 303 mmol) was added portion-wise to a suspension of 3-(2,3-dichlorophenyl)-6-hydroxy-2-sulfanylidene-1,2,3,4-tetrahydropyrimidin-4-one (71 g, 246 mmol) in methanol (1000 mL). Methyl iodide (38 g, 268 mmol) was then added dropwise and the reaction mixture was stirred overnight at RT. Water was added (2000 mL) and the precipitate was filtered, washed with water and dried to give the title compound (42 g, 56%).

Step 3: 6-chloro-3-(2,3-dichlorophenyl)-2-(methylsulfanyl)-3,4-dihydropyrimidin-4-one Phosphoryl chloride (27 g, 176 mmol) was added dropwise to a suspension of 3-(2,3-dichlorophenyl)-6-hydroxy-2-(methylsulfanyl)-3,4-dihydropyrimidin-4-one (45 g, 148 mmdl) in MeCN (1000 mL). Solvent was removed under reduced pressure and the crude was purified by flash chromatography on silica to give the title compound as a white solid (4.4 g, 10%). 1H NMR (400 MHz, CDCl$_3$): 7.8 (d, 1H), 7.75 (t, 1H), 7.4 (m, 1H), 6.7 (s, 1H), 2.5 (s, 3H).

Intermediate 2: 6-chloro-3-(2,3-dichlorophenyl)-2-methyl-3,4-dihydropyrimidin-4-one

Step 1: N'-(2,3-dichlorophenyl)ethanimidamide

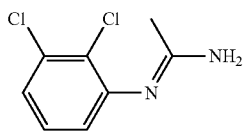

1-(methylsulfanyl)ethan-1-imine (55 g, 253 mmol, hydroiodide salt) was added to a solution of 2,3-dichloroaniline (37.5 g, 231 mmol) in dioxane (300 mL) and DMF (50 mL) maintained at 0° C. The reaction mixture was heated at 100° C. for two days. It was then cooled down to RT and the solvents were removed under reduced pressure. The residue was washed with ethyl acetate—MTBE mixture (500 mL, 1:5), dissolved in dichloromethane (200 mL) and filtered. The filtrate was concentrated in vacuo to provide the title compound as a yellow solid (28.0 g, 37%).

Step 2: Methyl 2-{[(1E)-1-[(2,3-dichlorophenyl)imino]ethyl]carbamoyl}acetate

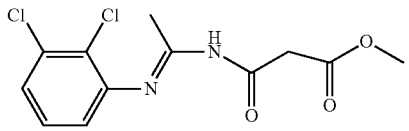 [SMILES: COC(=O)CC(=O)N/C(C)=N/c1cccc(Cl)c1Cl]

4-methylmorpholine (12.6 g, 127 mmol) and methyl malonyl chloride (17.4 g, 127 mmol) were added to a solution of N'-(2,3-dichlorophenyl)ethanimidamide (28 g, 85 mmol) in dichloromethane (400 mL) maintained at 0° C. The reaction mixture was allowed to warm to RT and stirred for 18 h. The reaction mixture was then diluted with a saturated sodium bicarbonate solution, extracted with dichloromethane, washed with brine, dried over magnesium sulfate, filtered and concentrated to give the title compound as brown oil (18 g, 70%).

Step 3: 6-chloro-3-(2,3-dichlorophenyl)-2-methyl-3,4-dihydropyrimidin-4-one

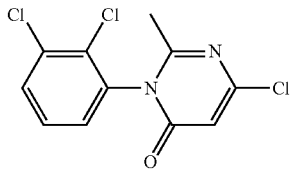 [SMILES: Cc1nc(Cl)cc(=O)n1-c1cccc(Cl)c1Cl]

A solution of methyl 2-{[(1E)-1-[(2,3-dichorophenyl)imino]ethyl]carbamoyl}acetate (18 g, 59 mmol) and 1,8-diazabicyclo[5.4.0]undec-7-ene (9 g, 60 mmol) in 1,4-dioxane (100 mL) was heated at 60° C. for 4 h. The reaction mixture was then concentrated under reduced pressure and phosphoryl chloride was added to the residue. The reaction mixture was heated at 100° C. for 4 h. Excess phosphorus chloride was removed under reduced pressure and the residue was added to ice-water with stirring. Sodium carbonate was added to the stirred mixture until no more effervescence was observed. The mixture was extracted with DCM (2×200 mL) and combined organic layers were dried over magnesium sulfate, filtered and concentrated. Purification by flash chromatography on silica (hexane-MTBE) afforded the title compound as a white solid (2.5 G, 23%). 1H NMR (500 MHz, CDCl$_3$): 7.67 (d, J=11.5 Hz, 1H), 7.45 (m, 1H), 7.21 (m, 1H), 6.56 (s, 1H), 2.21 (s, 3H). LC/MS (M+1): 289.0

Intermediate 3: 6-chloro-3-(2,3-dichlorophenyl)-2-methanesulfonyl-3,4-dihydropyrimidin-4-one

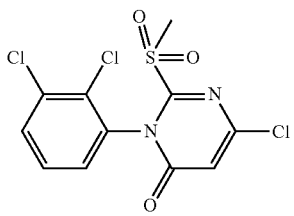 [SMILES: CS(=O)(=O)c1nc(Cl)cc(=O)n1-c1cccc(Cl)c1Cl]

A solution of mCPBA 3-chloroperoxybenzoic acid (523 mg; 2.33 mmol) in DCM (5 mL) was slowly added to a solution of 6-chloro-3-(2,3-dichlorophenyl)-2-(methylsulfanyl)-3,4-dihydropyrimidin-4-one (Intermediate 1; 1.25 g; 0.78 mmol) in DCM (5 mL) maintained at 0° C. The reaction mixture was allowed to warm at RT and stirred for 2 h. As the reaction was not completed, a solution of 3-chloroperoxybenzoic acid (348 mg; 1.55 mmol) in DCM (2.5 mL) was added at 0° C. and the reaction mixture was stirred for another 2 h at room temperature. The precipitate was filtered off and the filtrate was concentrated under reduced pressure. The residue was re-dissolved in DCM and the precipitate filtered again. Purification by flash chromatography on silica (hexane:EtOAc, gradient from 95:5 to 20:80) afforded the title compound as a white solid (272 mg, 98%). 1H NMR (400 MHz, DMSO-d6): 7.78-7.73 (m, 1H), 7.51 (s, 1H), 7.50 (d, J=1.7 Hz, 1H), 6.11 (s, 1H), 2.34 (s, 3H). LC/MS (M+1): 352.9

Intermediate 4: 2-amino-6-chloro-3-(2,3-dichlorophenyl)-3,4-dihydropyrimidin-4-one

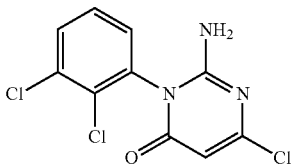 [SMILES: Nc1nc(Cl)cc(=O)n1-c1cccc(Cl)c1Cl]

A solution of 6-chloro-3-(2,3-dichlorophenyl)-2-methanesulfonyl-3,4-dihydropyrimidin-4-one (175 mg; 0.49 mmol) and ammonia (0.99 ml of a 0.5 mmol solution in dioxane 0.49 mmol) in THF (3.5 mL) was stirred at room temperature for 1 h. Solvent was removed under reduced pressure and the crude was purified by flash chromatography on NH-silica (hexane:EtOAc, gradient from 95:5 to 0:100) to give the title compound as a white solid 1H NMR (Bruker 400 MHz, DMSO-d6) 7.79 (dd, J=6.9, 2.8 Hz, 1H), 7.57-7.48 (m, 2H), 5.82 (s, 1H).

Intermediate 5: 6-chloro-2-methyl-3-phenyl-3,4-dihydropyrimidin-4-one

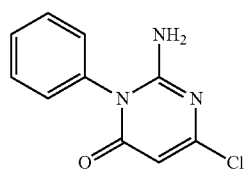 [SMILES: Nc1nc(Cl)cc(=O)n1-c1ccccc1]

The title compound was obtained following procedure described for intermediate 2 but starting from aniline as an orange solid. 1H NMR (500 MHz, DMSO-d6): 7.57 (m, 3H), 7.34 (m, 2H), 6.48 (s, 1H), 2.11 (s, 3H). LC/MS (M+1): 221.2

Intermediate 6: 6-chloro-3-(2,3-dichlorophenyl)-2-(difluoromethyl)-3,4-dihydropyrimidin-4-one

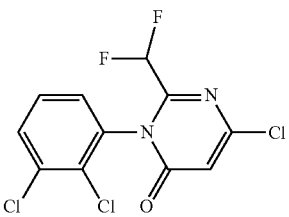 [SMILES: O=c1cc(Cl)nc(C(F)F)n1-c1cccc(Cl)c1Cl]

The title compound was obtained following procedure described for intermediate 2 but starting from N'-(2,3-dichlorophenyl)-2,2-difluoroethanimidamide.

Intermediate 7: 3-(2,3-dichlorophenyl)-6-hydroxy-2,5-dimethyl-3,4-dihydropyrimidin-4-one

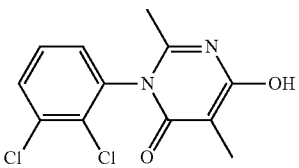 [SMILES: Cc1c(O)nc(C)n(-c2cccc(Cl)c2Cl)c1=O]

A mixture of N-(2,3-dichlorophenyl)ethanimidamide (20 g; 98.5 mmol), 2-methoxyethanol (300 mL), 1,3-diethyl 2-methylpropanedioate (24 mL; 147 mmol) and sodium methoxide (21 g; 394.0 mmol) was heated to 110° C. under argon for 12 h. The reaction mixture was then allowed to cool to RT and diluted with water (200 mL). Concentrated sulfuric acid was added until pH reached 2-3. The precipitate was filtered, washed with water and dried to give the title compound as a white solid (27 g, 90%). 1H NMR (DMSO-d6): 11.45 (1H), 7.82 (dd, J=6.6, 3.0 Hz, 1H), 7.59 (m, 2H), 2.02 (s, 3H), 1.74 (s, 3H). LC/MS (M+1): 285.0

Intermediates 7a and 7b: (3P)-3-(2,3-dichlorophenyl)-6-hydroxy-2,5-dimethyl-3,4-dihydropyrimidin-4-one and (3M)-3-(2,3-dichlorophenyl)-6-hydroxy-2,5-dimethyl-3,4-dihydropyrimidin-4-one 7a

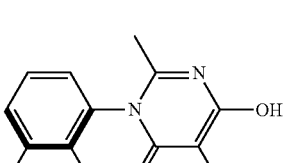

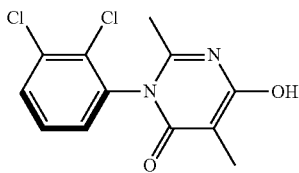

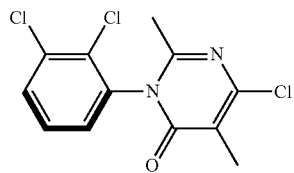

Separation of isomers of intermediate 7 by chiral SFC (column Cel2; 250×21 mm; 5 micron; Methanol+20 mM NH₄OH:CO₂; 40/60% v/v) afforded the two possible atropisomers:

First eluting atropisomer (intermediate 7a): white solid; Rt=3.24 min (analytical column CeI₂); de=100%; LC/MS (M+1): 285.0 Second eluting atropisomer (intermediate 7b): white solid; Rt=4.06 min (analytical column CeI₂); de=100; LC/MS (M+1): 285.0

Intermediate 8: 6-chloro-3-(2,3-dichlorophenyl)-2,5-dimethyl-3,4-dihydropyrimidin-4-one

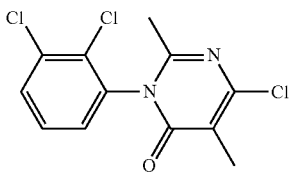 [SMILES: Cc1c(Cl)nc(C)n(-c2cccc(Cl)c2Cl)c1=O]

A mixture of 3-(2,3-dichlorophenyl)-6-hydroxy-2,5-dimethyl-3,4-dihydropyrimidin-4-one (intermediate 7; 5.0 g; 17.54 mmol) and phosphoroyl trichloride (30 mL; 327 mmol) was heated at 100° C. O/N. Excess phosphorus oxychloride was removed under reduced pressure and the residue was added to ice-water with stirring. Sodium carbonate was added to the stirred mixture until there was no more effervescence. The mixture was extracted with methylene chloride (2×200 mL) and the extracts were dried over magnesium sulfate, filtered and concentrated. Purification by flash chromatography on silica (Hex:EtOAc, gradient from 0% to 50%) afforded the title compound as a white solid (3 g, 57%). H NMR (DMSO-d6): ¹H NMR (400 MHz, DMSO-d): 7.87 (dd, J=8.0, 1.7 Hz, 1H), 7.65 (m, 1H), 7.61 (m, 1H), 2.07 (s, 6H). LC/MS (M+1): 303.0

Intermediate 8a and 8b: (3P)-6-chloro-3-(2,3-dichlorophenyl)-2,5-dimethyl-3,4-dihydropyrimidin-4-one and (3M)-6-chloro-3-(2,3-dichlorophenyl)-2,5-dimethyl-3,4-dihydropyrimidin-4-one

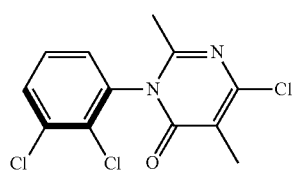

Separation of isomers of intermediate 8 by chiral SFC (column ADH; 250×21 mm; 5 micron; Methanol+20 mM NH₄OH:CO₂; 10/90) afforded the two possible atropisomers:

First eluting atropisomer (intermediate 8a): white solid; Rt=2.91 min (analytical column ADH-Methanol+20 mM NH₄OH:CO₂; gradient 5 to 45%); de=100%; 1H NMR (400 MHz, DMSO-d6): 7.86 (dd, J=8.0, 1.7 Hz, 1H), 7.67 (dd, J=8.0, 1.7 Hz, 1H), 7.61 (t, J=8.0 Hz, 1H), 2.07 (s, 6H); LC/MS (M+1): 302.9

Second eluting atropisomer (intermediate 8b): white solid; Rt=3.26 min (analytical column ADH-Methanol+20 mM NH4OH:CO2; gradient 5 to 45%); de=100%;

1H NMR (400 MHz, DMSO-d6): 7.86 (dd, J=8.0, 1.7 Hz, 1H), 7.67 (dd, J=7.9, 1.7 Hz, 1H), 7.61 (t, J=8.0 Hz, 1H), 2.07 (s, 6H); LC/MS (M+1): 302.9

Intermediate 9: 3-(2,3-dichlorophenyl)-6-hydroxy-2-methyl-3,4-dihydropyrimidin-4-one

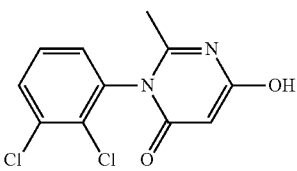 [SMILES: Cc1nc(O)cc(=O)n1-c1cccc(Cl)c1Cl]

A solution of AlMe₂Cl (5.5 mL of a 0.9M solution in hexane, 59.3 mmol) was added dropwise to a stirred solution of 2,3-dichloroaniline (810 mg, 4.75 mmol) and MeCN (248 mg, 6.0 mmol) in toluene (4 mL) maintained under inert atmosphere. The reaction 0.15 mixture was stirred at RT for 15 min and then heated in MW at 150° C. for 30 min. Solvent was removed under reduced pressure before the addition of 2-methoxyethan-1-ol (10 mL, 131.4 mmol), diethyl malonate (3.36 g, 20 mmol) and NaOMe (1.13 g, 20 mmol). The resulting mixture was stirred for an additional 24 h at 130° C. It was then diluted with water and neutralized to pH 6 by addition of aq. HCl (6M). The precipitate was filtered and washed with water (3×10 mL), Et₂O (3×20 mL) and dried to give the title compound as a yellow solid (1.2 g, 86%). 1H NMR (300 MHz, DMSO-d6) 11.94 (s, 1H), 7.80 (dd, J=7.3, 2.4 Hz, 1H), 7.64-7.47 (m, 2H), 5.36 (s, 1H), 2.01 (s, 3H). LC/MS (M+1): 271.1. mp: 260-262° C.

Intermediate 10: 1-(2,3-dichlorophenyl)-2-methyl-6-oxo-1,6-dihydropyrimidin-4-yl 4-methylbenzene-1-sulfonate

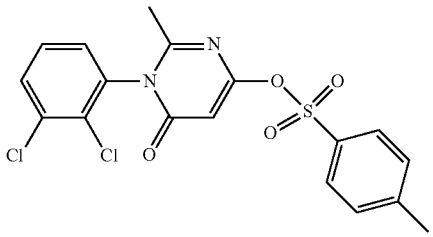 [SMILES: Cc1ccc(S(=O)(=O)Oc2cc(=O)n(-c3cccc(Cl)c3Cl)c(C)n2)cc1]

A mixture of 3-(2,3-dichlorophenyl)-6-hydroxy-2-methylpyrimidin-4-one (intermediate 9; 700 mg, 2.04 mmol), para-toluenesulfonyl chloride (953 mg, 4.07 mmol) and $K_2CO_3$ (1.04 g, 7.12 mmol) in THF (20 mL) was stirred for 6 h at 60° C. The resulting mixture was filtered, the filter cake was washed with EtOAc (3×100 mL) and the filtrate was concentrated under reduced pressure. The residue was purified by flash chromatography on silica (PE:EtOAc, gradient from 100:0 to 0:100) to give the title compound as a white solid (800 mg, 75%). LC/MS (M+1): 424.9.

Intermediate 11: 6-chloro-3-(2,3-dichlorophenyl)-2-methyl-5-(trifluoromethyl)-3,4-dihydropyrimidin-4-one

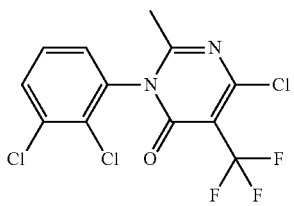 [SMILES: Cc1nc(Cl)c(C(F)(F)F)c(=O)n1-c1cccc(Cl)c1Cl]

The title compound was obtained by trifluoromethylation of intermediate 9 followed by a chlorination using same condition as for intermediate 1, step 3.

Intermediate 12: 6-chloro-3-(2,3-dichloro-6-fluorophenyl)-2-methyl-3,4-dihydropyrimidin-4-one

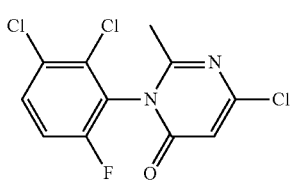 [SMILES: Cc1nc(Cl)cc(=O)n1-c1c(F)ccc(Cl)c1Cl]

The title compound was obtained following procedure described for intermediate 2 but starting from 2,3-dichlo-6-fluororoaniline as a yellow solid. 1H NMR (400 MHz, $CDCl_3$): 7.64 (m, 1H), 7.21 (m, 1H), 6.53 (s, 1H), 2.21 (s, 3H). LC/MS (M+1): 307.0

Intermediate 13: 3-(2,3-dichlorophenyl)-5-ethyl-6-hydroxy-2-methyl-3,4-dihydropyrimidin-4-one

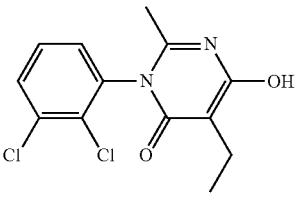 [SMILES: CCc1c(O)nc(C)n(-c2cccc(Cl)c2Cl)c1=O]

A mixture of N-(2,3-dichlorophenyl)ethanimidamide (6.50 g; 32.0 mmol), 2-methoxyethanol (75 mL), 1,3-diethyl 2-ethylpropanedioate (8.57 mL; 48.1 mmol) and sodium methoxide (6.92 g; 128.0 mmol) was heated to 110° C. under argon for 12 h. The reaction mixture was then allowed to cool to RT and diluted with water (200 mL). Concentrated sulfuric acid was added until pH reached 2-3. The precipitate was filtered, washed with water and dried to give the title compound as a white solid (8.3 g, 87%). $^1$H NMR (400 MHz, DMSO-d6): 11.45 (s, 1H), 7.81 (dd, J=7.5, 2.2 Hz, 1H), 7.63-7.51 (m, 2H), 2.31 (q, J=7.3 Hz, 2H), 2.00 (s, 3H), 0.98 (t, J=7.4 Hz, 3H).

Intermediate 14: 1-(2,3-dichlorophenyl)-6-methyl-4-(methylsulfanyl)-1,2-dihydro-1,3,5-triazin-2-one A solution of {[(E)-[1-(dimethylamino)ethylidene]amino](methylsulfanyl)-methylidene}azanium iodide (prepared as described in *J. of Heterocyclic Chem.*, 38(1), 93-98; 2001; 500 mg; 1.74 mmol) and 2,3-dichlorophenyl isocyanate (260 ul; 1.92 mmol) in THF (5 mL) was stirred for 4 h at RT under inert atmosphere. The reaction mixture was cooled down to 0° C. before the addition of TEA (0.5 mL, 3.83 mmol). It was then stirred overnight at RT. The precipitate was filtered off and the filtrate was concentrated under reduced pressure. Purification by flash chromatography on silica (hexane:EtOAc, 20:80) afforded the title compound as a white powder (105 mg, 20%). 1H NMR (400 MHz, Chloroform-d): 7.64 (dd, J=8.2, 1.4 Hz, 1H), 7.41 (t, J=8.0 Hz, 1H), 7.30-7.21 (m, 1H), 2.58 (s, 3H), 2.14 (s, 3H). LC/MS (M+1): 302.0.

Intermediate 15: 2,5-dimethyl-1-(naphthalen-2-yl)-6-oxo-1,6-dihydropyrimidin-4-yl 4-methylbenzene-1-sulfonate

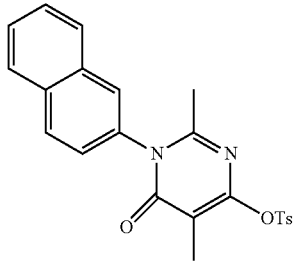 [SMILES: Cc1ccc(S(=O)(=O)Oc2nc(C)n(-c3ccc4ccccc4c3)c(=O)c2C)cc1]

The title compound was obtained following procedure described for intermediate 10 but starting from naphthalen-2-amine as a white solid (500 mg, 23%—two steps). LC/MS (M+1): 421.2

Intermediate 16: 3-(2,3-dichlorophenyl)-2-methyl-6-(4-oxopiperidin-1-yl)-3,4-dihydropyrimidin-4-one

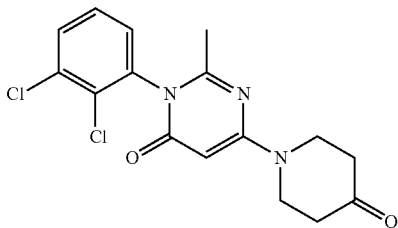 [SMILES: Cc1nc(N2CCC(=O)CC2)cc(=O)n1-c1cccc(Cl)c1Cl]

A solution of 6-chloro-3-(2,3-dichlorophenyl)-2-methyl-3,4-dihydropyrimidin-4-one (300 mg; 1.04 mmol), piperidin-4-one hydrochloride (281 mg; 2.07 mmol) and DIEA (1.08 mL, 6.22 mmol) in EtOH (6 mL) was heated at 50° C. for 5 h. The reaction mixture was then concentrated under reduced pressure and purified by flash chromatography on silica (EtOAc, 100%) to give the title compound as a white solid (307 mg, 82%). 1H NMR (Bruker 400 MHz, DMSO-d6): 7.80 (dd, J=6.0, 3.6 Hz, 1H), 7.62-7.49 (m, 2H), 5.46 (s, 1H), 3.98-3.78 (m, 4H), 2.59-2.39 (m, 4H), 2.02 (s, 3H).

Intermediate 17: 1-(1,3-benzothiazol-7-yl)-2,5-dimethyl-6-oxo-1,6-dihydro pyrimidin-4-yl 4-methylbenzene-1-sulfonate

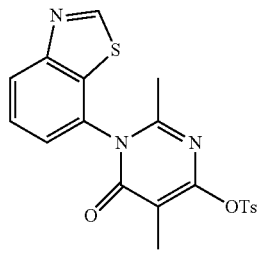 [SMILES: Cc1ccc(S(=O)(=O)Oc2nc(C)n(-c3cccc4ncsc34)c(=O)c2C)cc1]

The title compound was obtained following procedure described for intermediate 10 but starting from 1,3-benzothiazol-7-amine as a yellow solid (950 mg, 53%—two steps). LC/MS (M+1): 428.1

Intermediate 18: 6-hydroxy-2,5-dimethyl-3-(quinoxalin-6-yl)-3,4-dihydropyrimidin-4-one

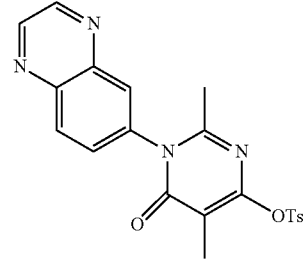 [SMILES: Cc1ccc(S(=O)(=O)Oc2nc(C)n(-c3ccc4nccnc4c3)c(=O)c2C)cc1]

The title compound was obtained following procedure described for intermediate 10 but starting from quinoxalin-6-amine as a brown solid (1.2 g, two steps). LC/MS (M+1): 423.1.

Intermediate 19: 1-(1-chloronaphthalen-2-yl)-2,5-dimethyl-6-oxo-1,6-dihydropyrimidin-4-yl 4-methylbenzene-1-sulfonate

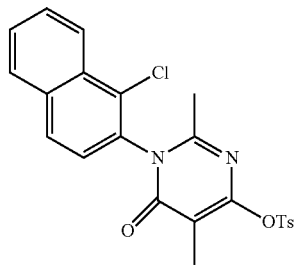 [SMILES: Cc1ccc(S(=O)(=O)Oc2nc(C)n(-c3ccc4ccccc4c3Cl)c(=O)c2C)cc1]

The title compound was obtained following procedure described for intermediate 10 but starting from 1-chloronaphthalen-2-amine as a brown solid (0.6 g, 61%, two steps). LC/MS (M+1): 455.1.

Intermediate 20: 1-(2,3-dichlorophenyl)-5-methyl-2-(methylsulfanyl)-6-oxo-1,6-dihydropyrimidin-4-yl 4-methylbenzene-1-sulfonate Step 1: 3-(2,3-dichlorophenyl)-6-hydroxy-5-methyl-2-sulfanyl-3,4-dihydropyrimidin-4-one

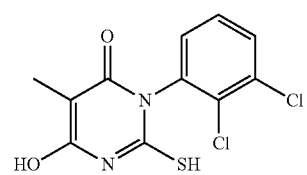 [SMILES: Cc1c(O)nc(S)n(-c2cccc(Cl)c2Cl)c1=O]

A solution of 2,3-dichlorophenylthiourea (3.0 g, 12.9 mmol), dimethyl malonate (3.6 g, 25.8 mmol), 18-Crown-6

(1.8 g, 6.45 mmol) and MeONa (4.64 g, 25.8 mmol) in dioxane (30 mL) was stirred for 3 h at 70° C. under nitrogen atmosphere. The reaction mixture was then concentrated under reduced pressure and the residue was purified by flash chromatography on silica (PE:EtOAc, 1:1) to afford the title compound as an off-white solid (4 g, 834%). LC/MS (M+1): 303.2.

Step 2: 3-(2,3-dichlorophenyl)-6-hydroxy-5-methyl-2-(methylsulfanyl)-3,4-dihydro-pyrimidin-4-one

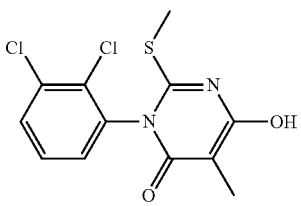 [SMILES: CSc1nc(O)c(C)c(=O)n1-c1cccc(Cl)c1Cl]

A solution of 3-(2,3-dichlorophenyl)-6-hydroxy-5-methyl-2-sulfanylpyrimidin-4-one (100 mg, 0.27 mmol) and $CH_3I$ (1 mL) in THF (1 mL) was stirred for 3 hr at room temperature under nitrogen atmosphere. The resulting mixture was concentrated and the residue was purified by flash chromatography on silica (PE:EtOAc, 1:1) to afford the title compound as an off-white solid (300 mg, 33%). LC/MS (M+1): 317.2.

Step 3: 1-(2,3-dichlorophenyl)-5-methyl-2-(methylsulfanyl)-6-oxo-1,6-dihydro-pyrimidin-4-yl 4-methylbenzene-1-sulfonate

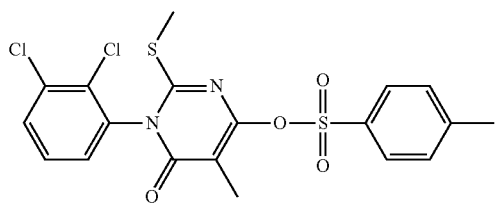 [SMILES: CSc1nc(OS(=O)(=O)c2ccc(C)cc2)c(C)c(=O)n1-c1cccc(Cl)c1Cl]

The title compound was obtained following procedure described for intermediate 10, step 2 but starting from 3-(2,3-dichlorophenyl)-6-hydroxy-5-methyl-2-(methylsulfanyl)pyrimidin-4-one (80 mg, 0.23 mmol) as an off-white solid (50 mg, 28%). LC/MS (M+1): 471.2

Intermediate 21: 3-(2,3-dichlorophenyl)-6-hydroxy-5-methoxy-2-methyl-3,4-dihydropyrimidin-4-one

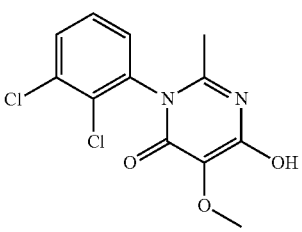 [SMILES: COc1c(O)nc(C)n(-c2cccc(Cl)c2Cl)c1=O]

The title compound was obtained following procedure described for intermediate 13, but starting from N-(2,3-dichlorophenyl)ethanimidamide (2 g, 9.8 mmol) and 1,3-diethyl 2-methoxypropanedioate (2.8 g, 14.8 mmol) as a white solid (1.6 g, 54%). 1H NMR (400 MHz, DMSO-d6): 11.5 (brs, 1H), 7.85 (m, 1H), 7.61 (m, 2H), 3.64 (s, 3H), 1.98 (s, 3H). LC/MS (M+1): 301.0.

Intermediate 22: N-[(6R)-5,6-dihydrospiro[cyclopenta[b]pyridine-7,4'-piperidin]-6-yl]-2-methylpropane-2-sulfinamide; trifluoroacetic acid Step 1: 1-tert-butyl 4-ethyl 4-(3-methylpyridin-2-yl)piperidine-1,4-dicarboxylate

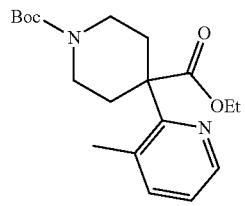 [SMILES: CCOC(=O)C1(c2ncccc2C)CCN(C(=O)OC(C)(C)C)CC1]

A solution of NaHMDS (1.00 M, 896 mL of a 1M solution in toluene) was added dropwise to a solution of 2-fluoro-3-methylpyridine (65.0 g, 585 mmol) and 1-tert-butyl 4-ethyl piperidine-1,4-dicarboxylate (166 g, 643 mmol) in toluene (600 mL) maintained at 0° C. The reaction mixture was then stirred at 20° C. for 24 h. It was quenched with brine (500 mL). The organic layer was separated and dried over $Na_2SO_4$, filtered and concentrated. Purification by flash chromatography on silica (PE:EtOAc, gradient from 10:0 to 0:10 afforded the title compound as a yellow oil (50.0 g, 23%). $^1$H NMR (400 MHz, $CDCl_3$): 8.40 (dd, J=4.8, 1.6 Hz, 1H), 7.40 (d, J=7.6 Hz, 1H), 7.10 (dd, J=8.0, 4.8 Hz, 1H), 4.19-4.13 (m, 2H), 3.70-3.64 (m, 2H), 3.50-3.48 (m, 1H), 2.86-2.66 (m, 1H), 2.25 (s, 4H), 2.18-2.13 (m, 1H), 1.91-1.85 (m, 1H), 1.67-1.56 (m, 1H), 1.45 (s, 9H), 1.29-1.14 (m, 3H); LC/MS (M+1-Boc): 293.2

Step 2: Tert-Butyl 6-oxo-5,6-dihydrospiro[cyclopenta[b]pyridine-7,4'-piperidine]-1'-carboxylate

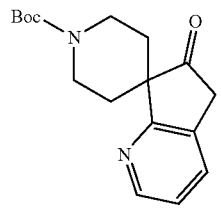 [SMILES: CC(C)(C)OC(=O)N1CCC2(CC1)C(=O)Cc1cccnc12]

LDA (140 mL of a 2 M solution in THF, 2.50 eq) was added to a solution of 1-tert-butyl 4-ethyl 4-(3-methylpyridin-2-yl)piperidine-1,4-dicarboxylate (39 g, 112 mmol) in THF (390 mL) maintained at 0° C. The reaction mixture was stirred at 0° C. for 1 h, poured into ice saturated $NH_4Cl$ (500 mL) and extracted with ethyl acetate (400 mL×2). The organic layer was washed with brine (300 mL×2), dried over $Na_2SO_4$, filtered and concentrated. Purification by flash chromatography on silica (PE:EtOAc, gradient from 10:0 to 0:10) afforded the title compound as a yellow solid (18 g, 52%). ¹H NMR (400 MHz, CDCl₃): 8.52-8.50 (m, 1H), 7.63-7.61 (m, 1H), 7.20 (dd, J=8.0, 4.2 Hz, 1H), 3.98-3.95 (m, 2H), 3.60 (s, 4H), 1.93-1.86 (m, 2H), 1.78-1.73 (m, 2H), 1.48 (s, 9H). LC/MS (M+1): 247.1.

Step 3: Tert-Butyl (6R)-6-{[(R)-2-methylpropane-2-sulfinyl]amino}-5,6-dihydro spiro[cyclopenta[b]pyridine-7,4'-piperidine]-1'-carboxylate

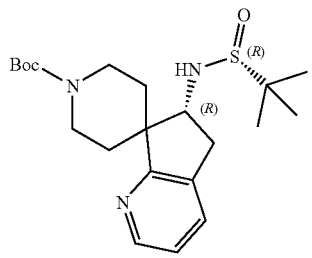

A mixture of tert-butyl 6-oxo-5,6-dihydrospiro[cyclopenta[b]-pyridine-7,4'-piperidine]-1'-carboxylate (12.0 g, 39.7 mmol), Ti(OEt)₄ (70.0 g, 307 mmol) and (R)-2-methylpropane-2-sulfinamide (14.4 g, 119 mmol) in 2-Me-THF (72.0 mL) was stirred at 80° C. for 1.5 h. The reaction mixture was then cooled to −5° C. and LiBH₄ (4.24 g, 195 mmol) was added portion-wise to the mixture maintained at 0° C. After 1 h at 0° C., the reaction mixture was poured into ice-water (300 mL) and filtered. The filter cake was washed with ethyl acetate (300 mL×3). The filtrate was washed with brine (200 mL), dried over Na₂SO₄, filtered and concentrated. The residue was purified by flash chromatography on silica (PE:EtOAC, gradient from 10:0 to 0:10) to afford the title compound as a yellow solid (8.00 g, 44.6% yield). ¹H NMR (400 MHz, CDCl₃): 8.39-8.37 (m, 1H), 7.50 (d, J=7.2 Hz, 1H), 7.09 (dd, J=7.6, 4.8 Hz, 1H), 4.03-4.93 (m, 2H), 3.76 (brs, 2H), 3.41 (s, 1H), 3.27-3.24 (m, 1H), 2.94 (dd, J=16.0, 6.4 Hz, 1H), 1.82-1.79 (m, 2H), 1.74-1.70 (m, 2H), 1.47 (s, 9H), 1.20 (s, 9H). LC/MS (M+1): 406.2.

Step 4: N-[(6R)-5,6-dihydrospiro[cyclopenta[b]pyridine-7,4'-piperidin]-6-yl]-2-methylpropane-2-sulfinamide; trifluoroacetic acid

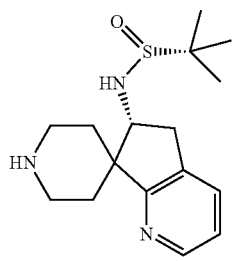

A solution of tert-butyl (6R)-6-{[(R)-2-methylpropane-2-sulfinyl]amino}-5,6-dihydro spiro[cyclopenta[b]pyridine-7,4'-piperidine]-1'-carboxylate (6.0 g, 14.7 mmol) in DCM (60 mL) and TFA (10.9 mL) was stirred at 25° C. for 2 h. Solvent was removed under reduced pressure and the residue was purified by preparative HPLC (0.1% TFA condition) to afford the title compound as a yellow solid (2.41 g, 38.0% yield). ¹H NMR (400 MHz, DMSO-d6): 8.81 (s, 1H), 8.52 (s, 1H), 8.38 (d, J=3.6 Hz, 1H), 7.67 (d, J=7.6 Hz, 1H), 7.24 (dd, J=7.6, 4.2 Hz, 1H), 5.80 (d, J=9.2 Hz, 1H), 3.99-3.95 (m, 1H), 3.83-3.78 (m, 1H), 3.32-3.12 (m, 3H), 3.01-2.96 (m, 1H), 2.19-2.01 (m, 2H), 1.85-1.71 (m, 2H), 1.18 (s, 9H). LC/MS (M+1): 308.2.

Intermediate 23: 5-cyclopropyl-1-(2,3-dichlorophenyl)-2-methyl-6-oxo-1,6-dihydropyrimidin-4-yl 4-methylbenzene-1-sulfonate

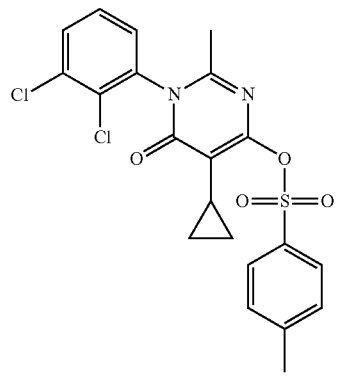 [SMILES: Cc1ccc(S(=O)(=O)Oc2nc(C)n(-c3cccc(Cl)c3Cl)c(=O)c2C2CC2)cc1]

The title compound was obtained following procedure described for intermediate 10 but starting from 1,3-diethyl 2-cyclopropylpropanedioate and 2,3-dichloroaniline as a yellow solid (0.4 g, 15%, two steps). LC/MS (M+1): 465.2.

Intermediate 24:1-(2,3-dichlorophenyl)-5-(D3) methyl-2-methyl-6-oxo-1,6-dihydropyrimidin-4-yl 4-methylbenzene-1-sulfonate

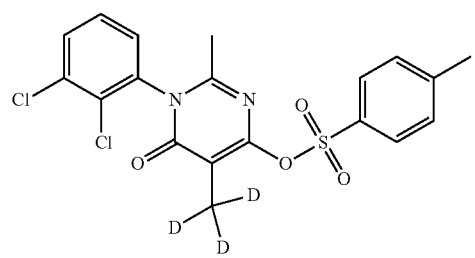 [SMILES: [2H]C([2H])([2H])c1c(OS(=O)(=O)c2ccc(C)cc2)nc(C)n(-c2cccc(Cl)c2Cl)c1=O]

The title compound was obtained following procedure described for intermediate 10 but starting from 2,3-dichloroaniline and 1,3-diethyl 2-(D3)methylpropanedioate as a yellow solid (1 g, 79%). LC/MS (M+1): 441.9.

Intermediate 25: 1-(3-bromo-2-chlorophenyl)-2,5-dimethyl-6-oxo-1,6-dihydropyrimidin-4-yl 4-methylbenzene-1-sulfonate

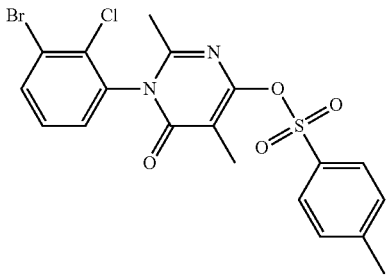

The title compound was obtained following procedure described for intermediate 10 but starting from 3-bromo-2-chloroaniline and 1,3-diethyl 2-methylpropanedioate as a yellow solid. LC/MS (M+1): 485.0.

Intermediate 26: 1-(2-chloro-3-fluorophenyl)-2,5-dimethyl-6-oxo-1,6-dihydropyrimidin-4-yl 4-methylbenzene-1-sulfonate

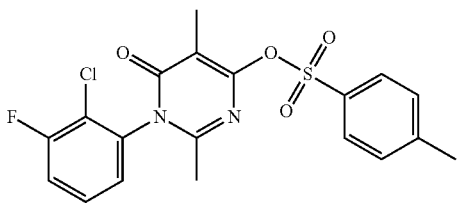 [SMILES: Cc1ccc(S(=O)(=O)Oc2nc(C)n(-c3cccc(F)c3Cl)c(=O)c2C)cc1]

The title compound was obtained following procedure described for intermediate 10 but starting from 2-chloro-3-fluoroaniline and 1,3-diethyl 2-methylpropanedioate as a white solid. LC/MS (M+1): 423.0.

Intermediate 27: 1-(2-bromo-3-chlorophenyl)-2,5-dimethyl-6-oxo-1,6-dihydropyrimidin-4-yl 4-methylbenzene-1-sulfonate

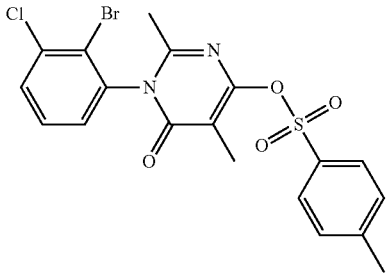 [SMILES: Cc1ccc(S(=O)(=O)Oc2nc(C)n(-c3cccc(Cl)c3Br)c(=O)c2C)cc1]

The title compound was obtained following procedure described for intermediate 10 but starting from 2-bromo-3-chloroaniline and 1,3-diethyl 2-methylpropanedioate as a white solid. LC/MS (M+1): 485.1.

Intermediate 28: 1-(2,3-dichloro-4-methoxyphenyl)-2,5-dimethyl-6-oxo-1,6-dihydropyrimidin-4-yl 4-methylbenzene-1-sulfonate

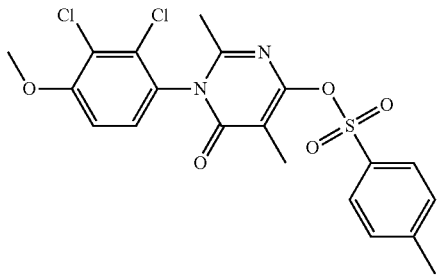

The title compound was obtained following procedure described for intermediate 10 but starting from 2,3-dichloro-4-fluoroaniline and 1,3-diethyl 2-methylpropanedioate as a white solid. LC/MS (M+1): 469.0.

Intermediate 29: 1-(2,3-dichloro-4-fluorophenyl)-2,5-dimethyl-6-oxo-1,6-dihydropyrimidin-4-yl 4-methylbenzene-1-sulfonate

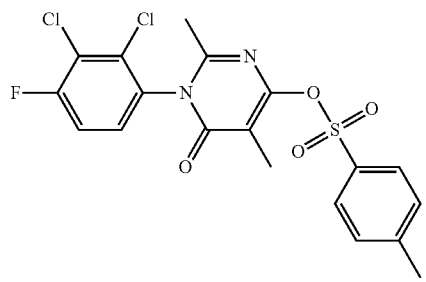

The title compound was obtained following procedure described for intermediate 10 but starting from 2,3-dichloro-4-fluoroaniline and 1,3-diethyl 2-methylpropanedioate as a white solid. LC/MS (M+1): 452.9.

Intermediate 30: 1-(2,3-dichloro-6-methylphenyl)-2,5-dimethyl-6-oxo-1,6-dihydropyrimidin-4-yl 4-methylbenzene-1-sulfonate

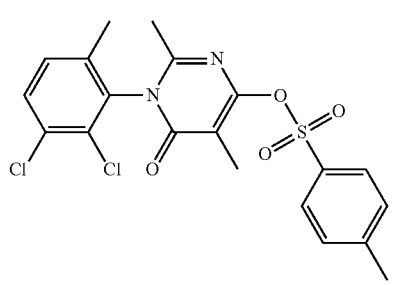

The title compound was obtained following procedure described for intermediate 10 but starting from 2,3-dichloro-6-methylaniline and 1,3-diethyl 2-methylpropanedioate as a white solid. LC/MS (M+1): 456.9.

Intermediate 31: 1-(2-chloro-4-fluoro-3-methylphenyl)-2,5-dimethyl-6-oxo-1,6-dihydropyrimidin-4-yl 4-methylbenzene-1-sulfonate

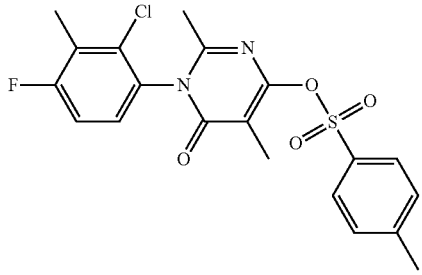 [SMILES: Cc1ccc(S(=O)(=O)Oc2nc(C)n(-c3ccc(F)c(Cl)c3Cl)c(=O)c2C)cc1]

The title compound was obtained following procedure described for intermediate 10 but starting from 2-chloro-4-fluoro-3-methylaniline and 1,3-diethyl 2-methylpropanedioate as a white solid. LC/MS (M+1): 436.9.

Intermediate 32: 1-(2,4-difluoro-3-methoxyphenyl)-2,5-dimethyl-6-oxo-1,6-dihydropyrimidin-4-yl 4-methylbenzene-1-sulfonate

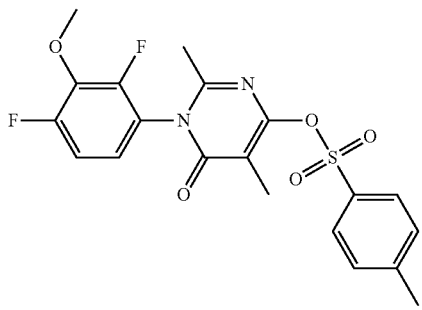 [SMILES: COc1c(F)ccc(-n2c(C)nc(OS(=O)(=O)c3ccc(C)cc3)c(C)c2=O)c1F]

The title compound was obtained following procedure described for intermediate 10 but starting from 2,4-difluoro-3-methoxyaniline and 1,3-diethyl 2-methylpropanedioate as a brown solid. LC/MS (M+1): 437.1.

Intermediate 33: 1-(2-chloro-3-cyanophenyl)-2,5-dimethyl-6-oxo-1,6-dihydropyrimidin-4-yl 4-methylbenzene-1-sulfonate

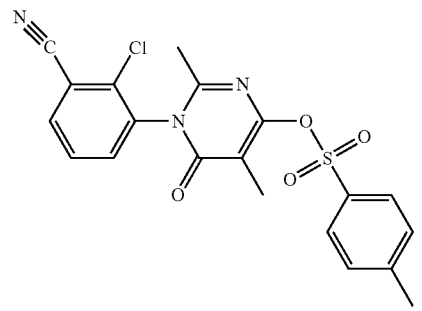 [SMILES: Cc1ccc(S(=O)(=O)Oc2nc(C)n(-c3cccc(C#N)c3Cl)c(=O)c2C)cc1]

The title compound was obtained following procedure described for intermediate 10 but starting from 3-amino-2-chlorobenzonitrile and 1,3-diethyl 2-methylpropanedioate as a yellow solid. LC/MS (M+1): 430.1.

Intermediate 34: 1-(2-chloro-3,4-difluorophenyl)-2,5-dimethyl-6-oxo-1,6-dihydropyrimidin-4-yl 4-methylbenzene-1-sulfonate

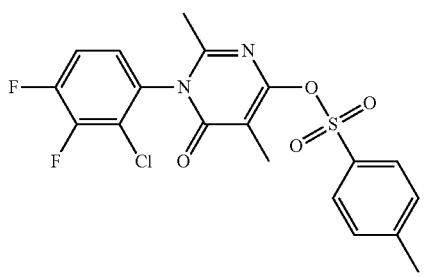 [SMILES: Cc1ccc(S(=O)(=O)Oc2nc(C)n(-c3ccc(F)c(F)c3Cl)c(=O)c2C)cc1]

The title compound was obtained following procedure described for intermediate 10 but starting from 2-chloro-3,4-difluoroaniline and 1,3-diethyl 2-methylpropanedioate as a yellow solid. LC/MS (M+1): 441.1.

Intermediate 35: 2-amino-1-(2,3-dichorophenyl)-5-methyl-6-oxo-1,6-dihydropyrimidin-4-yl 4-methylbenzene-1-sulfonate

Step 1: 3-(2,3-dichlorophenyl)-6-hydroxy-5-methyl-2-sulfanyl-3,4-dihydropyrimidin-4-one

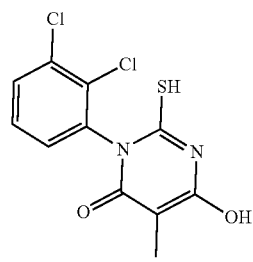 [SMILES: Cc1c(O)nc(S)n(-c2cccc(Cl)c2Cl)c1=O]

A solution of 2,3-dichlorophenylthiourea (3.0 g, 12.9 mmol), 1,3-diethyl 2-methylpropanedioate (3.59 g, 25.8 mmol), 18-Crown-6 (1.79 g, 6.445 mmol) and MeONa (4.64 g, 25.8 mmol) in dioxane (30 mL) was stirred for 3 h at 70° C. under nitrogen atmosphere. Solvent was removed under reduced pressure and the residue was purified by flash chromatography on silica (PE:EtOAc, 1:1) to afford the title compound as an off-white solid (4 g, 83.6%). LC/MS (M+1): 302.9.

Step 2: 3-(2,3-dichlorophenyl)-6-hydroxy-5-methyl-2-(methylsulfanyl)-3,4-dihydro pyrimidin-4-one

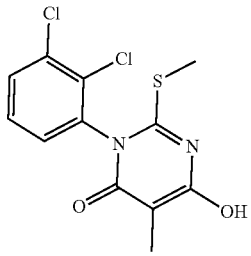 [SMILES: CSc1nc(O)c(C)c(=O)n1-c1cccc(Cl)c1Cl]

Methyliodide (2.0 mL, 14.1) was added to a solution of 3-(2,3-dichlorophenyl)-6-hydroxy-5-methyl-2-sulfanylpyrimidin-4-one (2.0 g, 5.4 mmol) in THF (2 mL) maintained at 0° C. under nitrogen atmosphere. The reaction mixture was then stirred for 3 h at room temperature and partially concentrated under reduced pressure. Precipitate was filtered-off, washed with DCM and dried under reduced pressure to give the title compound as an off-white solid (1.5 g, 88.7%). LC/MS (M+1): 317.0.

Step 3: 3-(2,3-dichlorophenyl)-6-hydroxy-5-methyl-2-(methylsulfanyl)-3,4-dihydropyrimidin-4-one

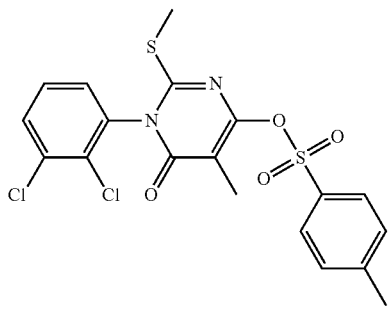 [SMILES: CSc1nc(OS(=O)(=O)c2ccc(C)cc2)c(C)c(=O)n1-c1cccc(Cl)c1Cl]

The title compound was obtained following procedure described for intermediate 10 but starting from 3-(2,3-dichlorophenyl)-6-hydroxy-5-methyl-2-(methylsulfanyl)-3,4-dihydropyrimidin-4-one as an off-white solid. LC/MS (M+1): 471.0.

Step 4: 1-(2,3-dichlorophenyl)-2-methanesulfonyl-5-methyl-6-oxo-1,6-dihydropyrimidin-4-yl 4-methylbenzene-1-sulfonate

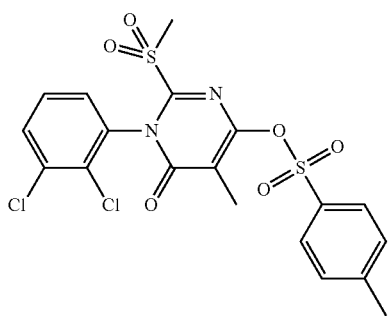 [SMILES: Cc1ccc(S(=O)(=O)Oc2nc(S(C)(=O)=O)n(-c3cccc(Cl)c3Cl)c(=O)c2C)cc1]

A solution of m-CPBA (1.5 g, 6.1 mmol) in DCM (10 mL) was added dropwise to a solution of 1-(2,3-dichlorophenyl)-5-methyl-2-(methylsulfanyl)-6-oxopyrimidin-4-yl 4-methylbenzenesulfonate (650 mg, 1.3 mmol) in DCM (20 mL) maintained at 0° C. The reaction mixture was then stirred at RT for 4 h. Solvent was removed under reduced pressure and the residue was purified by flash chromatography on silica (PE/EtOAc; 5:1) to afford the title compound as a white solid (550 mg, 89%). LC/MS: 503.0 (M+1); 566.0 (M+ACN+Na).

Step 5: 2-amino-1-(2,3-dichlorophenyl)-5-methyl-6-oxo-1,6-dihydropyrimidin-4-yl 4-methylbenzene-1-sulfonate

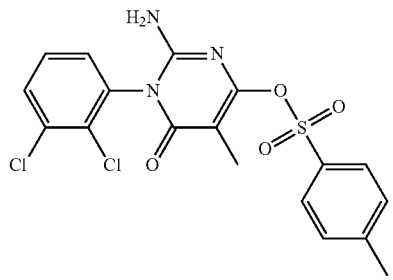 [SMILES: Cc1ccc(S(=O)(=O)Oc2nc(N)n(-c3cccc(Cl)c3Cl)c(=O)c2C)cc1]

A solution of 1-(2,3-dichlorophenyl)-2-methanesulfonyl-5-methyl-6-oxopyrimidin-4-yl 4-methylbenzenesulfonate (500 mg, 0.992 mmol) in MeOH/NH$_3$ (5.0 mL) was stirred for 1 h at room temperature. The resulting mixture was concentrated under reduced pressure to afford the title compound as a white solid (500 mg, 92.8%). LC/MS (M+1): 440.0.

Intermediate 36b: (1M)-1-(2,3-dichlorophenyl)-2,5-dimethyl-6-oxo-1,6-dihydropyrimidin-4-yl trifluoromethanesulfonate

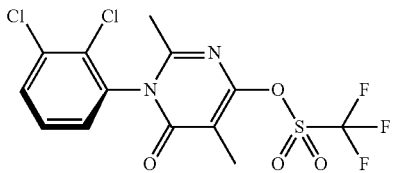

Trifluoromethanesulfonic anhydride (0.89 ml; 5.26 mmol) was added over 10 minutes to a solution of (3M)-3-(2,3-dichlorophenyl)-6-hydroxy-2,5-dimethyl-3,4-dihydropyrimidin-4-one (Intermediate 7b, 1.00 g; 3.51 mmol) and pyridine (0.57 mL; 7.01 mmol) in DCM (6 mL) maintained at 0° C. The reaction mixture was stirred at 0° C. for an additional 20 minutes before the addition of methanol (1 mL) followed by water (5 mL). The mixture was stirred at 0° C. for an additional 30 minutes. The phases were separated, and the organic phase was washed with water (4 mL), brine (4 mL), dried over sodium sulfate, filtered and concentrated. Purification by flash chromatography on silica (hexanes:EtOAc, gradient from 90:10 to 60:40) afforded the title compound as a gum (1.38 g, 94%). 1H NMR (400 MHz, DMSO-d6): 7.89 (dd, J=8.1, 1.5 Hz, 1H), 7.73 (dd, J=8.0, 1.6 Hz, 1H), 7.63 (t, J=8.0 Hz, 1H), 2.13 (s, 3H), 2.01 (s, 3H). LC/MS (M+1): 416.9.

Intermediate 36: 1-(2,3-dichlorophenyl)-2,5-dimethyl-6-oxo-1,6-dihydropyrimidin-4-yl trifluoromethanesulfonate

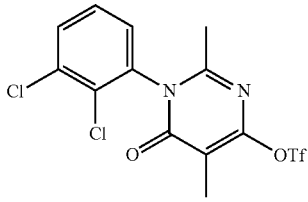 [SMILES: Cc1c(OS(=O)(=O)C(F)(F)F)nc(C)n(-c2cccc(Cl)c2Cl)c1=O]

The title compound was obtained following procedure described for intermediate 36b but starting from racemic mixture 3-(2,3-dichlorophenyl)-6-hydroxy-2,5-dimethyl-3,4-dihydropyrimidin-4-one (Intermediate 7) as a yellow oil. LC/MS (M+1): 419.

Intermediate 37: 2-amino-1-(2,3-dichlorophenyl)-5-methyl-6-oxo-1,6-dihydro-pyrimidin-4-yl trifluoromethanesulfonate

Step 1: 1-(2,3-dichlorophenyl)-5-methyl-2-(methylsulfanyl)-6-oxo-1,6-dihydropyrimidin-4-yl trifluoromethanesulfonate

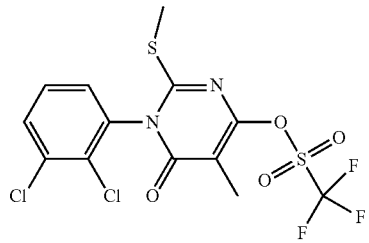 [SMILES: CSc1nc(OS(=O)(=O)C(F)(F)F)c(C)c(=O)n1-c1cccc(Cl)c1Cl]

The title compound was obtained following procedure described for intermediate 36 but starting from 3-(2,3-dichlorophenyl)-6-hydroxy-5-methyl-2-(methylsulfanyl)-3,4-dihydropyrimidin-4-one as a white solid. LC/MS (M+1): 448.9.

Step 2: 2-amino-1-(2,3-dichlorophenyl)-5-methyl-6-oxo-1,6-dihydropyrimidin-4-yl trifluoroinethanesulfonate

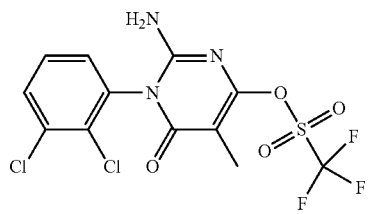 [SMILES: Cc1c(OS(=O)(=O)C(F)(F)F)nc(N)n(-c2cccc(Cl)c2Cl)c1=O]

The title compound was obtained following procedure described for intermediate 35, step 3 to 5 but starting from 1-(2,3-dichlorophenyl)-5-methyl-2-(methylsulfanyl)-6-oxo-1,6-dihydropyrimidin-4-yl trifluoromethanesulfonate as a white solid. LC/MS (M+1): 417.9.

Intermediate 38: 3H-spiro[furo[2,3-b]pyridine-2,4'-piperidin]-3-amine

Step 1: 3-(1,3-dithian-2-yl)-2-fluoropyridine

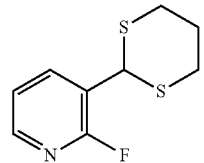 [SMILES: Fc1ncccc1C1SCCCS1]

To a solution of 2-fluoropyridine-3-carbaldehyde (46.0 g, 349.3 mmol) and 1,3-propanedithiol (43.8 g, 384.2 mmol) in DCM (500 mL) was added $BF_3 \cdot Et_2O$ (29 mL, 107.6 mmol, 0.31 eq., 47%) dropwise at room temperature. The resulting mixture was stirred for 16 h at room temperature. The reaction was quenched with saturated $NaHCO_3$ (200 mL) and extracted with EtOAc (3×200 mL). The combined organic layers were dried over anhydrous $Na_2SO_4$, filtered and concentrated. Purification by flash chromatography on silica (PE:EtOAc, 10:1) afforded the title compound as a white solid (59 g, 63%). LC/MS (M+1): 216.

Step 2: Tert-Butyl 4-[2-(2-fluoropyridin-3-yl)-1,3-dithian-2-yl]-4-hydroxypiperidine-1-carboxylate

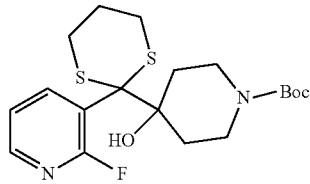 [SMILES: CC(C)(C)OC(=O)N1CCC(O)(C2(c3cccnc3F)SCCCS2)CC1]

A solution of LDA (240 mL, 2M in THF) was added dropwise to a solution of 3-(1,3-dithian-2-yl)-2-fluoropyridine (59.0 g, 220.3 mmol) in THF (150 mL) maintained at −78° C. The resulting mixture was then stirred for 60 min at −20° C. before the addition of a solution of tert-butyl 4-oxopiperidine-1-carboxylate (92.4 g, 440.6 mmol) in THF (30 mL) at −78° C. The resulting mixture was stirred for an additional 1 h at −78° C. and quenched with saturated $NH_4Cl$ (500 mL) at 0° C. It was extracted with EtOAc (3×300 mL). The combined organic layers were dried over anhydrous $Na_2SO_4$, filtered and concentrated. Purification by flash chromatography on silica (PE:EtOAc, 5:1) afforded the title compound as a white solid ((80 g, 87%). LC/MS: 359 (M+H-56)

Step 3: Tert-Butyl 4-(2-fluoropyridine-3-carbonyl)-4-hydroxypiperidine-1-carboxylate

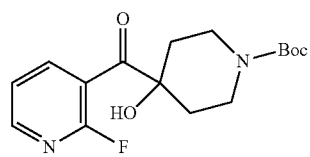 [SMILES: CC(C)(C)OC(=O)N1CCC(O)(C(=O)c2cccnc2F)CC1]

A solution of tert-butyl 4-[2-(2-fluoropyridin-3-yl)-1,3-dithian-2-yl]-4-hydroxypiperidine-1-carboxylate (90.0 g, 213.6 mmol), TBAB (21.7 g, 64.1 mmol), 21^[2]-tribromane.pyridine (143.8 g, 427.2 mmol) and pyridine (27.2 mL, 320.4 mmol, 1.50 eq.) in DCM (1 L) and H$_2$O (200 mL) was stirred for 10 h at room temperature. The reaction mixture was then extracted with DCM (3×300 mL). The combined organic layers were dried over anhydrous Na$_2$SO$_4$, filtered and concentrated. Purification by flash chromatography on silica (PE:EtOAc, 2:1) afforded the title compound as a yellow solid (50.0 g, 71%). LC/MS: 269 (M+H-56).

Step 4: Tert-Butyl 3-oxospiro[furo[2,3-b]pyridine-2,4-piperidine]-1-carboxylate

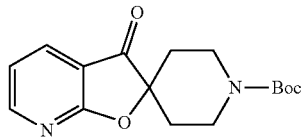 [SMILES: CC(C)(C)OC(=O)N1CCC2(CC1)Oc1ncccc1C2=O]

t-BuOK (6.51 g, 55.1 mmol) was added to a solution of tert-butyl 4-(2-fluoropyridine-3-carbonyl)-4-hydroxypiperidine-1-carboxylate (17.0 g, 50.1 mmol) in dioxane (170 mL) at room temperature. After stirring for 2 h, the resulting mixture was poured into water (200 mL) and extracted with EtOAc (3×200 mL). The combined organic layers were dried over anhydrous Na$_2$SO$_4$, filtered and concentrated. Purification by flash chromatography on silica (PE:EtOAc 5:1) afforded the title compound as a white solid (8.5 g, 53%). LC/MS: 249 (M+H-56).

Step 5: Tert-butyl 3-[[(R)-2-methylpropane-2-sulfinyl]imino]spiro[furo[2,3-b]pyridine-2,4'-piperidine]-1'-carboxylate

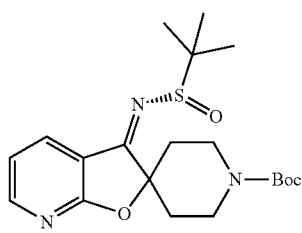

A mixture of tert-butyl 3-oxospiro[furo[2,3-b]pyridine-2,4-piperidine]-1-carboxylate (8.50 g, 26.8 mmol), (R)-2-methylpropane-2-sulfinamide (20.5 g, 160.7 mmol) and Ti(OEt)$_4$'(60 mL) was stirred for 2 h at 90° C. The resulting mixture was cooled to room temperature and poured into with H$_2$O (150 mL). it was filtered, and the filtrate was extracted with EtOAc (3×150 mL). The combined organic layers were dried over anhydrous Na$_2$SO$_4$, filtered and concentrated. Purification by flash chromatography on silica (PE:EtOAc, 5:1) afforded the title compound as a yellow solid (11 g, 96%). LC/MS (M+1): 408.0.

Step 6: Tert-butyl-3-[[(S)-2-methylpropane-2-sulfinyl]amino]-3H-spiro[furo[2,3-b]pyridine-2,4'-piperidine]-1'-carboxylate

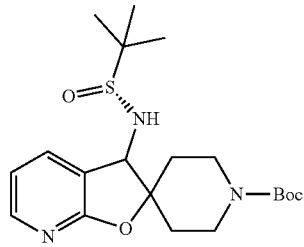 [SMILES: CC(C)(C)OC(=O)N1CCC2(CC1)Oc1ncccc1C2N[S@](=O)C(C)(C)C]

Sodium borohydride (4.66 g, 117 mmol) was added in portions to a stirred solution of tert-butyl 3-[[(R)-2-methylpropane-2-sulfinyl]imino]spiro[furo[2,3-b]pyridine-2,4-piperidine]-1-carboxylate (10.0 g, 23.4 mmol) in THF (100 mL) and MeOH (100 mL) at -50° C. The resulting mixture was stirred for 1 h at -50° C. and quenched with water (10 mL). Solvent was removed under reduced pressure, then the mixture was diluted with water (100 mL) and extracted with ethyl acetate (3×100 mL). Combined organic layers were washed with brine (100 mL), dried over anhydrous sodium sulfate, filtered and concentrated to afford the title compound as a yellow solid (10 g, 62%). LC/MS (M+1): 410.0.

Step 7: 3H-spiro[furo[2,3-b]pyridine-2,4'-piperidin]-3-amine

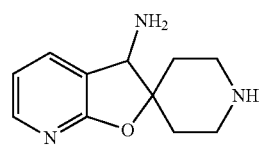 [SMILES: NC1c2cccnc2OC12CCNCC2]

A solution of HC(gas) in 1,4-dioxane (100 mL) was added dropwise to a solution of tert-butyl-3-[[(S)-2-methylpropane-2-sulfinyl]amino]-3H-spiro[furo[2,3-b]pyridine-2,4'-piperidine]-1'-carboxylate (10.0 g, 24.4 mmol) in DCM (60 mL) maintained at 0° C. After stirring for 1 h at room temperature, the resulting mixture was concentrated under reduced pressure. The resulting HCl salt was loaded onto the SiliaBond Propylsulfonic Acid (SCX-2) resin, which was pre-wetted with methanol, eluting with methanol until no HCl was detected. Then the free amine was washed out with 7M NH$_3$ in methanol. The eluent was concentrated under vacuum to give the title compound as an orange oil (4.0 g, 77.7%). LC/MS (M+1): 206.

Intermediate 39: (S)-2-methyl-N-[spiro[furo[2,3-c]pyridine-2,4'-piperidin]-3-ylidene]propane-2-sulfinamide trifluoroacetic acid

Step 1: 4-[(3-bromopyridin-4-yl)methyl]-4-hydroxypiperidine-1-carboxylate

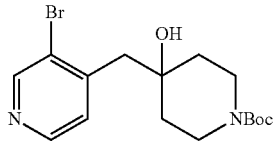 [SMILES: CC(C)(C)OC(=O)N1CCC(O)(Cc2ccncc2Br)CC1]

NaHMDS (3.3 mL of a 1 M solution in THF, 3.3 mmol) was added into a solution of 3-bromo-4-methylpyridine (500 mg, 2.76 mmol) in THF (10 mL) at −60° C. The resulting mixture was stirred for 1 h at −15° C. before the addition of BF₃.Et₂O (2.2 mL, 7.4 mmol, 3.0 eq., 47%) and a solution of tert-butyl 4-oxopiperidine-1-carboxylate (694 mg, 3.31 mmol) in THF (2 mL) at −60° C. After stirring for 2 h at −60° C., the resulting mixture was quenched water (20 mL) and extracted with EtOAc (3×30 mL). Combined organic layers were washed with brine (1×30 mL), dried over anhydrous sodium sulfate, filtered and concentrated under reduced pressure. Purification by flash chromatography on silica (PE:EtOAc, 1:2) afforded the title compound as a yellow oil (5.7 g, 55%). LC/MS (M+1): 372, 374.

Step 2: 3H-spiro[furo[2,3-c]pyridine-2,4'-piperidine]-1'-carboxylate

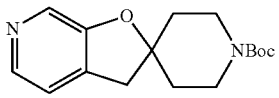

A mixture of tert-butyl 4-[(3-bromopyridin-4-yl)methyl]-4-hydroxypiperidine-1-carboxylate (3.0 g, 7.96 mmol), quinolin-8-ol (267 mg, 1.75 mmol), Cs₂CO₃ (5.10 g, 14.9 mmol) and CuI (143 mg, 0.713 mmol) in toluene (75 mL) was stirred for 16 h at 110° C. The resulting mixture was cooled down, filtered, and concentrated under reduced pressure. The residue was purified by flash chromatography on silica (DCM:MeOH, 12:1) to afford the title compound as a green solid (2.3 g, 95%). LC/MS (M+1): 291.

Step 3: 3-bromo-3H-spiro[furo[2,3-c]pyridine-2,4'-piperidine]-1'-carboxylate

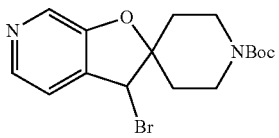 [SMILES: CC(C)(C)OC(=O)N1CCC2(CC1)Oc1cnccc1C2Br]

A solution of tert-butyl 3H-spiro[furo[2,3-c]pyridine-2,4-piperidine]-1-carboxylate (100 mg, 0.328 mmol), AIBN (6 mg, 0.035 mmol) and NBS (92 mg, 0.491 mmol) in CHCl₃ (5.0 mL) was stirred for 4 h at 90° C. The resulting mixture was cooled down to room temperature, poured into a saturated solution of NaHCO₃ (30 mL) and extracted with DCM (3×30 mL). Combined organic layers were washed with brine (1×30 mL), dried over anhydrous sodium sulfate, filtered and concentrated under reduced pressure. The residue was purified by silica gel column chromatography (PE:EtOAc, 1:1) to afford the title compound as a yellow solid (1.0 g, 16% yield, 63% purity). LC/MS (M+1): 369, 371.

Step 4: 3-oxospiro[furo[2,3-c]pyridine-2,4'-piperidine]-1'-carboxylate

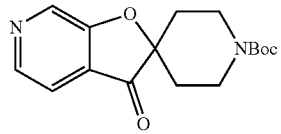 [SMILES: CC(C)(C)OC(=O)N1CCC2(CC1)Oc1cnccc1C2=O]

A mixture of tert-butyl 3-bromo-3H-spiro[furo[2,3-c]pyridine-2,4-piperidine]-1-carboxylate (240 mg, 0.409 mmol, 1.0 eq., 63%), NaHCO₃ (198 mg, 2.25 mmol, 5.49 eq.), DMSO (4 mL) and 4A molecular sieves (20 mg) was stirred for 2.5 h at 120° C. The resulting mixture was cooled down to room temperature, poured into water (30 mL) and extracted with EtOAc (3×30 mL). Combined organic layers were washed with brine (1×30 mL), dried over anhydrous sodium sulfate, filtered and concentrated under reduced pressure. The residue was purified by silica gel column chromatography (PE:EtOAc, 1:1) to afford the title compound as a yellow solid (280 mg, 41% yield, 43% purity). LC/MS (M+1): 305.

Step 5: (3E)-3-[[(S)-2-methylpropane-2-sulfinyl]imino]spiro[furo[2,3-c]pyridine-2,4'-piperidine]-1'-carboxylate

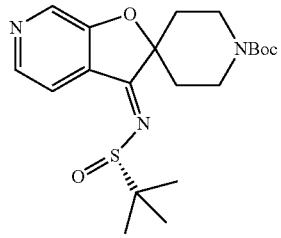 [SMILES: CC(C)(C)OC(=O)N1CCC2(CC1)Oc1cnccc1/C2=N\[S@@](=O)C(C)(C)C]

A mixture of tert-butyl 3-oxospiro[furo[2,3-c]pyridine-2,4-piperidine]-1-carboxylate (280 mg, 0.394 mmol), (S)-2-methylpropane-2-sulfinamide (170 mg, 1.33 mmol) and Ti(OEt)₄ (3 mL) was stirred for 2 h at 90° C. The resulting mixture was cooled down to room temperature, diluted with water (25 mL) and EtOAc (25 mL), filtered. The filter cake was washed with EtOAc (30 mL) and the filtrate was extracted with EtOAc (3×30 mL). Combined organic layers were washed with brine (1×50 mL), dried over anhydrous sodium sulfate, filtered and concentrated under reduced pressure. The residue was purified by flash chromatography on silica (PE:EtOAc, 1:1) to afford the title compound as a yellow solid (180 mg, 99% yield). LC/MS (M=1): 408.

Step 6: (S)-2-methyl-N-[spiro[furo[2,3-c]pyridine-2,4'-piperidin]-3-ylidene]propane-2-sulfinamide Trifluoroacetic Acid

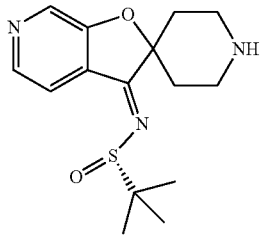 [SMILES: CC(C)(C)[S@](=O)/N=C1\c2ccncc2OC12CCNCC2]

A mixture of tert-butyl (3E)-3-[[(S)-2-methylpropane-2-sulfinyl]imino]spiro-[furo[2,3-c]pyridine-2,4-piperidine]-1-carboxylate (160 mg, 0.345 mmol), TFA (2.0 mL) and DCM (4.0 mL) was stirred for 1 h at 25° C. The resulting mixture was concentrated under reduced pressure to give the title compound as a yellow solid (108 mg, 99%). LC/MS (M+1): 308.

Intermediate 40: 5,7-dihydrospiro[cyclopenta[b]pyridine-6,4'-piperidin]-5-amine Dihydrochloride

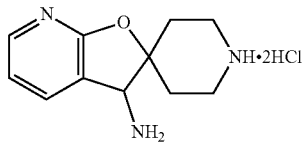

The title compound was obtained following procedure described for intermediate 38, step 4 to 7 but starting from tert-butyl 5-oxo-5,7-dihydrospiro[cyclopenta-[b]pyridine-6,4'-piperidine]-1'-carboxylate (Pharmablock) as light yellow solid (isolated at the HCl salt). LC/MS (M+1): 204.1.

Intermediate 41: (1R)-1,3-dihydrospiro[indene-2,4'-piperidin]-1-amine Dihydrochloride

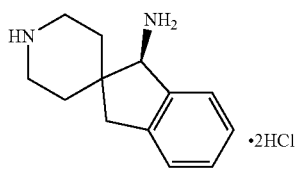 [SMILES: N[C@H]1c2ccccc2CC12CCNCC2]

The title compound was obtained following procedure described for intermediate 38, step 5 to 7 but starting from n-boc-1-oxo-1,3-dihydrospiro[indene-2,4'-piperidine] (Chemshuttle) and (S)-(−)-2-methyl-2-propanesulfinamide as a white solid. LC/MS (M+1):203.1

Intermediate 42: 1-[2-chloro-3-(trifluoromethyl)phenyl]-2-methyl-6-oxo-1,6-dihydropyrimidin-4-yl 4-methylbenzene-1-sulfonate

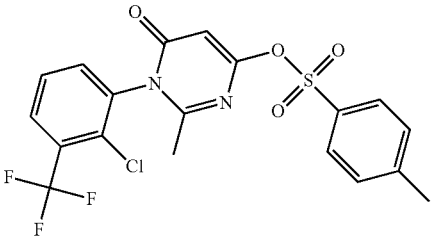 [SMILES: Cc1ccc(S(=O)(=O)Oc2cc(=O)n(-c3cccc(C(F)(F)F)c3Cl)c(C)n2)cc1]

The title compound was obtained following procedure described for intermediate 10 but starting from 2-chloro-3-(trifluoromethyl)aniline (489 mg, 2.4 mmol) as a white solid (350 mg, 24%, 2 steps). LC/MS (M+1): 458.9.

Intermediate 43: Methyl 2-[1-(2,3-dichlorophenyl)-2-methyl-4-[(4-methylbenzenesulfonyl)oxy]-6-oxo-1,6-dihydropyrimidin-5-yl]acetate

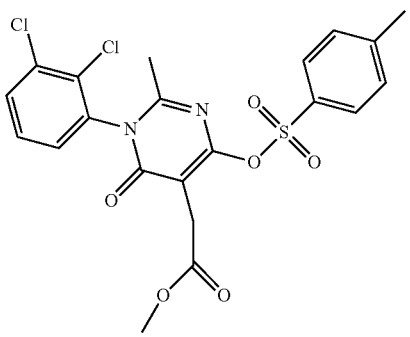 [SMILES: COC(=O)Cc1c(OS(=O)(=O)c2ccc(C)cc2)nc(C)n(-c2cccc(Cl)c2Cl)c1=O]

The title compound was obtained following procedure described for intermediate 10 but starting from 2,3-dichloroaniline (200 mg, 1.2 mmol) and 1,1,2-triethyl ethane-1,1,2-tricarboxylate (246 mg, 4.7 mmol) as a yellow solid (250 mg, 68%, 2 steps). LC/MS (M+1): 496.9.

Compound 1: 6-(4-amino-4-methylpiperidin-1-yl)-3-(2,3-dichlorophenyl)-2-(methylsulfanyl)-3,4-dihydropyrimidin-4-one

Step 1: Tert-Butyl N-{1-[1-(2,3-dichlorophenyl)-2-(methylsulfanyl)-6-oxo-1,6-dihydropyrimidin-4-yl]-4-methylpiperidin-4-yl}carbamate

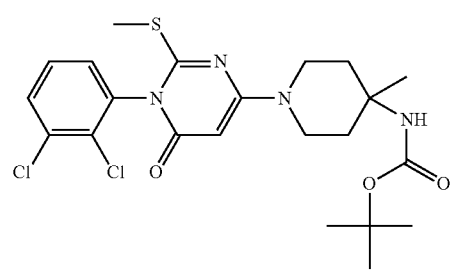 [SMILES: CSc1nc(N2CCC(C)(NC(=O)OC(C)(C)C)CC2)cc(=O)n1-c1cccc(Cl)c1Cl]

A solution of 6-chloro-3-(2,3-dichlorophenyl)-2-(methylsulfanyl)-3,4-dihydropyrimidin-4-one (intermediate 1, 100 mg; 0.31 mmol) and tert-butyl (4-methylpiperidin-4-yl)carbamate (133 mg; 0.62 mmol) in EtOH (1 mL) was heated at 100° C. for 16 h. Solvent was removed under reduced pressure and the residue was purified by flash chromatography on silica (Hexane:EtOAc, gradient from 70:30 to 0:100) to afford the title compound (60 mg, 98%). LC/MS (M+1): 499.2.

Step 2: 6-(4-amino-4-methylpiperidin-1-yl)-3-(2,3-dichlorophenyl)-2-(methylsulfanyl)-3,4-dihydropyrimidin-4-one

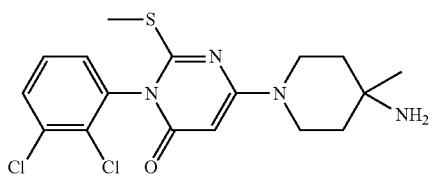 [SMILES: CSc1nc(N2CCC(C)(N)CC2)cc(=O)n1-c1cccc(Cl)c1Cl]

A solution of tert-butyl N-{1-[1-(2,3-dichlorophenyl)-2-(methylsulfanyl)-6-oxo-1,6-dihydropyrimidin-4-yl]-4-methylpiperidin-4-yl}carbamate (34 mg; 0.07 mmol) in DCM (2 mL) and TFA (0.5 mL) was stirred at RT for 2 h. Solvent were removed under reduced pressure and the crude was purified by preparative HPLC (Xbridge Prep. C18. 5 μm, 30 mm×50 mm, ACN in water/0.1% NH$_4$OH, gradient from 20 to 80% in 12 min) to afford the title compound as a white powder (18 mg, 67%). 1H NMR (400 MHz, DMSO-d6) δ 7.82 (dd, J=7.2, 2.5 Hz, 1H), 7.57-7.48 (m, 2H), 5.27 (s, 1H), 3.73 (brs, 2H), 3.51 (m, 2H), 2.42 (s, 3H), 1.67 (brs, 2H), 1.43 (m, 4H), 1.10 (s, 3H). LC/MS (M+1): 399.0. HPLC purity: 99.0%.

Compound 2: 6-(4-amino-4-methylpiperidin-1-yl)-3-(2,3-dichlorophenyl)-2-methyl-3,4-dihydropyrimidin-4-one

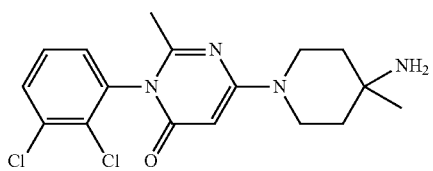 [SMILES: Cc1nc(N2CCC(C)(N)CC2)cc(=O)n1-c1cccc(Cl)c1Cl]

The title compound was obtained following procedure described in compound 1 but starting from 6-chloro-3-(2,3-dichlorophenyl)-2-methyl-3,4-dihydropyrimidin-4-one (intermediate 2, 100 mg; 0.35 mmol) and tert-butyl (4-methylpiperidin-4-yl)carbamate (111 mg; 0.52 mmol) as a white powder (29 mg, 45%). 1H NMR (400 MHz, DMSO-d6) δ 7.78 (dt, J=6.3, 2.7 Hz, 1H), 7.59-7.48 (m, 2H), 5.35 (s, 1H), 3.70 (m, 2H), 3.47 (m, 2H), 1.98 (s, 3H), 1.47 (brs, 2H), 1.40 (m, 4H), 1.09 (d, J=2.1 Hz, 3H). LC/MS (M+1): 367.1

Compounds 2a and 2b: (3P)-6-(4-amino-4-methylpiperidin-1-yl)-3-(2,3-dichlorophenyl)-2-methyl-3,4-dihydropyrimidin-4-one and (3M)-6-(4-amino-4-methylpiperidin-1-yl)-3-(2,3-dichlorophenyl)-2-methyl-3,4-dihydropyrimidin-4-one

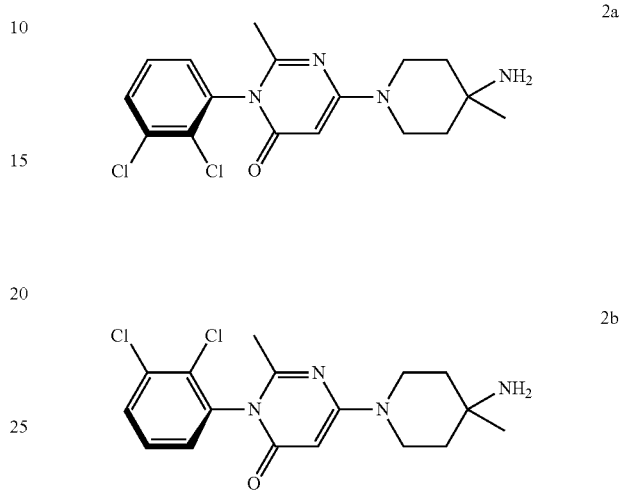

Racemic mixture of 6-(4-amino-4-methylpiperidin-1-yl)-3-(2,3-dichlorophenyl)-2-methyl-3,4-dihydropyrimidin-4-one was separated by Preparative SFC on an AD-H column (250×21 mm, 5 micron) using McOH-NH$_4$OH 20 mM: CO$_2$ 25:75 (% v/v) as eluent.

First eluting isomer (compound 2a): 62 mg, Rt=2.41 min, purity: 100%, 1H NMR (400 MHz, DMSO-d6) 7.84-7.74 (m, 1H), 7.58-7.48 (m, 2H), 5.35 (s, 1H), 3.70 (m, 2H), 3.49 (m, 2H), 1.98 (s, 3H), 1.54 (s, 2H), 1.41 (m, 4H), 1.09 (s, 3H).

Second eluting isomer (compound 2b): 75 mg, Rt=2.87 min, purity: 100%. 1H NMR (400 MHz, DMSO-d6) 7.81 (dd, J=7.8, 1.9 Hz, 1H), 7.62-7.45 (m, 2H), 5.47 (s, 1H), 4.01 (m, 2H), 2.01 (s, 3H), 1.72 (m, 4H), 1.38 (s, 3H).

Compound 3: 6-[(3S,4S)-4-amino-3-methyl-2-oxa-8-azaspiro[4.5]decan-8-yl]-3-(2,3-dichlorophenyl)-2-methyl-3,4-dihydropyrimidin-4-one

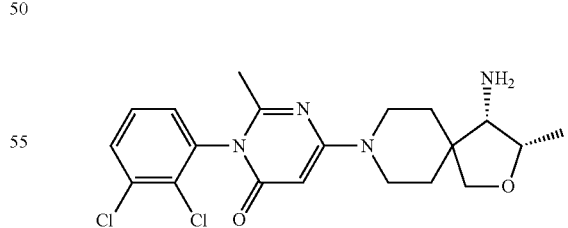

The title compound was obtained following procedure described in compound 1 but starting from 6-chloro-3-(2,3-dichlorophenyl)-2-methyl-3,4-dihydropyrimidin-4-one (intermediate 2, 150 mg; 0.52 mmol) and tert-butyl N-[(3S,4S)-3-methyl-2-oxa-8-azaspiro[4.5]decan-4-yl]carbamate (154 mg; 0.57 mmol) as a white powder (12 mg, 19%). 1:1 mixture of two atropisomers. LC/MS (M+1): 424.2.

Compounds 3a and 3b: (3P)-6-[(3S,4S)-4-amino-3-methyl-2-oxa-8-azaspiro[4.5]decan-8-yl]-3-(2,3-dichlorophenyl)-2-methyl-3,4-dihydropyrimidin-4-one and (3M)-6-[(3S,4S)-4-amino-3-methyl-2-oxa-8-azaspiro[4.5]decan-8-yl]-3-(2,3-dichlorophenyl)-2-methyl-3,4-dihydropyrimidin-4-one

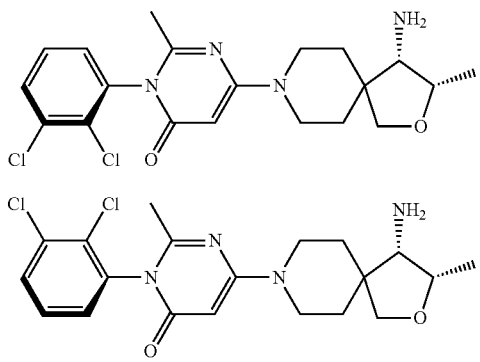

The atropisomers from 6-[(3S,4S)-4-amino-3-methyl-2-oxa-8-azaspiro[4.5]decan-8-yl]-3-(2,3-dichlorophenyl)-2-methyl-3,4-dihydropyrimidin-4-one were separated by Preparative SFC (AS-H column, 250×21 mm, 5 micron, MeOH—NH$_4$OH 20 mM: CO$_2$ 30:70).

First eluting isomer (compound 3a): 33 mg, Rt=3.88 min, purity=100%. 1H NMR (400 MHz, DMSO-d6) 7.86-7.73 (m, 1H), 7.58-7.46 (m, 2H), 5.37 (s, 1H), 4.11-4.01 (m, 1H), 3.80 (m, 2H), 3.67 (d, J=8.4 Hz, 1H), 3.48 (d, J=8.4 Hz, 1H), 3.36-3.28 (m, 2H), 2.90 (m, 1H), 1.99 (s, 3H), 1.78-1.36 (m, 6H), 1.09 (d, J=6.5 Hz, 3H).

Second eluting isomer (compound 3b): 30 mg, Rt=4.50 min, purity=100%. 1H NMR (400 MHz, DMSO-d6) 7.86-7.74 (m, 1H), 7.60-7.44 (m, 2H), 5.37 (s, 1H), 4.14-4.00 (m, 1H), 3.78 (brs, 2H), 3.67 (d, J=8.5 Hz, 1H), 3.48 (d, J=8.4 Hz, 1H), 3.41 (m, 1H), 3.28 (m, 1H), 2.90 (d, J=5.1 Hz, 1H), 1.99 (s, 3H), 1.80-1.33 (m, 6H), 1.08 (d, J=6.4 Hz, 3H).

Compound 4: 6-[4-(aminomethyl)-4-methylpiperidin-1-yl]-3-(2,3-dichlorophenyl)-2-methyl-3,4-dihydropyrimidin-4-one

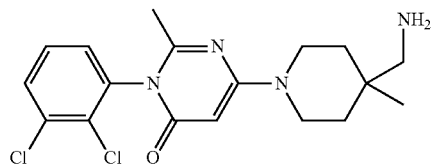 [SMILES: Cc1nc(N2CCC(C)(CN)CC2)cc(=O)n1-c1cccc(Cl)c1Cl]

The title compound was obtained following procedure described for compound 1 but starting from 6-chloro-3-(2,3-dichlorophenyl)-2-methyl-3,4-dihydropyrimidin-4-one (intermediate 2, 150 mg; 0.52 mmol) and 4-(boc-aminomethyl)-4-methylpiperidine hydrochloride (151 mg; 0.57 mmol) as a white powder (5 mg, 3%). 1H NMR (400 MHz, DMSO-d6) 7.79 (t, J=5.4 Hz, 1H), 7.59-7.50 (m, 2H), 5.34 (s, 1H), 3.80 (m, 2H), 3.28 (m, 4H), 2.41 (s, 2H), 1.98 (s, 3H), 1.51-1.38 (m, 2H), 1.27 (d, J=13.7 Hz, 2H), 0.93 (s, 3H). LC/MS (M+1): 381.2.

Compound 5: 2-amino-6-[(3S,4S)-4-amino-3-methyl-2-oxa-8-azaspiro[4.5]decan-8-yl]-3-(2,3-dichlorophenyl)-3,4-dihydropyrimidin-4-one

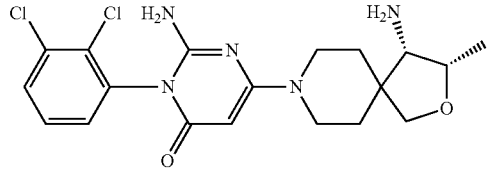 [SMILES: C[C@@H]1OCC2(CCN(c3cc(=O)n(-c4cccc(Cl)c4Cl)c(N)n3)CC2)[C@@H]1N]

A solution of 2-amino-6-chloro-3-(2,3-dichlorophenyl)-3,4-dihydropyrimidin-4-one (intermediate 4, 75 mg; 0.18 mmol) and tert-butyl N-[(3S,4S)-3-methyl-2-oxa-8-azaspiro[4.5]decan-4-yl]carbamate (71 mg; 0.26 mmol) in EtOH (2.3 mL) was stirred for 20 h at 100° C. Solvent was removed under reduced pressure and the residue was diluted with water (10 mL) and extracted with EtOAc (25 mL). Organic layer was washed with water (2×) and brine, dried over anhydrous sodium sulfate, filtered and concentrated. This crude was directly re-dissolved in DCM (1.8 mL) and TFA (0.9 mL) and stirred at RT for 1 h. Solvents were removed under reduced pressure and the residue was co-evaporated with toluene three times. Purification by preparative HPLC (XBridge Prep C-18 OBD 10 μM, 30×250.10-45% ACN/Water (0.1% Ammonium Hydroxide), 12 minutes gradient) afforded the title compound as a white powder (8 mg, 22%). 1H NMR (400 MHz, DMSO-d6) 7.71 (dd, J=8.2, 1.5 Hz, 1H), 7.45 (t, J=8.0 Hz, 1H), 7.32 (dd, J=7.9, 1.5 Hz, 1H), 6.44 (s, 2H), 4.90 (s, 1H), 4.11-3.99 (m, 1H), 3.81-3.67 (m, 2H), 3.65 (d, J=8.5 Hz, 1H), 3.47 (dd, J=8.4, 1.5 Hz, 1H), 3.28-3.08 (m, 2H), 2.88 (dd, J=5.1, 1.1 Hz, 1H), 1.68 (ddd, J=13.2, 9.2, 3.8 Hz, 1H), 1.63-1.51 (m, 1H), 1.51-1.24 (m, 4H), 1.07 (d, J=6.4 Hz, 3H). LC/MS (M+1): 424.1. HPLC purity: 100%.

Compounds 6a and 6b: (+/−)-(3M)-6-[(4S)-4-amino-4-methylcyclohex-1-en-1-yl]-3-(2,3-dichlorophenyl)-2-methyl-3,4-dihydropyrimidin-4-one (racemic-relative configuration) and (+/−)-(3P)-6-[(4S)-4-amino-4-methylcyclohex-1-en-1-yl]-3-(2,3-dichlorophenyl)-2-methyl-3,4-dihydropyrimidin-4-one (Racemic, Relative Configuration)

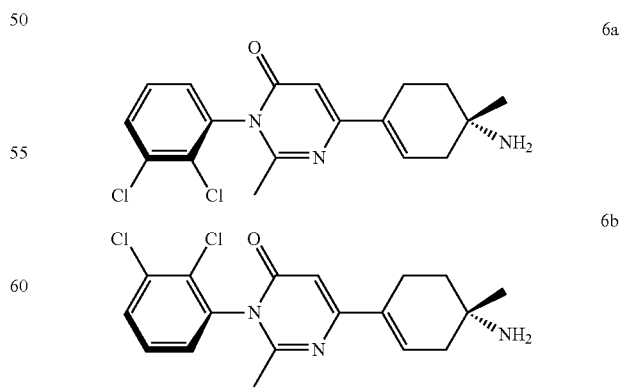

A mixture of 6-chloro-3-(2,3-dichlorophenyl)-2-methyl-3,4-dihydropyrimidin-4-one (intermediate 2, 25 mg; 0.09 mmol), tert-butyl N-[1-methyl-4-(4,4,5,5-tetramethyl-1,3,2-dioxaborolan-2-yl)cyclohex-3-en-1-yl]carbamate (35 mg; 0.10 mmol), tetrakis(triphenylphosphine)palladium(0) (20 mg; 0.02 mmol) and cesium carbonate (62 mg; 0.19 mmol) in dioxane (1 mL) and water (0.3 mL) was stirred at room temperature for 48 h. It was then diluted with water and extracted with EtOAc. Organic layer was dried over anhydrous sodium sulfate, filtered and concentrated. A solution of HCl in dioxane (4 mL of a 4N solution) was then added and the reaction mixture was stirred at RT for 30 min. Solvent was removed under reduced pressure and the crude was purified by preparative HPLC (XBridge C18. 5 um, 30 mm×250 mm, MeCN in H$_2$O (0.1% ammonia) gradient from 5 to 80% in 25 min) to give the title compounds (mixture of isomers, stereochemistry attributed arbitrarily).

First eluting isomer (compound 6a): 3.5 mg, 1H NMR (400 MHz, DMSO-d6) 7.84 (dd, J=7.8, 1.9 Hz, 1H), 7.65-7.56 (m, 2H), 7.09 (d, J=4.5 Hz, 1H), 6.32 (s, 1H), 3.28 (s, 1H), 2.18 (d, J=8.8 Hz, 1H), 2.08 (s, 3H), 1.56 (t, J=6.5 Hz, 2H), 1.05 (s, 3H). LC/MS (M+1): 364.1

Second eluting isomer (compound 6b): 2 mg. LC/MS (M+1): 364.1

Compound 7: 6-[(3S,4S)-4-amino-3-methyl-2-oxa-8-azaspiro[4.5]decan-8-yl]-2-methyl-3-phenyl-3,4-dihydropyrimidin-4-one

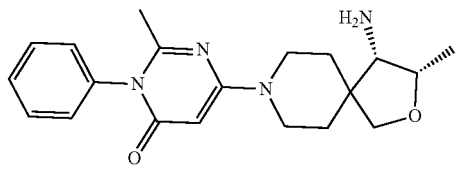 [SMILES: Cc1nc(N2CCC3(CC2)CO[C@@H](C)[C@H]3N)cc(=O)n1-c1ccccc1]

The title compound was obtained following procedure described in compound 1 but starting from 6-chloro-2-methyl-3-phenyl-3,4-dihydropyrimidin-4-one (intermediate 5, 50 mg; 0.23 mmol) and tert-butyl N-[(3S,4S)-3-methyl-2-oxa-8-azaspiro[4.5]decan-4-yl]carbamate (61 mg; 0.23 mmol) as a white powder (21 mg, 33%). 1H NMR (400 MHz, DMSO-d6) 7.55-7.42 (m, 3H), 7.32-7.25 (m, 2H), 5.35 (s, 1H), 4.10-4.02 (m, 1H), 3.78 (m, 2H), 3.67 (d, J=8.4 Hz, 1H), 3.48 (d, J=8.4 Hz, 1H), 3.42-3.33 (m, 1H), 3.29-3.22 (m, 1H), 2.90 (d, J=5.1 Hz, 1H), 1.99 (s, 3H), 1.71 (m, 1H), 1.60 (m, 1H), 1.54-1.40 (m, 2H), 1.08 (d, J=6.4 Hz, 3H). LC/MS (M+1):355.2.

Compound 8: 2-amino-6-[(1R)-1-amino-3,3-difluoro-8-azaspiro[4.5]decan-8-yl]-3-(2,3-dichlorophenyl)-3,4-dihydropyrimidin-4-one

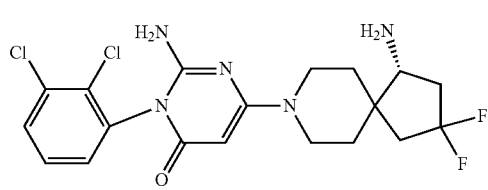 [SMILES: Nc1nc(N2CCC3(CC2)CC(F)(F)C[C@H]3N)cc(=O)n1-c1cccc(Cl)c1Cl]

The title compound was obtained following procedure described in compound 5 but starting from 2-amino-6-chloro-3-(2,3-dichlorophenyl)-3,4-dihydropyrimidin-4-one (intermediate 4, 31 mg; 0.11 mmol) and tert-butyl N-[(1R)-3,3-difluoro-8-azaspiro[4.5]decan-1-yl]carbamate (46 mg; 0.16 mmol) as a white powder (16 mg, 33%). 1H NMR (400 MHz, DMSO-d6) 7.71 (dd, J=8.1, 1.5 Hz, 1H), 7.45 (t, J=8.0 Hz, 1H), 7.32 (dd, J=7.9, 1.5 Hz, 1H), 6.45 (s, 2H), 4.91 (s, 1H), 4.23-3.97 (m, 2H), 3.05-2.80 (m, 3H), 2.79-2.57 (m, 2H), 2.46-2.26 (m, 2H), 2.10-1.86 (m, 2H), 1.72-1.50 (m, 2H), 1.39-1.18 (m, 2H). LC/MS (M+1): 444.1

Compound 9: 6-[4-(aminomethyl)-4-methylcyclohex-1-en-1-yl]-3-(2,3-dichlorophenyl)-2-methyl-3,4-dihydropyrimidin-4-one

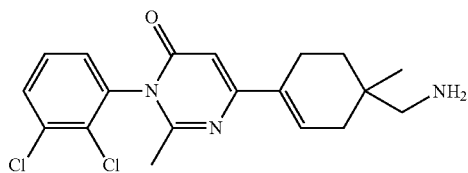 [SMILES: Cc1nc(C2=CCC(C)(CN)CC2)cc(=O)n1-c1cccc(Cl)c1Cl]

The title compound was obtained following procedure described for compound 6 but starting from 6-chloro-3-(2,3-dichlorophenyl)-2-methyl-3,4-dihydropyrimidin-4-one (intermediate 2, 100 mg; 0.35 mmol) and tert-butyl-N-{[1-methyl-4-(4,4,5,5-tetramethyl-1,3,2-dioxaborolan-2-yl)cyclohex-3-en-1-yl]methyl}carbamate (145 mg; 0.41 mmol) as a white powder (mixture of diastereoisomers, 58 mg, 43%). LC/MS (M+1):378.1

Compound 10: 6-(4-amino-4-methylpiperidin-1-yl)-5-chloro-3-(2,3-dichlorophenyl)-2-methyl-3,4-dihydropyrimidin-4-one Step 1: Tert-Butyl N-{1-[5-chloro-1-(2,3-dichlorophenyl)-2-methyl-6-oxo-1,6-dihydropyrimidin-4-yl]-4-methylpiperidin-4-yl}carbamate

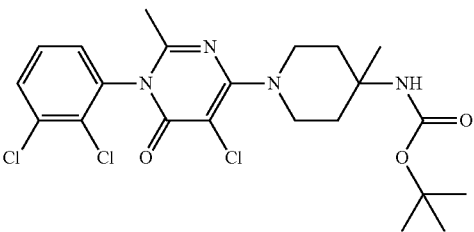 [SMILES: Cc1nc(N2CCC(C)(NC(=O)OC(C)(C)C)CC2)c(Cl)c(=O)n1-c1cccc(Cl)c1Cl]

N-chlorosuccinimide (25 mg; 0.19 mmol) was added to a solution of tert-butyl N-{1-[1-(2,3-dichlorophenyl)-2-methyl-6-oxo-1,6-dihydropyrimidin-4-yl]-4-methylpiperidin-4-yl}carbamate (prepared in compound 2, step 1, 63 mg; 0.13 mmol) in DCM (1 mL) maintained at 0° C. The reaction mixture was then stirred at 0° C. for 2 h. It was then quenched by adding a saturated Na$_2$S$_2$O$_3$ solution and stirring at RT for 10 min. The mixture was extracted with EtOAc, filtered and concentrated. Purification by flash chromatography on silica (hexanes:EtOAc, gradient from 90:10 to 50:50) afforded the title compound (54 mg, 80%). LC/MS (M+1): 501.1.

Step 2: 6-(4-amino-4-methylpiperidin-1-yl)-5-chloro-3-(2,3-dichlorophenyl)-2-methyl-3,4-dihydropyrimidin-4-one

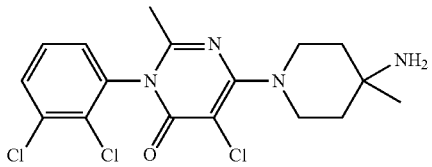 [SMILES: Cc1nc(N2CCC(C)(N)CC2)c(Cl)c(=O)n1-c1cccc(Cl)c1Cl]

The title compound was obtained following procedure describe in compound 1, step 2 but starting from tert-butyl N-{-[5-chloro-1-(2,3-dichlorophenyl)-2-methyl-6-oxo-1,6-dihydropyrimidin-4-yl]-4-methylpiperidin-4-yl}carbamate (54 mg; 0.10 mmol) as a white powder (14 mg, 34%). 1H NMR (400 MHz, DMSO-d6) 7.83 (dd, J=7.9, 1.7 Hz, 1H), 7.65-7.47 (m, 2H), 3.89-3.77 (m, 2H), 3.64 (dd, J=13.5, 8.9 Hz, 2H), 2.00 (s, 3H), 1.51 (d, J=11.8 Hz, 4H), 1.12 (s, 3H); LC/MS (M+1): 401.1.

Compound 11: 6-(4-amino-4-methylpiperidin-1-yl)-3-(2,3-dichlorophenyl)-2-(difluoromethyl)-3,4-dihydropyrimidin-4-one

Step 1: Tert-Butyl N-{1-[1-(2,3-dichlorophenyl)-2-(difluoromethyl)-6-oxo-1,6-dihydropyrimidin-4-yl]-4-methylpiperidin-4-yl}carbamate

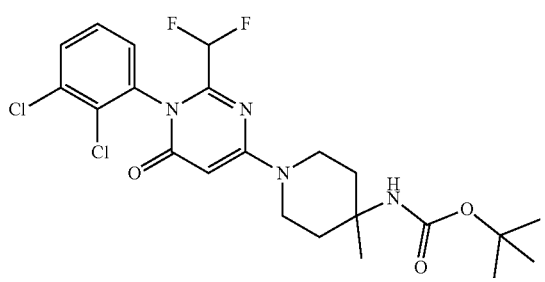 [SMILES: CC1(NC(=O)OC(C)(C)C)CCN(c2cc(=O)n(-c3cccc(Cl)c3Cl)c(C(F)F)n2)CC1]

A solution of 6-chloro-3-(2,3-dichlorophenyl)-2-(difluoromethyl)-3,4-dihydro-pyrimidin-4-one (Intermediate 6, 75 mg), tert-butyl (4-methylpiperidin-4-yl)carbamate (148 mg; 0.69 mmol) and DIEA (0.16 µL, 0.92 mmol) in anhydrous DMSO (1.50 mL) was stirred for 6 h at 70° C. The reaction mixture was then diluted with water (5 mL) and extracted with EtOAc (10 mL). The organic layer was dried over anhydrous sodium sulfate, filtered and concentrated. Purification by flash chromatography over silica (hexanes:EtOAc, gradient from 80:20 to 0:100) afforded the title compound as a white solid (84 mg, 71%). H NMR (400 MHz, DMSO-d6) 7.81 (dd, J=8.0, 1.7 Hz, 1H), 7.58 (dt, J=8.0, 1.4 Hz, 1H), 7.52 (t, J=8.0 Hz, 1H), 6.53 (t, J=52.1 Hz, 1H), 5.58 (s, 1H), 3.28-3.17 (m, 2H), 2.64-2.52 (m, 2H), 2.19-2.05 (m, 2H), 1.53-1.41 (m, 2H), 1.40 (s, 9H), 1.26 (s, 3H). LC/MS (M+1): 503.1.

Step 2: 6-(4-amino-4-methylpiperidin-1-yl)-3-(2,3-dichlorophenyl)-2-(difluoromethyl)-3,4-dihydropyrimidin-4-one

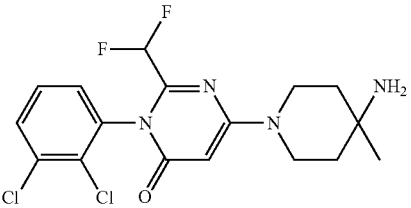 [SMILES: CC1(N)CCN(c2cc(=O)n(-c3cccc(Cl)c3Cl)c(C(F)F)n2)CC1]

The title compound was obtained following procedure described for compound 1, step 2 but starting from N-{-[1-(2,3-dichlorophenyl)-2-(difluoromethyl)-6-oxo-1,6-dihydropyrimidin-4-yl]-4-methylpiperidin-4-yl}carbamate (84 mg; 0.17 mmol) as a white solid (58 mg, 86%). 1H NMR (Bruker 400 MHz, DMSO-d6) δ 7.98 (s, 2H), 7.84 (dd, J=7.8, 1.9 Hz, 1H), 7.63-7.48 (m, 2H), 6.55 (t, J=51.9 Hz, 1H), 5.69 (s, 1H), 4.25-3.84 (m, 2H), 3.42-3.34 (m, 2H), 1.84-1.63 (m, 4H), 1.38 (s, 3H). LC/MS (M+1): 403.0. HPLC purity: 100%.

Compound 12: 6-(4-amino-4-methylpiperidin-1-yl)-3-(2,3-dichlorophenyl)-2,5-dimethyl-3,4-dihydropyrimidin-4-one

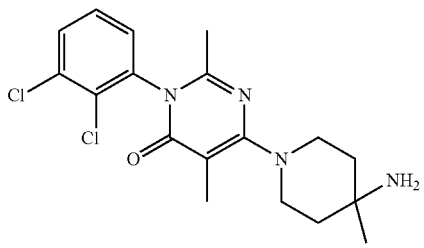 [SMILES: Cc1c(N2CCC(C)(N)CC2)nc(C)n(-c2cccc(Cl)c2Cl)c1=O]

The title compound was obtained following procedure described for compound 11 but starting from 6-chloro-3-(2,3-dichlorophenyl)-2,5-dimethyl-3,4-dihydro-pyrimidin-4-one (Intermediate 6, 75 mg) and tert-butyl (4-methylpiperidin-4-yl)carbamate (156 mg; 0.74 mmol) as a white powder (64 mg, 65%). 1H NMR (Bruker 400 MHz, DMSO-d6) δ 7.95 (s, 2H), 7.82 (dd, J=7.4, 2.3 Hz, 1H), 7.61-7.47 (m, 2H), 3.72-3.59 (m, 2H), 3.27-3.11 (m, 2H), 1.99 (s, 3H), 1.89 (s, 3H), 1.83-1.67 (m, 4H), 1.36 (s, 3H). LC/MS (M+1): 382.9. HPLC purity: 100%.

Compound 13: 6-[1-(aminomethyl)-6-azaspiro[2.5]octan-6-yl]-3-(2,3-dichlorophenyl)-2-methyl-3,4-dihydropyrimidin-4-one

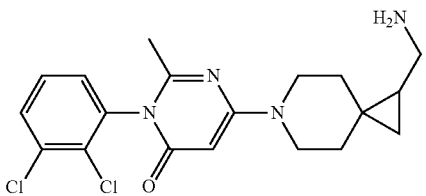 [SMILES: Cc1nc(N2CCC3(CC2)CC3CN)cc(=O)n1-c1cccc(Cl)c1Cl]

The title compound was obtained following procedure described for compound 1, step 1 but starting from 6-chloro-3-(2,3-dichlorophenyl)-2-methyl-3,4-dihydro-pyrimidin-4-one (intermediate 2, 50 mg; 0.17 mmol) and 6-azaspiro[2.5]octane-1-methanamine (36 mg; 0.26 mmol) as a white foam (20 mg, 27%). 1H NMR (400 MHz, DMSO-d6): 7.80 (dd, J=7.1, 2.5 Hz, 1H), 7.59-7.49 (m, 2H), 5.42 (s, 1H), 3.90 (m, 2H), 3.40 (m, 2H), 2.94 (dd, J=13.1, 7.1 Hz, 1H), 2.73 (dd, J=13.1, 7.8 Hz, 1H), 2.00 (s, 3H), 1.70 (m, 1H), 1.57 (m, 1H), 1.39 (m, 1H), 1.20 (m, 1H), 0.87 (m, 1H), 0.65 (m, 1H), 0.38 (t, J=4.9 Hz, 1H); LC/MS (M+1): 393.1.

Compound 14: 6-[3a-(aminomethyl)-octahydrocyclopenta[c]pyrrol-2-yl]-3-(2,3-dichlorophenyl)-2-methyl-3,4-dihydropyrimidin-4-one

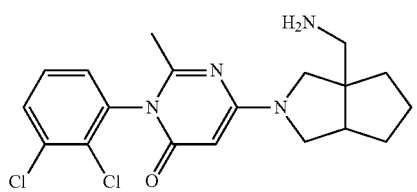 [SMILES: Cc1nc(N2CC3CCCC3(CN)C2)cc(=O)n1-c1cccc(Cl)c1Cl]

The title compound was obtained following procedure described in compound 1 but starting from 6-chloro-3-(2,3-dichlorophenyl)-2-methyl-3,4-dihydropyrimidin-4-one (Intermediate 2, 50 mg; 0.17 mmol), rac-tert-butyl n-([(3ar,6ar)-octahydro-cyclopenta[c]pyrrol-3a-yl]methyl)carbamate hydrochloride (72 mg; 0.26 mmol) as a white foam (40 mg, 55%). $^1$H NMR (400 MHz, DMSO-d6) 7.79 (dd, J=6.9, 2.8 Hz, 1H), 7.58-7.47 (m, 2H), 4.99 (d, J=1.1 Hz, 1H), 3.14-3.71 (m 4H), 2.55 (s, 2H), 2.38 (s, 1H), 1.97 (s, 3H), 1.86-1.48 (m, 6H). LC/MS (M+1): 393.1.

Compound 15: 6-[1-(aminomethyl)-8-azaspiro[4.5]decan-8-yl]-3-(2,3-dichlorophenyl)-2-methyl-3,4-dihydropyrimidin-4-one

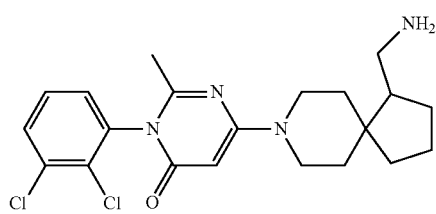 [SMILES: Cc1nc(N2CCC3(CCCC3CN)CC2)cc(=O)n1-c1cccc(Cl)c1Cl]

The title compound was obtained following procedure described in compound 1 but starting from 6-chloro-3-(2,3-dichlorophenyl)-2-methyl-3,4-dihydropyrimidin-4-one (intermediate 2, 50 mg; 0.17 mmol) and tert-butyl n-((8-azaspiro[4.5]decan-1-yl)methyl)carbamate (69 mg; 0.26 mmol) as a white foam (25 mg, 33%). $^1$H NMR (400 MHz, DMSO-d6): 7.80 (dd, J=7.7, 1.9 Hz, 1H), 7.59-7.47 (m, 2H), 5.39 (s, 1H), 4.16 (s, 1H), 3.23 (m, 2H), 3.05-2.93 (m, 2H), 2.58 (m, 2H), 1.99 (s, 3H), 1.97-1.87 (m, 1H), 1.69 (m, 1H), 1.74-1.28 (m, 4H). LC/MS (M+1): 393.1

Compound 16: 6-[4-(2-aminoethyl)-4-(hydroxymethyl)piperidin--yl]-3-(2,3-dichlorophenyl)-2-methyl-3,4-dihydropyrimidin-4-one

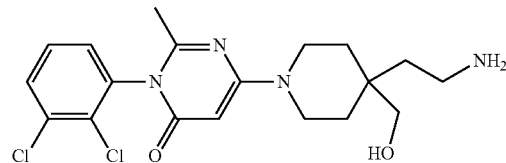 [SMILES: Cc1nc(N2CCC(CO)(CCN)CC2)cc(=O)n1-c1cccc(Cl)c1Cl]

The title compound was obtained following procedure described or compound 1, step 1 but starting from 6-chloro-3-(2,3-dichlorophenyl)-2-methyl-3,4-dihydro-pyrimidin-4-one (intermediate 2, 50 mg; 0.17 mmol.) and [4-(2-aminoethyl)piperidin-4-yl]methanol (60 mg; 0.26 mmol) as a beige powder (30 mg, 38%). $^1$H NMR (400 MHz, DMSO-d6) 7.79 (m, 1H), 7.53 (m, 2H), 3.54 (m, 4H), 3.28 (s, 2H), 2.59 (t, J=6.8 Hz, 2H), 1.98 (s, 3H), 1.47 (m, 4H), 1.40 (m, 2H). LC/MS (M+1): 411.2

Compound 17: 6-[4-(aminomethyl)-4-methylpiperidin-1-yl]-3-(2,3-dichlorophenyl)-2-(difluoromethyl)-3,4-dihydropyrimidin-4-one

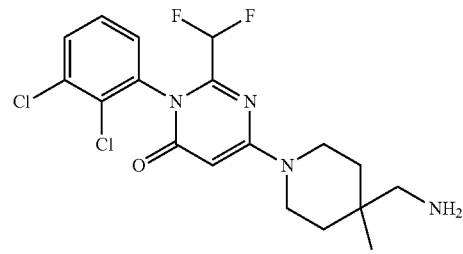 [SMILES: CC1(CN)CCN(c2cc(=O)n(-c3cccc(Cl)c3Cl)c(C(F)F)n2)CC1]

The title compound was obtained following procedure described for compound 11 but starting from 6-chloro-3-(2,3-dichlorophenyl)-2-(difluoromethyl)-3,4-dihydropyrimidin-4-one (intermediate 6, 75 mg; 0.23 mmol) and 4-(boc-aminomethyl)-4-methylpiperidine hydrochloride (183 mg; 0.69 mmol) as a white powder (55 mg, 55%). 1H NMR (Bruker 400 MHz, DMSO-d6) 7.83 (dd, J=7.8, 1.9 Hz, 1H), 7.74 (s, 2H), 7.61-7.46 (m, 2H), 6.55 (t, J=52.0 Hz, 1H), 5.63 (s, 1H), 4.02-3.70 (m, 2H), 3.51-3.36 (m, 2H), 2.87-2.73 (m, 2H), 1.59-1.36 (m, 4H), 1.07 (s, 3H). LC/MS (M+1): 417.0. HLPC purity: 96%.

Compound 18: 6-[4-(aminomethyl)-4-methylpiperidin-1-yl]-3-(2,3-dichlorophenyl)-2,5-dimethyl-3,4-dihydropyrimidin-4-one

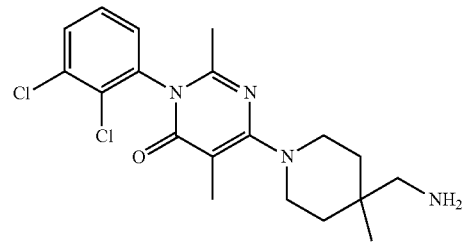 [SMILES: Cc1c(N2CCC(C)(CN)CC2)nc(C)n(-c2cccc(Cl)c2Cl)c1=O]

The title compound was obtained following procedure described for compound 11 but starting from 6-chloro-3-(2,3-dichlorophenyl)-2,5-dimethyl-3,4-dihydropyrimidin-4-one (intermediate 8, 75 mg; 0.25 mmol) and 4-(boc-aminomethyl)-4-methylpiperidine hydrochloride (196 mg; 0.74 mmol) as a white solid (26 mg, 27%). 1H NMR (Bruker 400 MHz, DMSO-d6) 7.81 (dd, J=7.3, 2.3 Hz, 1H), 7.73 (s, 2H), 7.62-7.44 (m, 2H), 3.60-3.45 (m, 2H), 3.28-3.16 (m, 2H), 2.80 (s, 3H), 1.98 (s, 3H), 1.89 (s, 3H), 1.63-1.49 (m, 2H), 1.49-1.36 (m, 2H), 1.06 (s, 3H). LC/MS (M+1): 395.0. HPLC purity: 100%.

Compound 19: (+/−)-6-[(3aS,7aR)-7a-(aminomethyl)-octahydropyrano[3,4-c]pyrrol-2-yl]-3-(2,3-dichlorophenyl)-2-methyl-3,4-dihydropyrimidin-4-one (Relative Configuration)

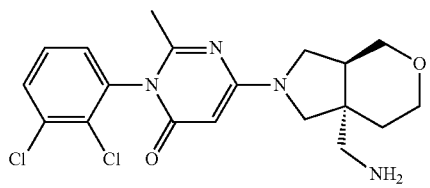 [SMILES: Cc1nc(N2C[C@H]3COCC[C@@]3(CN)C2)cc(=O)n1-c1cccc(Cl)c1Cl]

The title compound was obtained following procedure described for compound 1 but starting from 6-chloro-3-(2,3-dichlorophenyl)-2-methyl-3,4-dihydropyrimidin-4-one (50 mg; 0.17 mmol) and (+/−)-tert-butyl N-{[(3aS,7aS)-octahydropyrano[3,4-c]pyrrol-7a-yl]methyl}carbamate (56 mg, 0.2 mmol) as a white foam (20 mg, 28%). ¹H NMR (400 MHz, DMSO-d6) 7.80 (m, 1H), 7.53 (m, 2H), 4.99 (d, J=1.3 Hz, 1H), 3.57 (m, 4H), 3.35 (m, 1H), 3.29 (s, 2H), 3.17 (m, 1H), 2.67 (m, 1H), 2.55 (m, 1H), 2.45 (m, 0.5H), 2.34 (m, 0.5H), 2.16 (m, 0.5H), 2.07 (m, 0.5H), 1.98 (s, 3H), 1.60 (m, 2H), 1.45 (m, 2H). LC/MS (M+1): 410.1

Compound 20a and 20b: (3P)-6-[(3S,4S)-4-amino-3-methyl-2-oxa-8-azaspiro[4.5]decan-8-yl]-3-(2,3-dichlorophenyl)-2-(difluoromethyl)-3,4-dihydropyrimidin-4-one and (3M)-6-[(3S,4S)-4-amino-3-methyl-2-oxa-8-azaspiro[4.5]decan-8-yl]-3-(2,3-dichlorophenyl)-2-(difluoromethyl)-3,4-dihydropyrimidin-4-one

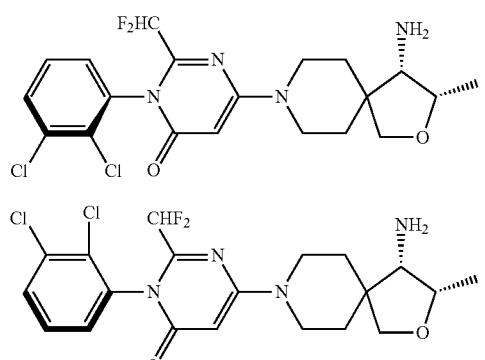

The title compounds were obtained following procedure described for compound 11 but starting from 6-chloro-3-(2,3-dichlorophenyl)-2-(difluoromethyl)-3,4-dihydropyrimidin-4-one (Intermediate 6, 75 mg; 0.23 mmol) and tert-butyl N-[(3S,4S)-3-methyl-2-oxa-8-azaspiro[4.5]decan-4-yl]carbamate (124 mg; 0.46 mmol). The atropisomers were separated by preparative SFC (Chiral column Whelk-O, 250×21 mm, 5 micron, Methanol/20 mM NH4OH and C02, 30/70).

First eluting isomer (compound 20a): 17 mg, Rt=3.72 min, ed=100%, white solid. 1H NMR (Bruker 400 MHz, DMSO-d6) 7.81 (dd, J=8.0, 1.7 Hz, 1H), 7.59 (dt, J=8.0, 1.3 Hz, 1H), 7.52 (t, J=8.0 Hz, 1H), 6.53 (t, J=52.1 Hz, 1H), 5.58 (s, 1H), 4.12-4.01 (m, 1H), 3.93-3.71 (m, 2H), 3.67 (d, J=8.5 Hz, 1H), 3.48 (d, J=8.5 Hz, 1H), 3.46-3.33 (m, 2H), 2.92 (d, J=5.1 Hz, 1H), 1.75 (ddd, J=13.2, 9.1, 3.8 Hz, 1H), 1.63 (ddd, J=13.2, 9.0, 4.0 Hz, 1H), 1.58-1.32 (m, 4H), 1.08 (d, J=6.4 Hz, 3H). LC/MS (M+1): 459.0. HPLC purity: 100%.

Second eluting isomer (compound 20b): 19 mg, Rt=4.46 min, ed=100%, white solid. 1H NMR (DMSO) 1H NMR (Bruker 400 MHz, DMSO-d6) 7.81 (dd, J=8.0, 1.7 Hz, 1H), 7.59 (dt, J=8.0, 1.3 Hz, 1H), 7.52 (t, J=8.0 Hz, 1H), 6.53 (t, J=52.1 Hz, 1H), 5.58 (s, 1H), 4.12-4.01 (m, 1H), 3.93-3.71 (m, 2H), 3.67 (d, J=8.5 Hz, 1H), 3.48 (d, J=8.5 Hz, 1H), 3.46-3.33 (m, 2H), 2.92 (d, J=5.1 Hz, 1H), 1.75 (ddd, J=13.2, 9.1, 3.8 Hz, 1H), 1.63 (ddd, J=13.2, 9.0, 4.0 Hz, 1H), 1.58-1.32 (m, 4H), 1.08 (d, J=6.4 Hz, 3H). LC/MS (M+1): 459.0. HPLC purity: 100%.

Compound 21: 6-(4-amino-4-methylazepan-1-yl)-3-(2,3-dichlorophenyl)-2-methyl-3,4-dihydropyrimidin-4-one hydrochloride Step 1: benzyl N-{1-[1-(2,3-dichlorophenyl)-2-methyl-6-oxo-1,6-dihydropyrimidin-4-yl]-4-methyl-azepan-4-yl}carbamate

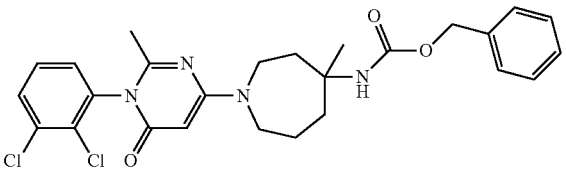 [SMILES: Cc1nc(N2CCCC(C)(NC(=O)OCc3ccccc3)CC2)cc(=O)n1-c1cccc(Cl)c1Cl]

A solution of 1-(2,3-dichlorophenyl)-2-methyl-6-oxopyrimidin-4-yl 4-methylbenzene-sulfonate (intermediate 10, 100 mg, 0.223 mmol), benzyl N-(4-methylazepan-4-yl)carbamate (74 mg, 0.268 mmol) and Cs2CO3 (115 mg, 0.335 mmol) in DMF (10 mL) was stirred for 2 h at 100° C. The reaction was diluted with water (16 mL) and extracted with EtOAc (3×10 mL). The combined organic layers were dried over anhydrous sulfate, filtered and concentrated. Purification by flash chromatography on silica (PE:EtOAc, gradient from 100:0 to 0:100) afforded the title compound as a white solid (50 mg, 32%). LC/MS (M+1): 515.3

Step 2: 6-(4-amino-4-methylazepan-1-yl)-3-(2,3-dichlorophenyl)-2-methyl-3,4-dihydropyrimidin-4-one hydrochloride

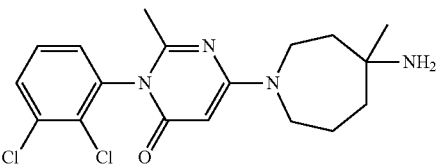

A solution of HBr in AcOH (1.50 mL, 40%) was added dropwise to a stirred solution of benzyl N-[1-[1-(2,3-dichlorophenyl)-2-methyl-6-oxopyrimidin-4-yl]-4-methylazepan-4-yl]carbamate (50 mg, 0.072 mmol) in DCM (5.00 mL) maintained at 0° C. The reaction mixture was then stirred at RT for 1 h and concentrated under reduced pressure. Purification by preparative HPLC (XBridge Prep C18 OBD Column, 19×150 mm, 5 um; Water (0.05% HCl) and ACN, 20% to 50% in 8 min) afforded the title compound as a yellow powder (14 mg, 46%). 1H NMR (DMSO-d6+D20) 7.74 (dd, J=8.0, 1.6 Hz, 1H), 7.55-7.36 (m, 2H), 3.92 (s, 1H), 3.40 (s, 4H), 2.02 (s, 3H), 1.97-1.71 (m, 6H), 1.26 (s, 3H). LC/MS (M+1): 381.0. HPLC (purity) 99%. mp: 158-160° C.

Compound 22: 4-amino-1-[1-(2,3-dichlorophenyl)-2-methyl-6-oxo-1,6-dihydropyrimidin-4-yl]piperidine-4-carboxamide

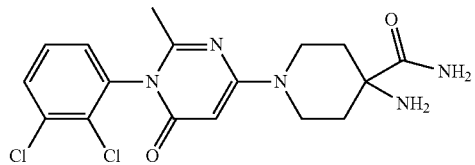 [SMILES: Cc1nc(N2CCC(N)(C(N)=O)CC2)cc(=O)n1-c1cccc(Cl)c1Cl]

The title compound was obtained following procedure described in compound 1 but starting from 6-chloro-3-(2,3-dichlorophenyl)-2-methyl-3,4-dihydropyrimidin-4-one (intermediate 2, 50 mg; 0.17 mmol) and tert-butyl (4-cyanopiperidin-4-yl)carbamate (58 mg; 0.26 mmol) as a white foam (5 mg, 7%). $^{1}$H NMR (400 MHz, DMSO-d6) 7.79 (dd, J=6.6, 3.1 Hz, 1H), 7.59-7.49 (m, 2H), 7.43 (s, 1H), 6.96 (s, 1H), 5.38 (s, 1H), 3.98 (m, 2H), 3.34 (m, 2H), 1.99 (s, 3H), 1.88 (t, J=12.6 Hz, 2H), 1.39 (m, 2H). LC/MS (M+1): 396.1

Compound 23a and 23b: (3P)-6-[(3S,4S)-4-amino-3-methyl-2-oxa-8-azaspiro[4.5]decan-8-yl]-3-(2,3-dichlorophenyl)-2,5-dimethyl-3,4-dihydropyrimidin-4-one and (3M)-6-[(3S,4S)-4-amino-3-methyl-2-oxa-8-azaspiro[4.5]decan-8-yl]-3-(2,3-dichlorophenyl)-2,5-dimethyl-3,4-dihydropyrimidin-4-one Step 1: Tert-Butyl N-[(3S,4S)-8-[1-(2,3-dichlorophenyl)-2,5-dimethyl-6-oxo-1,6-dihydropyrimidin-4-yl]-3-methyl-2-oxa-8-azaspiro[4.5]decan-4-yl]carbamate

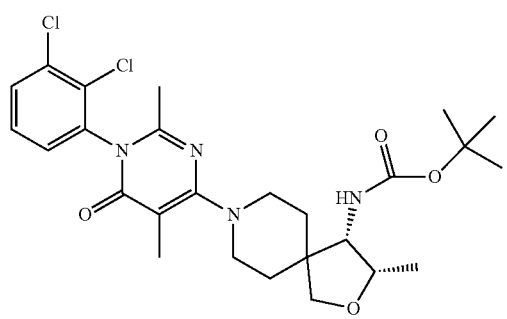 [SMILES: Cc1c(N2CCC3(CC2)CO[C@@H](C)[C@H]3NC(=O)OC(C)(C)C)nc(C)n(-c2cccc(Cl)c2Cl)c1=O]

A solution of 6-chloro-3-(2,3-dichlorophenyl)-2,5-dimethyl-3,4-dihydropyrimidin-4-one (intermediate 8, 75 mg; 0.25 mmol), tert-butyl N-[(3S,4S)-3-methyl-2-oxa-8-azaspiro[4.5]decan-4-yl]carbamate (133 mg; 0.49 mmol) and DIEA (170 µL, 0.99 mmol) in anhydrous DMSO (1.50 mL) was heated at 70° C. for 6 h. The reaction mixture was then diluted with water and extracted with EtOAc (10 mL). Organic layer was washed with water (2×5 mL) and brine (5 mL). It was dried over anhydrous sodium sulfate, filtrated and concentrated. Purification by flash chromatography on silica (hexanes:EtOAc, gradient from 80:20 to 0:100) afforded the title compound as a white solid (108 mg; 80%). LC/MS (M+1): 537.0.

Step 2: (3P)-6-[(3S,4S)-4-amino-3-methyl-2-oxa-8-azaspiro[4.5]decan-8-yl]-3-(2,3-dichlorophenyl)-2,5-dimethyl-3,4-dihydropyrimidin-4-one and (3M)-6-[(3S,4S)-4-amino-3-methyl-2-oxa-8-azaspiro[4.5]decan-8-yl]-3-(2,3-dichlorophenyl)-2,5-dimethyl-3,4-dihydropyrimidin-4-one

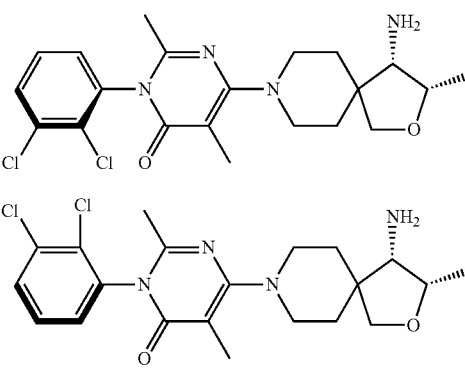

A solution of tert-butyl N-[(3S,4S)-8-[1-(2,3-dichlorophenyl)-2,5-dimethyl-6-oxo-1,6-dihydropyrimidin-4-yl]-3-methyl-2-oxa-8-azaspiro[4.5]decan-4-yl]carbamate (108 mg; 0.20 mmol) in DCM (2.2 mL) and TFA (2.2 mL) was stirred at RT for 1 h. Solvents were removed under reduced pressure and the residue was co-evaporated three times with toluene. Purification by preparative SFC (Chiral column IA 250×21 mm, 5 micron) with Methanol/20 mM NH₄OH 20 mM and CO₂, gradient from 5 to 45% v/v in 4 min as eluent afforded the two atropisomers of the expected compound:

First eluting isomer (compound 23a): 27 mg, white solid, Rt=2.82 min, ee=100%, 1H NMR (400 MHz, DMSO-d6) 7.80 (dd, J=5.8, 3.9 Hz, 1H), 7.54 (m, 2H), 4.07 (m, 1H), 3.68 (d, J=8.5 Hz, 1H), 3.62-3.53 (m, 2H), 3.51 (d, J=8.5 Hz, 1H), 3.24-3.06 (m, 4H), 2.96 (d, J=5.1 Hz, 1H), 1.97 (s, 3H), 1.89 (s, 3H), 1.84-1.73 (m, 1H), 1.73-1.62 (m, 1H), 1.62-1.45 (m, 2H), 1.10 (d, J=6.4 Hz, 3H). LC/MS (M+1): 437.0.

Second eluting isomer (compound 23b): 27 mg, white solid, Rt=4.29 min, ee=100%, 1H NMR (400 MHz, DMSO-d6) 7.84-7.76 (m, 1H), 7.58-7.49 (m, 2H), 4.05 (qd, J=6.5, 5.1 Hz, 1H), 3.65 (d, J=8.4 Hz, 1H), 3.61-3.50 (m, 2H), 3.49 (d, J=8.4 Hz, 1H), 3.26-3.17 (m, 1H), 3.17-3.07 (m, 2H), 2.89 (d, J=5.1 Hz, 1H), 1.97 (s, 3H), 1.89 (s, 3H), 1.77 (ddt, J=16.9, 11.0, 5.4 Hz, 1H), 1.67 (ddd, J=13.1, 9.1, 3.7 Hz, 1H), 1.60-1.44 (m, 2H), 1.42-1.21 (m, 2H), 1.08 (d, J=6.4 Hz, 3H). LC/MS (M+1): 437.0.

Compound 24: 6-[(3S,4S)-4-amino-3-methyl-2-oxa-8-azaspiro[4.5]decan-8-yl]-3-(2,3-dichlorophenyl)-2-methyl-5-(trifluoromethyl)-3,4-dihydropyrimidin-4-one

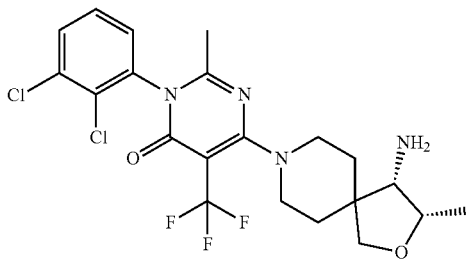 [SMILES: Cc1nc(N2CCC3(CC2)CO[C@@H](C)[C@H]3N)c(C(F)(F)F)c(=O)n1-c1cccc(Cl)c1Cl]

The title compound was obtained following procedure described for compound 11, step 1 but starting from 6-chloro-3-(2,3-dichlorophenyl)-2-methyl-5-(trifluoromethyl)-3,4-dihydropyrimidin-4-one (intermediate 11, 50 mg; 0.14 mmol) and (3S,4S)-3-methyl-2-oxa-8-azaspiro[4.5]decan-4-amine (48 mg; 0.28 mmol) as a white solid (two atropisomers, 25 mg, 36%). LC/MS (M+1) 491.0.

Compound 25: (+/−)-6-[(3aS,6aR)-3a-(aminomethyl)-octahydrocyclopenta[c]pyrrol-2-yl]-3-(2,3-dichlorophenyl)-2-methyl-5-(trifluoromethyl)-3,4-dihydropyrimidin-4-one (relative configuration)

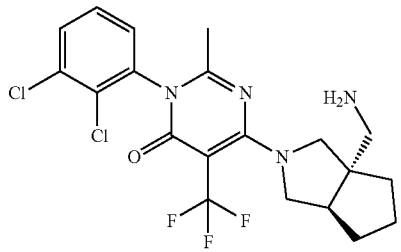 [SMILES: Cc1nc(N2C[C@@H]3CCC[C@]3(CN)C2)c(C(F)(F)F)c(=O)n1-c1cccc(Cl)c1Cl]

The title compound was obtained following procedure described in compound 11, step 1 but starting from 6-chloro-3-(2,3-dichlorophenyl)-2-methyl-5-(trifluoromethyl)-3,4-dihydropyrimidin-4-one (Intermediate 11, 50 mg; 0.14 mmol) and (+/−)-1-[(3aS,6aR)-octahydrocyclopenta[c]pyrrol-3a-yl]methanamine dihydrochloride (60 mg; 0.28 mmol) as a white solid (mixture of atropisomers, 8 mg, 12%). LC/MS (M+1): 461.0.

Compound 26: 6-[4-amino-4-(2-hydroxyethyl)piperidin-1-yl]-3-(2,3-dichlorophenyl)-2-methyl-3,4-dihydropyrimidin-4-one

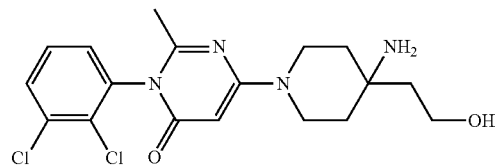 [SMILES: Cc1nc(N2CCC(N)(CCO)CC2)cc(=O)n1-c1cccc(Cl)c1Cl]

The title compound was obtained following procedure described in compound 1, step 1 but starting from 6-chloro-3-(2,3-dichlorophenyl)-2-methyl-3,4-dihydropyrimidin-4-one (intermediate 2, 50 mg; 0.17 mmol) and 2-(4-aminopiperidin-4-yl)ethan-1-ol dihydrochloride (56 mg; 0.26 mmol) as a white foam (mixture of atropisomers, 13 mg, 18%). $^1$H NMR (400 MHz, DMSO-d6) δ 7.79 (m, 1H), 7.56-7.50 (m, 2H), 5.35 (s, 1H), 3.76 (m, 2H), 3.60 (t, J=6.6 Hz, 2H), 3.44 (m, 2H), 1.98 (s, 3H), 1.56 (t, J=6.3 Hz, 2H), 1.46 (m, 2H). LC/MS (M+1): 397.1.

Compound 27: 6-{(R)-1-amino-8-azaspiro[4.5]decan-8-yl}-3-(2,3-dichlorophenyl)-2-methyl-3,4-dihydropyrimidin-4-one

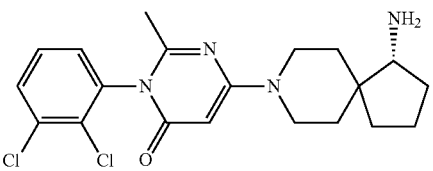 [SMILES: Cc1nc(N2CCC3(CCC[C@H]3N)CC2)cc(=O)n1-c1cccc(Cl)c1Cl]

The title compound was obtained following procedure described for compound 1 but starting from 6-chloro-3-(2,3-dichlorophenyl)-2-methyl-3,4-dihydropyrimidin-4-one (intermediate 2, 50 mg; 0.17 mmol) and tert-butyl N-[(1R)-8-azaspiro[4.5]decan-1-yl]carbamate (WUXI, 53 mg, 0.2 mmol) as a white foam (mixture of atropisomers, 30 mg, 39%). $^1$H NMR (400 MHz, DMSO-d$_6$) 7.80 (m, 1H), 7.58-7.48 (m, 2H), 5.35 (s, 1H), 3.29 (m, 2H), 3.14-2.96 (m, 2H), 2.69 (t, J=7.4 Hz, 1H), 1.99 (s, 3H), 1.92-1.72 (m, 2H), 1.69-1.47 (m, 2H), 1.43-1.77 (m, 6H). LC/MS (M+1): 407.2

Compound 28: 6-[4-(aminomethyl)-4-hydroxypiperidin-1-yl]-3-(2,3-dichlorophenyl)-2-methyl-3,4-dihydropyrimidin-4-one

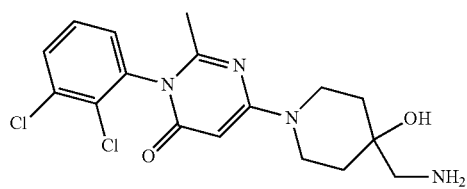 [SMILES: Cc1nc(N2CCC(O)(CN)CC2)cc(=O)n1-c1cccc(Cl)c1Cl]

The title compound was obtained following procedure described for compound 1, step 1, but starting from 6-chloro-3-(2,3-dichlorophenyl)-2-methyl-3,4-dihydropyrimidin-4-one (Intermediate 2, 50 mg; 0.17 mmol) and 4-(aminomethyl)piperidin-4-ol bis(trifluoroacetic acid) (93 mg; 0.26 mmol) as a white foam (21 mg, 31%). $^1$H NMR (400 MHz, DMSO-d$_6$) 7.80 (m, 1H), 7.52 (m, 2H), 5.35 (d, J=6.9 Hz, 1H), 4.29 (s, 1H), 4.00 (m, 2H), 3.33-3.17 (m, 2H), 2.45 (s, 2H), 1.99 (s, 3H), 1.47 (m, 4H). LC/MS (M+1): 383.1

Compound 29: 6-[4-amino-4-(hydroxymethyl)piperidin-1-yl]-3-(2,3-dichlorophenyl)-2-methyl-3,4-dihydropyrimidin-4-one

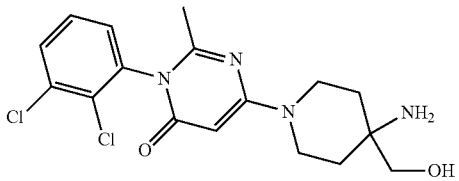 [SMILES: Cc1nc(N2CCC(N)(CO)CC2)cc(=O)n1-c1cccc(Cl)c1Cl]

The title compound was obtained following procedure described for compound 1 but starting from 6-chloro-3-(2,3-dichlorophenyl)-2-methyl-3,4-dihydropyrimidin-4-one (intermediate 2, 50 mg; 0.17 mmol) and tert-butyl n-[4-(hydroxymethyl)piperidin-4-yl]carbamate (60 mg; 0.26 mmol) as an white powder (26 mg, 31%). $^1$H NMR (400 MHz, DMSO-d$_6$) 7.83-7.74 (m, 1H), 7.58-7.48 (m, 2H), 5.33 (d, J=2.2 Hz, 1H), 4.74 (d, J=3.9 Hz, 1H), 3.82 (m 2H), 3.57 (m, 1H), 3.36 (m 1H), 3.22 (m, 1H), 2.91 (m, 1H), 1.98 (s, 3H), 1.55 (m, 4H). LC/MS (M+1): 383.1.

Compound 30: (+/−)-6-[(3S,4R)-4-amino-3-hydroxypiperidin-1-yl]-3-(2,3-dichlorophenyl)-2-methyl-3,4-dihydropyrimidin-4-one

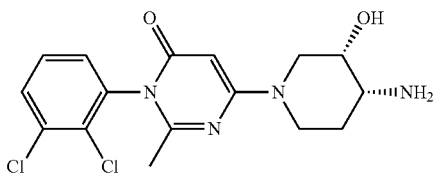 [SMILES: Cc1nc(N2CC[C@@H](N)[C@@H](O)C2)cc(=O)n1-c1cccc(Cl)c1Cl]

The title compound was obtained following procedure described for compound 1 but starting from 6-chloro-3-(2,3-dichlorophenyl)-2-methyl-3,4-dihydropyrimidin-4-one (intermediate 2, 50 mg; 0.17 mmol), tert-butyl n-[(3s,4r)-rel-3-hydroxypiperidin-4-yl]carbamate (56 mg; 0.26 mmol) as a white foam (30 mg, 47%). $^1$H NMR (400 MHz, DMSO-d$_6$) 7.80 (m, 1H), 7.57-7.50 (m, 2H), 5.36 (s, 1H), 4.74 (s, 1H), 3.87 (m, 2H), 3.21 (s, 1H), 1.99 (s, 2H), 1.53 (t, J=11.0 Hz, 2H), 1.34 (d, J=13.7 Hz, 2H). LC/MS (M+1): 369.1

Compound 31: 3-(2,3-dichlorophenyl)-2-methyl-6-[4-methyl-4-(methylamino)piperidin-1-yl]-3,4-dihydropyrimidin-4-one

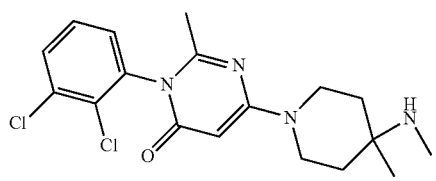 [SMILES: CNC1(C)CCN(c2cc(=O)n(-c3cccc(Cl)c3Cl)c(C)n2)CC1]

The title compound was obtained following procedure described for compound 1 but starting from 6-chloro-3-(2,3-dichlorophenyl)-2-methyl-3,4-dihydropyrimidin-4-one (intermediate 2, 50 mg; 0.17 mmol) and tert-butyl n-methyl-n-(4-methylpiperidin-4-yl)carbamate (59 mg; 0.26 mmol) as a white foam (20 mg, 30%). $^1$H NMR (400 MHz, DMSO-d$_6$) 7.80 (m, 1H), 7.54 (m, 2H), 5.34 (s, 1H), 3.67 (m, 2H), 3.44 (q, J=10.7 Hz, 2H), 3.27 (m, 2H), 2.20 (s, 3H), 1.98 (s, 3H), 1.55 (m, 1H), 1.40 (m, 2H), 1.04 (s, 3H). LC/MS (M+1): 381.1

Compound 32a and 32b: (3P)-6-[(3S,4S)-4-amino-3-methyl-2-oxa-8-azaspiro[4.5]decan-8-yl]-3-(2,3-dichloro-6-fluorophenyl)-2-methyl-3,4-dihydropyrimidin-4-one and (3M)-6-[(3S,4S)-4-amino-3-methyl-2-oxa-8-azaspiro[4.5]decan-8-yl]-3-(2,3-dichloro-6-fluorophenyl)-2-methyl-3,4-dihydropyrimidin-4-one

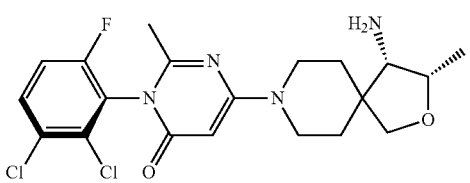

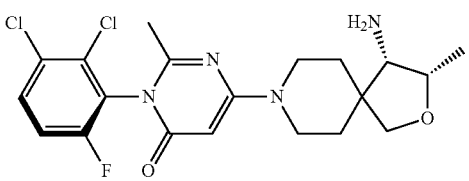

The title compound was obtained following procedure described in compound 11, step 1 but starting from 6-chloro-3-(2,3-dichloro-6-fluorophenyl)-2-methyl-3,4-dihydropyrimidin-4-one (intermediate 12; 80 mg; 0.26 mmol) and (3S,4S)-3-methyl-2-oxa-8-azaspiro[4.5]decan-4-amine (WUXI; 88 mg; 0.52 mmol). The two atropisomers were separated by preparative SFC (column Whelk-01 (R,R), 250×21 mm, 5 micron, Methanol+20 mM NH$_4$OH: CO$_2$ 30/70% v/v.

First eluting isomer (Compound 32a): 28 mg, white foam, Rt=2.62 min purity=98.5, 1H NMR (DMSO-d6) δ 7.91 (dd, J=9.2, 5.3 Hz, 1H), 7.59 (t, J=8.9 Hz, 1H), 5.39 (s, 1H), 4.10-3.99 (m, 1H), 3.89-3.72 (m, 2H), 3.66 (d, J=8.4 Hz, 1H), 3.48 (d, J=8.4 Hz, 1H), 3.45-3.30 (m, 2H), 2.90 (d, J=5.2 Hz, 1H), 2.05 (s, 3H), 1.73 (ddd, J=13.2, 9.2, 3.8 Hz, 1H), 1.61 (ddd, J=13.1, 9.0, 4.0 Hz, 1H), 1.56-1.39 (m, 4H), 1.08 (d, J=6.4 Hz, 3H). LC/MS (M+1): 441.0

Second eluting isomer (compound 32b): 27 mg, white foam, Rt=5.12 min, purity=100%, 1H NMR (DMSO-d6) δ 7.91 (dd, J=9.2, 5.3 Hz, 1H), 7.59 (t, J=8.9 Hz, 1H), 5.39 (s, 1H), 4.10-4.01 (m, 1H), 3.91-3.72 (m, 2H), 3.66 (d, J=8.4 Hz, 1H), 3.47 (d, J=8.4 Hz, 1H), 3.45-3.36 (m, 1H), 3.30 (s, 1H), 2.91 (d, J=5.1 Hz, 1H), 2.05 (s, 3H), 1.73 (ddd, J=13.3, 9.2, 3.8 Hz, 1H), 1.62 (ddd, J=13.2, 9.0, 4.0 Hz, 1H), 1.57-1.39 (m, 4H), 1.08 (d, J=6.4 Hz, 3H). LC/MS (M+1): 441.0.

Compound 33a and 33b: (3P)-6-[4-(aminomethyl)-4-methylpiperidin-1-yl]-3-(2,3-dichloro-6-fluorophenyl)-2-methyl-3,4-dihydropyrimidin-4-one and (3M)-6-[4-(aminomethyl)-4-methylpiperidin-1-yl]-3-(2,3-dichloro-6-fluorophenyl)-2-methyl-3,4-dihydropyrimidin-4-one

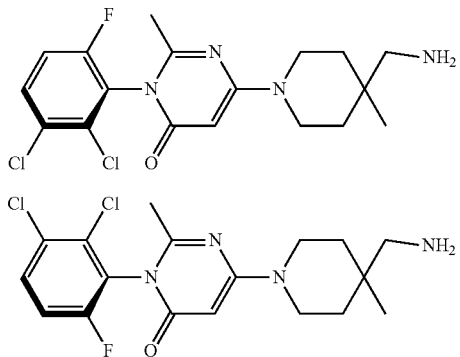

33a

33b

The title compound was obtained following procedure described for compound 11 but starting from 6-chloro-3-(2,3-dichloro-6-fluorophenyl)-2-methyl-3,4-dihydropyrimidin-4-one (intermediate 12, 40 mg; 0.13 mmol; 1.0 eq.) and 4-(boc-aminomethyl)-4-methylpiperidine hydrochloride (70 mg, 0.3 mmol). The two atropisomers were separated by preparative SFC (column AD-H, 250×21 mm, 5 micron, methanol+20 mM NH$_4$OH:CO$_2$, 25/75% v/v.

First eluting isomer (compound 33a): 16 mg, white solid, Rt=3.0 min, ee=100%, 1H NMR (400 MHz, DMSO-d6) 7.91 (dd, J=9.1, 5.3 Hz, 1H), 7.59 (t, J=8.9 Hz, 1H), 5.35 (s, 1H), 3.93-3.65 (m, 2H), 3.44-3.17 (m, 2H), 2.41 (s, 2H), 2.05 (s, 3H), 1.79-1.50 (m, 2H), 1.50-1.36 (m, 2H), 1.33-1.21 (m, 2H), 0.92 (s, 3H).

Second eluting isomer (compound 33b): 18 mg, white solid, Rt=3.33 min, ee=100%, 1H NMR (400 MHz, DMSO-d6) 7.91 (dd, J=9.2, 5.3 Hz, 1H), 7.59 (t, J=8.9 Hz, 1H), 5.35 (s, 1H), 3.92-3.67 (m, 2H), 3.44-3.29 (m, 2H), 2.41 (s, 2H), 2.05 (s, 3H), 1.87-1.54 (m, 2H), 1.44 (ddt, J=14.2, 8.6, 4.3 Hz, 2H), 1.27 (dt, J=13.5, 4.4 Hz, 2H), 0.92 (s, 3H).

Compound 34: (+/−)-6-[(3aS,6aS)-3a-(aminomethyl)-hexahydro-1H-furo[3,4-c]pyrrol-5-yl]-3-(2,3-dichlorophenyl)-2,5-dimethyl-3,4-dihydropyrimidin-4-one

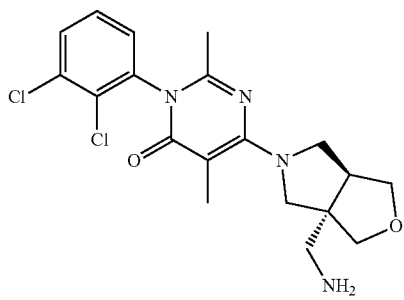 [SMILES: Cc1c(N2C[C@H]3COC[C@@]3(CN)C2)nc(C)n(-c2cccc(Cl)c2Cl)c1=O]

The title compound was obtained following procedure described for compound 11, step 1 but starting from 6-chloro-3-(2,3-dichlorophenyl)-2,5-dimethyl-3,4-dihydropyrimidin-4-one (intermediate 8, 100 mg; 0.33 mmol) and (+/−)-1-[(3aS,6aS)-hexahydro-1H-furo[3,4-c]pyrrol-3a-yl] methanamine (Enamine; 140 mg; 0.99 mmol) as a white foam (mixture of isomers, 60 mg, 42%). $^1$H NMR (DMSO-d$_6$) 7.79 (dd, J=7.0, 2.6 Hz, 1H), 7.59-7.48 (m, 2H), 3.92 (ddd, J=9.2, 7.3, 2.1 Hz, 1H), 3.86-3.49 (m, 6H), 3.29 (m, 2H), 2.68 (s, 2H), 2.02 (s, 3H), 1.93 (s, 3H). L/MS (M+1)=409.0

Compound 35: 6-{1-amino-7-azaspiro[3.5]nonan-7-yl}-3-(2,3-dichlorophenyl)-2-methyl-3,4-dihydropyrimidin-4-one

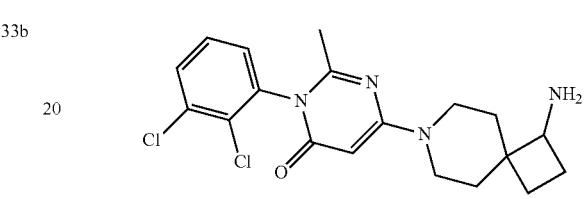

The title compound was obtained following procedure described for compound 11 but starting from 6-chloro-3-(2,3-dichlorophenyl)-2-methyl-3,4-dihydropyrimidin-4-one (intermediate 2, 50 mg; 0.17 mmol) and tert-butyl n-(7-azaspiro[3.5]nonan-1-yl)carbamate (62 mg; 0.26 mmol) as a white foam (25 mg, 37%). $^1$H NMR (DMSO-d$_6$) 7.83-7.74 (m, 1H), 7.58-7.48 (m, 2H), 5.37 (d, J=1.1 Hz, 1H), 4.00 (m, 2H), 3.21-2.92 (m, 2H), 2.16-2.02 (m, 1H), 1.99 (s, 3H), 1.73-1.47 (m, 6H), 1.39 (m, 2H). LC/MS (M+1): 393.1.

Compound 36: 6-[(3S,4S)-4-amino-3-methyl-2-oxa-8-azaspiro[4.5]decan-8-yl]-3-(2,3-dichlorophenyl)-5-ethyl-2-methyl-3,4-dihydropyrimidin-4-one

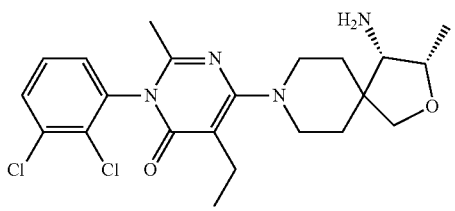 [SMILES: CCc1c(N2CCC3(CC2)CO[C@@H](C)[C@H]3N)nc(C)n(-c2cccc(Cl)c2Cl)c1=O]

A mixture of 3-(2,3-dichlorophenyl)-5-ethyl-6-hydroxy-2-methyl-3,4-dihydro-pyrimidin-4-one (intermediate 13, 100 mg; 0.33 mmol) and 1,8-diazabicyclo(5.4.0)undec-7-ene (DBU) (153 mg; 1.00 mmol) in DMF (3 mL) was stirred for 15 minutes at RT. (Benzotriazol--yloxy)tris(dimethylamino)phosphonium hexafluorophosphate (BOP) (0.28 ml; 0.67 mmol) was added and the reaction mixture was stirred for another 15 minutes before the addition of (3S,4S)-3-methyl-2-oxa-8-azaspiro[4.5]decan-4-amine (60 mg; 0.35 mmol) and TEA (507 μL) The reaction mixture was stirred O/N. Purification by preparative HPLC (XBridge, water+ 0.1% NH$_4$OH and ACN, gradient from 20 to 100% in 10 min) afforded the title compound as a white foam (mixture of atropisomers, 18 mg, 12%). $^1$H NMR (400 MHz, DMSO-d$_6$) 7.80 (m, 1H), 7.57-7.50 (m, 2H), 4.04 (m, 1H), 3.66 (d, J=8.4 Hz, 1H), 3.52 (m, 2H), 3.49 (d, J=8.2 Hz, 1H), 3.18 (m, 3H), 2.90 (d, J=5.1 Hz, 1H), 2.37 (q, J=7.3 Hz, 2H), 1.97

(s, 3H), 1.74 (m, 1H), 1.68 (m, 1H), 1.53 (m, 2H), 1.37 (s, 2H), 1.11 (t, J=7.2 Hz, 3H), 1.06 (d, J=6.4 Hz, 3H); LC/MS (M+1): 451.2.

Compound 37a and 37b: (1M)-4-[(3S,4S)-4-amino-3-methyl-2-oxa-8-azaspiro[4.5]decan-8-yl]-1-(2,3-dichlorophenyl)-6-methyl-1,2-dihydro-1,3,5-triazin-2-one and (1P)-4-[(3S,4S)-4-amino-3-methyl-2-oxa-8-azaspiro[4.5]decan-8-yl]-1-(2,3-dichlorophenyl)-6-methyl-1,2-dihydro-1,3,5-triazin-2-one

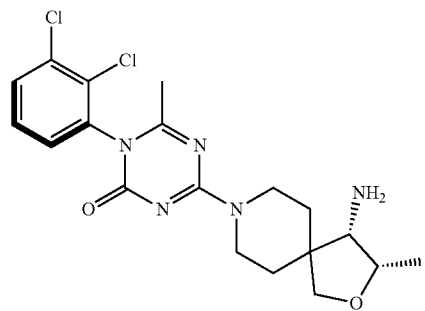

37a

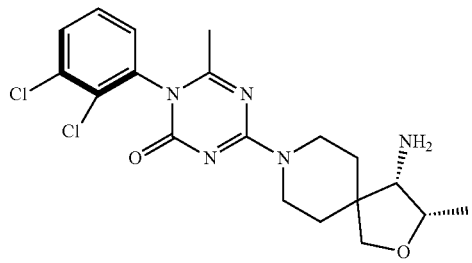

37b

A solution of 1-(2,3-dichlorophenyl)-6-methyl-4-(methylsulfanyl)-1,2-dihydro-1,3,5-triazin-2-one (intermediate 14, 100 mg; 0.33 mmol), (3S,4S)-3-methyl-2-oxa-8-azaspiro[4.5]decan-4-amine (113 mg; 0.66 mmol) and DIEA (0.23 μL, 1.32 mmol) in anhydrous 1,4-dioxane (3.00 mL) was stirred for 16 h at 100° C. The mixture was concentrated under reduced pressure and purified by preparative SFC (column Whelk-01 (R,R), 250×21 mm, 5 micron, methanol+ 20 mM NH₄OH:CO₂, 30/70% v/v) to afford the two atropisomers.

First eluting isomer (compound 37a): 35 mg, white solid, Rt=5.58 min, purity: 97.9%, 1H NMR (400 MHz, DMSO-d6) δ 7.79 (dd, J=8.1, 1.6 Hz, 1H), 7.61 (m, 1H), 7.53 (m, 1H), 4.20 (m, 0.5H), 4.12-3.99 (m, 2H), 3.92 (m, 0.5H), 3.75 (m, 0.5H), 3.68 (dd, J=14.2, 8.5 Hz, 1H), 3.57 (m, 0.5H), 3.52-3.41 (m, 2H), 2.95 (d, J=5.1 Hz, 0.5H), 2.90 (d, J=5.3 Hz, 0.5H), 1.99 (s, 3H), 1.84-1.29 (m, 6H), 1.08 (dd, J=6.4, 2.9 Hz, 3H). LC/MS (M+1): 424.0.

Second eluting isomer (compound 37b): 27 mg, white solid, Rt=6.78%, purity: 98.9%. 1H NMR (400 MHz, DMSO-d6) 7.79 (dd, J=8.0, 1.6 Hz, 1H), 7.61 (m, 1H), 7.53 (t, J=8.0 Hz, 1H), 4.17 (m, 0.5H), 4.11-3.99 (m, 2H), 3.94 (m, 0.5H), 3.68 (m, 1.5H), 3.60 (m, 1H), 3.48 (dd, J=18.1, 8.5 Hz, 1H), 3.44-3.36 (m, 0.5H), 2.95 (d, J=5.1 Hz, 0.5H), 2.89 (d, J=5.3 Hz, 0.5H), 1.99 (s, 3H), 1.89-1.30 (m, 6H), 1.08 (d, J=6.4 Hz, 3H). LC/MS (M+1): 424.0.

Compound 41: 3-(2,3-dichlorophenyl)-6-(4-{[(2R)-2,3-dihydroxypropyl]-amino}piperidin-1-yl)-2-methyl-3,4-dihydropyrimidin-4-one

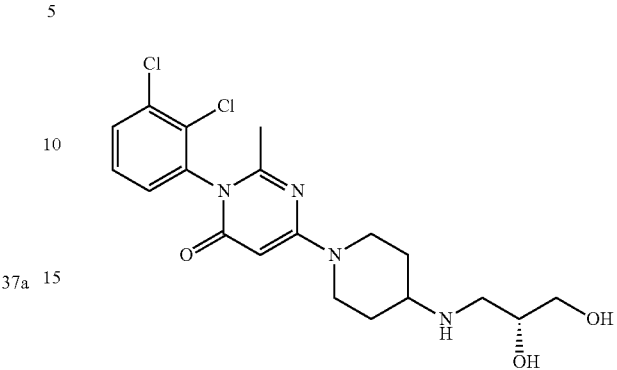

A solution of 3-(2,3-dichlorophenyl)-2-methyl-6-4-oxopiperidin-1-yl)-3,4-dihydropyrimidin-4-one (70 mg; 0.20 mmol) and (R)-3-amino-1,2-propanediol (27 mg; 0.30 mmol) in DCM (1.4 mL) and MeOH (0.3 mL) was stirred at RT for 30 min before the addition of sodium triacetoxyborohydride (126 mg; 0.60 mmol). The resulting reaction mixture was stirred at RT overnight. It was hen diluted with DCM and a saturated solution of sodium bicarbonate. The aqueous was extracted with DCM. Combined organic phases were washed with brine, dried over anhydrous sodium sulfate, filtered and concentrated. The crude was purified by SFC (column 2EP, MeOH—NH4OH 20 nM) to give the title compound as a white slid (23 mg, 27%). 1H NMR (Bruker 400 MHz, DMSO-d6+D20) δ 7.76 (dd, J=7.6, 2.0 Hz, 1H), 7.56-7.43 (m, 2H), 5.35 (s, 1H), 4.31-4.04 (m, 2H), 3.54-3.45 (m, 1H), 3.40-3.25 (m, 2H), 2.97 (tdd, J=13.6, 9.8, 2.7 Hz, 2H), 2.63 (ddd, J=11.3, 8.2, 4.1 Hz, 2H), 2.45 (dd, J=11.7, 7.3 Hz, 1H), 1.97 (s, 3H), 1.84 (dq, J=12.4, 4.1 Hz, 2H), 1.29-1.10 (m, 2H). LC/MS (M+1): 427.0.

Compound 42: 3-(2,3-dichlorophenyl)-6-(4-{[(2S)-2,3-dihydroxypropyl]amino}-piperidin-1-yl)-2-methyl-3,4-dihydropyrimidin-4-one

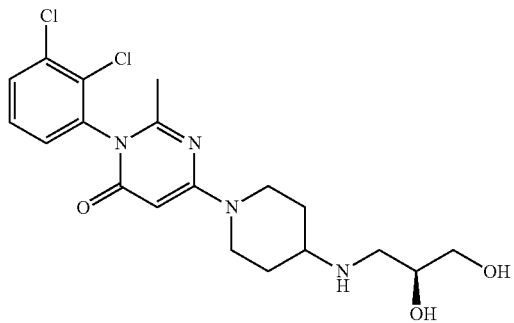 [SMILES: Cc1nc(N2CCC(NC[C@H](O)CO)CC2)cc(=O)n1-c1cccc(Cl)c1Cl]

The title compound was obtained following procedure described for compound 41 but starting from 3-(2,3-dichlorophenyl)-2-methyl-6-(4-oxopiperidin-1-yl)-3,4-dihydropyrimidin-4-one (intermediate 16; 70 mg; 0.20 mmol) and (S)-3-amino-1,2-propanediol (27.16 mg; 0.30 mmol; 1.50 eq.) as a white solid (57 mg, 100%). 1H NMR (400 MHz, DMSO-d6+D2O): 7.76 (dd, J=7.7, 2.0 Hz, 1H), 7.56-7.44 (m, 2H), 5.34 (s, 1H), 4.25-4.05 (m, 2H), 3.54-3.46 (m, 1H), 3.38-3.25 (m, 2H), 3.04-2.90 (m, 2H), 2.63 (ddd, J=11.6, 8.7, 4.1 Hz, 2H), 2.44 (dd, J=11.7, 7.3 Hz, 1H), 1.97 (s, 3H), 1.84 (dt, J=13.2, 3.8 Hz, 2H), 1.27-1.12 (m, 2H); LC/MS (M+1): 427.0.

Compound 46: 3-(2,3-dichlorophenyl)-6-{4-[(2-hydroxy-3-methoxypropyl)-amino]piperidin-1-yl}-2-methyl-3,4-dihydropyrimidin-4-one

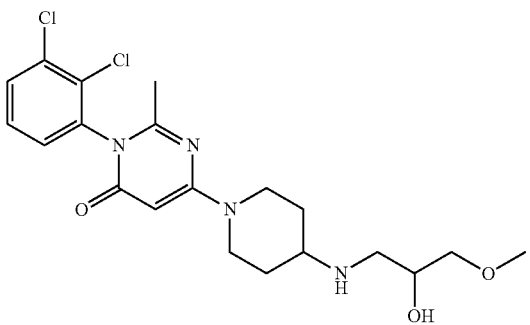 [SMILES: COCC(O)CNC1CCN(c2cc(=O)n(-c3cccc(Cl)c3Cl)c(C)n2)CC1]

The title compound was obtained following procedure described for compound 41 but starting from 3-(2,3-dichlorophenyl)-2-methyl-6-(4-oxopiperidin-1-yl)-3,4-dihydropyrimidin-4-one (Intermediate 16, 70 mg; 0.20 mmol) and 1-amino-3-methoxypropan-2-ol (31 mg; 0.30 mmol) as a white powder (6 mg, 6%). 1H NMR (400 MHz, DMSO-d6): 7.88-7.72 (m, 1H), 7.64-7.42 (m, 2H), 5.37 (s, 1H), 4.83-4.59 (m, 1H), 4.30-3.96 (m, 2H), 3.74-3.54 (m, 1H), 3.31-3.26 (m, 2H), 3.23 (s, 3H), 3.11-2.88 (m, 2H), 2.73-2.55 (m, 2H), 1.98 (s, 3H), 1.92-1.74 (m, 2H), 1.70-1.47 (m, 1H), 1.47-1.30 (m, 1H), 1.30-1.08 (m, 2H); LC/MS (M+1): 441.0.

Compounds 49a and 49b: (3P)-6-[(3S,4S)-4-amino-3-methyl-2-oxa-8-azaspiro[4.5]decan-8-yl]-3-(2,3-dichlorophenyl)-2-methyl-5-(propan-2-yl)-3,4-dihydropyrimidin-4-one and (3M)-6-[(3S,4S)-4-amino-3-methyl-2-oxa-8-azaspiro[4.5]decan-8-yl]-3-(2,3-dichlorophenyl)-2-methyl-5-(propan-2-yl)-3,4-dihydropyrimidin-4-one

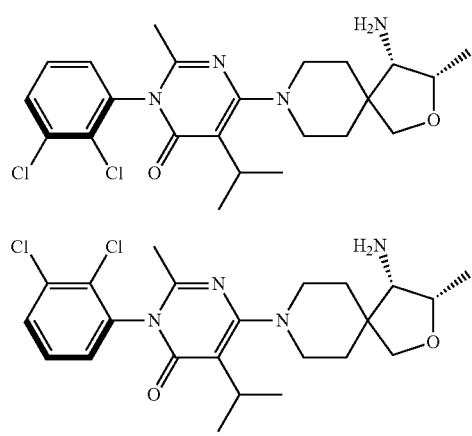

The title compound was obtained following procedure described for compound 36 but starting from 3-(2,3-dichlorophenyl)-6-hydroxy-2-methyl-5-(propan-2-yl)-3,4-dihydropyrimidin-4-one (300 mg; 0.10 mmol) and (3S,4S)-3-methyl-2-oxa-8-azaspiro[4.5]decan-4-amine (171 mg; 0.1 mmol). Purification of the crude by preparative SFC (column Cel₂ 250×21 mm, 5 micron, Methanol+20 mM NH4OH:CO2, 25:75) afforded the two atropisomers.

First eluting atropisomer: 9.1 mg; white solid; Rt=3.48 min.; de=100% (column Cel₂ analytical); 1H NMR (400 MHz, DMSO-d6): 7.79346 (1H), 7.5495 (2H), 4.0583 (1H), 3.65 (1H), 3.55 (1H), 3.47 (1H), 3.21 (1H), 3.14 (1H), 2.90 (1H), 2.37 (1H), 1.973 (3H), 1.78 91H), 1.68 (1 H), 1.54 (1 H), 1.39 (1H),1.2416 (9H); LC/MS (M+1): 465.3

Second eluting isomer: 6.6 mg; white powder; Rt=3.63 min; de=97% (column Cel2 analytical); 1H NMR (400 MHz, DMSO-d6): 7.79346 (1H), 7.5495 (2H), 4.0583 (1H), 3.65 (1H), 3.55 (1H), 3.47 (1H), 3.21 (1H), 3.14 (1H), 2.90 (1H), 2.37 (1H), 1.973 (3H), 1.78 91H), 1.68 (1H), 1.54 (1H), 1.39 (1H), 1.2576 (3H), 1.2115 (3H), 1.0720 (3H); LC/MS (M+1): 465.3

Compound 50: 3-(2,3-dichlorophenyl)-6-(4-{[(4-hydroxycyclohexyl)methyl]amino}-4-methylpiperidin-1-yl)-2-methyl-3,4-dihydropyrimidin-4-one

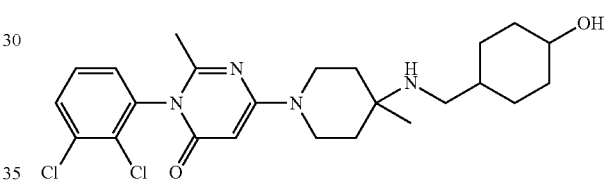

A solution of 6-(4-amino-4-methylpiperidin-1-yl)-3-(2,3-dichlorophenyl)-2-methyl-3,4-dihydropyrimidin-4-one, bis (trifluoroacetic acid) (50 mg; 0.08 mmol), 4-(chloromethyl) cyclohexan-1-ol (161 mg; 1.1 mmol) and potassium carbonate (205 mg, 1.4 mmol) in DMSO (2 mL) was stirred at RT at 80° C. overnight. The crude was directly purified by preparative SFC (column 2EP; Methanol+20 mM NH4OH) to afford the title compound as a white solid (6.3 mg, 14%). LC/MS (M+1): 479.1

Compound 51: 6-(8-amino-1,2,3,4-tetrahydroisoquinolin-2-yl)-3-(2,3-dichlorophenyl)-2,5-dimethyl-3,4-dihydropyrimidin-4-one

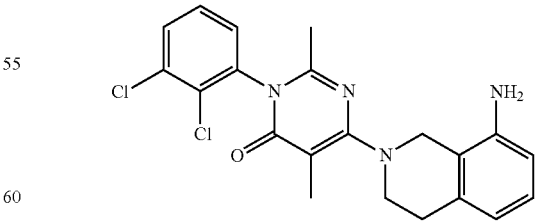

A solution of 6-chloro-3-(2,3-dichlorophenyl)-2,5-dimethyl-3,4-dihydropyrimidin-4-one (intermediate 8; 30 mg; 0.10 mmol), 1,2,3,4-tetrahydroisoquinolin-8-amine (29 mg; 0.20 mmol) and DIEA (70 µL; 0.40 mmol) in anhydrous DMSO (1.5 mL) was stirred overnight at 70° C. The crude was directly purified by preparative HPLC (X-Bridge, ACN: water with 0.1% NH4OH, gradient from 20:80 to 100:0 in 10 min @60 mL/min) to give the title compound a white powder (14 mg, 33%). 1H NMR (DMSO-d6): 7.80 (d, J=8.1, 1.5 Hz, 1H), 7.57 (m, 2H), 6.88 (d, J=8.0 Hz, 1H), 6.52 (t, J=8.0 Hz, 1H), 6.41 (dd, J=8.0 Hz, 1H), 4.87 (br, 2H), 4.32 (m, 2H), 3.62 (m, 2H), 2.85 (m, 2H), 2.018 (s, 3H), 2.000 (s, 3H). LC/MS (M+1): 417.2.

Compounds 57a and 57b: (+/−)-(3M)-6-{4-[(1S)-2-amino-1-hydroxyethyl]-4-methylpiperidin-1-yl}-3-(2,3-dichlorophenyl)-2-methyl-3,4-dihydropyrimidin-4-one and (+/−)-(3P)-6-{4-[(1S)-2-amino-1-hydroxyethyl]-4-methylpiperidin-1-yl}-3-(2,3-dichlorophenyl)-2-methyl-3,4-dihydropyrimidin-4-one

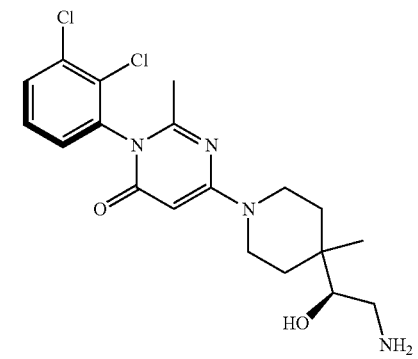

57a

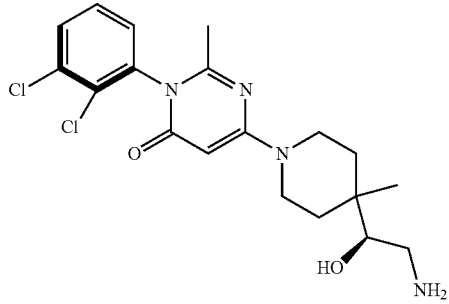

57b (arbitrarily assigned)

The title compound was obtained following procedure described for compound 1, step 1 but starting from 6-chloro-3-(2,3-dichlorophenyl)-2-methyl-3,4-dihydropyrimidin-4-one (intermediate 2; 75 mg; 0.3 mmol) and 2-amino-1-(4-methylpiperidin-4-yl)ethan-1-ol dihydrochloride (Enamine; 120 mg; 0.5 mmol). Purification of the crude by preparative SFC (column Whelk-01 (R,R); 250×21 mm, 5 micron; Methanol+20 mM NH4OH:CO2, 30:70% v/v) afforded two isomers:

First eluting isomer (compound 57a): white solid; 15 mg; ¹H NMR (400 MHz, DMSO-d₆) δ 7.76 (dd, J=7.2, 2.4 Hz, 1H), 7.56-7.44 (m, 2H), 5.31 (s, 1H), 4.11-3.78 (m, 2H), 3.22-3.09 (m, 2H), 3.07 (d, J=9.9 Hz, 1H), 2.66-2.59 (m, 1H), 2.40-2.27 (m, 1H), 1.97 (s, 3H), 1.59-1.45 (m, 2H), 1.41-1.31 (m, 1H), 1.28-1.18 (m, 1H), 0.90 (s, 3H); LC/MS (M+1): 411.0.

Second eluting isomer (compound 57b): white solid; 17 mg; ¹H NMR (400 MHz, DMSO-d₆) δ 7.84-7.72 (m, 1H), 7.58-7.46 (m, 2H), 5.33 (s, 1H), 4.12-3.80 (m, 2H), 3.23-3.10 (m, 2H), 3.10-3.01 (m, 1H), 2.72-2.61 (m, 1H), 2.42-2.30 (m, 1H), 1.98 (s, 3H), 1.62-1.47 (m, 2H), 1.42-1.32 (m, 1H), 1.31-1.20 (m, 1H), 0.91 (s, 3H); LC/MS (M+1): 411.0.

Compounds 58a and 58b: (+/−)-(3M)-6-4-[(1R)-4-amino-4-(2,2-difluoroethyl)-azepan-1-yl]-3-(2,3-dichlorophenyl)-2-methyl-3,4-dihydropyrimidin-4-one and (+/−)-(3P)-6-4-[(1R)-4-amino-4-(2,2-difluoroethyl)-azepan-1-yl]-3-(2,3-dichlorophenyl)-2-methyl-3,4-dihydropyrimidin-4-one

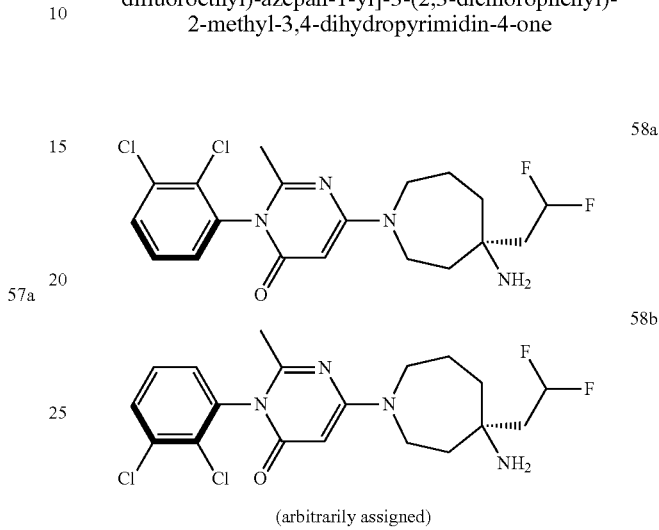

(arbitrarily assigned)

The title compound was obtained following procedure described for compound 1, step 1 but starting from 6-chloro-3-(2,3-dichlorophenyl)-2-methyl-3,4-dihydropyrimidin-4-one (intermediate 2; 75 mg; 0.3 mmol) and 4-(2,2-difluoroethyl)azepan-4-amine dihydrochloride (Chemspace; 130 mg; 0.5 mmol). Purification of the crude by preparative SFC (column Whelk-01 (R,R); 250×21 mm, 5 micron; Methanol+20 mM NH₄OH:CO₂, 30/70% v/v) afforded two isomers:

First eluting isomer (compound 59a): white solid; 15.5 mg; ¹H NMR (400 MHz, DMSO-d₆) δ 7.82-7.72 (m, 1H), 7.59-7.44 (m, 2H), 6.25 (tt, J=56.4, 4.5 Hz, 1H), 5.14 (s, 1H), 4.43-3.34 (m, 4H), 1.98 (s, 3H), 1.91 (td, J=18.3, 4.5 Hz, 3H), 1.82-1.35 (m, 8H); LC/MS (M+1): 431.1.

Second eluting isomer (compound 58b): white solid; 33 mg; ¹H NMR (400 MHz, DMSO-d₆) δ 7.93-7.71 (m, 1H), 7.69-7.46 (m, 2H), 6.26 (tt, J=56.4, 4.4 Hz, 1H), 5.14 (s, 1H), 4.29-3.66 (m, 2H), 3.72-3.42 (m, 2H), 1.99 (s, 3H), 1.92 (td, J=18.3, 4.5 Hz, 2H), 1.85-1.35 (m, 8H); LC/MS (M+1): 430.9.

Compounds 62a and 62b: (3P)-6-{(R)-1-amino-8-azaspiro[4.5]decan-8-yl}-3-(2,3-dichlorophenyl)-2-methyl-3,4-dihydropyrimidin-4-one and (3M)-6-{(R)-1-amino-8-azaspiro[4.5]decan-8-yl}-3-(2,3-dichlorophenyl)-2-methyl-3,4-dihydropyrimidin-4-one

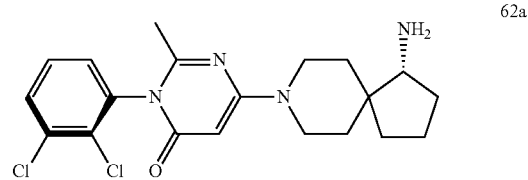

-continued

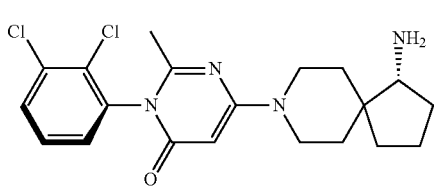

62b

The two atropisomers from compound 27 were separated by preparative SFC (column IG, 300×150 mm, 5 micron, Methanol+20 mM NH$_4$OH:CO$_2$, 40/60% v/v).

First eluting atropisomer (compound 62a): 4.2 mg, RT=3.27 min (AD-H column), ed=100%, $^1$H NMR (400 MHz, DMSO-d): 7.79 (dd, J=6.3, 3.3 Hz, 1H), 7.58-7.47 (m, 2H), 5.36 (s, 1H), 4.10 (brs, 2H), 3.16-2.96 (m, 2H), 2.79 (t, J=7.3 Hz, 1H), 1.99 (s, 3H), 1.95-1.84 (m, 1H), 1.83-1.73 (m, 1H), 1.70-1.59 (m, 2H), 1.59-1.48 (m, 2H), 1.48-1.24 (m, 4H), LC/MS (M+1): 407.1

Second eluting atropisomer (compound 62b): 4.2 mg, RT=4.23 min (AD-H column), ed=100%, $^1$H NMR (400 MHz, DMSO-d$_6$): 7.85-7.73 (m, 1H), 7.58-7.44 (m, 2H), 5.36 (s, 1H), 4.10 (d, J=35.5 Hz, 2H), 3.05 (ddd, J=13.7, 11.8, 3.0 Hz, 2H), 2.80 (t, J=7.3 Hz, 1H), 1.99 (d, J=1.7 Hz, 3H), 1.95-1.83 (m, 1H), 1.78 (ddd, J=12.4, 9.0, 5.6 Hz, 1H), 1.70-1.33 (m, 6H), 1.25 (dd, J=25.9, 13.7 Hz, 2H), LC/MS (M+1):407.1

Compound 63: 6-[(3S,4S)-4-amino-3-methyl-2-oxa-8-azaspiro[4.5]decan-8-yl]-3-(2,3-dichlorophenyl)-5-($^2$H3)methyl-2-methyl-3,4-dihydropyrimidin-4-one

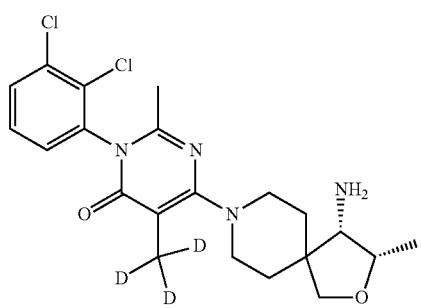 [SMILES: [2H]C([2H])([2H])c1c(N2CCC3(CC2)CO[C@@H](C)[C@H]3N)nc(C)n(-c2cccc(Cl)c2Cl)c1=O]

A solution of 1-(2,3-dichlorophenyl)-5-(2H)-3-methyl-2-methyl-6-oxopyrimidin-4-yl 4-methylbenzenesulfonate (intermediate 24, 140 mg, 0.253 mmol) and (3S,4S)-3-methyl-2-oxa-8-azaspiro[4.5]decan-4-amine (Pharmablock, 85 mg, 0.474 mmol) in NMP (2.0 mL) was stirred for 2 h at 140° C. The resulting mixture was concentrated under vacuum and purified by reverse flash chromatography on C18 silica gel (ACN in water, gradient from 10% to 50%) to give the title compound as a white solid (20 mg, 17.3%). 1H NMR (300 MHz, DMSO-d6): 7.77 (q, J=4.3, 3.8 Hz, 1H), 7.52 (d, J=4.9 Hz, 2H), 4.10-3.96 (m, 1H), 3.64 (d, J=8.4 Hz, 1H), 3.55 (s, 1H), 3.48 (t, J=8.0 Hz, 2H), 3.26 ? 3.08 (m, 1H), 2.88 (d, J=5.1 Hz, 1H), 1.95 (s, 3H), 1.76 (t, J=10.0 Hz, 1H), 1.63 (d, J=8.7 Hz, 1H), 1.50 (s, 4H), 1.06 (d, J=6.4 Hz, 3H), LC/MS (M+1):440.2; m.p: 170-172° C.

Compound 63a and 63b: (3P)-6-[(3S,4S)-4-amino-3-methyl-2-oxa-8-azaspiro[4.5]decan-8-yl]-3-(2,3-dichlorophenyl)-5-(D$_3$)methyl-2-methyl-3,4-dihydropyrimidin-4-one and (3M)-6-[(3S,4S)-4-amino-3-methyl-2-oxa-8-azaspiro[4.5]decan-8-yl]-3-(2,3-dichlorophenyl)-5-(D$_3$)methyl-2-methyl-3,4-dihydropyrimidin-4-one

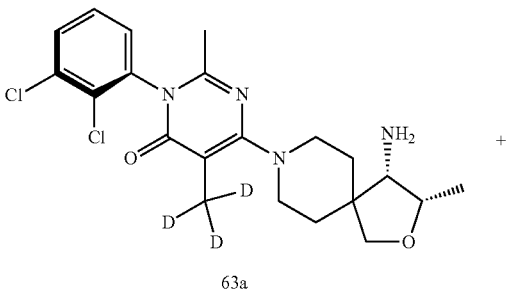

63a

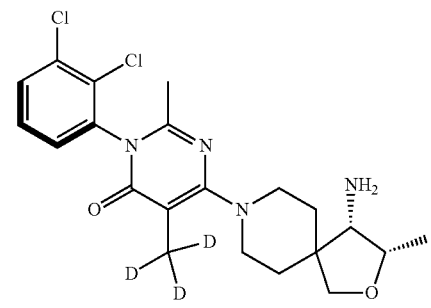

63b

The isomers from compound 63 were separated by preparative SFC (column AD-H, 250×21 mm, 5 micron, Methanol+20 mM NH$_4$OH:CO$_2$, 30:70).

First eluting atropisomer (compound 63a): 14 mg; Rt=2.47 min; ed=100%; 1H NMR (400 MHz, DMSO-d6) δ 7.83-7.76 (m, 1H), 7.57-7.51 (m, 21), 4.11-4.00 (m, 1H), 3.66 (d, J=8.4 Hz, 1H), 3.61-3.51 (m, 2H), 3.49 (d, J=8.4 Hz, 1H), 3.26-3.08 (m, 2H), 2.90 (d, J=5.1 Hz, 1H), 1.97 (s, 3H), 1.84-1.72 (m, 1H), 1.72-1.61 (m, 1H), 1.60-1.44 (m, 2H), 1.42-1.27 (m, 2H), 1.08 (d, J=6.4 Hz, 3H); LC/MS (M+1): 440.2.

Second eluting atropisomer (compound 63b): 15 mg; RT=3.53 min, ed=96.5%; 1H NMR (400 MHz, DMSO-d6) δ 7.83-7.76 (m, 1H), 7.56-7.51 (m, 2H), 4.06 (td, J=6.4, 5.1 Hz, 1H), 3.66 (d, J=8.4 Hz, 1H), 3.61-3.50 (m, 2H), 3.49 (d, J=8.5 Hz, 1H), 3.26-3.07 (m, 2H), 2.90 (d, J=5.1 Hz, 1H), 1.97 (s, 3H), 1.84-1.73 (m, 1H), 1.73-1.61 (m, 1H), 1.62-1.38 (m, 4H), 1.08 (d, J=6.4 Hz, 3H); LC/MS (M+1): 440.2.

Compounds 66a and 66b: (3P)-6-[(5R)-5-amino-5,7-dihydrospiro[cyclopenta[b]pyridine-6,4'-piperidin]-1'-yl]-3-(2,3-dichlorophenyl)-2,5-dimethyl-3,4-dihydropyrimidin-4-one and (3M)-6-[(5S)-5-amino-5,7-dihydrospiro[cyclopenta[b]pyridine-6,4'-piperidin]-1'-yl]-3-(2,3-dichlorophenyl)-2,5-dimethyl-3,4-dihydropyrimidin-4-one

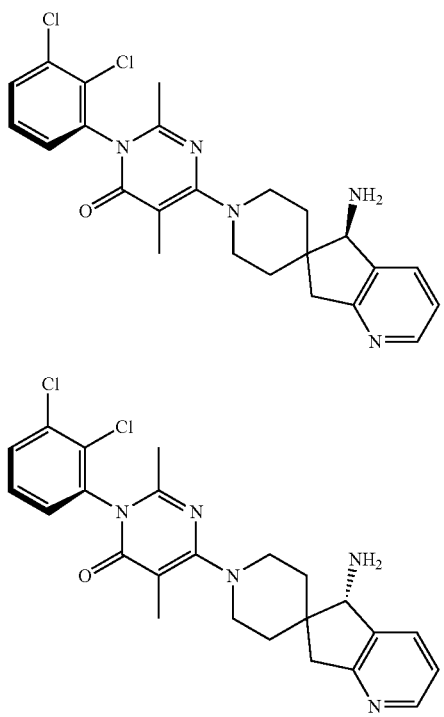

66a

66b

A solution of (1M)-1-(2,3-dichlorophenyl)-2,5-dimethyl-6-oxo-1,6-dihydropyrimidin-4-yl trifluoromethane sulfonate (Intermediate 36b; 1.2 g, 2.9 mmol), 5,7-dihydrospiro [cyclopenta[b]pyridine-6,4'-piperidin]-5-amine dihydrochloride (Intermediate 40, 1.2 g, 4.3 mmol) and DIEA (3 mL, 17.3 mmol) in ethanol (12 mL) was stirred at 60° C. overnight. Solvent was removed under reduced pressure and the residue was partitioned between DCM (10 mL) and NaOH (23 mL of a 0.5N aqueous solution). The mixture was stirred for 30 minutes. Organic phase was washed with brine (10 mL), dried over sodium sulfate, filtered and concentrated. Purification by flash chromatography on silica (EtOAc:MeOH, gradient from 99:1 to 70:30) afforded the title compound as a white powder (550 mg, 38%). The mixture was separated by chiral SFC (column OJH, 250×21 mm, 5 micron, Methanol+20 mM NH$_4$OH:CO$_2$, 45:55) to afford the two pure atropisomers:

First eluting isomer (compound 66a): 138 mg, white solid, RT=2.04 min, ed=100%, 1H NMR (400 MHz, DMSO-d6) δ 8.31 (dd, J=5.0, 1.6 Hz, 1H), 7.84-7.76 (m, 1H), 7.66 (dt, J=7.5, 1.4 Hz, 1H), 7.59-7.51 (m, 2H), 7.16 (dd, J=7.5, 4.9 Hz, 1H), 3.90 (s, 1H), 3.86-3.71 (m, 2H), 3.21-3.10 (m, 2H), 3.08 (d, J=16.2 Hz, 1H), 2.73 (d, J=16.2 Hz, 1H), 1.98 (s, 3H), 1.91 (s, 3H), 1.90-1.71 (m, 2H), 1.54 (d, J=13.2 Hz, 1H), 1.14 (d, J=13.0 Hz, 1H); LC/MS (M+1): 470.1.

Second eluting isomer (compound 66b): 283 mg, white solid, RT=2.22 min, ed=100%, 1H NMR (400 MHz, DMSO-d6) δ 8.31 (dd, J=4.9, 1.6 Hz, 1H), 7.84-7.76 (m, 1H), 7.66 (dt, J=7.4, 1.3 Hz, 1H), 7.59-7.50 (m, 2H), 7.16 (dd, J=7.5, 4.9 Hz, 1H), 3.90 (s, 1H), 3.84-3.72 (m, 2H), 3.20-3.10 (m, 2H), 3.08 (d, J=16.3 Hz, 1H), 2.73 (d, J=16.3 Hz, 1H), 1.98 (s, 3H), 1.91 (s, 3H), 1.89-1.72 (m, 2H), 1.54 (d, J=14.3 Hz, 1H), 1.15 (d, J=12.6 Hz, 1H); LC/MS (M+1): 470.1

Compounds 67a and 67b: (3P)-6-[(1R)-1-amino-8-azaspiro[4.5]decan-8-yl]-3-(2,3-dichlorophenyl)-2,5-dimethyl-3,4-dihydropyrimidin-4-one and (3M)-6-[(1R)-1-amino-8-azaspiro[4.5]decan-8-yl]-3-(2,3-dichlorophenyl)-2,5-dimethyl-3,4-dihydropyrimidin-4-one Step 1: Tert-Butyl N-[(1R)-8-[1-(2,3-dichlorophenyl)-2,5-dimethyl-6-oxo-1,6-dihydropyrimidin-4-yl]-8-azaspiro[4.5]decan-1-yl]carbamate

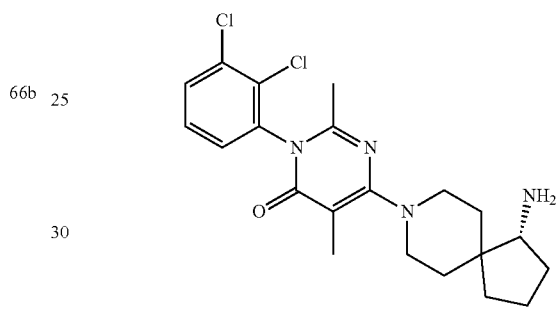

A solution of 6-chloro-3-(2,3-dichlorophenyl)-2,5-dimethyl-3,4-dihydropyrimidin-4-one (Intermediate 8; 100 mg; 0.30 mmol), tert-butyl N-[(1R)-8-azaspiro[4.5]decan-1-yl]carbamate (WUXI; 167 mg; 0.7 mmol) and DIEA (200 µL) in anhydrous DMSO (2.0 mL) was stirred overnight at 70° C. The reaction mixture was then diluted with water (5 mL) and extracted with EtOAc (10 mL). organic phase was washed with water (2×5 mL) and brine (10 mL), dried over sodium sulfate, filtered and concentrated. Purification by flash chromatography on silica (Hexanes:EtOAc, gradient 80:20 to 0:100) afforded the title compound as a white solid (118 mg, 69%). LC/MS (M+1): 521.1.

Step 2: (3P)-6-[(1R)-1-amino-8-azaspiro[4.5]decan-8-yl]-3-(2,3-dichlorophenyl)-2,5-dimethyl-3,4-dihydropyrimidin-4-one and (3M)-6-[(1R)-1-amino-8-azaspiro[4.5]decan-8-yl]-3-(2,3-dichlorophenyl)-2,5-dimethyl-3,4-dihydropyrimidin-4-one

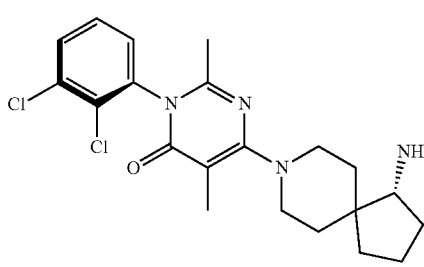

67a

-continued

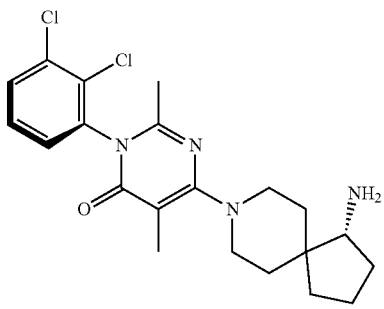

67b

A solution of tert-butyl N-[(1R)-8-[1-(2,3-dichlorophenyl)-2,5-dimethyl-6-oxo-1,6-dihydropyrimidin-4-yl]-8-azaspiro[4.5]decan--yl]carbamate (118 mg, 0.2 mmol) in TFA (1.2 mL) and DCM (2.4 mL) was stirred at RT for 1 h. Solvent was then removed under reduced pressure. Toluene was added to the crude and concentrated to remove residual TFA. Purification by preparative SFC (column AD-H; 250× 21 mm, 5 micron; Methanol+20 mM $NH_4OH:CO_2$, 20/80% v/v) afforded two atropisomers:

First eluting atropisomer (compound 67a): 36 mg; white foam; RT=4.13 min; ed=100% (AD-H column); 1H NMR (Bruker 400 MHz, DMSO-d6): 7.83-7.74 (m, 1H), 7.59-7.48 (m, 2H), 3.78-3.66 (m, 2H), 3.12-2.94 (m, 2H), 2.71 (t, J=7.3 Hz, 1H), 1.97 (s, 3H), 1.89 (s, 3H), 1.88-1.70 (m, 3H), 1.70-1.56 (m, 3H), 1.57-1.43 (m, 2H), 1.43-1.13 (m, 4H); LC/MS (M+1): 421.0

Second eluting atropisomer (compound 67b): 39 mg; white foam; RT=5.42 min (AD-H column); ed=100%; 1H NMR (Bruker 400 MHz, DMSO-d6) δ 7.82-7.74 (m, 1H), 7.57-7.46 (m, 2H), 3.78-3.63 (m, 2H), 3.09-2.96 (m, 2H), 2.71 (t, J=7.3 Hz, 1H), 1.97 (s, 3H), 1.89 (s, 3H), 1.86-1.69 (m, 3H), 1.69-1.56 (m, 3H), 1.56-1.42 (m, 2H), 1.41-1.15 (m, 4H); LC/MS (M+1): 421.0

Compound 70: 6-(4-Amino-4-methyl-piperidin-1-yl)-3-(2,3-dichloro-phenyl)-5-methyl-3H-pyrimidin-4-one Step 1: Tert-Butyl N-{1-[1-(2,3-dichlorophenyl)-5-methyl-2-(methylsulfanyl)-6-oxo-1,6-dihydropyrimidin-4-yl]-4-methylpiperidin-4-yl}carbamate

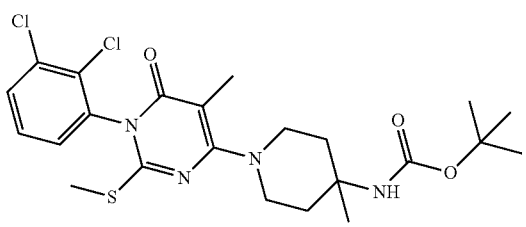 [SMILES: CSc1nc(N2CCC(C)(NC(=O)OC(C)(C)C)CC2)c(C)c(=O)n1-c1cccc(Cl)c1Cl]

A solution of 1-(2,3-dichlorophenyl)-5-methyl-2-(methylsulfanyl)-6-oxopyrimidin-4-yl 4-methylbenzenesulfonate (intermediate 35, step 3; 80 mg, 0.12 mmol), tert-butyl N-(4-methylpiperidin-4-yl)carbamate (104 mg, 0.46 mmol), $Cs_2CO_3$ (118 mg, 0.346 mmol) in DMF (4.0 mL) maintained in nitrogen atmosphere was heated for 2 h at 100° C. in a sealed tube. The reaction was cooled down to room temperature and quenched with water. The aqueous layer was extracted with EtOAc (3×40 mL). Combined organic phases were the dried over sodium sulfate, filtered and concentrated to give the title compound as an off-white solid (50 mg, 26%). LC/MS (M+1): 513.2.

Step 2: 6-(4-amino-4-methylpiperidin-1-yl)-3-(2,3-dichlorophenyl)-5-methyl-2-(methylsulfanyl)-3,4-dihydropyrimidin-4-one

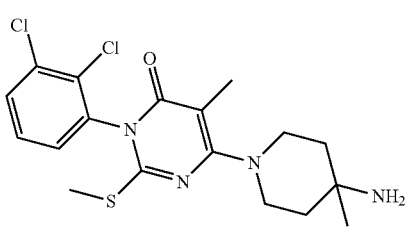 [SMILES: CSc1nc(N2CCC(C)(N)CC2)c(C)c(=O)n1-c1cccc(Cl)c1Cl]

A solution of tert-butyl N-[1-[1-(2,3-dichlorophenyl)-5-methyl-2-(methylsulfanyl)-6-oxopyrimidin-4-yl]-4-methylpiperidin-4-yl]carbamate (20 mg, 0.026 mmol) in MeOH/ HC (2.0 mL, 14%) was stirred for 1 h at room temperature. The resulting mixture was concentrated under reduced pressure to give the title compound as a brown solid (15 mg, 83%). LC/MS (M+1): 413.2.

Step 3: 6-(4-Amino-4-methyl-piperidin-1-yl)-3-(2,3-dichloro-phenyl)-5-methyl-3H-pyrimidin-4-one

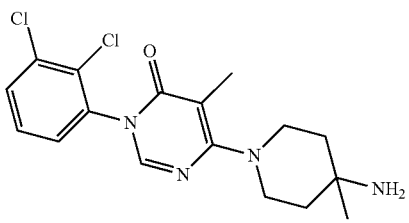 [SMILES: Cc1c(N2CCC(C)(N)CC2)ncn(-c2cccc(Cl)c2Cl)c1=O]

Raney Ni (12 mg, 0.130 mmol) was added to a solution of 6-(4-amino-4-methylpiperidin-1-yl)-3-(2,3-dichlorophenyl)-5-methyl-2-(methylsulfanyl)pyrimidin-4-one (15 mg, 0.022 mmol) in DMA (2.0 mL) maintained under inert atmosphere. The resulting solution was heated for 16 h at 70° C. it was then filtered through a celite pad. The filter cake was washed with MeOH (30 mL) and the filtrate was concentrated under reduced pressure. The residue was purified by reverse flash chromatography on C18 silica gel (ACN:water+$NH_4HCO_3$, gradient from 10:90 to 50:50 in 10 min) to give the title compound as an off-white solid (5 mg, 59%). 1H NMR (400 MHz, DMSO-d6): 8.14 (s, 1H), 7.81 (dd, J=6.9, 2.8 Hz, 1H), 7.61 (d, J=7.9 Hz, 1H), 7.58-7.48 (m, 2H), 7.44 (d, J=7.9 Hz, 1H), 3.53-3.45 (m, 3H), 3.40 (s, 4H), 1.55-150 (m, 4H), 1.24 (s, 3H); LC/MS (M+1): 367.2; mp: 136-138° C.

Compounds 71a and 71b: 3-(2,3-dichlorophenyl)-2-methyl-6-{methyl[(trans)-4-amino-4-methylcyclohexyl]amino}-3,4-dihydropyrimidin-4-one and 3-(2,3-dichlorophenyl)-2-methyl-6-{methyl[(cis)-4-amino-4-methylcyclohexyl]amino}-3,4-dihydropyrimidin-4-one

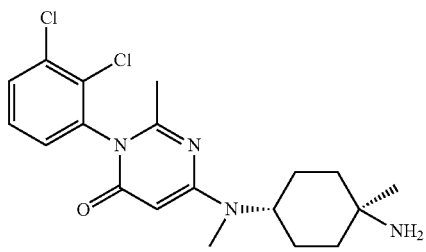

71a

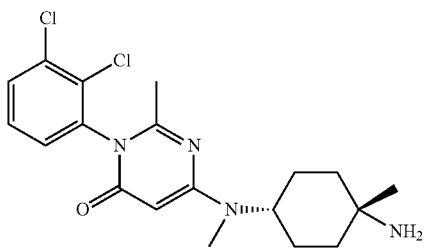

71b

The title compounds were obtained following procedure described for compound 1, step 1 but starting from 6-chloro-3-(2,3-dichlorophenyl)-2-methyl-3,4-dihydro-pyrimidin-4-one (intermediate 2; 75 mg; 0.3 mmol) and N-1,4-dimethylcyclohexane-1,4-diamine dihydrochloride (Enamine; 112 mg; 0.5 mmol). Purification of the crude by preparative SFC (column column 2EP; Methanol+20 mM NH₄OH) afforded two isomers (arbitrarily assigned):

First eluting isomer (compound 71a): 27 mg, white solid; LC/MS (M+1): 395.1

Second eluting isomer (compound 71b): 26 mg, white solid; LC/MS (M+1): 395.1

Compounds 72a and 72b: (+/−)-(3P)-3-(2,3-dichlorophenyl)-6-{4-[(3R)-3-hydroxypyrrolidin-1-yl]-4-methylpiperidin-1-yl}-2-methyl-3,4-dihydro-pyrimidin-4-one and (+/−)-(3M)-3-(2,3-dichlorophenyl)-6-{4-[(3R)-3-hydroxy-pyrrolidin-1-yl]-4-methylpiperidin-1-yl}-2-methyl-3,4-dihydropyrimidin-4-one

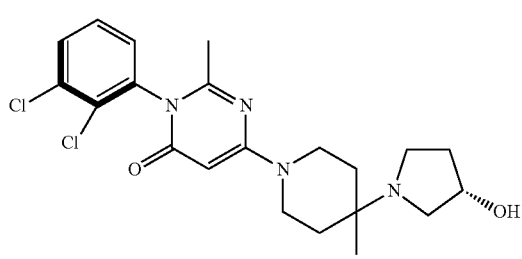

72a

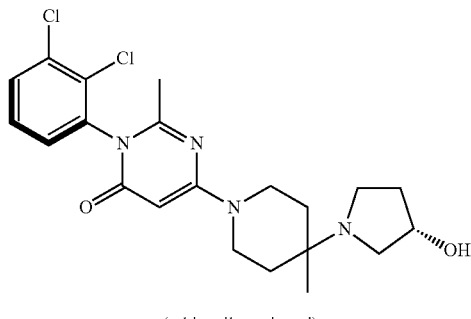

72b (arbitrarily assigned)

The title compounds were obtained following procedure described for compound 1, step 1 but starting from 6-chloro-3-(2,3-dichlorophenyl)-2-methyl-3,4-dihydropyrimidin-4-one (intermediate 2; 75 mg; 0.3 mmol) and 1-(4-methyl-4-piperidinyl)-3-pyrrolidinol dihydrochloride (Matrix; 133 mg; 0.5 mmol). Purification of the crude by preparative SFC (column column 2EP; Methanol+20 mM NH₄OH) afforded two atropisomers (arbitrarily assigned):

First eluting isomer (compound 72a): 27 mg, white solid; LC/MS (M+1): 437.0

Second eluting isomer (compound 72b): 26 mg, white solid; LC/MS (M+1): 437.1

Compounds 73a and 73b: (3P)-6-[(3S,4S)-4-amino-3-methyl-2-oxa-8-azaspiro-[4.5]decan-8-yl]-3-(2,3-dichlorophenyl)-5-methoxy-2-methyl-3,4-dihydropyrimidin-4-one and (3M)-6-[(3S,4S)-4-amino-3-methyl-2-oxa-8-azaspiro-[4.5]decan-8-yl]-3-(2,3-dichlorophenyl)-5-methoxy-2-methyl-3,4-dihydropyrimidin-4-one

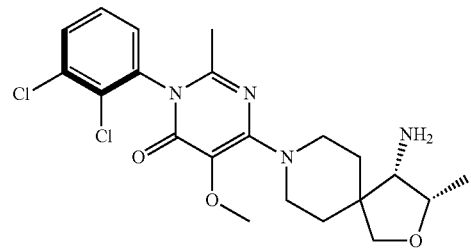

73a

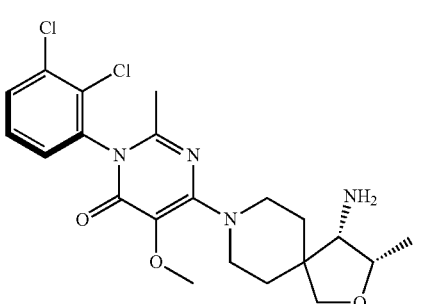

73b

The title compounds were obtained following procedure described for compound 36 but starting from 3-(2,3-dichlorophenyl)-6-hydroxy-5-methoxy-2-methyl-3,4-dihydropyrimidin-4-one (Intermediate 21, 300 mg, 1 mmol) and (3S,4S)-3-methyl-2-oxa-8-azaspiro[4.5]decan-4-amine dihydrochloride (WUXI, 254 mg, 1 mmol). The atropisomers were separated by preparative SFC (column ADH, 250×21 mm, 5 micron, Methanol+20 mM NH₄OH:CO₂, 30:70).

First eluting atropisomer (compound 73a): 36 mg; Rt=2.97 min; ed=100%; 7.76 (dd, J=8.1, 1.5 Hz, 1H), 7.55 (m, 2H), 4.04 (m, 3H), 3.65 (d, J=6.8 Hz, 1H), 3.59 (s, 3H), 3.480 (m, 2H), 2.891 (d, J=6.5 Hz, 2H), 1.96 (s, 3H), 1.79 (m, 1H), 1.62 (m, 1H), 1.54-1.44 (m, 2H), 1.07 (d, J=6.8 Hz, 3H); LC/MS (M+1): 453.2.

Second eluting atropisomer (compound 73b): 34 mg; RT=3.98 min, ed=98.5%; 8.27 (s, 1H), 7.76 (m, 1H), 7.55 (m, 2H), 4.04 (m, 3H), 3.65 (d, J=6.8 Hz, 1H), 3.59 (s, 3H), 3.510 (d, J=6.8 Hz, 2H), 2.891 (d, J=6.5 Hz, 2H), 1.96 (s, 3H), 1.79 (m, 1H), 1.62 (m, 1H), 1.54-1.44 (m, 2H), 1.07 (d, J=6.6 Hz, 3H); LC/MS (M+1): 453.2.

Compound 74a: (3M)-6-[(1S)-1-amino-1,3-dihydrospiro[indene-2,4'-piperidin]-1'-yl]-3-(2,3-dichlorophenyl)-2,5-dimethyl-3,4-dihydropyrimidin-4-one Step 1: (3M)-N-[(1S)-1'-[(1P)-1-(2,3-dichlorophenyl)-2,5-dimethyl-6-oxo-1,6-dihydro pyrimidin-4-yl]-1,3-dihydrospiro[indene-2,4'-piperidin]-1-yl]-2-methylpropane-2-sulfinamide

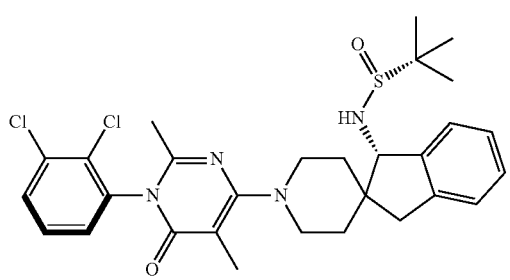

The title compound was obtained following procedure described for compound 36 but starting from (3M)-3-(2,3-dichlorophenyl)-6-hydroxy-2,5-dimethyl-3,4-dihydropyrimidin-4-one (intermediate 7b; 300 mg; 1.1 mmol) and N-[(1S)-1,3-dihydrospiro[indene-2,4'-piperidin]-1-yl]-2-methylpropane-2-sulfinamide; trifluoroacetic acid (WUXI; 531 mg; 1.3 mmol). Purification of the crude by preparative HPLC (Column Waters XBridge Prep C-18 OBD 10 uM, 30×250, ACN:water with 0.1% NH₄OH, gradient from 20:100 to 100:0 in 10 min@ 60 mL/min) afforded the title compound as a white foam. 1H NMR (400 MHz, DMSO-d6): 7.81 (dd, J=5.6, 4.1 Hz, 1H), 7.54 (m, 2H), 7.28-7.23 (m, 4H), 5.65 (d, J=10.4 Hz, 2H), 4.45 (d, J=10.3 Hz, 2H), 3.86 (m, 2H), 3.16 (m, 2H), 3.11 (d, J=15.8 Hz, 1H), 2.72 (m, 1H), 1.91 (s, 3H), 1.89 (s, 3H), 1.62 (m, 1H), 1.29 (m, 1H), 1.23 (s, 9H); LC/MS (M+1): 573.2.

Step 2: (3M)-6-[(1S)-1-amino-1,3-dihydrospiro[indene-2,4'-piperidin]-1'-yl]-3-(2,3-dichlorophenyl)-2,5-dimethyl-3,4-dihydropyrimidin-4-one

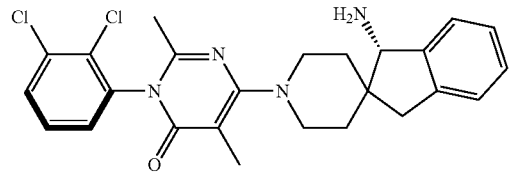

A solution of N-[(1S)-1'-[(1P)-1-(2,3-dichlorophenyl)-2,5-dimethyl-6-oxo-1,6-dihydropyrimidin-4-yl]-1,3-dihydrospiro[indene-2,4'-piperidin]-1-yl]-2-methylpropane-2-sulfinamide (200 mg; 0.35 mmol) in MeOH/HCl (3M, 3 mL) was stirred at RT for 3 hours. The solvent was removed under reduced pressure and the crude was purified by preparative HPLC (Column Waters XBridge Prep C-18 OBD 10 uM, 30×250, ACN:water with 0.1% NH₄OH, gradient from 20:100 to 100:0 in 10 min@ 60 mL/min) to afford the title compound as a white foam (94 mg, 57%).

1H NMR (400 MHz, DMSO-d6): 7.80 (t, J=4.8 Hz, 1H), 7.58-7.50 (m, 2H), 7.35-7.28 (m, 1H), 7.22-7.11 (m, 3H), 3.85 (s, 1H), 3.78 (ddd, J=13.6, 8.6, 5.5 Hz, 2H), 3.21-3.08 (m, 2H), 3.05 (d, J=15.6 Hz, 1H), 2.61 (d, J=15.6 Hz, 1H), 1.98 (s, 3H), 1.91 (s, 3H), 1.89-1.65 (m, 2H), 1.57-1.47 (m, 1H), 1.18-1.07 (m, 1H). LC/MS (M+1): 469.2

Compound 74b: (3P)-6-[(1S)-1-amino-1,3-dihydrospiro[indene-2,4'-piperidin]-1'-yl]-3-(2,3-dichlorophenyl)-2,5-dimethyl-3,4-dihydropyrimidin-4-one

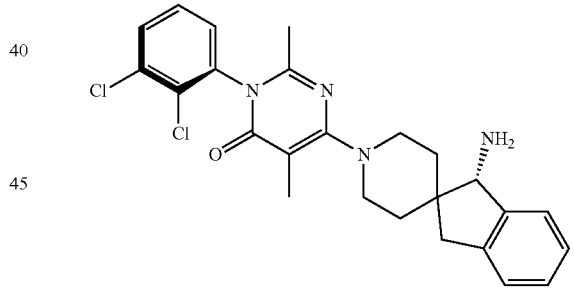

A solution of (3P)-6-chloro-3-(2,3-dichlorophenyl)-2,5-dimethyl-3,4-dihydro-pyrimidin-4-one (intermediate 8a, 200 mg; 0.7 mmol), (3S)-1,3-dihydrospiro[indene-2,4'-piperidin]-3-amine dihydrochloride (Pharmablock, 113 mg; 0.66 mmol) and DIEA (0.7 mL, 4 mmol) in EtOH (2.0 mL) was stirred overnight at 60° C. The mixture was concentrated under reduced pressure and partitioned between DCM (10 mL) and aq. NaOH, 2.2 mL of a 0.5N solution). Organic layer was washed with brine (3 mL), dried over sodium sulfate, filtered and concentrated. Purification by flash chromatography on silica afforded the title compounds as a white solid (127 mg, 40%). 1H NMR (400 MHz, DMSO-d6) ? 7.80 (dd, J=5.3, 4.3 Hz, 1H), 7.58-7.51 (m, 2H), 7.34-7.28 (m, 1H), 7.22-7.11 (m, 3H), 3.84 (s, 1H), 3.83-3.69 (m, 2H), 3.21-3.08 (m, 2H), 3.05 (d, J=15.6 Hz, 1H), 2.61 (d, J=15.6 Hz, 1H), 1.98 (s, 3H), 1.91 (s, 3H), 1.89-1.67 (m, 4H), 1.56-1.47 (m, 1H), 1.16-1.08 (m, 1H); LC/MS (M+1):

469.2; ed=100%; Rt=3.04 min (SFC, column IA, 4.6×100 mm, 5 micron, Methanol+20 mM NH₄OH:CO₂, gradient 5-60 to 60-5).

Compound 74c: (3M)-6-[(1R)-1-amino-1,3-dihydrospiro[indene-2,4'-piperidin]-1'-yl]-3-(2,3-dichlorophenyl)-2,5-dimethyl-3,4-dihydropyrimidin-4-one

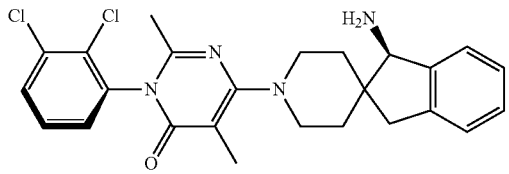

A solution of (1M)-1-(2,3-dichlorophenyl)-2,5-dimethyl-6-oxo-1,6-dihydropyrimidin-4-yl trifluoromethane sulfonate (Intermediate 36b; 325 mg; 0.8 mmol), (1R)-1,3-dihydrospiro[indene-2,4'-piperidin]-1-amine dihydrochloride (Intermediate 41; 322 mg; 1.2 mmol) and DIEA (0.8 mL, 4.7 mmol) in ethanol (3.3 mL) was stirred at 60° C. overnight. Solvent was removed under reduced pressure and the residue was partitioned between DCM (10 mL) and NaOH (6 mL of a 0.5N aqueous solution). The mixture was stirred for 30 minutes. Organic phase was washed with brine (3 mL), dried over sodium sulfate, filtered and concentrated. Purification by flash chromatography on silica (EtOAc:MeOH, gradient from 99:1 to 70:30) afforded the title compound as a white solid (186 mg, 51%). 1H NMR (400 MHz, DMSO-d6) δ 7.84-7.76 (m, 1H), 7.59-7.51 (m, 2H), 7.34-7.27 (m, 1H), 7.23-7.10 (m, 3H), 3.84 (s, 1H), 3.83-3.69 (m, 2H), 3.21-3.08 (m, 2H), 3.04 (d, J=15.4 Hz, 1H), 2.60 (d, J=15.5 Hz, 1H), 1.98 (s, 3H), 1.91 (s, 3H), 1.89-1.79 (m, 1H), 1.79-1.65 (m, 3H), 1.52 (d, J=13.3 Hz, 1H), 1.11 (d, J=13.2 Hz, 1H); LC/MS (M+1): 469.2; ed=100%; Rt=2.3 min (SFC, column OJH, 4.6×100 mm, 5 micron, Methanol+20 mM NH₄OH:CO₂, 35:65).

Compound 74d: (3P)-6-[(1R)-1-amino-1,3-dihydrospiro[indene-2,4'-piperidin]-1'-yl]-3-(2,3-dichlorophenyl)-2,5-dimethyl-3,4-dihydropyrimidin-4-one

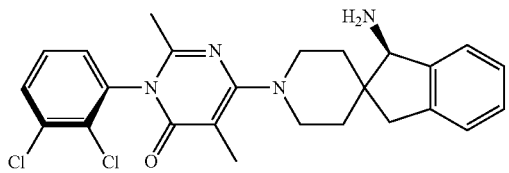

The title compound was obtained following procedure described for compound 74b but starting from (3P)-6-chloro-3-(2,3-dichlorophenyl)-2,5-dimethyl-3,4-dihydropyrimidin-4-one (Intermediate 7a) and (1R)-1,3-dihydrospiro[indene-2,4'-piperidin]-1-amine dihydrochloride (intermediate 41) as a white solid. 1H NMR (400 MHz, DMSO-d6) δ 7.80 (t, J=4.8 Hz, 1H), 7.61-7.48 (m, 2H), 7.38-7.24 (m, 1H), 7.24-7.06 (m, 3H), 3.84 (s, 1H), 3.77 (t, J=12.2 Hz, 2H), 3.20-3.07 (m, 2H), 3.04 (d, J=15.7 Hz, 1H), 2.61 (d, J=15.6 Hz, 1H), 1.98 (s, 3H), 1.91 (s, 3H), 1.87-1.63 (m, 4H), 1.59-1.43 (m, 1H), 1.18-1.07 (m, 1H); LC/MS (M+1): 469.1; ed=100%; Rt=6.6 min (SFC, column Whelk-01(R,R), 4.6×100 mm, 5 micron, Methanol+20 mM NH₄OH:CO₂, 45:55).

Compound 75: (3M)-6-[(6R)-6-amino-5,6-dihydrospiro[cyclopenta[b]pyridine-7,4'-piperidin]-1'-yl]-3-(2,3-dichlorophenyl)-2,5-dimethyl-3,4-dihydropyrimidin-4-one

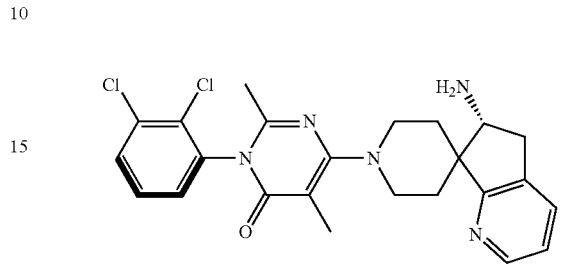

The title compound was obtained following procedure described for compound 74a but starting from (3M)-3-(2,3-dichlorophenyl)-6-hydroxy-2,5-dimethyl-3,4-dihydro-pyrimidin-4-one (Intermediate 7b, 300 mg, 1.1 mmol) and N-[(6R)-5,6-dihydrospiro[cyclopenta[b]pyridine-7,4'-piperidin]-6-yl]-2-methylpropane-2-sulfinamide; trifluoroacetic acid (intermediate 22, 532 mg, 1.3 mmol) as a white foam (18 mg, 4%—two steps). 1H NMR (DMSO-d6): 8.32 (s, 1H), 7.79 (s, 1H), 7.59 (d, J=8.1 Hz, 1H), 7.56 (m, 2H), 7.14 (t, J=8.1 Hz, 1H), 3.99 (brs, 1H), 3.67 (m, 1H), 3.57 (m, 2H), 3.41 (m, 1H), 3.12-309 (m, 1H), 2.84 (m, 1H), 2.60-2.57 (m, 1H), 1.97 (s, 3H), 1.93 (s, 3H), 1.74 (m, 2H), 1.62 (m, 1H); LC/MS (M+1): 470.2.

Compound 76: 6-[(3S,4S)-4-amino-3-methyl-2-oxa-8-azaspiro[4.5]decan-8-yl]-3-(2,3-dichlorophenyl)-5-(2-hydroxyethyl)-2-methyl-3,4-dihydropyrimidin-4-one Hydrochloride Step 1: Methyl 2-{4-[(3S,4S)-4-amino-3-methyl-2-oxa-8-azaspiro[4.5]decan-8-yl]-1-(2,3-dichlorophenyl)-2-methyl-6-oxo-1,6-dihydropyrimidin-5-yl}acetate

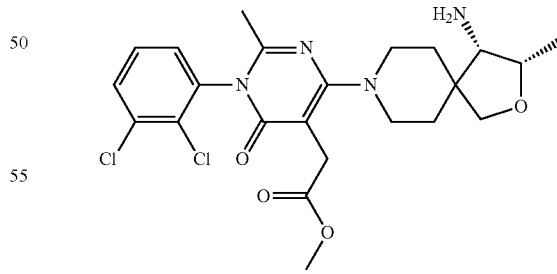

The title compound was obtained following procedure described for compound 21, step 1 but starting from methyl 2-[1-(2,3-dichlorophenyl)-2-methyl-4-[(4-methyl-benzenesulfonyl)oxy]-6-oxo-1,6-dihydropyrimidin-5-yl]acetate (Intermediate 43) and (3S,4S)-3-methyl-2-oxa-8-azaspiro[4.5]decan-4-amine (Pharmablock) as a yellow solid. LC/MS (M+1): 495.2.

Step 2: 6-[(3S,4S)-4-amino-3-methyl-2-oxa-8-azaspiro[4.5]decan-8-yl]-3-(2,3-dichlorophenyl)-5-(2-hydroxyethyl)-2-methyl-3,4-dihydropyrimidin-4-one Hydrochloride

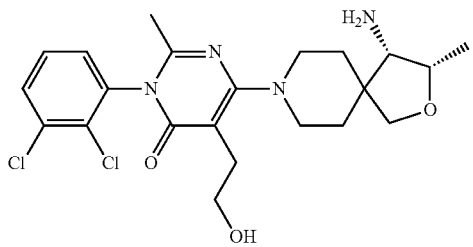 [SMILES: Cc1nc(N2CCC3(CC2)CO[C@@H](C)[C@H]3N)c(CCO)c(=O)n1-c1cccc(Cl)c1Cl]

Lithium borohydride (6 mg, 0.24 mmol) was added to a solution of methyl 2-[4-[(3S,4S)-4-amino-3-methyl-2-oxa-8-azaspiro[4.5]decan-8-yl]-1-(2,3-dichlorophenyl)-2-methyl-6-oxopyrimidin-5-yl]acetate (30 mg, 0.060 mmol) in THF (2.10 mL) maintained under nitrogen atmosphere at 0° C. The reaction mixture was then stirred at the same temperature for 4 h and quenched with MeOH. Solvent was removed under reduced pressure and the residue was purified by preparative HPLC (XBridge Prep C18 OBD Column, 19×150 mm, 5 µm; water (0.05% HCl) and ACN gradient from 20 to 50%) to afford the title compound as an off-white solid (10 mg, 31%). 1H NMR (300 MHz, Methanol-d4): 7.75 (d, J=8.0 Hz, 1H), 7.53 (t, J=7.8 Hz, 1H), 7.43 (d, J=7.9 Hz, 1H), 4.31 (s, 1H), 3.99 (d, J=9.2 Hz, 1H), 3.87 (d, J=9.2 Hz, 1H), 3.80 (s, 3H), 3.49 (s, 1H), 3.21 (d, J=13.1 Hz, 1H), 2.79 (t, J=6.6 Hz, 2H), 2.12 (s, 3H), 1.98 (d, J=14.9 Hz, 4H), 1.33 (d, J=6.3 Hz, 3H); LC/MS (M+1): 467.00; mp: 102-103° C.

Compound 77: (3M)-6-[(1R,3R)-1-amino-3-methyl-8-azaspiro[4.5]decan-8-yl]-3-(2,3-dichlorophenyl)-2,5-dimethyl-3,4-dihydropyrimidin-4-one

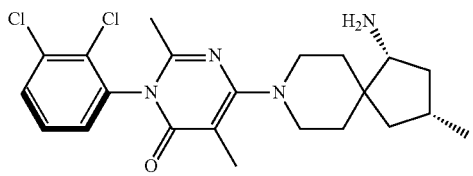

A solution of (1M)-1-(2,3-dichlorophenyl)-2,5-dimethyl-6-oxo-1,6-dihydropyrimidin-4-yl trifluoromethane sulfonate (Intermediate 36; 150 mg; 0.36 mmol), (1R,3R)-3-methyl-8-azaspiro[4.5]decan-1-amine dihydrochloride (Pharmablock; 108 mg; 0.45 mmol) and DIEA (0.25 mL, 1.44 mmol) in ethanol (1.5 mL) was stirred at 60° C. overnight. Solvent was removed under reduced pressure and the residue was partitioned between DCM (10 mL) and NaOH (2.2 mL of a 0.5N aqueous solution). The mixture was stirred for 30 minutes. Organic phase was washed with brine (3 mL), dried over sodium sulfate, filtered and concentrated. Purification by flash chromatography on silica (EtOAc:MeOH, gradient from 95:5 to 60:40) afforded the title compound as a white solid (116 mg, 74%). 1H NMR (Bruker 400 MHz, DMSO-d6): 7.84-7.75 (m, 1H), 7.57-7.50 (m, 2H), 3.79-3.62 (m, 2H), 3.11-2.93 (m, 2H), 2.73 (dd, J=8.9, 6.0 Hz, 1H), 2.09-1.93 (m, 5H), 1.89 (s, 3H), 1.81-1.63 (m, 2H), 1.63-1.51 (m, 1H), 1.33-1.16 (m, 3H), 1.09-0.91 (m, 4H); LC/MS (M+): 435; ed=100% (chiral SFC, column IA, MeOH+20 mM NH4OH).

Compounds 78a, 78b, 78c, 78d: (3P)-2-amino-6-[(1S)-1-amino-8-azaspiro-[4.5]decan-8-yl]-3-(2,3-dimethylphenyl)-5-methyl-3,4-dihydropyrimidin-4-one; (3P)-2-amino-6-[(1R)-1-amino-8-azaspiro[4.5]decan-8-yl]-3-(2,3-dimethyl-phenyl)-5-methyl-3,4-dihydropyrimidin-4-one; (3M)-2-amino-6-[(1S)-1-amino-8-azaspiro[4.5]decan-8-yl]-3-(2,3-dichlorophenyl)-5-methyl-3,4-dihydropyrimidin-4-one; (3M)-2-amino-6-[(1R)-1-amino-azaspiro[4.5]decan-8-yl]-3-(2,3-dichlorophenyl)-5-methyl-3,4-dihydropyrimidin-4-one

Step 1: Tert-Butyl N-{8-[2-amino-1-(2,3-dichloro-phenyl)-5-methyl-6-oxo-1,6-dihydro-pyrimidin-4-yl]-8-azaspiro[4.5]decan-1-yl}carbamate

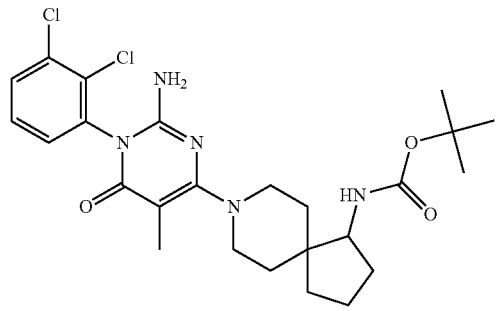 [SMILES: Cc1c(N2CCC3(CCCC3NC(=O)OC(C)(C)C)CC2)nc(N)n(-c2cccc(Cl)c2Cl)c1=O]

The title compound was obtained following procedure described for compound 77 but starting from 2-amino-1-(2,3-dichlorophenyl)-5-methyl-6-oxo-1,6-dihydropyrimidin-4-yl trifluoromethanesulfonate (intermediate 37) and tert-butyl N-{8-azaspiro[4.5]decan-1-yl}carbamate (Chembridge) as a white solid. LC/MS (M+1): 522.2.

Step 2: Isomers Separation and Boc Deprotection

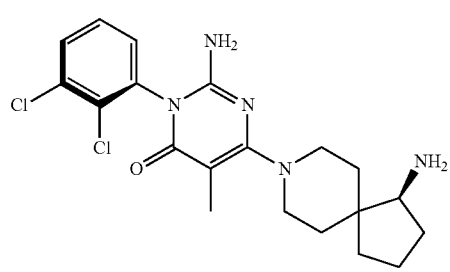

78a

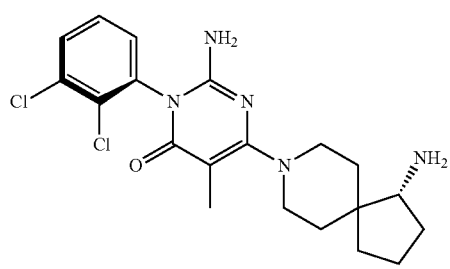

78b

-continued

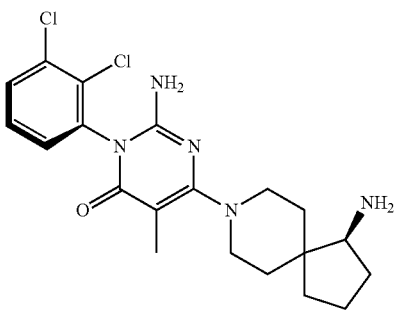

78c

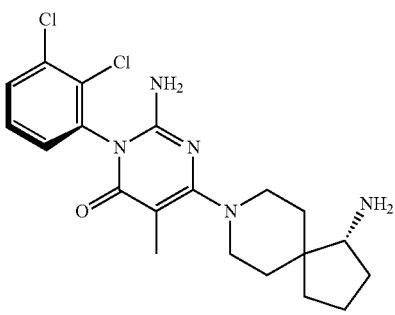

78d

The four diastereoisomers of tert-butyl N-{8-[2-amino-1-(2,3-dichlorophenyl)-5-methyl-6-oxo-1,6-dihydropyrimidin-4-yl]-8-azaspiro[4.5]decan-1-yl}carbamate were separated by preparative chiral HPLC. After treatment with TFA, the four diastereoisomers were obtained.

First purification (CHIRALPAK IA, 3×25 cm, 5 µm; Hexane+8 mM $NH_3$.MeOH and EtOH, 30:70%) provided two fractions A and B.

Fraction A (RT=4.5 min, 100 mg, mixture of two isomers) was separated (CHIRALPAK IG, 2×25 cm, 5 µm; Hexane+8 mM $NH_3$.MeOH and EtOH, 15:85%) to give:

First eluting isomer (Boc): Rt=3.61 min; ed=100%.

First eluting isomer after Boc deprotection (compound 78a): Rt=5.73 min (column Cellulose SB4, hexane+0.1% DEA:IPA, 70:30); ed=100; 1H NMR (400 MHz, DMSO-d6): 7.72 (dd, J=8.1, 1.5 Hz, 1H), 7.46 (t, J=8.0 Hz, 1H), 7.34 (dd, J=7.9, 1.6 Hz, 1H), 6.36 (s, 2H), 3.65-3.54 (m, 2H), 2.90 (t, J=12.1 Hz, 2H), 2.73 (s, 1H), 1.79 (s, 5H), 1.62 (td, J=32.2, 30.1, 11.8 Hz, 5H), 1.36 (s, 2H), 1.21 (dd, J=26.8, 13.5 Hz, 2H); LC/MS (M+1): 422.2; mp: 140-141° C.

Second eluting isomer: RT=4.5 min; ed=98.9%

Second eluting isomer after Boc deprotection (compound 78b): Rt=5.01 min (column Cellulose SB4, hexane+0.1% DEA:IPA, 70:30); ed=100; 1H NMR (400 MHz, DMSO-d6): 7.72 (dd, J=8.1, 1.5 Hz, 1H), 7.46 (t, J=8.0 Hz, 1H), 7.34 (dd, J=7.9, 1.5 Hz, 1H), 6.36 (s, 2H), 3.69-3.53 (m, 2H), 2.90 (q, J=12.3 Hz, 2H), 2.70 (t, J=7.3 Hz, 1H), 1.89-1.68 (m, 5H), 1.68-1.44 (m, 4H), 1.42-1.09 (m, 4H); LC/MS (M+1): 422.1; mp: 117-118° C.

Fraction B (100 mg, RT=6.1 min) was separated (CHIRALPAK IG, 2×25 cm, 5 um; Hexane+8 mM $NH_3$.MeOH and EtOH, 25:75%) to give:

Third eluting isomer: RT=2.0 min; ed=100%

Third eluting isomer after Boc deprotection (Compound 78c): Rt=6.52 min (column chiralpak IC-3, hexane-DCM 3:1+0.1% DEA:EtOH, 90:10); ed=100; 1 H NMR (400 MHz, DMSO-d6): 7.72 (dd, J=8.2, 1.5 Hz, 1H), 7.46 (t, J=8.0 Hz, 1H), 7.34 (dd, J=7.9, 1.5 Hz, 1H), 6.36 (s, 2H), 3.65-3.55 (m, 2H), 2.90 (q, J=12.4 Hz, 3H), 2.70 (t, J=7.3 Hz, 1H), 1.89-1.68 (m, 5H), 1.68-1.44 (m, 4H), 1.41-1.26 (m, 2H), 1.19 (dd, J=28.1, 12.8 Hz, 2H); LC/MS (M+1): 422.1; mp: 120-121° C.

Forth eluting isomer: RT=2.78 min; ed=97.8%

Forth eluting isomer after Boc deprotection (compound 78d): Rt=7.49 min (column chiralpak IC-3, hexane-DCM 3:1+0.1% DEA:EtOH, 90:10); ed=96.9; 1H NMR (400 MHz, DMSO-d6): 7.72 (dd, J=8.1, 1.5 Hz, 1H), 7.46 (t, J=8.0 Hz, 1H), 7.34 (dd, J=7.9, 1.5 Hz, 1H), 6.36 (s, 2H), 3.59 (t, J=12.4 Hz, 2H), 2.90 (t, J=12.5 Hz, 2H), 2.71 (s, 1H), 1.79 (s, 5H), 1.68-1.44 (m, 4H), 1.33 (s, 2H), 1.19 (dd, J=25.4, 12.9 Hz, 2H); LC/MS (M+1): 422.1; mp: 110-112° C.

Compounds 79a and 79b: (3M)-6-[(3R)-3-amino-3H-spiro[furo[2,3-b]pyridine-2,4'-piperidin]-1'-yl]-3-(2,3-dichlorophenyl)-2,5-dimethylpyrimidin-4-one (PH-MS-PMC608-722-0) and (3M)-6-[(3S)-3-amino-3H-spiro[furo[2,3-b]pyridine-2,4'-piperidin]-1'-yl]-3-(2,3-dichlorophenyl)-2,5-dimethylpyrimidin-4-one Step 1: (3M)-6-[3-amino-3H-spiro[furo[2,3-b]pyridine-2,4'-piperidin]-1'-yl]-3-(2,3-dichloro Phenyl)-2,5-dimethylpyrimidin-4-one

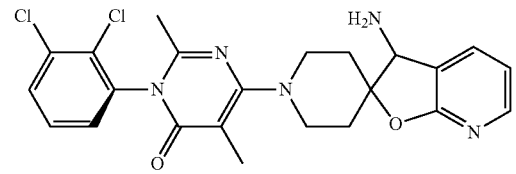

A solution of (1M)-1-(2,3-dichlorophenyl)-2,5-dimethyl-6-oxopyrimidin-4-yl trifluoromethanesulfonate (Intermediate 36b, 2.20 g, 4.32 mmol), 3H-spiro[furo[2,3-b]pyridine-2,4-piperidin]-3-amine (Intermediate 37, 1.43 g, 6.62 mmol) and DIEA (1.40 mL, 8.09 mmol) in EtOH (20 mL) was stirred for 4 h at 60° C. The resulting mixture was concentrated under vacuum and purified by flash chromatography on silica (DCM:MeOH, 1:1) to afford the title compound as an off-white solid (2.0 g, 97%). LC/MS (M+1): 472.

Step 2: (3M)-6-[(3R)-3-amino-3H-spiro[furo[2,3-b]pyridine-2,4'-piperidin]-1'-yl]-3-(2,3-dichlorophenyl)-2,5-dimethylpyrimidin-4-one and (3M)-6-[(3S)-3-amino-3H-spiro[furo[2,3-b]pyridine-2,4'-piperidin]-1'-yl]-3-(2,3-dichlorophenyl)-2,5-dimethylpyrimidin-4-one

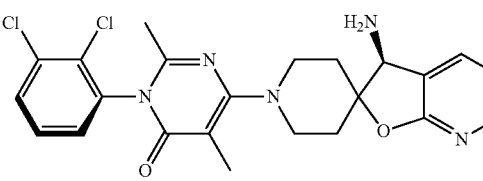

79a

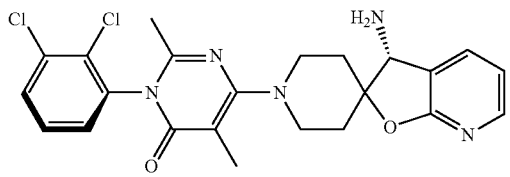

79b (3M)-6-[3-amino-3H-spiro[furo[2,3-b]pyridine-2,4'-piperidin]-1'-yl]-3-(2,3-dichlorophenyl)-2,5-dimethylpyrimidin-4-one (2.0 g) was separated via preparative HPLC (Column: CHIRALPAK IG, 2×25 cm, 5 μm; MTBE+10 mM MeOH—NH$_3$:EtOH; 85:15).

First eluting isomer (compound 79a): 750 mg, off-white solid, RT$_1$: 1.361 min, ed=94.1% (Column: CHIRALPAK IE-3, 4.6×50 mm, 3 μm; MeOH+0.1% DEA:CO$_2$; 1:1), $^1$H-NMR (400 MHz, DMSO-d$_6$): 8.00 (dd, J=4.8, 1.2 Hz, 1H), 7.83-7.80 (m, 1H), 7.79 (J=4.0 Hz, 1H), 7.57-7.50 (m, 2H), 6.91 (dd, J=7.2, 5.2 Hz, 1H), 4.14 (s, 1H), 3.85-3.75 (m, 2H), 3.39-3.31 (m, 3H), 2.15 (br s, 2H), 2.10-1.92 (m, 7H), 1.79-1.73 (m, 3H); LC/MS (M+1): 472, 474.

Second eluting isomer (compound 79b): 850 mg, off-white solid, RT$_1$: 2.01 min, ed=96.9% (Column: CHIRALPAK IE-3, 4.6×50 mm, 3 μm; MeOH+0.1% DEA:CO$_2$; 1:1), $^1$H-NMR (400 MHz, DMSO-d$_6$): 8.00 (dd, J=5.2, 1.6 Hz, 1H), 7.82-7.80 (m, 1H), 7.79 (J=4.4 Hz, 1H), 7.57-7.53 (m, 2H), 6.91 (dd, J=6.8, 4.8 Hz, 1H), 4.14 (s, 1H), 3.84-3.76 (m, 2H), 3.40-3.34 (m, 3H), 2.15 (brs, 1H), 2.07-1.91 (m, 7H), 1.89-1.78 (m, 3H); LC/MS (M+1): 472, 474

Compounds 80a; 80b; 80c; 80d: (3P)-6-[(3R)-3-amino-3H-spiro[furo[2,3-c]pyridine-2,4'-piperidin]-1'-yl]-3-(2,3-dichlorophenyl)-2,5-dimethylpyrimidin-4-one; (3M)-6-[(3R)-3-amino-3H-spiro[furo[2,3-c]pyridine-2,4'-piperidin]-1'-yl]-3-(2,3-dichlorophenyl)-2,5-dimethylpyrimidin-4-one; (3P)-6-[(3S)-3-amino-3H-spiro[furo[2,3-c]pyridine-2,4'-piperidin]-1'-yl]-3-(2,3-dichlorophenyl)-2,5-dimethylpyrimidin-4-one; (3M)-6-[(3S)-3-amino-3H-spiro[furo[2,3-c]pyridine-2,4'-piperidin]-1'-yl]-3-(2,3-dichlorophenyl)-2,5-dimethylpyrimidin-4-one Step 1: (S)—N-[1'-[1-(2,3-dichlorophenyl)-2,5-dimethyl-6-oxopyrimidin-4-yl]spiro[furo[2,3-c]pyridine-2,4'-piperidin]-3-ylidene]-2-methylpropane-2-sulfinamide

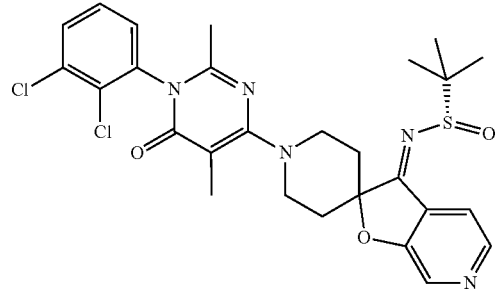 [SMILES: Cc1c(N2CCC3(CC2)Oc2cnccc2/C3=N\[S@@](=O)C(C)(C)C)nc(C)n(-c2cccc(Cl)c2Cl)c1=O]

A solution of (S)-2-methyl-N-[spiro[furo[2,3-c]pyridine-2,4'-piperidin]-3-ylidene]-propane-2-sulfinamide trifluoroacetic acid (Intermediate 39; 115 mg, 0.364 mmol), 1-(2,3-dichlorophenyl)-2,5-dimethyl-6-oxopyrimidin-4-yl trifluoromethanesulfonate (Intermediate 36; 150 mg, 0.359 mmol) and DIEA (0.192 mL, 1.10 mmol) in EtOH (5.0 mL) was stirred for 16 h at 60° C. The resulting mixture was cooled down to room temperature, concentrated under reduced pressure and purified by flash chromatography on silica (PE:EtOAc, 1:3) to afford the title compound as a yellow solid (208 mg, 99%). LC/MS (M+1): 574, 576.

Step 2: (S)—N-[1'-[1-(2,3-dichlorophenyl)-2,5-dimethyl-6-oxopyrimidin-4-yl]-3H-spiro[furo[2,3-c]pyridine-2,4'-piperidin]-3-yl]-2-methylpropane-2-sulfinamide

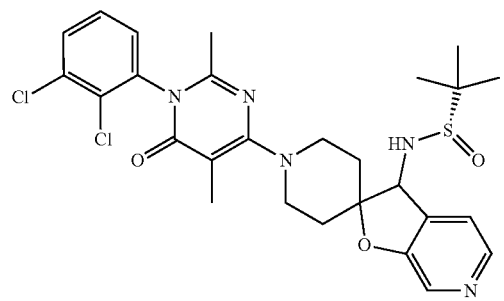 [SMILES: Cc1c(N2CCC3(CC2)Oc2cnccc2C3N[S@@](=O)C(C)(C)C)nc(C)n(-c2cccc(Cl)c2Cl)c1=O]

NaBH$_4$ (75 mg, 1.89 mmol) was added to a solution of (S)—N-[1-[1-(2,3-dichlorophenyl)-2,5-dimethyl-6-oxopyrimidin-4-yl]spiro[furo[2,3-c]pyridine-2,4-piperidin]-3-ylidene]-2-methylpropane-2-sulfinamide (200 mg, 0.348 mmol) in THF (10 mL) and H$_2$O (1.0 mL) at 0° C. The resulting mixture was stirred for 1 h at 25° C. The reaction was poured into water (15 mL) and extracted with EtOAc (3×20 mL). Combined organic layers were washed with brine (1×40 mL), dried over anhydrous sodium sulfate, filtered and concentrated under reduced pressure. The residue was purified by flash chromatography on silica (EP:EtOAc, 1:1) to afford the title compound as an off-white solid (200 mg, 73% yield). LC/MS (M+1): 576, 578.

Step 3: 6-[3-amino-3H-spiro[furo[2,3-c]pyridine-2,4-piperidin]-1-yl]-3-(2,3-dichlorophenyl)-2,5-dimethylpyrimidin-4-one

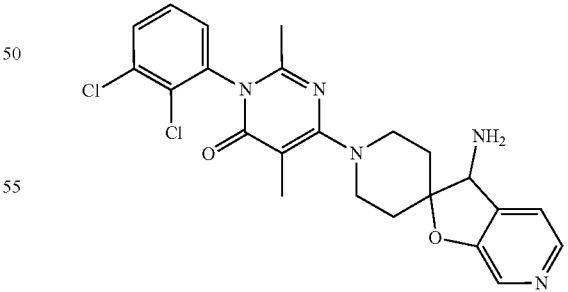

A mixture of (S)—N-[1-[1-(2,3-dichlorophenyl)-2,5-dimethyl-6-oxopyrimidin-4-yl]-3H-spiro[furo[2,3-c]pyridine-2,4-piperidin]-3-yl]-2-methylpropane-2-sulfinamide (190 mg, 0.242 mmol) and HCl in MeOH (5.0 mL, 6M) was stirred for 1 h at 25° C. The resulting mixture was concentrated under reduced pressure and purified by reverse phase chromatography (Column: C18 silica gel; Mobile phase, A: water (containing 10 mmol/L NH4HCO3) and B: ACN (3% to 50% in 40 min); Detector: UV 220/254 nm) to give 6-[3-amino-3H-spiro[furo[2,3-c]pyridine-2,4-piperidin]-1-yl]-3-(2,3-dichlorophenyl)-2,5-dimethylpyrimidin-4-one (120 mg, 95%) as an off-white solid.

Step 4: Separation of the Four Isomers, (3P)-6-[(3R)-3-amino-3H-spiro[furo[2,3-c]pyridine-2,4'-piperidin]-1'-yl]-3-(2,3-dichlorophenyl)-2,5-dimethylpyrimidin-4-one; (3P)-6-[(3S)-3-amino-3H-spiro[furo[2,3-c]pyridine-2,4'-piperidin]-1'-yl]-3-(2,3-dichlorophenyl)-2,5-dimethylpyrimidin-4-one; (3M)-6-[(3R)-3-amino-3H-spiro[furo[2,3-c]pyridine-2,4'-piperidin]-1'-yl]-3-(2,3-dichlorophenyl)-2,5-dimethylpyrimidin-4-one; (3M)-6-[(3S)-3-amino-3H-spiro[furo[2,3-c]pyridine-2,4'-piperidin]-1'-yl]-3-(2,3-dichlorophenyl)-2,5-dimethylpyrimidin-4-one

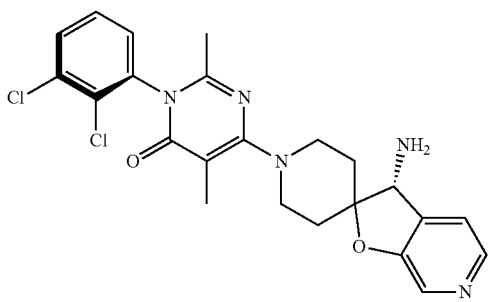 [SMILES: Cc1c(N2CCC3(CC2)Oc2cnccc2C3N)nc(C)n(-c2cccc(Cl)c2Cl)c1=O]

80a

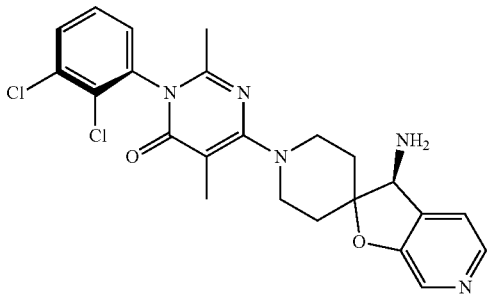

80b

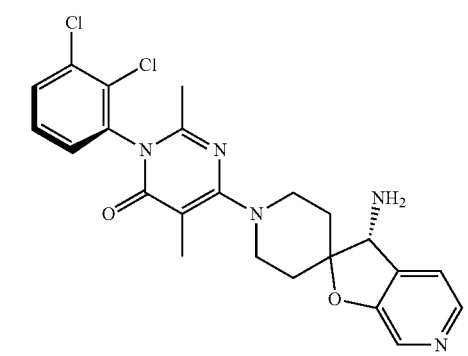

80c

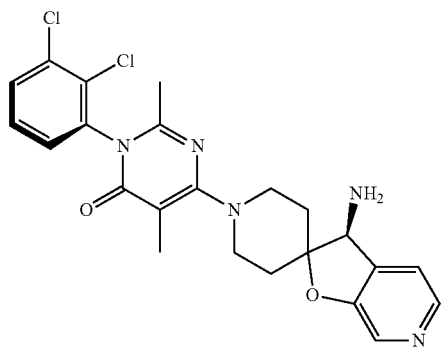

80d

6-[3-amino-3H-spiro[furo[2,3-c]pyridine-2,4-piperidin]-1-yl]-3-(2,3-dichlorophenyl)-2,5-dimethylpyrimidin-4-one was separated via preparative HPLC (Column: CHIRALPAK ID, 3×25 cm, 5 μm; MTBE+10 mM NH$_3$-MeOH:EtOH, 85:15).

The first eluting fraction (RT$_1$:14.23 min) was collected and concentrated under vacuum to give fraction A (50 mg). The second eluting fraction (RT$_2$:20.5 min) was collected and concentrated under vacuum to give fraction B (50 mg).

Fraction A (50 mg) was re-separated via preparative HPLC (Column: CHIRALPAK IA, 2×25 cm, 5 um; Hex-DCM, 3:+10 mM NH$_3$-MEOH:EtOH, 95:5).

First eluting isomer (compound 80a): off-white solid, 16.5 mg, RT=5.08 min, ed=95.6, (Column: CHIRALPAK IA-3, 4.6×50 mm, 3 μm; Hex/DCM, 3/+10 mM NH$_3$-MEOH:EtOH, 98:2); $^1$H-NMR (400 MHz, DMSO-d$_6$) δ8.13 (d, J=4.8 Hz, 2H), 7.83-7.79 (m, 1H), 7.57-7.53 (m, 2H), 7.38 (d, J=4.8 Hz, 1H), 4.16 (s, 1H), 3.83-3.74 (m, 2H), 3.35-3.30 (m, 2H), 2.03-1.95 (m, 4H), 1.93 (s, 3H), 1.88-1.75 (m, 3H). LC/MS (M+1): 472, 474.

Second eluting isomer (compound 80b): off-white solid; 9.8 mg; RT=5.7 min, ed=97.6, (Column: CHIRALPAK IA-3, 4.6×50 mm, 3 m; Hex/DCM, 3/+10 mM NH$_3$-MEOH:EtOH, 98:2); $^1$H-NMR (400 MHz, DMSO-d$_6$) δ8.15 (t, J=4.8 Hz, 2H), 7.83-7.78 (m, 1H), 7.57-7.52 (m, 2H), 7.39 (d, J=4.8 Hz, 1H), 4.17 (s, 1H), 3.83-3.74 (m, 2H), 3.35-3.30 (m, 2H), 2.04-1.97 (m, 4H), 1.93 (s, 3H), 1.88-1.73 (m, 3H); LC/MS (M+1): 472, 474.

Fraction B (50 mg) was re-separated via Prep-Chiral-HPLC (Column: CHIRALPAK IA, 2×25 cm, 5um; MTBE+2 mM NH$_3$-MEOH:EtOH, 65:35)

First eluting isomer (compound 80c): off-white solid; 24.5 mg; RT=3.8 min, ed=95.1 (CHIRALPAK IA, 4.6×50 mm, 3 um; MTBE+0.1% DEA:EtOH, 65:35); $^1$H-NMR (400 MHz, DMSO-d$_6$): 8.14 (d, J=4.8 Hz, 2H), 7.83-7.79 (m, 1H), 7.57-7.53 (m, 2H), 7.38 (d, J=4.8 Hz, 1H), 4.18 (s, 1H), 3.82-3.74 (m, 2H), 3.35-3.30 (m, 2H), 2.04-1.95 (m, 4H), 1.93 (s, 3H), 1.89-1.75 (m, 3H). LC/MS (M+1): 472, 474.

Second eluting isomer (compound 80d): off-white solid; 11.8 mg; RT=4.6 min, ed=98.8 (CHIRALPAK IA-3, 4.6×50 mm, 3 um; MTBE+0.1% DEA:EtOH, 65:35); $^1$H-NMR (400 MHz, DMSO-d$_6$): 8.14 (d, J=4.8 Hz, 2H), 7.83-7.79 (m, 1H), 7.57-7.53 (m, 2H), 7.38 (d, J=4.8 Hz, 1H), 4.16 (s, 1H), 3.83-3.74 (m, 2H), 3.35-3.30 (m, 2H), 2.04-1.95 (m, 4H), 1.93 (s, 3H), 1.88-1.75 (m, 3H). LC/MS (M+1): 472, 474.

Compounds 81a (3P)-6-[(3R)-3-amino-3H-spiro[1-benzofuran-2,4'-piperidin]-1'-yl]-3-(2,3-dichlorophenyl)-2,5-dimethyl-3,4-dihydropyrimidin-4-one and 81b (3M)-6-[(3R)-3-amino-3H-spiro[1-benzofuran-2,4'-piperidin]-1'-yl]-3-(2,3-dichlorophenyl)-2,5-dimethyl-3,4-dihydropyrimidin-4-one Step 1: 1'-[1-(2,3-dichlorophenyl)-2,5-dimethyl-6-oxo-1,6-dihydropyrimidin-4-yl]-3H-spiro[1-benzofuran-2,4'-piperidin]-3-one

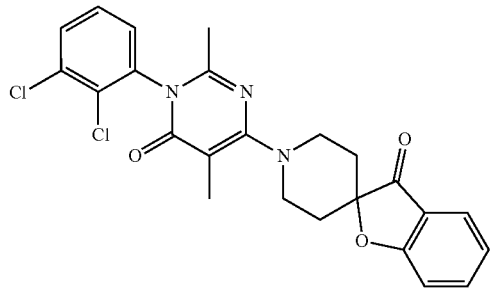 [SMILES: Cc1c(N2CCC3(CC2)Oc2ccccc2C3=O)nc(C)n(-c2cccc(Cl)c2Cl)c1=O]

The title compound was obtained following procedure described for compound 77 but starting from 1-(2,3-dichlorophenyl)-2,5-dimethyl-6-oxo-1,6-dihydropyrimidin-4-yl trifluoromethanesulfonate (intermediate 36) and 3H-spiro[1-benzofuran-2,4'-piperidin]-3-one (Pharmablock) as a yellow solid. LC/MS (M+1): 470.1

Step 2: (R)—N-{1'-[1-(2,3-dichlorophenyl)-2,5-dimethyl-6-oxo-1,6-dihydropyrimidin-4-yl]-3H-spiro[1-benzofuran-2,4'-piperidin]-3-ylidene}-2-methylpropane-2-sulfinamide

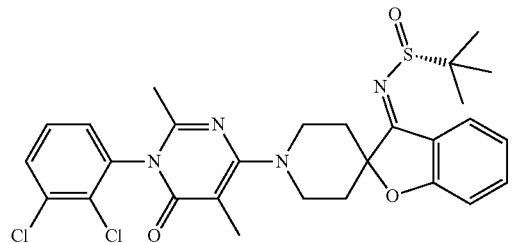 [SMILES: Cc1c(N2CCC3(CC2)Oc2ccccc2/C3=N\[S@](=O)C(C)(C)C)nc(C)n(-c2cccc(Cl)c2Cl)c1=O]

The title compound was obtained following procedure described for compound 77 but starting from 1'-[1-(2,3-dichlorophenyl)-2,5-dimethyl-6-oxo-1,6-dihydropyrimidin-4-yl]-3H-spiro[1-benzofuran-2,4'-piperidin]-3-one as an off-white solid. LC/MS (M+1): 573.2.

Step 3: (R)—N-[(3R)-1'-[1-(2,3-dichlorophenyl)-2,5-dimethyl-6-oxo-1,6-dihydropyrimidin-4-yl]-3H-spiro[1-benzofuran-2,4'-piperidin]-3-yl]-2-methyl-propane-2-sulfinamide The title compound was obtained following procedure described for compound 80 step 2, but starting from (R)—N-{1'-[1-(2,3-dichlorophenyl)-2,5-dimethyl-6-oxo-1,6-dihydropyrimidin-4-yl]-3H-spiro[1-benzofuran-2,4'-piperidin]-3-ylidene}-2-methylpropane-2-sulfinamide as an off-white solid. LC/MS (M+1): 575.1.

Step 4: 6-[(3R)-3-amino-3H-spiro[1-benzofuran-2,4'-piperidin]-1'-yl]-3-(2,3-dichlorophenyl)-2,5-dimethyl-3,4-dihydropyrimidin-4-one The title compound was obtained following procedure described for compound 80, step 3, but starting from (R)—N-[(3R)-1'-[1-(2,3-dichlorophenyl)-2,5-dimethyl-6-oxo-1,6-dihydropyrimidin-4-yl]-3H-spiro[1-benzofuran-2,4'-piperidin]-3-yl]-2-methylpropane-2-sulfinamide as an off-white solid. LC/MS (M+1): 471.1.

Step 5: Separation of the Two Atropisomers

The atropisomers of 6-[(3R)-3-amino-3H-spiro[1-benzofuran-2,4'-piperidin]-1'-yl]-3-(2,3-dichlorophenyl)-2,5-dimethyl-3,4-dihydropyrimidin-4-one (200 mg) were separated by preparative HPLC (column ChiralPAK IA-3, MtBE+ 0.1% DEA:EtOH, 70:30).

First eluting isomer (compound 81a): 68 mg, white solid, Rt=1.0 min, ed=100%; mp: 175-176° C.

Second eluting isomer (compound 81b): 76 mg, white solid, Rt=3.24 min, ed=99%; 1H NMR (400 MHz, DMSO-d6) δ 7.87-7.74 (m, 1H), 7.65-7.49 (m, 2H), 7.32 (d, J=7.4 Hz, 1H), 7.14 (td, J=7.7, 1.4 Hz, 1H) 6.86 (td, J=7.4, 1.0 Hz, 1H), 6.76 (d, J=7.9 Hz, 1H), 4.10 (s, 1H), 3.89-3.66 (m, 2H), 3.48-3.24 (m, 2H), 2.28-2.06 (m, 2H), 2.00 (s, 3H), 1.93 (s, 3H), 1.88-1.64 N,3H), 0.93-0.79 (m, 1H); LC/MS (M+1): 470.1; mp: 170-173C.

Compounds from Table 2 have been prepared following similar synthetic routes as described above:

TABLE 2

| No. | Description | Reactants and Procedure |
|---|---|---|
| 38 | white solid, 1H NMR (300 MHz, DMSO-d6): 7.99 (dd, J = 8.0, 1.6 Hz, 1H), 7.86 (dd, J = 8.0, 1.6 Hz, 1H), 7.77-7.67 (m, 1H), 5.34 (s, 1H), 3.93-3.66 (m, 2H), 3.36-3.24 (m, 2H), 2.39 (s, 2H), 1.95 (s, 3H), 1.65 (s, 2H), 1.46-1.37 (m, 2H), 1.33-1.20 (m, 2H), 0.91 (s, 3H), LC/MS (M + 1): 415.2, m.p.: 191-193° C. | similar procedure as compound 21, from Intermediate 41 and tert-butyl N-[(4-methylpiperidin-4-yl)methyl]carbamate |
| 39 | White solid; 1H NMR (400 MHz, DMSO-d6): 8.05-8.00 (m, 2H), 7.97-7.92 (m, 1H), 7.88 (d, J = 2.1 Hz, 1H), 7.64-7.56 (m, 2H), 7.39 (dd, J = 8.6, 2.1 Hz, 1H), 3.40 (t, J = 5.6 Hz, 4H), 2.02 (s, 3H), 1.90 (s, 3H), 1.59-1.39 (m, 4H), 1.11 (s, 3H); LC/M (M + 1): 363.15; mp: 101.0-103.0° C. | similar procedure as compound 21, from Intermediate 15 and tert-butyl N-(4-methylpiperidin-4-yl)carbamate (Pharmablock) |
| 43 | White solid; 1H NMR (300 MHz, DMSO-d6): 9.42 (s, 1H), 8.19 (dd, J = 8.2, 1.0 Hz, 1H), 7.68 (t, J = 7.9 Hz, 1H), 7.53 (d, J = 7.5 Hz, 1H), 3.42 (t, J = 5.5 Hz, 4H), 1.95 (s, 3H), 1.89 (s, 3H), 1.47 (q, J = 6.4, 5.3 Hz, 4H), 1.10 (s, 3H). LC/M (M + 1): 370.15; mp: 100-102° C. | similar procedure as compound 21, from Intermediate 17 and tert-butyl N-(4-methylpiperidin-4-yl)carbamate (Pharmablock) |
| 44 | white solid; 1H NMR (400 MHz, DMSO-d6): 8.05-8.00 (m, 2H), 7.96-7.94 (m, 1H), 7.88 (s, 1H), 7.62-7.59 (m, 2H), 7.39 (dd, J = 8.6, 2.1 Hz, 1H), 3.51-3.47 (m, 4H), 3.24-3.21 (m, 2H), 2.93 (d, J = 6.5 Hz, 1H), 2.45 (s, 1H), 2.03 (s, 3H), 1.90 (s, 3H), 1.51-1.48 (m, 2H), 1.32-1.29 (m, 2H), 0.94 (d, J = 3.3 Hz, 3H); LC/MS (M + 1): 377.2; mp: 102-104.0° C. | similar procedure as compound 21, from Intermediate 15 and tert-butyl N-[(4-methylpiperidin-4-yl)methyl]carbamate (Pharmablock) |
| 45 | White solid; 1H NMR (400 MHz, DMSO-d6): 8.06-8.01 (m, 2H), 7.97-7.92 (m, 1H), 7.89 (d, J = 2.1 Hz, 1H), 7.64-7.57 (m, 2H), 7.40 (dd, J = 8.6, 2.1 Hz, 1H), 4.11-4.03 (m, 1H), 3.67 (d, J = 8.4 Hz, 1H), 3.54-3.49 (m, 3H), 3.24-3.06 (m, 2H), 2.91 (d, J = 5.1 Hz, 1H), 2.03 (s, 3H), 1.91 (s, 3H), 1.85-1.75 (m, 1H), 1.71-1.66 (m, 2H), 1.58-1.53 (m, 2H), 1.09 (d, J = 6.4 Hz, 3H); LC/MS (M + 1): 418.5; mp: 105.0-107.0° C. | similar procedure as compound 21, from Intermediate 15 and (3S,4S)-3-methyl-2-oxa-8-azaspiro[4.5]decan-4-amine dihydrochloride (Pharmablock) |
| 47 | Off-white solid; 1H NMR (300 MHz, DMSO-d6): 9.06-8.97 (m, 2H), 8.26-8.09 (m, 2H), 7.78 (dd, J = 8.8, 2.3 Hz, 1H), 3.40 (s, 4H), 2.03 (s, 3H), 1.89 (s, 3H), 1.50 (d, J = 5.8 Hz, 3H), 1.12 (s, 3H); LC/MS (M + 1): 377.2; mp: 108.0-110.0° C. | similar procedure as compound 21, from Intermediate 18 and tert-butyl N-(4-methylpiperidin-4-yl)carbamate (Pharmablock) |
| 48 | White solid; 1H NMR (300 MHz, DMSO-d6): 8.28-8.21 (m, 1H), 8.17-8.05 (m, 2H), 7.82-7.69 (m, 2H), 7.56 (d, J = 8.6 Hz, 1H), 3.42 (t, J = 5.6 Hz, 4H), 2.06-1.89 (m, 8H), 1.59-1.39 (m, 4H), 1.10 (s, 3H); LC/MS (M + 1): 397.2; mp: 200.0-202° C. | similar procedure as compound 21, from 1-chloro-naphtalene-2-amine, Intermediate 19 and tert-butyl N-(4-methylpiperidin-4-yl)carbamate (Pharmablock) |
| 52 | white solid; 1H NMR (300 MHz, DMSO-d6): 8.24 (d, J = 8.1 Hz, 1H), 8.11 (t, J = 7.7 Hz, 2H), 7.79-7.70 (m, 2H), 7.57 (d, J = 8.7 Hz, 1H), 4.12-3.99 (m, 1H), 3.66 (d, J = 8.3 Hz, 1H), 3.57-3.48 (m, 3H), 3.25-3.05 (m, 2H), 2.90 (d, J = 5.1 Hz, 1H), 1.94 (d, J = 20.2 Hz, 6H), 1.82-1.42 (m, 6H), 1.07 (d, J = 6.4 Hz, 3H); LC/MS (M + 1): 453.2; mp: 170-172° C. | similar procedure as compound 21, from Intermediate 19 and (3S,4S)-3-methyl-2-oxa-8-azaspiro[4.5]decan-4-amine dihydrochloride (Pharmablock) |
| 53 | off-white solid; 1H NMR (300 MHz, DMSO-d6): 9.06-8.97 (m, 2H), 8.28-8.11 (m, 2H), 7.78 (dd, J = 8.8, 2.3 Hz, 1H), 4.12-3.98 (m, 1H), 3.65 (d, J = 8.4 Hz, 1H), 3.58-3.44 (m, 3H), 3.19-3.05 (m, 2H), 2.89 (d, J = 5.1 Hz, 1H), 2.04 (s, 3H), 1.90 (s, 3H), 1.83-1.44 (m, 6H), 1.07 (d, J = 6.4 Hz, 3H); LC/MS (M + 1): 421.3; mp: 138-140° C. | similar procedure as compound 21, from Intermediate 18 and (3S,4S)-3-methyl-2-oxa-8-azaspiro[4.5]decan-4-amine dihydrochloride (Pharmablock) |

TABLE 2-continued

| No. | Description | Reactants and Procedure |
|---|---|---|
| 54 | white solid; 1H NMR (300 MHz, DMSO-d6) ? 8.25 (dd, J = 7.9, 1.7 Hz, 1H), 8.17-8.05 (m, 2H), 7.80-7.70 (m, 2H), 7.57 (d, J = 8.7 Hz, 1H), 3.61-3.42 (m, 2H), 3.25-3.12 (m, 2H), 2.42 (s, 2H), 1.93 (d, J = 21.4 Hz, 6H), 1.71 (s, 1H), 1.54-1.46 (m, 1H), 1.32-1.28 (m, 2H), 0.92 (s, 3H); LC/MS (M + 1): 411.3; mp: 195-197° C. | similar procedure as compound 21, from Intermediate 19 and tert-butyl N-[(4-methylpiperidin-4-yl)methyl]carbamate (Pharmablock) |
| 55 | Light yellow solid; 1H NMR (300 MHz, DMSO-d6): 9.06-8.97 (m, 2H), 8.36-8.04 (m, 2H), 7.78 (m, 1H), 3.50 (d, J = 13.7 Hz, 2H), 3.19 (d, J = 11.6 Hz, 2H), 2.50 (s, 2H), 2.03 (s, 3H), 1.89 (s, 3H), 1.51 (t, J = 11.3 Hz, 2H), 1.33 (d, J = 13.1 Hz, 2H), 0.93 (d, J = 8.5 Hz, 3H); LC/MS (M + 1): 379.3; mp:160-162° C. | similar procedure as compound 21, from Intermediate 18 and tert-butyl N-[(4-methylpiperidin-4-yl)methyl]carbamate (Pharmablock) |
| 56 | white solid; 1H NMR (400 MHz, DMSO-d6): 7.78 (dd, J = 6.6, 3.0 Hz, 1H), 7.57-7.45 (m, 2H), 5.21 (s, 1H), 3.99-3.65 (m, 1H), 3.53-3.39 (m, 2H), 2.98-2.83 (m, 2H), 2.47-2.35 (m, 2H), 1.97 (s, 3H), 1.77-1.44 (m, 4H); LC/MS (M + 1): 365.0 | similar procedure as compound 1, from Intermediate 2 and tert-butyl 3,8-diazabicyclo[3.2.1]-octane-8-carboxylate (Anichem) |
| 59 | white solid; LC/MS (M + 1): 409.0 | similar procedure as compound 1, step 1, from Intermediate 2 and (3aR,6aS)-3a-(aminomethyl)-octahydrocyclo-penta[c]pyrrol-5-ol dihydrochloride (Enamine) |
| 60 | white solid; LC/MS (M + 1): 447.1 | similar procedure as compound 1, step 1, from Intermediate 2 and 1-{9,9-dimethyl-4-azatricyclo[6.1.1.0$^{2}$,6]decan-2-yl}methanamine (Enamine) |
| 61 | white solid; 1H NMR (400 MHz, DMSO-d6) d 7.79 (dd, J = 6.5, 3.2 Hz, 1H), 7.66-7.47 (m, 2H), 5.50 (dd, J = 5.1, 0.9 Hz, 1H), 4.69-4.21 (m, 2H), 3.95-3.76 (m, 1H), 3.69-3.45 (m, 1H), 2.99-2.72 (m, 2H), 2.72-2.56 (m, 1H), 2.49-2.37 (m, 1H), 2.01 (s, 3H), 1.97-1.75 (m, 1H), 1.38-1.17 (m, 1H); LC/MS (M + 1): 408.0 | similar procedure as compound 1, from Intermediate 2 and tert-butyl N-{6-oxo-octahydropyrrolo[1,2-a]pyrazin-7-yl}carbamate (Enamine) |
| 82 | white powder; 1H NMR (300 MHz, DMSO-d6): 7.80 (dd, J = 8.1 Hz, 1H), 7.55 (d, J = 8.0 Hz, 1H),7.53 (s, 1H), 3.73 (m, 1H), 3.59 (m, 1H), 3.06-2.96 (m, 2H), 2.07 (dd, J = 4.3 Hz, 2H), 1.97 (s, 3H), 1.89 (s, 3H), 1.64 (m, 4H), 1.43 (m, 1H), 1.36 (m, 1H); LC/MS (M + 1): 407.2 | similar procedure as compound 51, from Intermediate 8 and 7-azaspiro[3.5]nonan-1-amine dihydrochloride |
| 83 | white powder; 1H NMR (400 MHz, DMSO-d6): 7.80 (dd, J = 8.0 Hz, 1H), 7.56 (s, 1H), 7.54 (d, J = 8.0 Hz, 1H), 6.88 (t, J = 7.8 Hz, 1H), 6.52 (d, J = 7.8 Hz, 1H), 6.41 (d, J = 7.8 Hz, 1H), 4.87 (s, 2H), 4.32 (s, 2H), 3.62 (m, 2H), 3.17 (d, J = 5.9 Hz, 1H), 2.85 (m, 2H), 2.018 (s, 3H), 2.000 (s, 3H); LC/MS (M + 1): 415.2 | similar procedure as compound 1, from Intermediate 8 and 1,2,3,4-tetrahydroisoquinolin-6-amine |
| 84 | white solid; 1H NMR (300 MHz, Methanol-d4): 9.29 (s, 1H), 8.23-8.20 (m, 1H), 7.77-7.71 (m, 1H), 7.47 (d, J = 7.6 Hz, 1H), 4.31 ? 4.17 (m, 1H), 3.89-3.72 (m, 4H), 3.29 ? 3.15 (m, 2H), 3.04 (d, J = 4.9 Hz, 1H), 2.04 (d, J = 12.4 Hz, 6H), 1.95-1.75 (m, 2H), 1.71 (d, J = 13.4 Hz, 2H), 1.23 (s, 3H); LC/MS (M + 1): 426.2 | similar procedure as compound 21, step 1, from Intermediate 17 and (3S,4S)-3-methyl-2-oxa-8-azaspiro[4.5]decan-4-amine dihydrochloride (Pharmablock) |
| 85 | off-white solid; 1H NMR (400 MHz, DMSO-d6): 8.09 (s, 1H), 7.83-7.74 (m, 1H), 7.55-7.46 (m, 2H), 5.89 (d, J = 7.7 Hz, 1H), 3.99 (d, J = 8.8 Hz, 1H), 2.98 (s, 1H), 2.45 (s, OH), 1.82 (s, 3H), 1.79 (s, 2H), 1.55 (q, J = 5.1 Hz, 6H); LC/MS (M + 1): 367.1; mp : 137-138° C. | similar procedure as compound 70, from Intermediate 20 and tert-butyl N-[(1s,4s)-4-aminocyclohexyl]carbamate |
| 86 | white powder; 1H NMR (DMSO-d6): 8.410 (s, 1H), 7.798 (dd, J = 8.0 Hz, 1H), 7.5567 (d, J = 8.0 Hz, 1H), 7.5401 (s, 1H), 3.5886 (3H), 3.55 (m, 1H), 2.923 (m, 2H), 2.668 (m, 3H), 1.983 (s, 3H), 1.901 (s, 3H), 1.766 (m, 1H), 1.659 (m, 1H), 1.397 (m, 1H), 1.227 (m, 1H), 0.8734(m, | similar procedure as compound 51, from Intermediate 8 and 1-{6-azaspiro[2.5]octan-1-yl}methanamine dihydrochloride (Enamine) |

TABLE 2-continued

| No. | Description | Reactants and Procedure |
|-----|-------------|------------------------|
|     | 1H), 0.6252 (s, 1H), 0.3672 (s, 1H); LC/MS (M + 1): 407.2 | |
| 87  | white solid; 1H NMR (400 MHz, DMSO-d6): 8.39 (s, 1H), 7.79 (dd, J = 8.0 Hz, 1H), 7.51 (m, 2H), 3.87 (m, 2H), 3.58 (m, 2H), 2.86 (m, 2H), 2.61 (m, 2H), 2.03 (s, 3H), 1.94 (s, 3H), 1.08 (s, 3H), 0.89 (s, 3H); LC/MS (M + 1): 395.2 | similar procedure as compound 51, from Intermediate 8 and 1-(4,4-dimethylpyrrolidin-3-yl)methanamine dihydrochloride (Enamine) |
| 88  | white powder; 1H NMR (400 MHz, DMSO-d6): 7.76 (m, 1H), 7.55 (2H), 3.38 (6H), 2.59 (m, 2H), 1.9 (s, 3H), 1.89 (s, 3H), 1.44 (4H); LC/MS (M + 1): 411.2 | similar procedure as compound 51, from Intermediate 8 and [4-(aminomethyl)piperidin-4-yl]methanol dihydrochloride (AdvChemBlock; after Boc cleavage) |
| 89  | white solid; 1H NMR (400MHz, DMSO-d6): 7.91 (d, J = 8.0 Hz, 1H), 7.54 (m, 2H), 3.42 (m, 4H), 2.10 (m, 1H), 1.95 (s, 3H), 1.90 (s, 3H), 1.71 (m, 1H), 1.61 (m, 1H), 1.41 (m, 1H), 1.25 (m, 1H), 0.42 (s, 1H), 0.09 (s, 1H); LC/MS (M + 1): 393.1 | similar procedure as compound 51, from Intermediate 8 and tert-butyl 1-amino-6-azaspiro[2.5]-octane-6-carboxylate (AdvChemblock; after Boc cleavage) |
| 90  | white powder, 1 H NMR (40 MHz, DMSO-d6): 7.81 (s, 1H), 7.53 (m, 2H), 3.47 (m, 4H), 3.02 (m, 4H), 2.07 (m, 1H), 1.97 (s, 3H), 1.89 (s, 3H), 1.67-1.43 (m, 4H); LC/MS (M + 1): 407.1 | similar procedure as compound 51, from Intermediate 8 and tert-butyl 1-amino-6-azaspiro[3.5]-nonane-6-carboxylate (AdvChemblock) |
| 91  | White powder; 1H NMR (400 MHz, DSMO-d6): 8.41 (s, 1H), 7.786 (s, 1H), 7.52 (m, 2H), 3.76 (m, 4H), 3.46-3.44 (m, 5H), 1.96 (s, 3H), 1.89 (s, 3H), 1.80 (m, 1H), 1.69 (m, 1H), 1.48 (m, 1H), 1.40 (d, J = 5.2 Hz, 1H); LC/MS (M + 1): 395.1 | similar procedure as compound 51, from Intermediate 8 and tert-butyl 4-(aminomethyl)azepane-1-carboxylate (AdvChemblock) |
| 92  | white powder; 1H NMR (DMSO-d6): 7.77 (m, 1H), 7.55 (m, 2H), 3.89 (m, 1H), 3.84 (m, 1H), 3.69 (m, 1H), 3.59 (m, 1H), 3.41 (m, 1H), 3.01 (m, 1H), 2.73 (m, 1H), 2.65 (m, 2H), 1.99 (s, 3H), 1.91 (s, 3H); LC/MS (M + 1): 383.1 | similar procedure as compound 51, from Intermediate 8 and tert-butyl (2R)-2-(aminomethyl)-morpholine-4-carboxylate (AdvChemBlock) |
| 93  | White solid; 1H NMR (300 MHz, Methanol-d4): 7.71 (dd, J = 8.2, 1.5 Hz, 1H), 7.49 (t, J = 8.0 Hz, 1H), 7.36 (dd, J = 7.9, 1.5 Hz, 1H), 4.07-3.88 (m, 2H), 3.72-3.54 (m, 2H), 2.03 (s, 3H), 1.75-1.69 (m, 4H), 1.60-1.49 (m, 1H), 1.36-1.25 (m, 3H), 0.94-0.89 (m, 2H), 0.48-0.43 (m, 2H); LC/MS (M + 1): 407.1; mp: 100-102° C. | similar procedure as compound 21, from 5-cyclopropyl-1-(2,3-dichlorophenyl)-2-methyl-6-oxo-1,6-dihydropyrimidin-4-yl 4-methylbenzene-1-sulfonate (intermediate 23) and tert-butyl N-(4-methylpiperidin-4-yl)carbamate |
| 94  | White solid; 1H NMR (300 MHz, DMSO-d6): 7.81-7.75 (m, 1H), 7.58-7.46 (m, 2H), 3.40 (brs, 4H), 1.95 (s, 3H), 1.54 ? 1.43 (m, 4H), 1.11 (s, 3H); LC/MS (M + 1): 384.1; mp: 133-135° C. | similar procedure as compound 21, from 1-(2,3-dichlorophenyl)-5-(2H3)methyl-2-methyl-6-oxo-1,6-dihydropyrimidin-4-yl 4-methylbenzene-1-sulfonate (Intermediate24) and tert-butyl N-(4-methylpiperidin-4-yl)carbamate |
| 95  | White solid; 1H NMR (300 MHz, Methanol-d4) 7.87 (dd, J = 5.8, 3.8 Hz, 1H), 7.47-7.38 (m, 2H), 4.29-4.16 (m, 1H), 3.92-3.69 (m, 4H), 3.24-3.15 (m, 2H), 3.02 (d, J = 4.9 Hz, 1H), 2.06 (s, 3H), 2.00 (s, 3H), 1.96-1.75 (m, 2H), 1.75-1.57 (m, 2H), 1.22 (d, J = 6.5 Hz, 3H); LC/MS (M + 1): 481.1, 483.1; mp: 95-97° C. | similar procedure as compound 21, from 1-(3-bromo-2-chlorophenyl)-2,5-dimethyl-6-oxo-1,6-dihydropyrimidin-4-yl 4-methylbenzene-1-sulfonate (intermediate 25) and (3S,4S)-3-methyl-2-oxa-8-azaspiro[4.5]decan-4-amine dihydrochloride (Pharmablock) |
| 96  | White solid; 1H NMR (300 MHz, Methanol-d4): 7.61-7.37 (m, 2H), 7.28-7.24 (m, 1H), 4.31-4.17 (m, 1H), 3.91-3.66 (m, 4H), 3.29-3.09 (m, 2H), 3.03 (d, J = 4.9 Hz, 1H), 2.14-1.95 (m, 6H), 1.93-1.77 (m, 2H), 1.72-1.63 (m, 2H), 1.22 (d, J = 6.5 Hz, 3H). LC/MS (M + 1): 421.2; mp: 115-117° C. | similar procedure as compound 21, from 1-(2-chloro-3-fluorophenyl)-2,5-dimethyl-6-oxo-1,6-dihydropyrimidin-4-yl 4-methylbenzene-1-sulfonate (intermediate 26) and (3S,4S)-3-methyl-2-oxa-8- |

TABLE 2-continued

| No. | Description | Reactants and Procedure |
|---|---|---|
| | | azaspiro[4.5]decan-4-amine dihydrochloride (Pharmablock) |
| 97 | white solid; 1H NMR (300 MHz, Methanol-d4) 7.70 (dd, J = 8.1, 1.5 Hz, 1H), 7.54 (t, J = 8.0 Hz, 1H), 7.35 (dd, J = 7.9, 1.5 Hz, 1H), 4.29-4.17 (m, 1H), 3.90-3.68 (m, 4H), 3.29-3.14 (m, 2H), 3.04 (d, J = 4.9 Hz, 1H), 2.06 (s, 3H), 2.00 (s, 3H), 1.95-1.62 (m, 4H), 1.22 (d, J = 6.4 Hz, 3H); LC/MS (M + 1): 481.1, 483.1; mp: 100-102° C. | similar procedure as compound 21, from 1-(2-bromo-3-chlorophenyl)-2,5-dimethyl-6-oxo-1,6-dihydropyrimidin-4-yl 4-methylbenzene-1-sulfonate (Intermediate 27) and (3S,4S)-3-methyl-2-oxa-8-azaspiro[4.5]decan-4-amine dihydrochloride |
| 98 | White solid; 1H NMR (300 MHz, Methanol-d4) ? 7.35-7.18 (m, 2H), 4.27-4.19 (m, 1H), 3.99 (s, 3H), 3.85 (d, J = 8.6 Hz, 1H), 3.82-3.64 (m, 3H), 3.28-3.14 (m, 2H), 3.01 (d, J = 5.0 Hz, 1H), 2.06 (s, 3H), 2.00 (s, 3H), 1.95-1.74 (m, 2H), 1.69 (d, J = 10.4 Hz, 2H), 1.22 (d, J = 6.5 Hz, 3H); LC/MS (M + 1): 465.1, 467.1; mp: 100-102° C. | similar procedure as compound 21, 1-(2,3-dichloro-4-methoxyphenyl)-2,5-dimethyl-6-oxo-1,6-dihydropyrimidin-4-yl 4-methylbenzene-1-sulfonate (intermediate 28) and (3S,4S)-3-methyl-2-oxa-8-azaspiro[4.5]decan-4-amine dihydrochloride |
| 99 | White solid; 1H NMR (300 MHz, Methanol-d4): 7.50-7.42 (m, 2H), 4.28-4.17 (m, 1H), 3.93-3.68 (m, 4H), 3.29-3.13 (m, 2H), 3.02 (d, J = 4.9 Hz, 1H), 2.07 (s, 3H), 2.00 (s, 3H), 1.93-1.74 (m, 2H), 1.69 (d, J = 11.9 Hz, 2H), 1.22 (d, J = 6.4 Hz, 3H); LC/MS (M + 1): 455.2; mp: 121-123° C. | similar procedure as compound 21, from 1-(2,3-dichloro-4-fluorophenyl)-2,5-dimethyl-6-oxo-1,6-dihydropyrimidin-4-yl 4-methylbenzene-1-sulfonate (Intermediate 29) and (3S,4S)-3-methyl-2-oxa-8-azaspiro[4.5]decan-4-amine dihydrochloride (Pharmablock) |
| 100 | White solid; LC/MS (M + 1): 408.1 | similar procedure as compound 37, from (3M)-6-chloro-3-(2,3-dichlorophenyl)-2,5-dimethyl-3,4-dihydropyrimidin-4-one (Intermediate 8b) and octahydropyrrolo[1,2-a]pyrazin-7-amine trihydrochloride (Enamine) |
| 101 | White solid; 1H NMR (400 MHz, DMSO-d6): 7.76 (dd, J = 8.0, 1.7 Hz, 1H), 7.59-7.39 (m, 2H), 3.87 (dt, J = 11.2, 8.2 Hz, 1H), 3.73 (dd, J = 14.4, 11.4 Hz, 1H), 3.50-3.33 (m, 2H), 3.31 (d, J = 6.4 Hz, 1H), 2.70-2.53 (m, 2H), 2.40-2.16 (m, 2H), 2.00 (s, 3H), 1.93 (s, 3H), 1.78-1.63 (m, 1H), 1.63-1.49 (m, 2H), 1.31 (dd, J = 13.1, 9.3 Hz, 1H); LC/MS (M + 1): 437.2. | similar procedure as compound 37, from (3M)-6-chloro-3-(2,3-dichlorophenyl)-2,5-dimethyl-3,4-dihydropyrimidin-4-one 9Intermediate 8b) and [(3aR,6aS)-3a-(aminomethyl)-octahydrocyclopenta[c]pyrrol-5-yl]methanol (Enamine) |
| 102 | White solid; 1H NMR (300 MHz, MeOD): 6.79 (d, J = 8.4 Hz, 1H), 6.57 (d, J = 8.4 Hz, 1H), 4.25-4.21 (m, 1H), 3.88-3.71 (m, 4H), 3.32-3.16 (m, 2H), 3.02 (d, J = 4.8 Hz, 1H), 2.09 (s, 3H), 2.03 (s, 6H), 1.89-1.78 (m, 2H), 1.76-1.61 (m, 2H), 1.22 (d, J = 6.6 Hz, 3H); LC/MS (M + 1): 451.1. | similar procedure as compound 21, from 1-(2,3-dichloro-6-methylphenyl)-2,5-dimethyl-6-oxo-1,6-dihydropyrimidin-4-yl 4-methylbenzene-1-sulfonate (intermediate 30) and (3S,4S)-3-methyl-2-oxa-8-azaspiro[4.5]decan-4-amine dihydrochloride (Pharmablock) |
| 103 | White solid; 1H NMR (300 MHz, Methanol-d4): 7.32-7.19 (m, 2H), 4.23 (t, J = 6.0 Hz, 1H), 3.93-3.68 (m, 4H), 3.29-2.93 (m, 3H), 2.39 (d, J = 2.3 Hz, 3H), 2.03 (d, J = 16.1 Hz, 6H), 1.96-1.58 (m, 4H), 1.22 (d, J = 6.5 Hz, 3H); LC/MS (M + 1): 435.3; mp: 198-200° C. | similar procedure as compound 21, from 1-(2-chloro-4-fluoro-3-methylphenyl)-2,5-dimethyl-6-oxo-1,6-dihydropyrimidin-4-yl 4-methylbenzene-1-sulfonate (intermediate 31) and (3S,4S)-3-methyl-2-oxa-8-azaspiro[4.5]decan-4-amine dihydrochloride (Pharmablock) |
| 104 | White solid; 1H NMR (300 MHz, Methanol-d4): 7.89-7.86 (m, 1H), 7.43-7.36 (m, 3H), 7.21-7.18 (m, 3H), 3.97-3.90 (m, 3H), 3.33-3.20 (m, 2H), 3.14 (d, J = 15.9 Hz, 1H), 2.80 (d, J = | similar procedure as compound 74a, from 1-(3-bromo-2-chlorophenyl)-2,5-dimethyl-6-oxo-1,6- |

TABLE 2-continued

| No. | Description | Reactants and Procedure |
|-----|-------------|-------------------------|
|  | 15.9 Hz, 1H), 2.07 (s, 3H), 2.02 (s, 3H), 1.94-1.84 (m, 2H), 1.60-1.56 (m, 1H), 1.45-1.41 (m, 1H); LC/MS (M + 1): 513.1. | dihydropyrimidin-4-yl 4-methylbenzene-1-sulfonate (Intermediate 25) and (R)-N-[(1S)-1,3-dihydrospiro[indene-2,4'-piperidin]-1-yl]-2-methylpropane-2-sulfinamide (Pharmablock) |
| 105 | off-white solid; 1H NMR (400 MHz, DMSO-d6): 7.31-7.15 (m, 6H), 3.97 (s, 3H), 3.81-3.70 (m, 2H), 3.60-3.40 (m, 2H), 3.20-3.10 (m, 2H), 2.62-2.58 (m, 1H), 2.05 (s, 3H), 1.90 (s, 3H), 1.83-1.45 (m, 3H), 1.12-1.08 (m, 1H); LC/MS (M + 1): 467.1 | similar procedure as compound 74a, from 1-(2,4-difluoro-3-methoxyphenyl)-2,5-dimethyl-6-oxo-1,6-dihydropyrimidin-4-yl 4-methylbenzene-1-sulfonate (Intermediate 32) and (R)-N-[(1S)-1,3-dihydrospiro[indene-2,4'-piperidin]-1-yl]-2-methylpropane-2-sulfinamide (Pharmablock) |
| 106 | White solid; 1H NMR (300 MHz, DMSO-d6) 7.80-7.77 (m, 1H), 7.53 (d, J = 5.0 Hz, 2H), 7.36 (d, J = 4.1 Hz, 1H), 7.20 (s, 2H), 7.22-7.14 (m, 1H), 3.99 (s, 1H), 3.76 (d, J = 13.1 Hz, 2H), 3.09 ? 3.04(m, 3H), 2.70 (d, J = 15.7 Hz, 1H), 1.96 (s, 3H), 1.87 (m, 2H), 1.49 (d, J = 13.5 Hz, 1H), 1.23 (d, J = 11.0 Hz, 2H); LC/MS (M + 1): 472.2; mp: 90-92° C. | similar procedure as compound 74a, from 1-(2,3-dichlorophenyl)-5-(D3)methyl-2-methyl-6-oxo-1,6-dihydropyrimidin-4-yl 4-methylbenzene-1-sulfonate (intermediate 23) and (R)-N-[(1S)-1,3-dihydrospiro[indene-2,4'-piperidin]-1-yl]-2-methylpropane-2-sulfinamide (Pharmablock) |
| 107 | White powder; 1H NMR (400 MHz, DMSO-d6): 8.42-8.32 (m, 2H), 7.84-7.73 (m, 1H), 7.59-7.47 (m, 2H), 3.73-3.55 (m, 2H), 3.55-3.41 (m, 2H), 2.47-2.36 (m, 2H), 1.95 (s, 6H), 1.86-1.72 (m, 2H), 1.72-1.60 (m, 1H), 1.60-1.30 (m, 3H), 0.86 (d, J = 4.7 Hz, 3H); LC/MS (M + 1): 409.1. | similar procedure as compound 74a, from (3M)-6-chloro-3-(2,3-dichlorophenyl)-2,5-dimethyl-3,4-dihydropyrimidin-4-one (Intermediate 8b) and benzyl ((4-methylazepan-4-yl)methyl)-carbamate hydrochloride (Atatech) |
| 108 | Yellow solid; 1H NMR (300 MHz, Methanol-d4): 8.07-7.99 (m, 1H), 7.77-7.67 (m, 2H), 7.55 (d, J = 7.3 Hz, 1H), 7.47-7.30 (m, 3H), 4.45 (s, 1H), 4.00-3.87(m, 2H), 3.31-3.30 (m, 1H), 3.20 (s, 2H), 2.11 (s, 3H), 2.05 (s, 3H), 2.01-1.42 (m, 4H); LC/MS (M + 1): 492.2; mp: 160-162° C. | similar procedure as compound 74a, from 1-(2-chloro-3-cyanophenyl)-2,5-dimethyl-6-oxo-1,6-dihydropyrimidin-4-yl 4-methylbenzene-1-sulfonate (intermediate 33) and (R)-N-[(1S)-1,3-dihydrospiro[indene-2,4'-piperidin]-1-yl]-2-methylpropane-2-sulfinamide (Pharmablock) |
| 109 | White solid; 1H NMR (400 MHz, Methanol-d4): 7.51-7.47 (m, 2H), 7.44-7.38 (m, 1H), 7.26-7.21 (m, 3H), 4.00 (s, 1H), 3.97-3.93 (m, 2H), 3.33-3.26 (m, 2H), 3.16 (d, J = 15.6 Hz, 1H), 2.83 (d, J = 15.6 Hz, 1H), 2.09 (s, 3H), 2.03 (s, 3H), 1.95-1.84 (m, 2H), 1.60 (d, J = 14.4 Hz, 1H), 1.48 (d, J = 14.4 Hz, 1H); LC/MS (M + 1): 487.1 | similar procedure as compound 74a, from 1-(2,3-dichloro-4-fluorophenyl)-2,5-dimethyl-6-oxo-1,6-dihydropyrimidin-4-yl 4-methylbenzene-1-sulfonate (Intermediate 29) and (R)-N-[(1S)-1,3-dihydrospiro[indene-2,4'-piperidin]-1-yl]-2-methylpropane-2-sulfinamide (Pharmablock) |
| 110 | White solid; 1H NMR (400 MHz, Methanol-d4): 7.41-7.38 (m, 1H), 7.32-7.21 (m, 5H), 4.00 (s, 1H), 3.93 (d, J = 13.6 Hz, 2H), 3.33-3.32 (m, 2H), 3.16 (d, J = 16.0 Hz, 1H), 2.83 (d, J = 15.6 Hz, 1H), 2.41 (s, 3H), 2.08 (s, 3H), 2.03 (s, 3H), 1.96-1.84(m, 2H), 1.60 (d, J = 13.6 Hz, 1H), 1.46 (d, J = 13.6 Hz, 1H); LC?MS (M + 1): 467.1 | similar procedure as compound 74a, from 1-(2-chloro-4-fluoro-3-methylphenyl)-2,5-dimethyl-6-oxo-1,6-dihydropyrimidin-4-yl 4-methylbenzene-1-sulfonate (Intermediate 31) and (R)-N-[(1S)-1,3-dihydrospiro[indene-2,4'-piperidin]-1-yl]-2-methylpropane-2-sulfinamide (Pharmablock) |

TABLE 2-continued

| No. | Description | Reactants and Procedure |
|---|---|---|
| 111a | White solid; 1H NMR (400 MHz, DMSO-d6): 7.85-7.74 (m, 1H), 7.62-7.46 (m, 2H), 3.85-3.67 (m, 2H), 3.53-3.12 (m, 2H), 3.11-2.90 (m, 2H), 2.79 (t, J = 7.7 Hz, 1H), 2.20-2.02 (m, 2H), 1.97 (s, 3H), 1.89 (s, 3H), 1.77-1.66 (m, 1H), 1.65-1.51 (m, 2H), 1.51-1.42 (m, 1H), 1.30-1.13 (m, 2H), 0.98 (d, J = 6.3 Hz, 3H), 0.91-0.81 (m, 1H); LC/MS (M + 1): 435.2 | similar procedure as compound 77, from (1M)-1-(2,3-dichlorophenyl)-2,5-dimethyl-6-oxo-1,6-dihydropyrimidin-4-yl trifluoromethanesulfonate (intermediate 36) and (1R,3S)-3-methyl-8-azaspiro[4.5]decan-1-amine dihydrochloride (Hong Kong Chemhere Co., Ltd.) |
| 111b | White solid, 1H NMR (400 MHz, DMSO-d6): 7.84-7.75 (m, 1H), 7.57-7.50 (m, 2H), 3.79-3.62 (m, 2H), 3.11-2.93 (m, 2H), 2.73 (dd, J = 8.9, 6.0 Hz, 1H), 2.09-1.93 (m, 5H), 1.89 (s, 3H), 1.81-1.63 (m, 2H), 1.63-1.51 (m, 1H), 1.33-1.16 (m, 3H), 1.09-0.91 (m, 4H), LC/MS (M + 1): 435.2 | similar procedure as compound 77, from (1M)-1-(2,3-dichlorophenyl)-2,5-dimethyl-6-oxo-1,6-dihydropyrimidin-4-yl trifluoromethanesulfonate (intermediate 36) and (1R,3R)-3-methyl-8-azaspiro[4.5]decan-1-amine dihydrochloride (WUXI) |
| 112 | White solid; 1H NMR (400 MHz, Methanol-d4): 7.71-7.53 (m, 1H), 7.50-7.46 (m, 1H), 7.41-7.39 (m, 1H), 7.34-7.13 (m, 4H), 4.00-3.93 (m, 3H), 3.17 (d, J = 15.6 Hz, 1H), 2.85-2.77 (m, 1H), 2.62-2.50 (m, 1H), 2.10 (s, 3H), 2.04 (s, 3H), 1.97-1.84 (m, 3H), 1.61 (d, J = 12.8 Hz, 1H), 1.46 (d, J = 13.6 Hz, 1H); LC?MS (M + 1): 453.0 | similar procedure as compound 74a, from 1-(2-chloro-3-fluorophenyl)-2,5-dimethyl-6-oxo-1,6-dihydropyrimidin-4-yl 4-methylbenzene-1-sulfonate (intermediate 26) and (3S,4S)-3-methyl-2-oxa-8-azaspiro[4.5]decan-4-amine dihydrochloride (Pharmablock) |
| 113 | White solid; 1H NMR (400 MHz, DMSO-d6): 7.69 (q, J = 9.4 Hz, 1H), 7.52 (s, 1H), 7.34 (s, 1H), 7.19 (s, 3H), 3.90 (s, 1H), 3.79 (s, 2H), 3.25-2.88 (m, 5H), 2.65 (d, J = 16.9 Hz, 1H), 2.00 (s, 3H), 1.92 (s, 3H), 1.74 (s, 2H), 1.52 (d, J = 13.1 Hz, 1H), 1.21 (d, J = 27.7 Hz, 1H); LC/MS (M + 1): 471.2; mp: 88-90° C. | similar procedure as compound 74a, from 1-(2-chloro-3,4-difluorophenyl)-2,5-dimethyl-6-oxo-1,6-dihydropyrimidin-4-yl 4-methylbenzene-1-sulfonate (intermedaite 34) and (S)-N-[(1S)-1,3-dihydrospiro[indene-2,4'-piperidin]-1-yl]-2-methylpropane-2-sulfinamide (Pharmablock) |
| 114 | White solid; 1H NMR (400 MHz, DMSO-d6): 7.72 (d, J = 8.4 Hz, 1H), 7.58-7.24 (m, 2H), 6.63 (d, J = 200.0 Hz, 2H), 3.01 (d, J = 75.2 Hz, 4H), 2.41 (s, 2H), 1.79 (s, 3H), 1.47 (s, 2H), 1.29 (s, 2H), 0.91 (s, 3H); LC/MS (M + 1): 396.0; mp: 150-152° C. | similar procedure as compound 21, from 2-amino-1-(2,3-dichlorophenyl)-5-methyl-6-oxo-1,6-dihydropyrimidin-4-yl 4-methylbenzene-1-sulfonate (intermediate 35) and tert-butyl N-[(4-methylpiperidin-4-yl)methyl]carbamate |
| 115 | White solid; 1H NMR (400 MHz, DMSO-d6): 7.87-7.72 (m, 1H), 7.64-7.42 (m, 2H), 4.02-3.82 (m, 1H), 3.76-3.37 (m, 4H), 2.04-1.87 (m, 6H), 1.87-1.35 (m, 6H), 1.37-1.18 (m, 2H), 1.10-0.95 (m, 3H). LC/MS (M + 1): 439.2 | similar procedure as compound 74a, from (1M)-1-(2,3-dichlorophenyl)-2,5-dimethyl-6-oxo-1,6-dihydropyrimidin-4-yl trifluoromethanesulfonate (intermediate 36) and 1-(4-aminoazepan-4-yl)propan-2-ol dihydrochloride (Enamine) |
| 116 | White solid; 1H NMR (400 MHz, DMSO-d6): 7.72 (dd, J = 8.2, 1.5 Hz, 1H), 7.46 (t, J = 8.0 Hz, 1H), 7.34 (dd, J = 7.9, 1.5 Hz, 1H), 6.38 (s, 2H), 4.09-3.98 (m, 1H), 3.64 (d, J = 8.4 Hz, 1H), 3.46 (dd, J = 17.8, 10.9 Hz, 3H), 3.10-2.90 (m, 2H), 2.88 (d, J = 5.1 Hz, 1H), 1.79 (s, 4H), 1.65 (t, J = 9.6 Hz, 2H), 1.50 (t, J = 15.5 Hz, 2H), 1.08 (d, J = 6.4 Hz, 3H); LC/MS (M + 1): 438.1; mp: 125-127° C. | similar procedure as compound 21, from 2-amino-1-(2,3-dichlorophenyl)-5-methyl-6-oxo-1,6-dihydropyrimidin-4-yl 4-methylbenzene-1-sulfonate (intermediate 35) and (3S,4S)-3-methyl-2-oxa-8-azaspiro[4.5]decan-4-amine (Pharmablock) |
| 117 | White solid; 1H NMR (400 MHz, DMSO-d6): 7.73 (dd, J = 8.1, 1.5 Hz, 1H), 7.47 (t, J = 8.0 Hz, 1H), 7.34 (dd, J = 16.4, 7.2 Hz, 2H), 7.17 (q, J = 7.3, 6.2 Hz, 3H), 6.39 (s, 2H), 3.84 (s, 1H), 3.66 (t, J = 14.8 Hz, 2H), 3.01 (t, J = 13.8 Hz, 3H), 2.60 (d, J = 15.6 Hz, 1H), 1.82 (s, | similar procedure as compound 21, from 2-amino-1-(2,3-dichlorophenyl)-5-methyl-6-oxo-1,6-dihydropyrimidin-4-yl 4-methylbenzene-1-sulfonate |

TABLE 2-continued

| No. | Description | Reactants and Procedure |
|---|---|---|
|  | 4H), 1.70 (d, J = 12.5 Hz, 1H), 1.49 (d, J = 12.8 Hz, 1H), 1.09 (d, J = 13.1 Hz, 1H); LC/MS (M + 1): 470.1; mp: 130-132° C. | (intermediate 35) and (1S)-1,3-dihydrospiro[indene-2,4'-piperidin]-1-amine (Pharmablock) |
| 118 | White solid; 1H NMR (400 MHz, DMSO-d6): 7.71 (d, J = 8.1 Hz, 1H), 7.45 (t, J = 8.0 Hz, 1H), 7.32 (dd, J = 12.8, 7.3 Hz, 2H), 7.16 (q, J = 7.1, 5.9 Hz, 3H), 6.47 (s, 1H), 4.92 (s, 1H), 4.10 (s, 2H), 3.82 (s, 1H), 3.03 (t, J = 13.9 Hz, 3H), 2.60 (d, J = 15.5 Hz, 1H), 2.23 (d, J = 77.5 Hz, 1H), 1.71 (dt, J = 12.7, 7.7 Hz, 1H), 1.57 (d, J = 13.3 Hz, 1H), 1.45 (d, J = 13.3 Hz, 1H), 1.04 (d, J = 13.2 Hz, 1H); LC/MS (M + 1): 456.2; mp: 117-119° C. | similar procedure as compound 21, from 2-amino-1-(2,3-dichlorophenyl)-6-oxo-1,6-dihydropyrimidin-4-yl 4-methylbenzene-1-sulfonate (intermediate 4) and (1S)-1,3-dihydrospiro[indene-2,4'-piperidin]-1-amine (Pharmablock) |

Example 3: Testing Compounds of the Present Invention for Inhibitory Activities Against SHP2 and ERK12

SHP2 Biochemical Assay:

The inhibition of SHP2 by compounds of the invention was monitored using the surrogate substrate DiFMUP after protein activation by a peptide bearing two appropriately spaced phosphotyrosine. Full length SHP2 protein (Recombinant HumanSHP-2, E. coli derived Ser2Arg593, N-terminal 6His tag from R&D systems; 0.0.24 nM) was incubated with activating peptide, IRSI_2pY (New England Peptide, 140 nM) and DiFMUP (molecular probes, 80 uM) at RT in buffer (HEPES pH 7.2 60 mM, DDT 5 mM, KCl 75 mM, NaCl 75 mM, EDTA 1 mM, Tween 20 0.05%) in presence of compound (10 concentrations range, top concentration 50 µM) for 60 min. The generation of the DiFMU product by activated SHP2 was monitored through Fluorescence measurement with a PerkinElmer Envision reader. The inhibitor dose response curves were analyzed with Genedata Screener. $IC_{50}$ ranges for compounds of the invention are shown in table 3 below.

p-Erk Cellular Assay in KYSE520:

The effect of SHP2 inhibitors on pERK level was assessed using phospho-specific antibody using Mesoscale quantification platform. For measuring change in pERK levels using mesoscale, 30,000 cells of KYSE520 cells were plated in 96-well tissue culture treated plate in 175 µl volume of media. After an overnight incubation at 37° C., various SHP2 inhibitors were added in different concentration to each well maintaining duplicate wells across plates and incubated with compounds for 2 h at 37° C. followed by a wash with ice cold PBS buffer. The cells were then lysed in lysis buffer and processed and analyzed for p-ERK/ERK as per manufacturer's instructions (Mesoscale discovery, cat No. K15107D-3). $IC_{50}$ ranges for compounds of the invention are shown in Table 3 below.

TABLE 3

| Compound | SHP-2 biochemical assay $IC_{50}$ (µM) | pERK1/2 in Cell KYSE520 $IC_{50}$ (µM) |
|---|---|---|
| 1 | 8.600 | NT |
| 2 | 0.250 | 5.572 |
| 2a | >10 | NT |
| 2b | 0.180 | 4.250 |
| 3 | 0.200 | 5.586 |
| 3a | >10 | NT |
| 3b | 0.037 | 1.525 |
| 4 | 0.260 | NT |
| 5 | 0.760 | 14.491 |
| 6a | 19 | NT |
| 6b | >10 | NT |
| 7 | 4.80 | NT |
| 8 | 1.10 | NT |
| 9 | 16 | NT |
| 10 | 1.10 | NT |
| 11 | 3.80 | NT |
| 12 | 1.00 | NT |
| 13 | 4.30 | NT |
| 14 | 6.60 | NT |
| 15 | 2.10 | NT |
| 16 | 4.30 | NT |
| 17 | 3.00 | NT |
| 18 | 0.370 | 1.320 |
| 19 | 4.00 | NT |
| 20a | ND | NT |
| 20b | 1.10 | NT |
| 21 | 1.60 | NT |
| 22 | 2.10 | NT |
| 23a | 3.40 | NT |
| 23b | 0.009 | 0.094 |
| 24 | 0.710 | NT |
| 25 | 14 | NT |
| 26 | 0.380 | 2.290 |
| 27 | 0.051 | 0.239 |
| 28 | 3.500 | NT |
| 29 | 0.510 | 2.782 |
| 30 | 13 | NT |
| 31 | 0.560 | NT |
| 32a | >10 | NT |
| 32b | 1.90 | NT |
| 33a | >10 | NT |
| 33b | 5.70 | NT |
| 34 | 1.70 | NT |
| 35 | 0.560 | 0.600 |
| 36 | 5.00 | NT |
| 37a | 1.100 | 11.287 |
| 37b | >10 | NT |
| 38 | 1.5 | NT |
| 39 | >10 | NT |
| 41 | 2.50 | NT |
| 42 | 4.30 | NT |
| 43 | >10 | NT |
| 44 | 18 | NT |
| 45 | 1.20 | NT |
| 46 | >10 | NT |
| 47 | >10 | NT |
| 48 | 18 | NT |
| 49a | >10 | NT |
| 49b | >10 | NT |

TABLE 3-continued

| Compound | SHP-2 biochemical assay IC$_{50}$ (µM) | pERK1/2 in Cell KYSE520 IC$_{50}$ (µM) |
|---|---|---|
| 50 | 0.560 | NT |
| 51 | >10 | NT |
| 52 | 0.590 | NT |
| 53 | 6.10 | NT |
| 54 | 5.60 | NT |
| 55 | >10 | NT |
| 56 | 5.20 | NT |
| 57a | >10 | NT |
| 57b | 3.00 | NT |
| 58a | >10 | NT |
| 58b | 1.30 | NT |
| 59 | 2.60 | NT |
| 60 | 10 | NT |
| 61 | >10 | NT |
| 62a | >10 | NT |
| 62b | .081 | 0.526 |
| 63a | 6.00 | NT |
| 63b | .015 | 0.177 |
| 63 | 0.039 | 0.467 |
| 66a | 0.073 | NT |
| 66b | 0.001 | 0.005 |
| 67a | 19 | NT |
| 67b | 0.041 | 0.198 |
| 70 | >10 | NT |
| 71a | >50 | NT |
| 71b | 20 | NT |
| 72a | >10 | NT |
| 72b | 6.40 | NT |
| 73a | >10 | NT |
| 73b | 0.910 | NT |
| 74a | 0.001 | 0.002 |
| 74b | 0.026 | 0.624 |
| 74c | 0.250 | NT |
| 74d | >10 | NT |
| 75 | 0.120 | 0.824 |
| 76 | 7.00 | NT |
| 77 | 0.006 | 0.074 |
| 78a | >50 | NT |
| 78b | >10 | NT |
| 78c | 2.10 | NT |
| 78d | 0.190 | 1.327 |
| 79a | 0.300 | NT |
| 79b | 0.006 | 0.102 |
| 80a | 1.4 | >10 |
| 80b | >10 | 16 |
| 80c | 0.005 | 0.420 |
| 80d | 1.400 | NT |
| 81a | 0.470 | NT |
| 81b | 0.0014 | 0.0066 |
| 82 | 0.560 | 6.633 |
| 83 | >10 | NT |
| 84 | >10 | NT |
| 85 | >10 | NT |
| 86 | 4.60 | NT |
| 87 | 7.90 | NT |
| 88 | 0.590 | NT |
| 89 | 1.30 | NT |
| 90 | 3.90 | NT |
| 91 | 2.00 | NT |
| 92 | 16 | NT |
| 93 | 12 | NT |
| 94 | 1.40 | NT |
| 95 | 0.027 | 0.604 |
| 96 | 0.150 | 1.998 |
| 97 | 0.078 | 1.300 |
| 98 | 0.500 | NT |
| 99 | 0.028 | 0.955 |
| 100 | 5.80 | NT |
| 101 | 0.230 | NT |
| 102 | 7.300 | NT |
| 103 | 0.067 | 2.739 |
| 104 | 0.005 | 0.026 |
| 105 | 0.006 | 0.010 |
| 106 | 0.006 | 0.010 |
| 107 | 1.200 | NT |
| 108 | 0.007 | 0.032 |
| 109 | 0.002 | 0.004 |
| 110 | 0.002 | 0.007 |
| 111a | 0.093 | 0.720 |
| 112 | 0.004 | 0.014 |
| 113 | 0.006 | 0.015 |
| 114 | 1.400 | NT |
| 115 | 3.800 | NT |
| 116 | 0.200 | 2.191 |
| 117 | 0.015 | 0.006 |
| 118 | 0.016 | 0.051 |
| 119a | 0.27 | NT |
| 119b | 0.0008 | 0.005 |

Example 4: In-Vitro Safety Profile—Testing the Selectivity Over hErg

Inhibition of the ion channel hErg (or Kv11.1) current causes QT interval prolongation resulting in potentially fatal ventricular tachyarrhythmia called Torsade de Pointes. This is one of the major causes of cardiotoxicity and hErg channel activity is usually evaluated early in the drug development process to mitigate cardiotoxicity risk.

hERG ion channel activity was assessed using a patch clamp technique in stable Kv11.1 (hERG) transfected human embryonic kidney cell line (HEK293). Whole cell recordings were carried out with an automated patch clamp device Patchliner™ from Nanion Technologies, Munich following manufacturer recommendation. Different concentrations of the test compound or reference, quinidine, were applied to whole cells suspension and current was measured using a pulse pattern with fixed amplitudes. The effect on Kv11.1 (hERG) ion channel activity was judged from the tail current amplitude and Changes in Kv11.1 (hERG) ion channel activity between control value (defined as 100%) and test compound and reported as percent change of control value of COI.

TABLE 4
In-vitro safety profile
| Structure | Compound No. | hErg (patch clamp) Ki (μM) | Split between hErg and cell activity Ki (patch Clamp)/IC$_{50}$ (KYSE) |
|---|---|---|---|
| 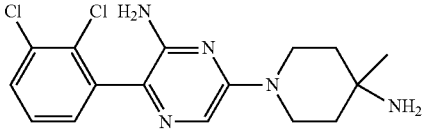 | SHP-099 (example 7 of WO15/107493) | 0.3 | 2.5 |
| 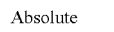 Absolute | 3b | >10 | >10 |
|  Absolute | RMC-4550 (example 228 of WO18/13597) | 0.6 | 26 |
|  Absolute | 23b | >10 | 136 |
| 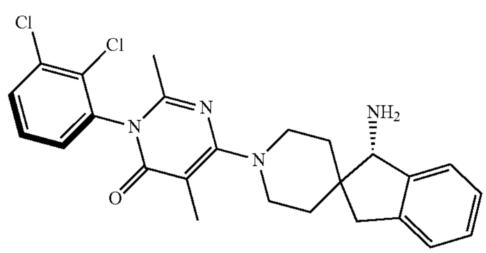 | 74a | 1.2 | 704 |
| 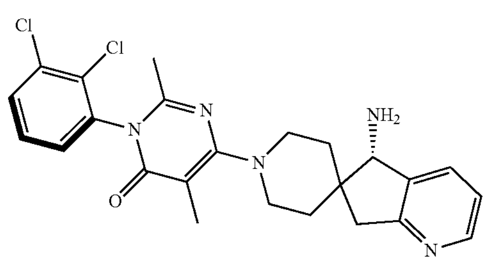 | 66b | 7.5 | 580 |

TABLE 4-continued

In-vitro safety profile

| Structure | Compound No. | hErg (patch clamp) Ki (μM) | Split between hErg and cell activity Ki (patch Clamp)/IC$_{50}$ (KYSE) |
|---|---|---|---|
| [structure] | 117 | 2.5 | 417 |

Result

The compounds of the present invention show a much better split between hErg activity (Ki in patch clamp assay) and cell activity (IC$_{50}$ in KYSE) as compared to known SHP2 inhibitors SHP-099 and RMC-4550. This should translate to less likelihood of cardio toxicity when administered to subjects.

Example 5: Testing the Pharmacokinetic Properties of the Compounds of the Present Invention in Mouse Female CD1 mice (N=3) received a single oral (gavage) or a single intravenous (bolus) injection of compound. Dosing vehicles were typically given by oral gavage as 0.5% Methocel K4M/0.25% Tween20 in sodium citrate buffer, 0.1M, pH 3.0 or, for IV administration, as a solution in 10% Kolliphor HS15 in Na acetate buffer, 0.01M, pH 4.5. Consecutive blood samples were taken sub-lingually under isofluorane inhalation from animals after 0.083 (IV), 0.25, 0.5, 1, 2, 4, 6 and 24 h and were further processed to obtain plasma. Samples were protein precipitated and analysed by LC/MS/MS.

TABLE 5

PK data in mouse

| Name, No. | Fz | Clearance L/h/kg | AUC ng/ml*h (normalized to 1 mp/k) | Vd ss (L/kg) | Cmax ng/mL (normalized to 1 mg/k) |
|---|---|---|---|---|---|
| SHP-099 | 74% | 5.7 | 129 | 5 | 48 |
| RMC-4550 | 86% | 1.2 | 735 | 6.1 | 85 |
| 3b | 85% | 0.48 | 1765 | 2.77 | 223 |
| 23b | 100% | 0.93 | 1222 | 4.64 | 177 |
| 66b | 100% | 0.5 | 2387 | 1.96 | 367 |
| 74a | 100% | 0.5 | 2108 | 5.1 | 129 |
| 81b | 48% | 0.15 | 3270 | 0.68 | 450 |

Result

In mouse PK, compounds of the present invention show a lower clearance and higher exposure as compared to the reference compounds SHP-099 and RMC-4550.

Example 6: Testing Compounds of the Present Invention for Inhibitory Activities Against SHP2 Active Mutant E76K with and without an Activating Peptide A selection of compounds have been tested in a biochemical assay using the same conditions as described in Example 3, but with an auto-activated mutant protein SHP2 E76K with and without the addition of the activating peptide IRSI_2pY (New England Peptide, 140 nM).

TABLE 6

| Compound | SHP-2 $IC_{50}$ (nM) peptide | SHP-2 E76Z $IC_{50}$ (nM) No peptide | SHP-2 E76Z $IC_{50}$ (nM) peptide |
|---|---|---|---|
| SHP-099 (example 7 of WO2015/107493) | 47 | 34 000 * | 250 000 * (+10 uM ppIRS-1) |
| 3b | 38 | 93 | 40 000 |
| 23b | 12 | 21 | 12 000 |
| 106 | 1.7 | 3.5 | 6.4 |
| 81b | 0.3 | 0.5 | 1.1 |
| 66a | 48 | 97 | 200 |
| 66b | 0.7 | 1.9 | 1.9 |

* From LaRochelle J. R. et al., Nature comm., 2018, 9:4508, 1-10

In strongly SHP2 activating conditions, the compounds of the invention retain a nM range potency while known inhibitor SHP099 loses efficacy in similar conditions. This can be an advantage for treating cancer with activating SHP2 mutations.

Example 7: SPR Binding Assay

Four SHP2 (R&D Systems) surfaces of different protein densities with one reference spot have been used. Recombinant human SHP2 protein (2-593) expressed from E. coli was covalently immobilized via amine coupling on a NTA chip at 25° C. to immobilization levels of 2,500 to 5,000 RU. The immobilization buffer contained 20 mM HEPES/NaOH (pH 7.4), 150 mM NaCl, 0.05% Tween 20. Inhibitors (stored as 10 mM stock solutions in 100% DMSO) were diluted in running buffer (20 mM HEPES/NaOH pH 7.4, 150 mM NaCl, 1 mM DTT, 5 mM MgCl2 0.1 mM EGTA, 0.05% Tween 20, 2% DMSO @25° C.) and analysed with a Biacore 4000 (Biacore AB, GE Healthcare Life Sciences, Uppsala, Sweden) using a 2-fold dilution series. The highest compound concentration varied according to the expected dissociation constant, but all compounds were tested at 10 different concentrations. Interaction analysis cycles were run at 30 µL/min and consisted of a 140 s sample injection followed by 600 s of buffer flow (dissociation phase). All sensograms were evaluated by first subtracting the binding response recorded from the control surface (reference spot), followed by subtracting a buffer blank injection. To determine kinetic rate constants, data sets were fitted to a simple 1:1 interaction model including a term for mass transport using numerical integration and nonlinear curve fitting. Equilibrium analysis was performed by fitting the response at the end of the association phase to a single-site binding isotherm.

TABLE 7

KD, kinetic profile and residence time on SHP2 SPR surface

| No. | KD [M] | kon [1/MS] | koff [1/s] | Residence time [min] |
|---|---|---|---|---|
| 23b | 7.14E−09 | 249000 | 0.0018 | 9.3 |
| 74a | ND | ND | <0.0001 | >160 |

Example 8: Activity in U937 Cells

Selected compounds were tested in a cytokine release assay in monocytic cells (U937) to test their anti-inflammatory properties. Cells were plated in a 96-well cell culture plate using serum-free media. The cells were treated with indicated concentrations of SHP-2 inhibitors for 30 minutes followed by overnight stimulation with recombinant IL-6 (50 ng/mL). The MCP-1 production was measured in the culture supernatant using a MCP-1 AlphaLISA kit (Perkin Elmer).

Compound 77 suppressed MCP-1 production in U937 cells stimulated with IL-6 with an $IC_{50}$=731 nM (FIG. 1). These results show that compounds of the invention may be useful to treat hyproliferative disorders beyond cancer, and including diseases and disorders associated with the immune system as well.

Example 9: Injection Vials

A solution of 100 g of a compound of the present invention and 5 g of disodium hydrogenphosphate in 3 L of bidistilled water is adjusted to pH 6.5 using 2 N hydrochloric acid, filtered under sterile conditions, transferred into injection vials, lyophilised under sterile conditions and sealed under sterile conditions. Each injection vial contains 5 mg of a compound of the present invention.

Example 10: Solution

A solution is prepared from 1 g of a compound of the present invention, 9.38 g of $NaH_2PO_4$ $2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation.

Example 11: Ampoules

A solution of 1 kg of a compound of the present invention in 60 L of bidistilled water is filtered under sterile conditions, transferred into ampoules, lyophilised under sterile conditions and sealed under sterile conditions. Each ampoule contains 10 mg of a compound of the present invention.

Example 12: In Vivo Studies—Monotherapy

Figure 2:
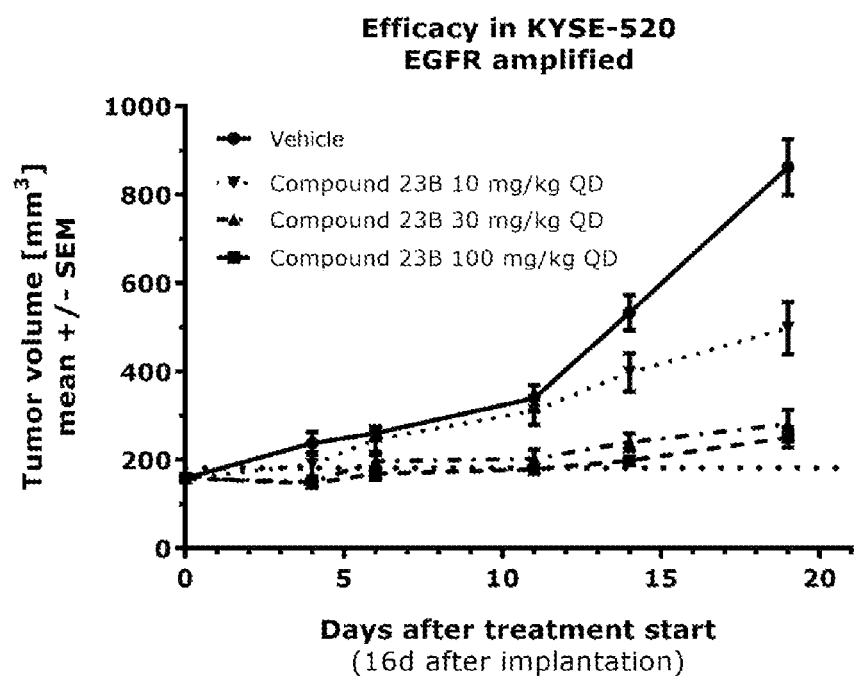
FIG. 2 depicts the effect of compound 23b administration at three dosage levels (10 mg/kg; 30 mg/kg; 100 mg/kg) QD in a xenograph model of EGFR amplified esophageal squamous carcinoma using a KYSE-520 cell line. The figure clearly shows multiple dosage levels reduce growth of the tumor a significant amount.

Selected compounds of the invention were evaluated in different in vivo models.
Kyse-520 (Esophageal Cancer)
In vivo efficacy of compound 23b in an EGFR amplified setting was investigated in Kyse-520 xenografts. H2D Rag2 mice were inoculated with 5 million KYSE-520 cells mixed with matrigel. After tumor engraftment mice were treated daily with oral gavage with either vehicle control or compound 23B at dose levels of 10 mg/kg, 30 mg/kg or 100 mg/kg. All doses were well tolerated. A dose-dependent significant tumor growth inhibition was observed (FIG. 2).

Figure 3:
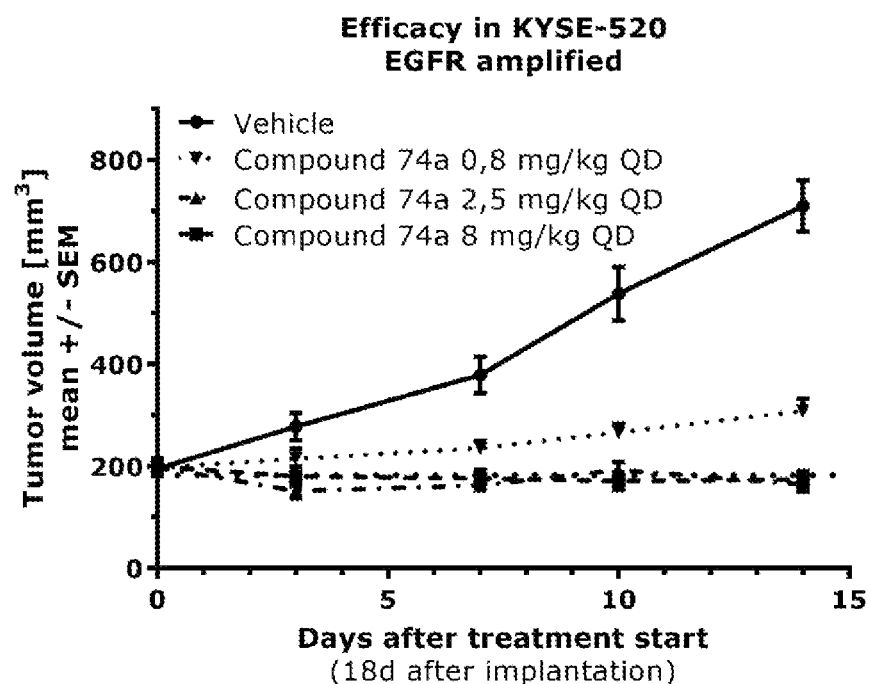
FIG. 3 depicts the effect of compound 74a administration at three dosage levels (0.8 mg/kg; 25 mg/kg; 8 mg/kg) QD in a xenograph model of esophageal squamous carcinoma using an EGFR amplified KYSE-520 cell line. The figure clearly shows all dosage levels reduce growth of the tumor a significant amount.

In vivo efficacy of compound 74a in an EGFR amplified setting was investigated in Kyse-520 xenografts. H2D Rag2 mice were inoculated with 5 million KYSE-520 cells mixed with matrigel. After tumor engraftment mice were treated daily with oral gavage with either vehicle control or compound 74a at dose levels of 0.8 mg/kg, 2.5 mg/kg or 8 mg/kg. All doses were well tolerated. A dose-dependent significant tumor growth inhibition was observed (FIG. 3). Other compounds of the invention could be tested using this methodology and adjusting the dose administered depending on $IC_{50}$ for each.

MiaPaCa-2 (Pancreatic Cancer)

Figure 4:
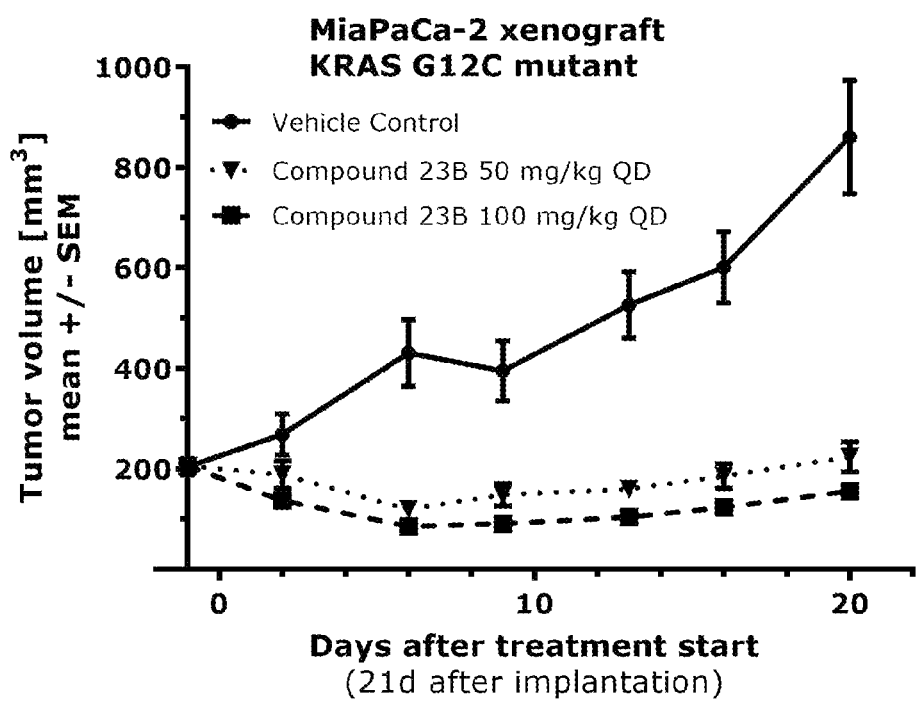
FIG. 4 depicts the effect of compound 23b administration at two dosage levels (50 mg/kg; 100 mg/kg) QD in a xenograph model of pancreatic carcinoma using a KRAS G12C mutant MiaPaCa-2 cell line. Both dosage levels clearly show significant reduction in tumor growth.

In vivo efficacy of compound 23b in a KRAS G12C mutant setting was investigated in MiaPaCa-2 xenografts. H2D Rag2 mice were inoculated with 3 million MiaPaCa-2 cells. After tumor engraftment mice were treated daily with oral gavage with either vehicle control or 50 mg/kg or 100 mg/kg compound 23B. All doses were well tolerated. Significant tumor growth inhibition was observed (FIG. 4). Other compounds of the invention could be tested using this methodology and adjusting the dose administered depending on $IC_{50}$ for each.

HPAF-2 (Pancreatic Adenocarcinoma)

Figure 5:
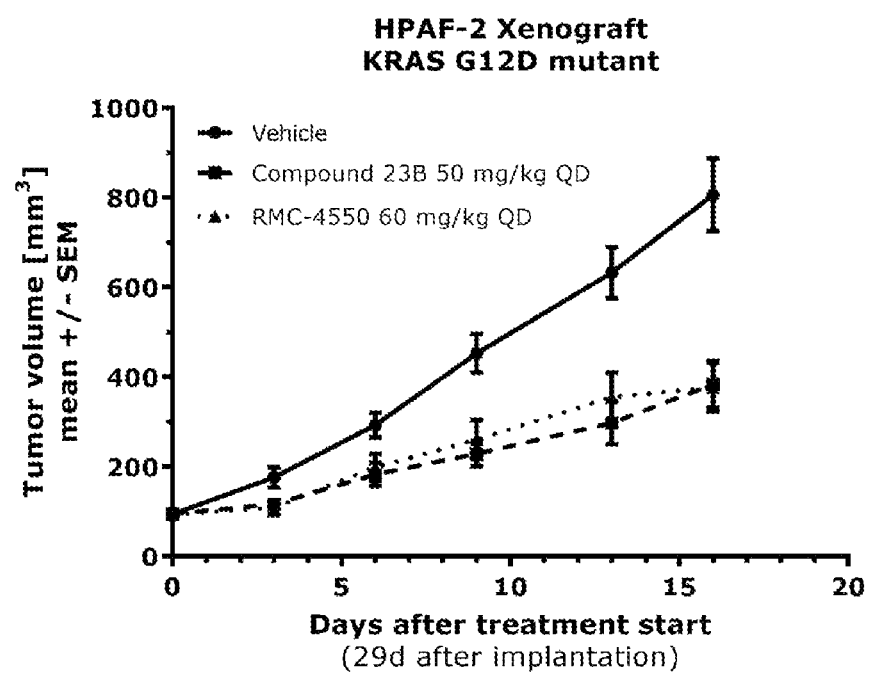
FIG. 5 depicts the effect of compound 23b administration at 50 mg/kg QD and administration of RMC-4550 at 60 mg/kg QD on a xenograph model of pancreatic cancer using a KRAS G12D mutant HPAF-2 cell line.

In vivo efficacy of compound 23b in a KRAS G12D mutant setting was investigated in HPAF-2 xenografts. CB17.SCID mice were inoculated with 5 million HPAF-2 cells. After tumor engraftment mice were treated daily with oral gavage with either vehicle control or 50 mg/kg compound 23B or 60 mg/kg reference compound RMC-4550. All doses were well tolerated. Significant tumor inhibition was observed (FIG. 5). Other compounds of the invention could be tested using this methodology and adjusting the dose administered depending on $IC_{50}$ for each.

U87-Mg (Glioblastoma)

Figure 6:
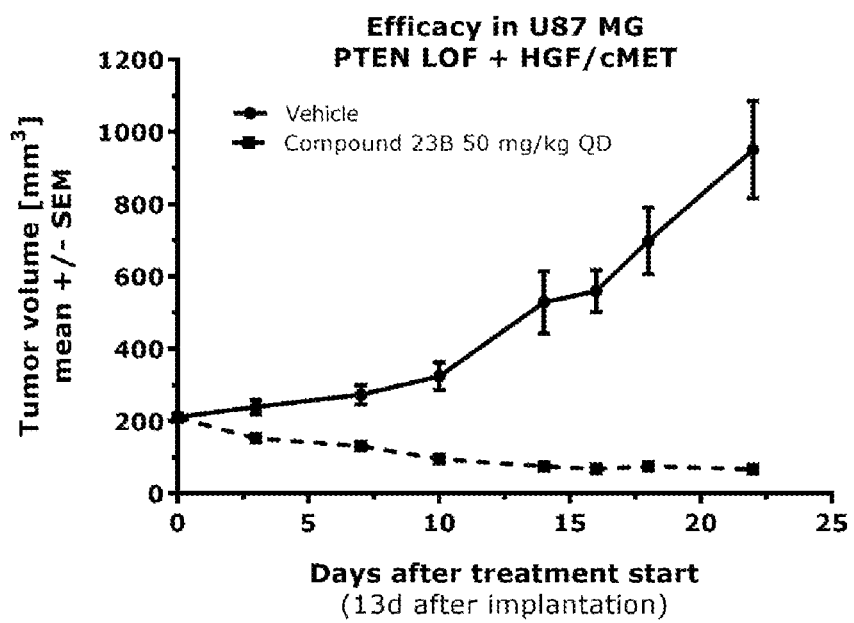
FIG. 6 depicts the effect of compound 23b administration at 50 mg/kg QD in a xenograph model of glioblastoma using U87 cell line with PTEN LOF+HGF/cMET mutations. Administration of the compound clearly prevents tumor growth and, in fact, actually reduces tumor size as compared to baseline.

In vivo efficacy of compound 23b in a PTEN LOF setting was investigated in U87-MG xenografts. CD-1 nude mice were inoculated with 10 million U87-MG cells. After tumor engraftment mice were treated daily with oral gavage with either vehicle control or 50 mg/kg compound 23B. Tumor regression was observed (FIG. 6). Other compounds of the invention could be tested using this methodology and adjusting the dose administered depending on $IC_{50}$ for each.

EBC-1 (Non-Small Cell Lung Cancer)

Figure 7:
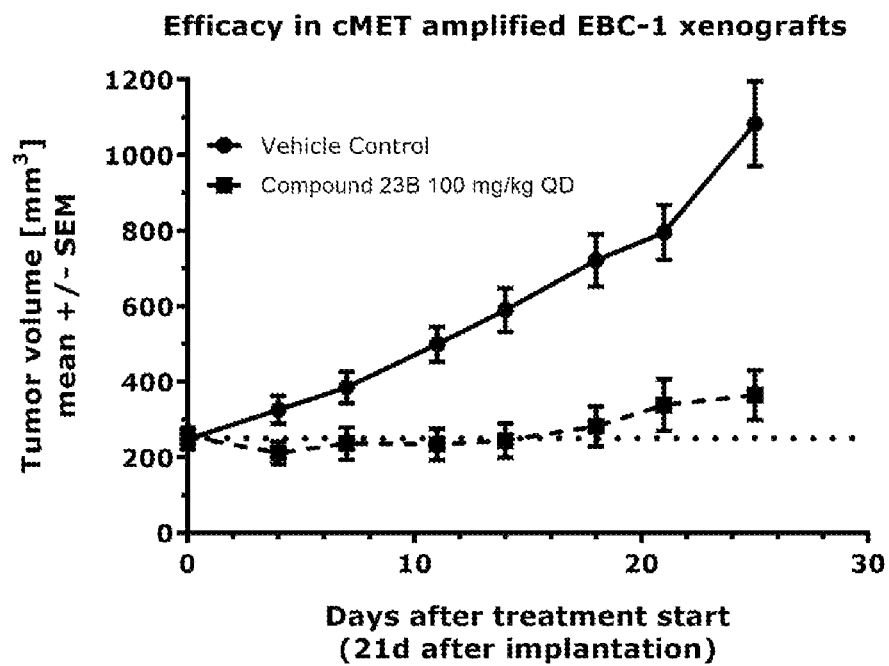
FIG. 7 depicts the effect of compound 23b administration at 100 mg/kg QD in a xenograph model of cMET amplified squamous cell carcinoma using an EBC-1 cell line. Administration of the compound clearly reduces tumor growth.

In vivo efficacy of compound 23b in a cMET amplified setting was investigated in EBC-1 xenografts. CD-1 nude mice were inoculated with 5 million EBC-1 cells. After tumor engraftment mice were treated daily with oral gavage with either vehicle control or 100 mg/kg compound 23b. All doses were well tolerated. Significant tumor growth inhibition was observed (FIG. 7). Other compounds of the invention could be tested using this methodology and adjusting the dose administered depending on $IC_{50}$ for each.

We claim:
1. A compound according to Formula (I):

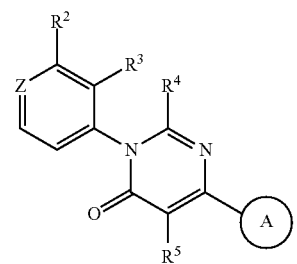

or a pharmaceutically acceptable salt thereof, wherein
Ring A is:

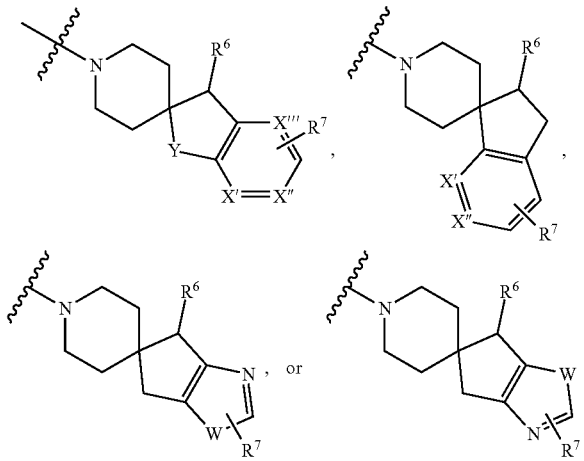

$R^1$ is:
hydrogen, —F, —Cl, —Br, —OPh,

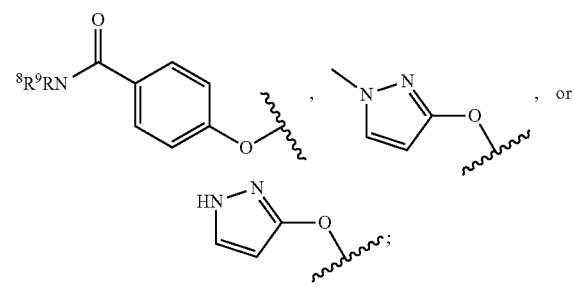

each of $R^2$, and $R^3$ are independently selected from hydrogen, —$CF_3$, —Cl, —Br, —F, —CN, —$NH_2$, —$OCH_3$, and —$CH_3$;
each of $R^4$ and $R^5$ are independently selected from hydrogen, —Br, —Cl, —$CF_3$, —$CH_3$, —$CD_3$ and —$NH_2$;
$R^6$ is —$NH_2$;
$R^7$ is hydrogen, —Cl, —Br, —F, —CN, —$OCH_3$, —$CH_3$, or —$NH_2$;
each of $R^8$ and $R^9$ is independently hydrogen or methyl;
each W is S or O;
Z is N or —$CR^1$;

each X' and X" is independently —CH— or —N—, provided that both X' and X" are not N at the same time; and Y, where present, is —CH$_2$— or —O—.

2. The compound of claim 1, or a pharmaceutically acceptable salt thereof, wherein Z is C—R$^1$; and R$^1$ is —H or —F.

3. The compound according to claim 2, or a pharmaceutically acceptable salt thereof, wherein R$^1$ is —H; R$^2$ and R$^3$ are both —Cl; and R$^4$ and R$^5$ are both —CH$_3$.

4. The compound according to claim 3, or a pharmaceutically acceptable salt thereof, wherein Ring A is selected from:

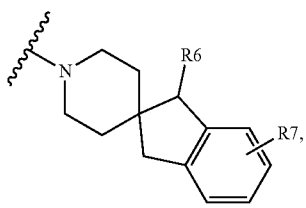

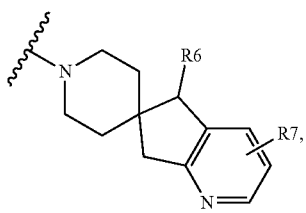

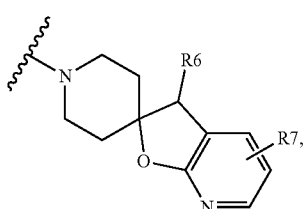

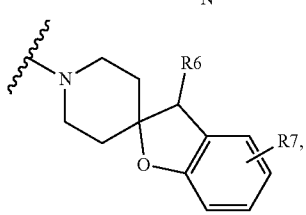

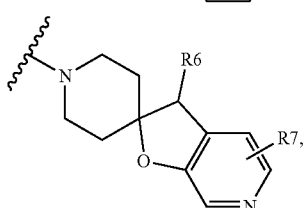

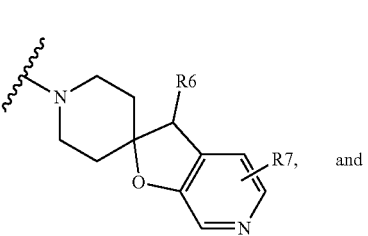 and

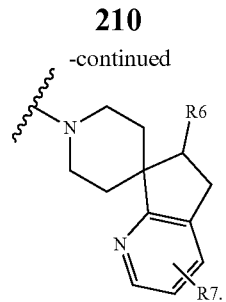

5. The compound according to claim 1, as shown by Formula (Ia') or Formula (Ib"):

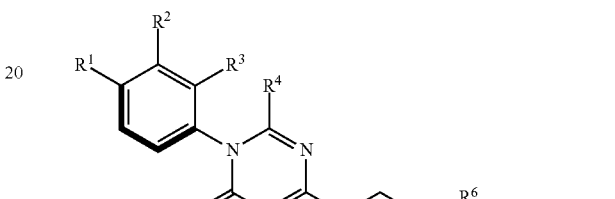

Ia"

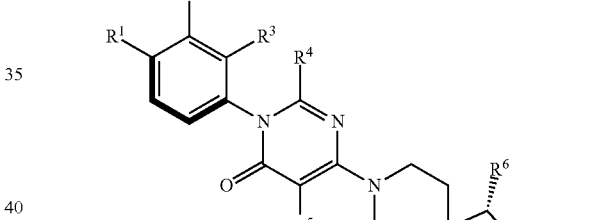

Ib"

or a pharmaceutically acceptable salt thereof.

6. The compound according to claim 5, or a pharmaceutically acceptable salt thereof, wherein R$^1$ is hydrogen.

7. The compound according to claim 5, or a pharmaceutically acceptable salt thereof, wherein R$^2$ and R$^3$ are independently —Cl, —Br, or —F.

8. The compound according to claim 5, or a pharmaceutically acceptable salt thereof, wherein R$^2$ and R$^3$ are both —Cl.

9. The compound according to claim 5, or a pharmaceutically acceptable salt thereof, wherein R$^4$ is —CH$_3$ or —NH$_2$; and R$^5$ is —CH$_3$ or —H.

10. The compound according to claim 5, or a pharmaceutically acceptable salt thereof, wherein R$^4$ and R$^5$ are both —CH$_3$.

11. The compound according to claim 5, or a pharmaceutically acceptable salt thereof, wherein R$^7$ is hydrogen.

12. The compound according to claim 5, or a pharmaceutically acceptable salt thereof, wherein X' is N and X" is CH.

13. The compound according to claim 5, or a pharmaceutically acceptable salt thereof, wherein X' is CH and X" is N.

14. The compound according to claim 5, or a pharmaceutically acceptable salt thereof, wherein both X' and X" are CH.

15. The compound according to claim 5, or a pharmaceutically acceptable salt thereof, wherein Y is O.

16. The compound according to claim 5, or a pharmaceutically acceptable salt thereof, wherein Y is CH$_2$.

17. The compound according to claim 1, selected from the group consisting of:

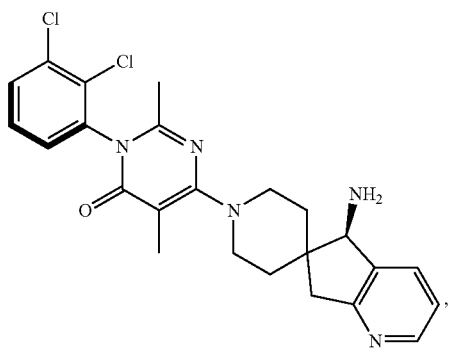

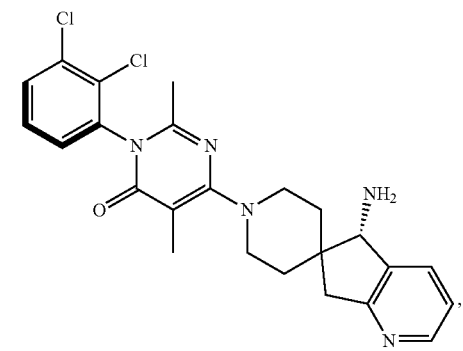

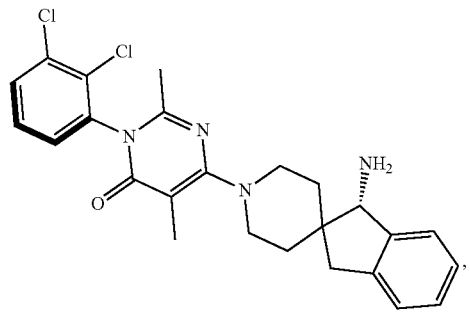

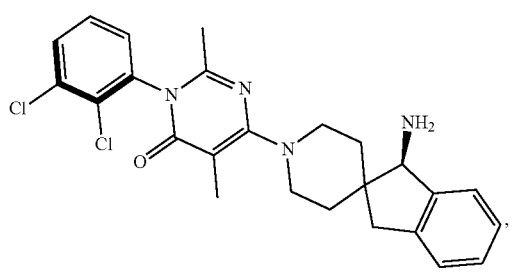

-continued

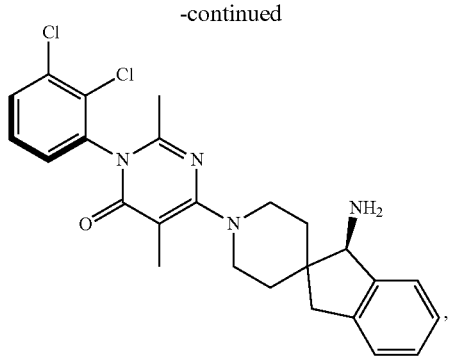

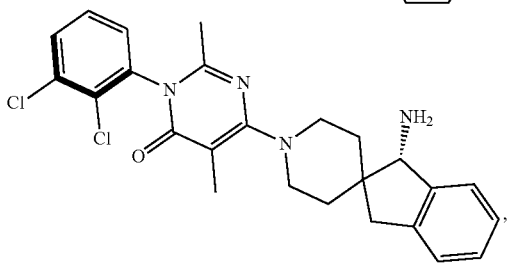

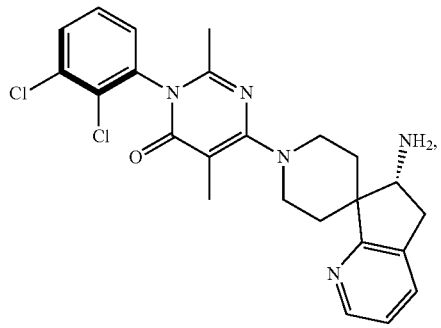

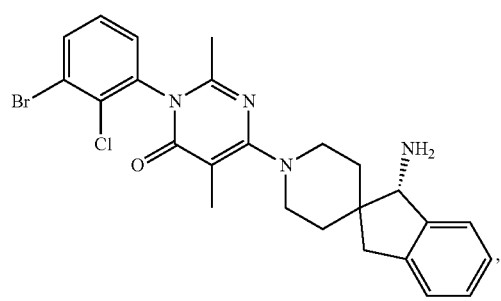

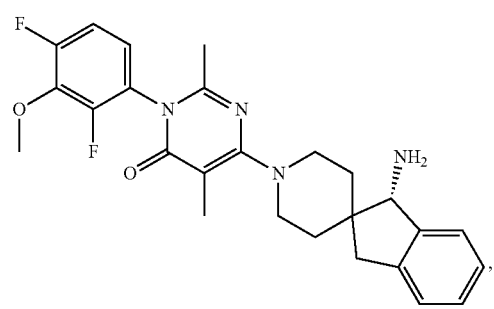

213
-continued
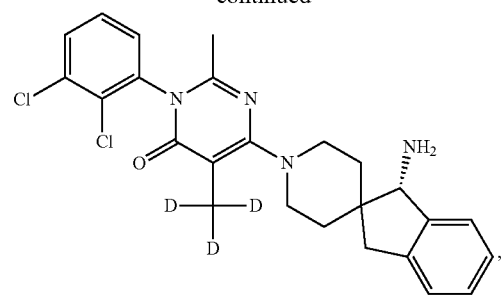
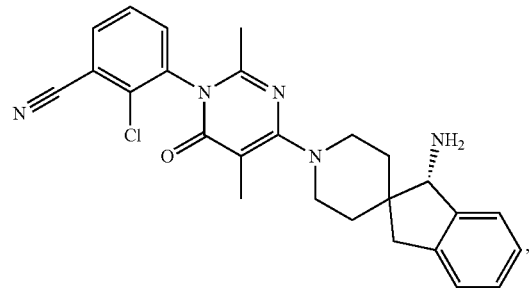
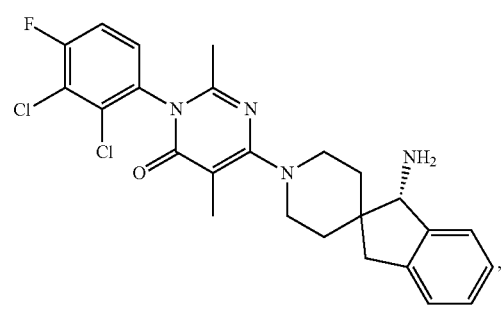
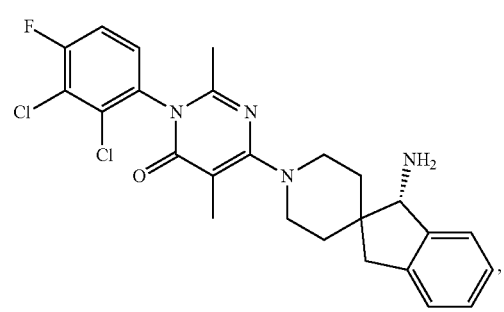
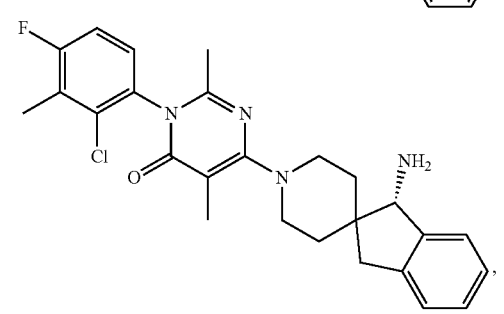
214
-continued
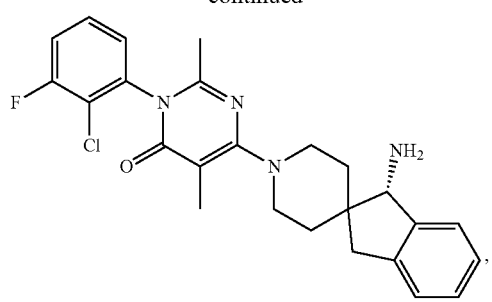
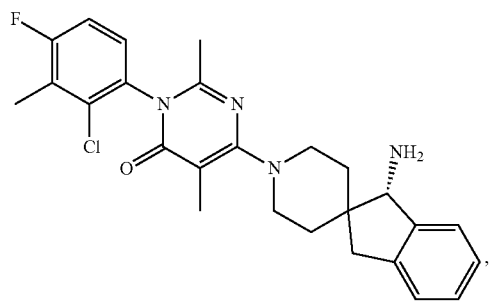
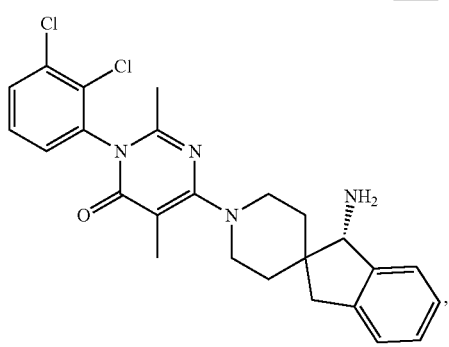
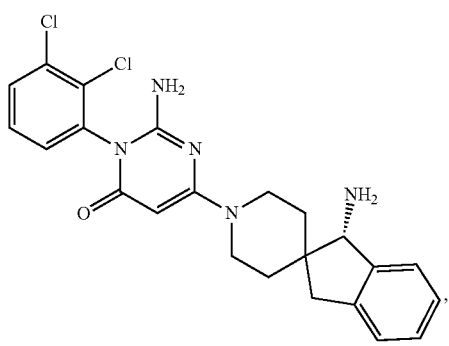
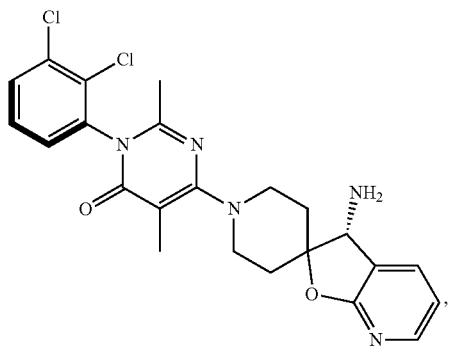

215
-continued
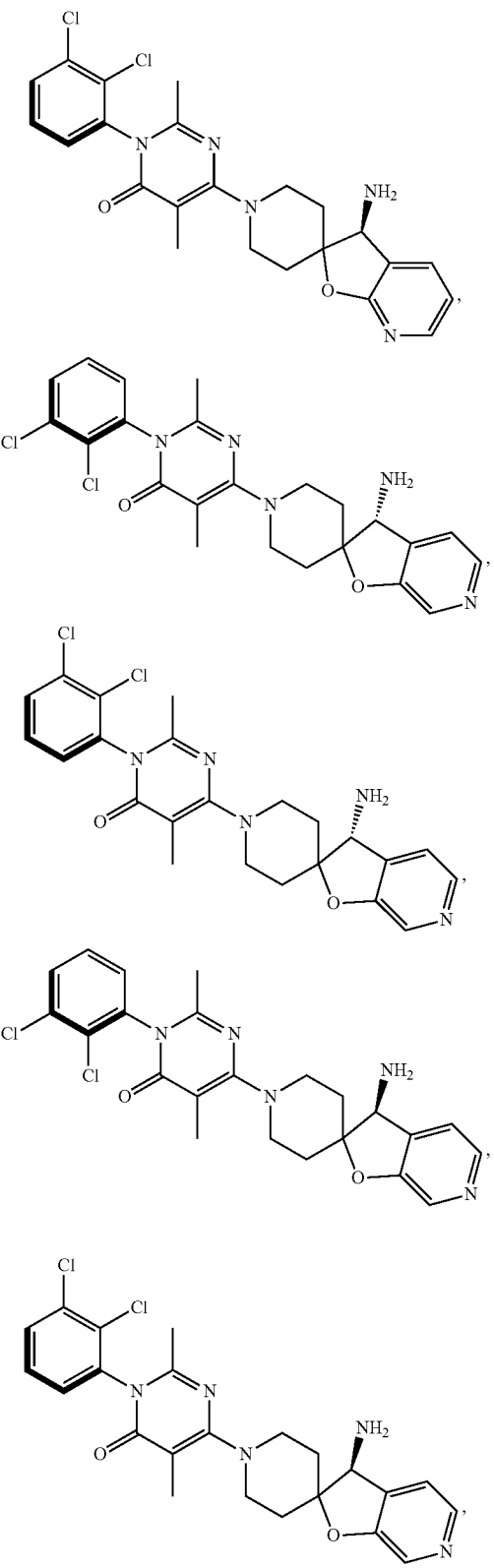
216
-continued
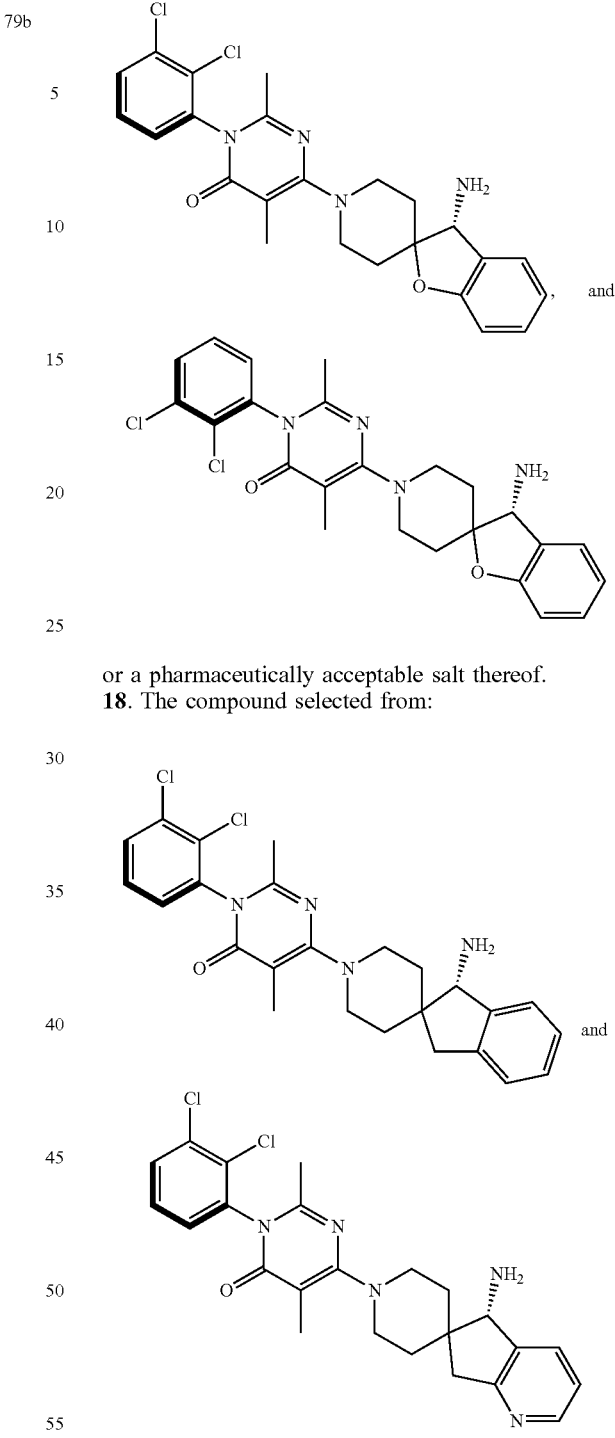
or a pharmaceutically acceptable salt thereof.
18. The compound selected from:
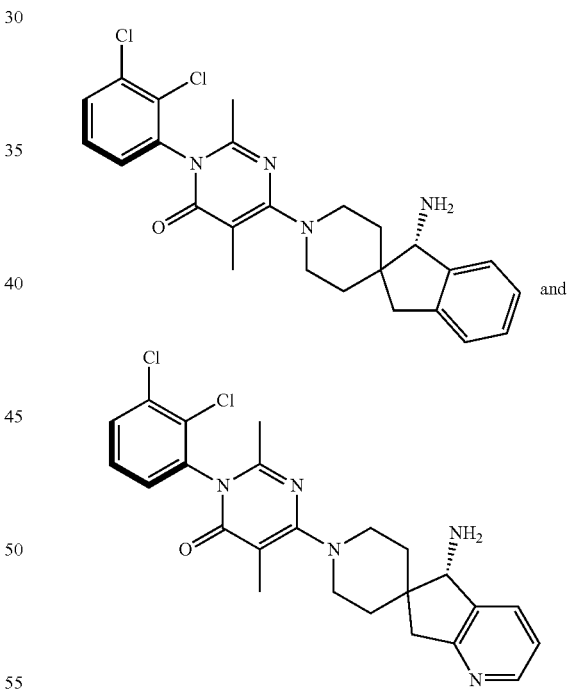
or a pharmaceutically acceptable salt thereof.
19. A pharmaceutical composition comprising a compound according to claim 1, or a pharmaceutically acceptable salt thereof, together with a pharmaceutically acceptable carrier, adjuvant and/or excipient.
* * * * *